United States Patent
Poma et al.

(10) Patent No.: US 12,037,367 B2
(45) Date of Patent: Jul. 16, 2024

(54) MHC CLASS I EPITOPE DELIVERING POLYPEPTIDES

(71) Applicant: Molecular Templates, Inc., Austin, TX (US)

(72) Inventors: Eric Poma, New York, NY (US); Erin Willert, Round Rock, TX (US)

(73) Assignee: Molecular Templates, Inc., Austin, TX (US)

( * ) Notice: Subject to any disclaimer, the term of this patent is extended or adjusted under 35 U.S.C. 154(b) by 123 days.

(21) Appl. No.: 17/705,619

(22) Filed: Mar. 28, 2022

(65) Prior Publication Data

US 2022/0306701 A1 Sep. 29, 2022

Related U.S. Application Data

(60) Division of application No. 17/231,526, filed on Apr. 15, 2021, now Pat. No. 11,312,751, which is a
(Continued)

(51) Int. Cl.
*C07K 14/25* (2006.01)
*A61K 39/00* (2006.01)
(Continued)

(52) U.S. Cl.
CPC ............ *C07K 14/25* (2013.01); *C07K 14/245* (2013.01); *C07K 16/00* (2013.01); *C07K 16/085* (2013.01);
(Continued)

(58) Field of Classification Search
CPC .. A61P 1/04; A61P 11/06; A61P 17/00; A61P 17/06; A61P 19/02; A61P 25/00;
(Continued)

(56) References Cited

U.S. PATENT DOCUMENTS

| 5,080,898 A | 1/1992 | Murphy |
| 5,135,736 A | 8/1992 | Anderson et al. |

(Continued)

FOREIGN PATENT DOCUMENTS

| AU | 750367 B2 | 7/2002 |
| AU | 2004202331 A1 | 6/2004 |

(Continued)

OTHER PUBLICATIONS

U.S. Appl. No. 17/314,563, filed May 7, 2021, Poma et al.
(Continued)

*Primary Examiner* — Jana A Hines
(74) *Attorney, Agent, or Firm* — COOLEY LLP

(57) ABSTRACT

The present invention is directed to T-cell epitope delivering polypeptides which deliver one or more CD8+ T-cell epitopes to the MHC class I presentation pathway of a cell, including toxin-derived polypeptides which comprise embedded T-cell epitopes and are de-immunized. The present invention provides cell-targeted, CD8+ T-cell epitope delivering molecules for the targeted delivery of cytotoxicity to certain cells, e.g., infected or malignant cells, for the targeted killing of specific cell types, and the treatment of a variety of diseases, disorders, and conditions, including cancers, immune disorders, and microbial infections. The present invention also provides methods of generating polypeptides capable of delivering one or more heterologous T-cell epitopes to the MHC class I presentation pathway, including polypeptides which are 1) B-cell and/or CD4+ T-cell de-immunized, 2) comprise embedded T-cell epitopes, and/or 3) comprises toxin effectors which retain toxin functions.

11 Claims, 4 Drawing Sheets

Specification includes a Sequence Listing.

Related U.S. Application Data continuation of application No. 16/220,468, filed on Dec. 14, 2018, now abandoned, which is a continuation of application No. 15/114,474, filed as application No. PCT/US2015/012968 on Jan. 26, 2015, now abandoned.

(60) Provisional application No. 62/049,325, filed on Sep. 11, 2014, provisional application No. 61/932,000, filed on Jan. 27, 2014.

(51) Int. Cl.
| | | |
|---|---|---|
| *C07K 14/245* | (2006.01) | |
| *C07K 16/00* | (2006.01) | |
| *C07K 16/08* | (2006.01) | |
| *C07K 16/10* | (2006.01) | |
| *C07K 16/28* | (2006.01) | |
| *C07K 16/32* | (2006.01) | |
| *C12N 9/10* | (2006.01) | |
| *C12N 9/24* | (2006.01) | |
| *C12N 15/62* | (2006.01) | |

(52) U.S. Cl.
CPC ........ *C07K 16/088* (2013.01); *C07K 16/1063* (2013.01); *C07K 16/286* (2013.01); *C07K 16/2863* (2013.01); *C07K 16/2866* (2013.01); *C07K 16/2887* (2013.01); *C07K 16/32* (2013.01); *C12N 9/1077* (2013.01); *C12N 9/2497* (2013.01); *C12N 15/62* (2013.01); *C12Y 204/02036* (2013.01); *C12Y 302/02022* (2013.01); *A61K 2039/6037* (2013.01); *C07K 2319/04* (2013.01); *C07K 2319/33* (2013.01); *C07K 2319/40* (2013.01); *C07K 2319/55* (2013.01); *Y02A 50/30* (2018.01)

(58) Field of Classification Search
CPC .. A61P 29/00; A61P 3/10; A61P 31/00; A61P 31/04; A61P 31/18; A61P 35/00; A61P 37/00; A61P 37/02; A61P 37/04; A61P 37/06; A61P 43/00; A61P 5/14; A61P 9/00; C07K 14/245; C07K 14/25; C07K 16/00; C07K 16/085; C07K 16/088; C07K 16/1063; C07K 16/286; C07K 16/2863; C07K 16/2866; C07K 16/2887; C07K 16/32; C07K 2317/22; C07K 2319/04; C07K 2319/33; C07K 2319/40; C07K 2319/55; C12N 15/63; C12N 9/1077; C12N 9/2497; C12Y 204/02036; C12Y 302/02022; A61K 2039/6037; A61K 38/00; Y02A 50/30
See application file for complete search history.

(56) References Cited

U.S. PATENT DOCUMENTS

| | | |
|---|---|---|
| 5,552,144 A | 9/1996 | Samuel et al. |
| 5,635,384 A | 6/1997 | Walsh et al. |
| 5,668,255 A | 9/1997 | Murphy |
| 5,858,682 A | 1/1999 | Gruenwald et al. |
| 6,022,950 A | 2/2000 | Murphy |
| 6,080,400 A | 6/2000 | Williams et al. |
| 6,492,498 B1 | 12/2002 | Vallera et al. |
| 6,652,857 B2 | 11/2003 | Williams et al. |
| 6,770,456 B1 | 8/2004 | Coulie et al. |
| 7,144,991 B2 | 12/2006 | Goshom et al. |
| 7,267,973 B2 | 9/2007 | Backer et al. |
| 7,527,787 B2 | 5/2009 | Chang et al. |
| 7,700,557 B2 | 4/2010 | Backer et al. |
| 7,713,915 B1 | 5/2010 | Gariepy et al. |
| 7,799,900 B2 | 9/2010 | Adams |
| 7,834,258 B2 | 11/2010 | Choe et al. |
| 7,887,801 B2 | 2/2011 | Wels et al. |
| 8,048,985 B2 | 11/2011 | Harrison et al. |
| 8,147,832 B2 | 4/2012 | Carr et al. |
| 8,337,844 B2 | 12/2012 | Carr et al. |
| 8,470,314 B2 | 6/2013 | Davis et al. |
| 8,530,637 B2 | 9/2013 | Wels et al. |
| 8,865,866 B2 | 10/2014 | Harrison et al. |
| 8,895,006 B2 | 11/2014 | Tumer et al. |
| 8,969,529 B2 | 3/2015 | O'Brien et al. |
| 9,175,059 B2 | 11/2015 | Pieczykolan et al. |
| 9,364,557 B2 | 6/2016 | Neville, Jr. et al. |
| 10,421,958 B2 | 9/2019 | Poma et al. |
| 10,815,469 B2 | 10/2020 | Poma et al. |
| 11,136,395 B2 | 10/2021 | Poma et al. |
| 11,225,509 B2 | 1/2022 | Poma et al. |
| 11,312,751 B2 | 4/2022 | Poma et al. |
| 11,365,223 B2 | 6/2022 | Poma et al. |
| 11,389,542 B1 | 7/2022 | Poma et al. |
| 11,406,692 B2 | 8/2022 | Poma et al. |
| 11,713,347 B2 | 8/2023 | Chattopadhyay et al. |
| 2002/0012658 A1 | 1/2002 | Williams et al. |
| 2002/0168370 A1 | 11/2002 | McDonald, Jr. et al. |
| 2003/0166196 A1 | 9/2003 | Better et al. |
| 2004/0141982 A1 | 7/2004 | Lust et al. |
| 2004/0166565 A1 | 8/2004 | Backer et al. |
| 2005/0054835 A1 | 3/2005 | Better et al. |
| 2005/0069545 A1 | 3/2005 | Carr et al. |
| 2006/0008475 A1 | 1/2006 | Johannes et al. |
| 2008/0286310 A1 | 11/2008 | Zhu et al. |
| 2009/0023649 A1 | 1/2009 | Backer et al. |
| 2009/0092578 A1 | 4/2009 | Su et al. |
| 2009/0156417 A1 | 6/2009 | Gariepy et al. |
| 2009/0156502 A1 | 6/2009 | Harrison et al. |
| 2010/0093563 A1 | 4/2010 | Williamson et al. |
| 2010/0285004 A1 | 11/2010 | Tesar et al. |
| 2011/0189209 A1 | 8/2011 | Neville, Jr. et al. |
| 2012/0039908 A1 | 2/2012 | Combs et al. |
| 2012/0149650 A1 | 6/2012 | Harrison et al. |
| 2012/0213781 A1 | 8/2012 | Hilbert |
| 2012/0251542 A1 | 10/2012 | Tumer et al. |
| 2012/0258104 A1 | 10/2012 | Echeverri |
| 2013/0071325 A1 | 3/2013 | Sahin et al. |
| 2013/0189271 A1 | 7/2013 | De Goeij et al. |
| 2013/0196928 A1 | 8/2013 | Gariepy et al. |
| 2013/0202598 A1 | 8/2013 | Benhar et al. |
| 2014/0030273 A1 | 1/2014 | Verploegen et al. |
| 2015/0044210 A1 | 2/2015 | Mechaly et al. |
| 2015/0259428 A1 | 9/2015 | Poma et al. |
| 2016/0017047 A1 | 1/2016 | Poma et al. |
| 2016/0017784 A1 | 1/2016 | Kumar |
| 2016/0068577 A1 | 1/2016 | Poma et al. |
| 2016/0130362 A1 | 5/2016 | de Weers |
| 2016/0177284 A1 | 6/2016 | Poma et al. |
| 2016/0340394 A1 | 11/2016 | Poma et al. |
| 2016/0347798 A1 | 12/2016 | Poma et al. |
| 2016/0376328 A1 | 12/2016 | Poma et al. |
| 2017/0002016 A1 | 1/2017 | Shishido et al. |
| 2017/0002046 A1 | 1/2017 | Poma et al. |
| 2017/0143814 A1 | 5/2017 | Poma et al. |
| 2017/0275382 A1 | 9/2017 | Poma et al. |
| 2018/0057544 A1 | 3/2018 | Poma et al. |
| 2018/0243432 A1 | 8/2018 | Poma et al. |
| 2018/0258143 A1 | 9/2018 | Poma et al. |
| 2018/0258144 A1 | 9/2018 | Poma et al. |
| 2018/0291359 A1 | 10/2018 | Poma et al. |
| 2019/0083644 A1 | 3/2019 | Yoo et al. |
| 2019/0100597 A1 | 4/2019 | Keyt et al. |
| 2019/0153044 A1 | 5/2019 | Poma et al. |
| 2019/0153471 A1 | 5/2019 | Paul et al. |
| 2019/0249145 A1 | 8/2019 | Jang et al. |
| 2019/0382755 A1 | 12/2019 | Poma et al. |
| 2020/0002387 A1 | 1/2020 | Poma et al. |
| 2020/0024312 A1 | 1/2020 | Poma et al. |
| 2020/0231650 A1 | 7/2020 | Chattopadhyay et al. |
| 2021/0008208 A1 | 1/2021 | Poma et al. |
| 2021/0017512 A1 | 1/2021 | Poma et al. |
| 2021/0253649 A1 | 8/2021 | Poma et al. |

(56) References Cited

U.S. PATENT DOCUMENTS

| | | |
|---|---|---|
| 2021/0268085 A1 | 9/2021 | Poma et al. |
| 2022/0152213 A1 | 5/2022 | Poma et al. |
| 2022/0267384 A1 | 8/2022 | Poma et al. |
| 2022/0275030 A1 | 9/2022 | Poma et al. |
| 2022/0281926 A1 | 9/2022 | Poma et al. |
| 2022/0306700 A1 | 9/2022 | Poma et al. |
| 2022/0354938 A1 | 11/2022 | Poma et al. |
| 2022/0401568 A1 | 12/2022 | Poma et al. |

FOREIGN PATENT DOCUMENTS

| | | |
|---|---|---|
| CN | 1272882 A | 11/2000 |
| CN | 101384614 A | 3/2009 |
| CN | 101622352 A | 1/2010 |
| CN | 101629158 A | 1/2010 |
| CN | 102257000 A | 11/2011 |
| CN | 103501818 A | 1/2014 |
| CN | 103648525 A | 3/2014 |
| CN | 105713087 A | 6/2016 |
| EP | 1 654 287 A2 | 8/2010 |
| EP | 2 778 173 A1 | 9/2014 |
| EP | 3 265 575 A2 | 1/2018 |
| EP | 3 448 874 A1 | 3/2019 |
| GB | 2 456 904 B | 10/2009 |
| GB | 2 519 786 A | 5/2015 |
| JP | 1993-502880 A | 5/1993 |
| JP | 2001-500730 A | 1/2001 |
| JP | 2002-521019 A | 7/2002 |
| JP | 2002-544173 A | 12/2002 |
| JP | 2003-531588 A | 10/2003 |
| JP | 2004-536778 A | 12/2004 |
| JP | 2006-502699 A | 1/2006 |
| JP | 2006-513691 A | 4/2006 |
| JP | 2007-536905 A | 12/2007 |
| JP | 2008-533977 A | 8/2008 |
| JP | 2009-502936 A | 1/2009 |
| JP | 2009-530468 A | 8/2009 |
| JP | 2011-050388 A | 3/2011 |
| JP | 2011-507389 A | 3/2011 |
| JP | 2012-044997 A | 3/2012 |
| JP | 2012-070737 A | 4/2012 |
| JP | 2012-515551 A | 7/2012 |
| JP | 2012-533587 A | 12/2012 |
| JP | 2014-515921 A | 7/2014 |
| KR | 2011-0033233 A | 3/2011 |
| KR | 2011-0119725 A | 11/2011 |
| TW | 201235469 A | 9/2012 |
| WO | WO 91/009871 A1 | 7/1991 |
| WO | WO 94/26910 A1 | 11/1994 |
| WO | WO 96/30043 A1 | 10/1996 |
| WO | WO 96/040200 A1 | 12/1996 |
| WO | WO 98/11229 A3 | 3/1998 |
| WO | WO 99/40185 A1 | 8/1999 |
| WO | WO 00/04926 A2 | 2/2000 |
| WO | WO 00/67795 A1 | 11/2000 |
| WO | WO 01/70945 A1 | 9/2001 |
| WO | WO 01/77342 A1 | 10/2001 |
| WO | WO 02/40506 A2 | 5/2002 |
| WO | WO 03/066854 A1 | 8/2003 |
| WO | WO 03/072746 A2 | 9/2003 |
| WO | WO 03/074567 A2 | 9/2003 |
| WO | WO 2004/056312 A2 | 7/2004 |
| WO | WO 2004/058158 A2 | 7/2004 |
| WO | WO 2005/000902 A1 | 1/2005 |
| WO | WO 2005/016969 A2 | 2/2005 |
| WO | WO 2005/017148 A1 | 2/2005 |
| WO | WO 2005/052006 A2 | 6/2005 |
| WO | WO 2005/052129 A2 | 6/2005 |
| WO | WO 2005/092917 A1 | 10/2005 |
| WO | WO 2006/047517 A2 | 5/2006 |
| WO | WO 2006/099875 A1 | 9/2006 |
| WO | WO 2007/005874 A2 | 1/2007 |
| WO | WO 2007/014238 A2 | 2/2007 |
| WO | WO 2007/033497 A1 | 3/2007 |
| WO | WO 2007/071061 A1 | 6/2007 |
| WO | WO 2007/098201 A2 | 8/2007 |
| WO | WO 2007/107779 A1 | 9/2007 |
| WO | WO 2008/080218 A1 | 7/2008 |
| WO | WO 2008/097817 A2 | 8/2008 |
| WO | WO 2009/014835 A2 | 1/2009 |
| WO | WO 2009/017823 A2 | 2/2009 |
| WO | WO 2009/032954 A1 | 3/2009 |
| WO | WO 2009/064815 A1 | 5/2009 |
| WO | WO 2009/088403 A2 | 7/2009 |
| WO | WO 2009/110944 A1 | 9/2009 |
| WO | WO 2010/011697 A1 | 1/2010 |
| WO | WO 2010/085539 A1 | 7/2010 |
| WO | WO 2011/009624 A1 | 1/2011 |
| WO | WO 2012/022985 A1 | 2/2012 |
| WO | WO 2012/093158 A1 | 7/2012 |
| WO | WO 2012/101235 A1 | 8/2012 |
| WO | WO 2012/104344 A1 | 8/2012 |
| WO | WO 2012/154530 A1 | 11/2012 |
| WO | WO 2012/162418 A1 | 11/2012 |
| WO | WO 2013/080147 A2 | 6/2013 |
| WO | WO 2014/086952 A1 | 6/2014 |
| WO | WO 2014/164680 A1 | 10/2014 |
| WO | WO 2014/164693 A2 | 10/2014 |
| WO | WO 2015/063187 A1 | 5/2015 |
| WO | WO 2015/113005 A1 | 7/2015 |
| WO | WO 2015/113007 A1 | 7/2015 |
| WO | WO 2015/120058 A2 | 8/2015 |
| WO | WO 2015/138435 A1 | 9/2015 |
| WO | WO 2015/138452 A1 | 9/2015 |
| WO | WO 2015/191764 A1 | 12/2015 |
| WO | WO 2015/191883 A1 | 12/2015 |
| WO | WO 2015/193411 A1 | 12/2015 |
| WO | WO 2016/126950 A1 | 8/2016 |
| WO | WO 2016/196344 A1 | 12/2016 |
| WO | WO 2017/019623 A2 | 2/2017 |
| WO | WO 2018/080812 A1 | 5/2018 |
| WO | WO 2018/106895 A1 | 6/2018 |
| WO | WO 2018/140427 A1 | 8/2018 |
| WO | WO 2018/159615 A1 | 9/2018 |
| WO | WO 2018/162749 A1 | 9/2018 |
| WO | WO 2019/059400 A1 | 3/2019 |
| WO | WO 2020/081493 A1 | 4/2020 |
| WO | WO 2020/154475 A1 | 7/2020 |

OTHER PUBLICATIONS

Amino Acids; https://www.promega.com/-/media/files/resources/technical-references/amino-acid-abbreviations-and-molecular-weights.pdf; retrieved on Feb. 26, 2018, 1 page.

https://www.genome.gov/genetics-glossary/antisense; retrieved on Jul. 17, 2021, 2 pages.

UniProtKB/Swiss-Prot P09385 (STXA_BP933), Shiga-like toxin 2 subunit A, retrieved from https://www.ncbi.nlm.nih.gov/protein/P09385.2 on Jan. 10, 2018, 7 pages.

Aatsinki, J. T. et al., "An alternative use of basic pGEX vectors for producing both N- and C-terminal fusion proteins for production and affinity purification of antibodies," Protein Expression and Purification, 40(2):287-291 (2005).

Ackerman, R. et al., "SLT-VEGF Reduces Lung Metastases, Decreases Tumor Recurrence, and Improves Survival in an Orthotropic Melanoma Model," Toxins (Basel), 2(9):224-257 (2010).

Adotevi, O. et al., "B Subunit of Shiga Toxin-Based Vaccines Synergize with α-Galactosylceramide to Break Tolerance against Self Antigen and Elicit Antiviral Immunity," The Journal of Immunology, 179(5):3371-3379 (2007).

Al-Jaufy, A. Y. et al., "Cytotoxicity of a Shiga toxin A Subunit-CD4 Fusion Protein to Human Immunodeficiency Virus-Infected Cells," Infection and Immunity, 62(3):956-960 (1994).

Al-Jaufy, A. Y. et al., "Purification and Characterization of a Shiga-Toxin A Subunit-CD4 Fusion Protein Cytotoxic to Human Immunodeficiency Virus-Infected Cells," Infection and Immunity, 63(8):3073-3078 (1995).

Antignani, A. & Fitzgerald, D., "Immunotoxins: The Role of the Toxin," Toxins, 5(8):1486-1502 (2013).

(56) References Cited

OTHER PUBLICATIONS

Apostolpoulos, V. et al., "MUC1 peptide epitopes associated with five different H-2 class I molecules," European Journal of Immunology, 27(10):2579-2587 (1997).
Backer, M. V. et al., "Shiga-like toxin-VEGF fusion proteins are selectively cytotoxic to endothelial cells overexpressing VEGFR-2," Journal of Controlled Release, 74(1-3):349-355 (2001).
Backer, M. V. & Backer, J. M., "Targeting Endothelial Cells Overexpressing VEGFR-2: Selective Toxicity of Shiga-like Toxin-VEGF Fusion Proteins," Bioconjugate Chemistry, 12(6):1066-1073 (2001).
Baker, M. P. et al., "Immunogenicity of Protein Therapeutics: the Key Causes, Consequences and Challenges," Self/Nonself, 1(4):314-322 (2010).
Ballard, J. D. et al., "Anthrax Toxin-Mediated Delivery In Vivo and In Vitro of a Cytotoxic T-Lymphocyte Epitope from Ovalbumin," Infection and Immunity, 66(2):615-619 (1998).
Ballard, J. D. et al., "Anthrax Toxin as a Molecular Tool for Stimulation of Cytotoxic T Lymphocytes: Disulfide-Linked Epitopes, Multiple Injections, and Role of CD4+ Cells," Infection and Immunity, 66(10):4696-4699 (1998).
Barnd, D. L. et al., "Specific, Major Histocompatibility Complex-Unrestricted Recognition of Tumor-Associated Mucins by Human Cytotoxic T cells," Proceedings of the National Academy of Sciences U.S.A., 86(18):7159-7163 (1989).
Barratt-Boyes, S. M. et al., "Immunization of Chimpanzees with Tumor Antigen MUC1 Mucin Tandem Repeat Peptide Elicits Both Helper and Cytotoxic T-cell Responses," Clinical Cancer Research, 5(7):1918-1924 (1999).
Beers, S. A. et al., "Type II (tositumomab) anti-CD20 monoclonal antibody out performs type I (rituximab-like) reagents in B-cell depletion regardless of complement activation," Blood, 112:4170-4177 (2008).
Beers, S. A. et al., "CD20 as A Target for Therapeutic type I and II Monoclonal Antibodies," Seminars in Hematology, 47(2):107-114 (2010).
Beers, S. A. et al., "Antigenic modulation limits the efficacy of anti-CD20 antibodies: implications for antibody selection," Blood, 1115(25):5191-5201 (2010).
Bera, T. K. et al., "A Bivalent Disulfide-stabilized Fv with Improved Antigen Binding to erbB2," Journal of Molecular Biology, 281(3):475-483 (1998).
Bera, T. K. et al., "Pharmacokinetics and Antitumor Activity of a Bivalent Disulfide-stabilized Fv Immunotoxin with Improved Antigen Binding to erbB2," Cancer Research, 59(16):4018-4022 (1999).
Beum, P. V. et al., "The Shaving Reaction: Rituximab/CD20 Complexes are Removed from Mantle Cell Lymphoma and Chronic Lymphocytic Leukemia Cells by THP-1 Monocytes," The Journal of Immunology, 176(4):2600-2609 (2006).
Beum, P. V. et al., "Loss of CD20 and Bound CD20 Antibody from Opsonized B Cells Occurs More Rapidly Because of Trogocytosis Mediated by Fc Receptor-Expressing Effector Cells than Direct Internalization by the B Cells," The Journal of Immunology, 187(6):3438-3447 (2011).
Bevan et al. "Real-time 96-well antibody internalization assays using IncuCyte FabFlour Red Antibody Labeling Reagent, Application Note, Sartorious", Essen BioScience (2017).
Bibby, M. C., "Orthotopic models of cancer for preclinical drug evaluation: advantages and disadvantages," European Journal of Cancer, 40(6):852-857 (2004).
Boes, A. et al., "Affinity Purification of a Framework 1 Engineered Mouse/Human Chimeric IgA2 Antibody From Tobacco," Biotechnology Bioengineering, 108(12):2804-2814 (2011).
Böldicke, T., "Blocking translocation of cell surface molecules from the ER to the cell surface by intracellular antibodies targeted to the ER," J. Cell. Mol., 11(1):54-70 (2007).
Bolognesi, A. et al., "A comparison of anti-lymphocyte immunotoxins containing different ribosome-inactivating proteins and antibodies," Clinical & Experimental Immunology, 89(3):341-346 (1992).
Bonifaz, L. et al., "Efficient targeting of protein antigen to the dendritic cell receptor DEC-205 in the steady state leads to antigen presentation on major histocompatibility complex class I products and peripheral CD8+ T cell tolerance," Journal of Experimental Medicine, 196(12):1627-1638 (2002).
Boross, P. et al., "Both activating and inhibitory Fc gamma receptors mediate rituximab-induced trogocytosis of CD20 in mice," Immunology Letters, 143(1):44-52 (2012).
Boross, P. et al., "Mechanisms of action of CD20 antibodies," American Journal of Cancer Research, 2(6):676-690 (2012).
Braslawsky, G. R. et al., "Adriamycin(hydrazone)-antibody conjugates require internalization and intracellular acid hydrolysis for antitumor activity," Cancer Immunology, Immunotherapy, 33:367-374 (1991).
Bray, M. R. et al., "Probing the surface of eukaryotic cells using combinatorial toxin libraries," Current Biology, 11(9):697-701 (2001).
Brieschke, B. et al., "Targeted Engineered Toxin Bodies provide a novel mechanism of action against HER2 positive cancers," Cancer Research, 78 (13 Suppl), (Jul. 2018), Abstract 5769.
Brieschke, B. et al., "Targeted Engineered Toxin Bodies provide a novel mechanism of action against HER2 positive cancers," Proceedings: American Association for Cancer Research (AACR) Annual Meeting 2018, (Apr. 18, 2018).
Brieschke, B. et al., "Identification and Functional Profiling of PD-L1 Targeted Engineered Toxin Bodies for Antigen Seeding Technology (AST) and Redirection of T cell Response to Tumors," 33rd Annual Meeting of the Society for Immunotherapy of Cancer (SITC), Washington, D.C., Poster # 11078, (Nov. 7-11, 2018).
Brieschke, B. et al., "Identification and functional profiling of PD-L1 targeted engineered toxin bodies for antigen seeding technology and redirection of T cell response to tumors," Journal of Immuno Therapy of Cancer, 6(Suppl 1): 114, (Nov. 6, 2018), Abstract P9.
Brieschke, B. et al., "Identification and functional profiling of PD-L1 targeted engineered toxin bodies for antigen seeding technology and redirection of T cell response to tumors," Journal for Immunotherapy of Cancer, 6(S1):p. 5 (2018).
Brieschke, B. et al., "Antigen Seeding Technology by engineered Toxin bodies Provides a Targeted Immuno-Oncology Approach for Treatment of Cancers," Proceedings: American Association for Cancer Research (AACR) Annual Meeting 2018, Poster 2777, Abstract #4912 (Apr. 14-18, 2018).
Brigotti, M. et al., "Damage to Nuclear DNA Induced by Shiga Toxin 1 and Ricin in Human Endothelial Cells," The FASEB Journal, 16(3):365-372 (2002).
Brigotti, M. et al., "Change in Conformation with Reduction of α-Helix Content Causes Loss of Neutrophil Binding Activity in Fully Cytotoxic Shiga toxin 1," The Journal of Biological Chemistry, 286(40):34514-34521 (2011).
Bujny, M. V. et al., "The retromer component sorting nexin-1 is required for efficient retrograde transport of Shiga toxin from early endosome to the trans Golgi network," Journal of Cell Science, 120(Pt 12):2010-2021 (2007).
Burgess, B. J. et al., "Proteolytic cleavage at arginine residues within the hydrophilic disulphide loop of the *Escherichia coli* Shiga-like toxin I A subunit is not essential for cytotoxicity," Molecular Microbiology, 10(1):171-179 (1993).
Cao, C. et al., "Construction of mutant genes for a non-toxic verotoxin 2 variant (VT2vp1) of *Escherichia coli* and characterization of purified mutant toxins," Microbiology and Immunology, 38(6):441-447 (1994).
Cao, Y. et al., "Design optimization and characterization of Her2/neu-targeted immunotoxins: comparative in vitro and in vivo efficacy studies," Oncogene, 33(4):1-11 (2013).
Cao, Y. et al., "Construction and characterization of novel, recombinant immunotoxins targeting the Her2/neu oncogene product: in vitro and in vivo studies," Cancer Research, 69(23): 8987-8995 (2009).
Carbonetti, N. H. et al., "Intracellular Delivery of a Cytolytic T-Lymphocyte Epitope Peptide by Pertussis Toxin to Major Histocompatibility Complex Class I without Involvement of the Cytosolic Class I Antigen Processing Pathway," Infection and Immunity, 67(2):602-607 (1999).

(56) References Cited

OTHER PUBLICATIONS

Carbonetti, N. H. et al., "Stimulation of HIV gp120-specific cytolytic T lymphocyte responses in vitro and in vivo using a detoxified pertussis toxin vector," AIDS Research and Human Retroviruses, 17(9):819-827 (2001).

Carbonetti, N. H., "Pertussis toxin and adenylate cyclase toxin: key virulence factors of Bordetella pertussis and cell biology tools," Future Microbiology, 5:455-469 (2010).

Casalini, P. et al., "Use of combination of Monoclonal Antibodies Directed Against three distinct epitopes of a Tumor-Associated Antigen: Analysis of Cell-Binding and Internalization," International Journal of Cancer, 48:2 284-290 (1991).

Casset, F. et al., "A peptide mimetic of an anti-CD4 monoclonal antibody by rational design," Biochemical and Biophysical Research Communications, 307(1):198-205 (2003).

Chatterjee, S. et al., "Noninvasive Imaging of Immune Checkpoint Ligand PD-L1 in Tumors and Metastases for Guiding Immunotherapy," Molecular Imaging, 16:1-5 (2017).

Cheung, M. C. et al., "An evolved ribo-inactivating protein targets and kills human melanoma cells in vitro and in vivo," Molecular Cancer, 9(28):1-14 (2010).

Cheung, M. C. et al., "A Ribosome-inactivating Protein Toxin as a Template for Cancer Drug Discovery", thesis, University of Toronto, (2012), retrieved from http://hdl.handle.net/1807/33952, 202 pages.

Cizeau, J. P. A. et al., "DeBouganin: A de-immunized toxin payload and its applications in oncology," 8th Fabisch-Symposium, 3rd Targeted Tumor Therapies, Berlin 2012, Mar. 21, 2012.

Cizeau, J. et al., "Fusogenics: A Recombinant Immunotoxin-Based Screening Platform to Select Internalizing Tumor-Specific Antibody Fragments," Journal of Biomolecular Screening 16(1):90-100 (2011).

Cleton-Jansen, A. et al., "A Single Amino Acid Substitution Changes the Substrate Specificity of Quinoprotein Glucose Dehydrogenase in Gluconobacter oxydans," Molecular and General Genetics, 229(2):206-212 (1991).

Cragg, M. S. et al., "Apparent modulation of CD20 by rituximab: an alternative explanation," Blood, 103(10):3889-3990 (2004).

Cuesta, A. M. et al., "Mutivalent antibodies: when design surpasses evolution," Trends in Biotechnology, 28(7):355-362 (2010).

Dadaglio, G, et al., "Induction of a Polarized Th1 Response by Insertion of Multiple Copies of a Viral T-Cell Epitope into Adenylate Cyclase of Bordetella pertussis," Infection and Immunity, 68(7):3867-3872 (2000).

Dadaglio, G, et al., "Recombinant adenylate cyclase toxin of Bordetella pertussis induces cytotoxic T lymphocyte responses against HLA*0201-restricted melanoma epitopes," International Immunology, 15(12):1423-1430 (2003).

De Pascalis, R. et al., "Grafting of "abbreviated" complementarity-determining regions containing specificity-determining residues essential for ligand contact to engineer a less immunogenic humanized monoclonal antibody," The Journal of Immunology, 169(6):3076-3084 (2002).

Dekker et al., "Engineered Toxin Bodies delivering immunogenic MHC class I peptides to tumor cells summon polyfunctional and relevant CTL responses against cancers," Presented at: Immunology 2019TM™, Annual Meeting of the American Association of Immunologists, May 10, 2019, The American Association of Immunologists, Inc., San Diego, Abstract 1791.

Dekker, J. D. et al., Abstract 1791, "Engineered toxin bodies delivering immunogenic MHC class I peptides to tumor cells summon polyfunctional and relevant CTL responses against cancers," Molecular Templates, AAI 2019 Poster, 2 pages.

Deresiewicz, R. L. et al., "Mutations Affecting the Activity of the Shiga-like Toxin I A-Chain," Biochemistry, 31(12):3272-3280 (1992).

Deresiewicz, R. L. et al., "The role of tyrosine-114 in the enzymatic activity of the Shiga-like toxin I A-chain," Mol. Gen. Genet., 241:467-473 (1993).

Déret, S. et al., "SUBIM: a program for analysing the Kabat database and determining the variability subgroup of a new immunoglobulin sequence," CABIOS, 11(4):435-439 (1995).

Dermer, G. B., "Another Anniversary for the War on Cancer," Bio/Technology 12:320 (1994).

Di, R. et al., "Identification of amino acids critical for the cytotoxicity of Shiga toxin 1 and 2 in *Saccharomyces cerevisiae*," Toxicon, 57(4):525-539 (2011).

Doling, A. M. et al., "Cytotoxic T-Lymphocyte Epitopes Fused to Anthrax toxin Induce protective Antiviral Immunity," Infection and Immunity, 67(7):3290-3296 (1999).
Donnelly, J. J. et al., "Targeted delivery of peptide epitopes to class I major histocompatibility molecules by a modified Pseudomonas exotoxin," Proceedings of the National Academy of Sciences U.S. A., 90:3530-3534 (1993).
Edelman, G. M. & Gally, J. A., "Degeneracy and complexity in biological systems," PNAS, 98(24):13763-13768 (2001).
Engedal, N. et al., "Shiga toxin and its use in targeted cancer therapy and imaging," Microbiology Biotechnology, 4(1):32-46 (2011).
Eriksson, K. et al., "Coupling of antigen to cholera toxin for dendritic cell vaccination promotes the induction of MHC class I-restricted cytotoxic T cells and the rejection of a cognate antigen-expressing model tumor," European Journal of Immunology, 34(5):1272-1281 (2004).
Ewers, H. & Helenius, A., "Lipid-Mediated Endocytosis," Cold Spring Harbor Perspectives in Biology, 3(8):1-14 (2011).
Fanale, M. A. et al., "Phase I/Ib study of the novel CD20-targeted immunotoxin MT-3724 in relapsed/refractory non-Hodgkin's B-cell lymphoma," Proceedings of the 107th Annual Meeting of the American Association for Cancer Research (AACR), Abstract # CT049, (Apr. 16-20, 2016), 2 pages.
Fanale, M. A. et al., "Phase I/Ib study of the novel CD20-targeted immunotoxin MT-3724 in relapsed/refractory non-Hodgkin's B-cell lymphoma," Cancer Research, 76(14 Suppl), (Jul. 2016), Abstract nr CT049.
Fayolle, C. et al., "Delivery of Multiple Epitopes by Recombinant Detoxified Adenylate Cyclase of Bordetella pertussis Induces Protective Antiviral Immunity," Journal of Virology, 75(16):7330-7338 (2001).
Fayolle, C, et al., "Therapy of Murine Tumors with Recombinant Bordetella pertussis Adenylate Cyclase Carrying a Cytotoxic T Cell Epitope," The Journal of Immunology, 162(7): 4157-4162 (1999).
Filpula, D., "Releasable PEGylation of Mesothelin Targeted Immunotoxin SSIP Achieves Single Dosage Complete Regression of a Human Carcinoma in Mice," Bioconjugate Chemistry, 18(3):773-784 (2007).
Freshney, R.I., "Culture of Animal Cells: A Manual of Basic Technique," Alan R. Liss, Inc., 1983, New York, pp. 3-4.
Gannon, V. P. et al., "Molecular cloning and nucleotide sequence of another variant of the *Escherichia coli* Shiga-like toxin II family," Journal of General Microbiology, 136(6):1125-1135 (1990).
Garred, O. et al., "Role of processing and intracellular transport for optimal toxicity of Shiga toxin and toxin mutants," Experimental Cell Research, 218(1):39-49 (1995).
Garred, O. et al., "Furin-induced cleavage and activation of Shiga toxin," Journal of Biological Chemistry, 270(18):10817-10821 (1995).
Gavrilov, B. K. et al., "Effects of Glycosylation on Antigenicity and Immunogenicity of Classical Swine Fever Virus Envelope Proteins," Virology, 420(2):135-145 (2011).
Gendler, S. et al., "A Highly Immunogenic Region of a Human Polymorphic Epithelial Mucin Expressed by Carcinomas is Made Up of Tandem Repeats," Journal of Biological Chemistry, 263(26):12820-12823 (1988).
Ghetie, M. A. et al., "Homodimers but not monomers of Rituxan (chimeric anti-CD20) induce apoptosis in human B-lymphoma cells and synergize with a chemotherapeutic agent and an immunotoxin," Blood, 97(5):1392-1398 (2001).
Giansanti, F. et al., "Strategies to Improve the Clinical Utility of Saporin-Based Targeted Toxins," Toxins, 10(82):1-32 (2018).
Gielis, S. et al., "Detection of Enriched T Cell Epitope Specificity in Full T Cell Receptor Sequence Repertoires," Frontiers in Immunology, vol. 10, Article 2820, pp. 1-13 (2019).
Gilliland, D. G. et al., "Antibody-directed cytotoxic agents: use of monoclonal antibody to direct the action of toxin A chains to colorectal carcinoma cells," Proceedings of the National Academy of Sciences of the United States of America, 77(8):4539-43 (1980).

(56) References Cited

OTHER PUBLICATIONS

Glennie, M. J. et al., "Mechanisms of killing by anti-CD20 monoclonal antibodies," Molecular Immunology, 44(16):3823-3837 (2007).
Gong, J. et al., "Selection and characterization of MUC1-specific CD8+ T cells from MUC1 transgenic mice immunized with dendritic-carcinoma fusion cells," Immunology, 101(3):316-324 (2000).
Gordon, V. M. et al., "An enzymatic Mutant of Shiga-like Toxin II Variant is a vaccine Candidate for Edema Disease of Swine," Infection and Immunity, 60(2):485-490 (1992).
Goulet, A. C. et al. ,"Conjugation of Blocked Ricin to an Anti-CD19 Monoclonal Antibody Increases Antibody-Induced cell Calcium Mobilization and CD19 Internalization," Blood 90(6): 2364-2375 (1995).
Grant, K. et al., "Abstract 1380: Engineered toxin bodies with specific activity against EGFR and HER2 expressing cells," Proceedings of the 102nd Annual Meeting of the American Association for Cancer Research (AACR); Apr. 2-6, 2011; The Journal of Cancer Research, 71 (8 Suppl): Abstract #1380, (Apr. 2011).
Grotzke, J. E. et al., "The ongoing saga of the mechanism(s) of MHC class I-restricted cross-presentation," Current Opinion in Immunology, 46:89-96 (2017).
Guermonprez, P. et al., "Les Toxines Bacteriennes Recombinantes: De Nouveaux Vecteurs Pour La Vaccination?" M/S Medicine Sciences, Societe Des Periodiques Flammarion, 16(5):653-662 (2000).
Guermonprez, P. et al., "The Adenylate Cyclase Toxin of *Bordetella pertussis* Binds to Target Cells via the αMβ2 Integrin (CD11b/CD18)," Journal of Experimental Medicine, 193(9):1035-1044 (2001).
Güssow, D. & Seeman, G., "Humanization of Monoclonal Antibodies," Methods in Enzymology, 203:99-121 (1991).
Haddad, J. E. et al., "Minimum Domain of the Shiga Toxin A subunit Required for Enzymatic Activity," Journal of Bacteriology, 175(16):4970-4978 (1993).
Haicheur, N. et al., "The B Subunit of Shiga Toxin Fused to a Tumor Antigen Elicits CTL and Targets Dendritic Cells to Allow MHC Class I-Restricted Presentation of Peptides Derived from Exogenous Antigens," The Journal of Immunology, 165(6):3301-3308 (2000).
Haisma, H. J. et al., "Construction and Characterization of a Fusion Protein Single-Chain Anti-CD20 Antibody and Human beta-glucuronidase for Antibody-Directed Enzyme Prodrug Therapy," Blood, 92(1):184-190 (1998).
Hamlin, P. A. et al., "Safety and Efficacy of Anti-CD20 Immunotoxin MT-3724 in Relapsed/refractory B-cell Non-Hodgkin Lymphoma (NHL) in a Phase 1 study," American Society of Clinical Oncology Annual Meeting-ABSTRACT 7580 (2018).
Harris, B., "Exploiting antibody-based technologies to manage environmental pollution," Trends in Biotechnology, DIAGRAM figure taken from 17(7):290-296 (1999).
Harwerth, I. M. et al., Monoclonal Antibodies against the Extracellular Domain of the erbB-2 Receptor Function as Partial Ligand Agonists, Journal of Biol. Chem, 267(21):15160-15167 (1992).
Head, S. C. et al., "Preparation of VT1 and VT2 hybrid toxins from their purified dissociated subunits. Evidence for B subunit modulation of a subunit function," Journal of Biological Chemistry, 266(6):3617-3621 (1991).
Hegde, N. R. et al., "The use of databases, data mining and immunoinformatics in vaccinology: where are we?" Expert Opinion on Drug Discovery, 13(2):117-130 (2018).
Hexham, J. M. et al., "Influence of relative binding affinity on efficacy in a panel of anti-CD3 scFv immunotoxins," Molecular Immunology, 38(5):397-408 (2001).
Higgins, J. P. et al., "Engineered toxin bodies with specific cell kill activity against mesenchymal cells," Cancer Research, 71(8 Suppl) (Apr. 2011), Abstract #1751.
Hiraga, J. et al., "Down-regulation of CD20 expression in B-cell lymphoma cells after treatment with rituximab-containing combination chemotherapies: its prevalence and clinical significance," Blood, 113(20):4885-4893 (2009).
Holubova, J. et al., "Delivery of Large Heterologous Polypeptides across the Cytoplasmic Membrane of Antigen-Presenting Cells by the Bordetella RTX Hemolysin Moiety Lacking the Adenylyl Cyclase Domain," Infection and Immunity, 80(3):1181-1192 (2012).
Hooijberg et al., "Characterization of a series of isotype switch variants of new CD20 monoclonal antibody," Hybridoma, 15(1):23-31 (1996).
Hotz, B. et al., "Specific Targeting of Tumor Endothelial Cells by a Shiga-like Toxin-Vascular Endothelial Growth Factor Fusion Protein as a Novel Treatment Strategy for Pancreatic Cancer," Neoplasia, 12(10):797-806 (2010).
Hovde, C. J. et al., "Evidence that glutamic acid 167 is an active-site residue of Shiga-like toxin-I," Proceedings of the National Academy of Sciences of the United States of America, 85(8):2568-2572 (1988).
Huang, S. et al., "The CD20-specific engineered toxin antibody MT-3724 exhibits lethal effects against mantle cell lymphoma," Blood Cancer Journal, 8(3):33 (2018).
Huang, S. et al. "Abstract 3651: Preclinical examination of the effects of MT-3724, an engineered toxin body targeting CD20, in mantle cell lymphoma," AACR Annual Meeting Abstract (2017).
Huang, S. et al. "AACR 2017 | Poster 3651/24—Preclinical examination of the effects of a CD20-specific engineered toxin body, MT-3724, in Mantle Cell Lymphoma," AACR Annual Meeting, Poster 3651/24 (2017).
Iberg, A. et al., "Design and Characterization of Bispecific Engineered Toxin Bodies for Targeted Cancer Therapy," Proceedings: American Association for Cancer Research (AACR) Annual Meeting 2019, Poster #2984 (2019).
Ishikawa, S. et al., "Protection against Shiga Toxin I Challenge by Immunization of Mice with Purified Mutant Shiga Toxin 1," Infection and Immunity, 71(6):3235-3239 (2003).
Jackson, R. L. et al., "Mutational analysis of the Shiga Toxin and Shiga-like toxin II enzymatic subunits," Journal of Bacteriology, 172(6):3346-3350 (1990).
Jackson, M. E. et al., "The KDEL retrieval system is exploited by Pseudomonas exotoxin A, but not by Shiga-like toxin-1, during retrograde transport from the Golgi complex to the endoplasmic reticulum," Journal of Cell Science, 112(4):467-475 (1999).
Jain, R. K., "Barriers to Drug Delivery in Solid Tumors," Scientific American, 271(1):58-65 (1994).
Jilani, I. et al., "Anti-Idiotype versus anti-mouse Ig for detecting ritumixab," Blood, 103(10):3990 (2004).
Jilani, I. et al., "Transient down-modulation of CD20 by ritumixab in patients with chronic lymphocytic leukemia," Blood ,102(10):3514-3520 (2003).
Johannes, L. et al., "Retrograde Transport of KDEL-bearing B-fragment of Shiga Toxin," Journal of Biological Chemistry, 272(31):19554-19561 (1997).
Johannes, L. et al., "Shiga toxins—from cell biology to biomedical applications," Nature Reviews Microbiology, 8(2):105-116 (2010).
Johannes, L. & Decaudin, D., "Protein toxins: intracellular trafficking for targeted therapy," Gene Therapy, 12(18):1360-1368 (2005).
Johnson, N. et al., "Construction of an epitope vector utilizing the diphtheria toxin B-subunit," FEMS Microbiology Letters, 146(1):91-96 (1997).
Jones, D. T., "Critically Assessing the State-of-the-art in Protein Structure Prediction," The Pharmacogenomics Journal, 1(2):126-134 (2001).
Jubala, C. M. et al., "CD20 Expression in Normal Canine B cells and in Canine non-Hodgkin Lymphoma," Veterinary Pathology, 42(4):468-476 (2005).
Kar, P. et al., "Current methods for the prediction of T-cell epitopes," Peptide Science, 110:e24046 (2018), 17 pages; https://doi.org/10.1002/pep2.24046.
Karanikas, V. et al., "Antibody and T Cell Responses of Patients with Adenocarcinoma Immunized with Mannan-MUC1 Fusion Protein," Journal of Clinical Investigation, 100(11): 2783-2792 (1997).
Karimova, G. et al., "Charge-dependent translocation of *Bordetella pertussis* adenylate cyclase toxin into eukaryotic cells: Implication for the in vivo delivery of CD8+ T cell epitopes into antigen-presenting cells," Proc. Natl. Acad. Sci. USA, 95:12532-12537 (1998).

(56) References Cited

OTHER PUBLICATIONS

Kelland, L. R., "'Of mice and men': values and liabilities of the athymic nude mouse model in anticancer drug development," European Journal of Cancer, 40(6):827-836 (2004).
Kim, G. B. et al., "A fold-back single chain diabody format enhances the bioactivity of an anti-monkey CD3 recombinant diphtheria toxin-based immunotoxin," Protein Engineering, 20(9):425-432 (2007).
Kotera, Y. et al., "Humoral Immunity against a Tandem Repeat Epitope of Human Mucin MUC-1 in Sera from Breast, Pancreatic, and Colon Cancer Patients," Cancer Research 54(11):2856-2860 (1994).
Kochenderfer, J. N. et al., "Construction and Pre-clinical Evaluation of an Anti-CD19 Chimeric Antigen Receptor," J Immunother., 32(7):689-702 (2009).
Kowanetz, M. et al., "Differential regulation of PD-L1 expression by immune and tumor cells in NSCLC and the response to treatment with atezolizumab (anti-PD-L1)," PNAS, 115(43):e10119-e10126 (2018).
Kurmanova, A. et al., "Structural requirements for furin-induced cleavage and activation of Shiga toxin," Biochemical and Biophysical Research Communications, 357(1):144-149 (2007).
Kyu, E., "Characterization of the A subunit mutants of Stx1 and Stx2 in *Saccharomyces cerevisiae*," Thesis, Rutgers, The State University of New Jersey, New Brunswick, retrieved from http://dx.doi.org/doi:10.7282/T34F1QWJ (2009), 57 pages.
Lakhrif, Z. et al., "A method to confer protein L binding ability to any antibody fragment," MAbs, 8(2):379-388 (2016).
Lambert, J. et al., "Purified Immunotoxins that are reactive with Human Lymphoid Cells: Monoclonal antibodies conjugated to the ribosome-inactivating proteins gelonin and the pokeweed antiviral proteins," Journal of Biological Chemistry, 260(22):12035-12041 (1985).
Lapointe, P. et al., "A Role for the Protease-sensitive Loop Region of Shiga-like Toxin 1 in the Retrotranslocation of its A Domain from the Endoplasmic Reticulum Lumen," Journal of Biological Chemistry, 280(24):23310-23318 (2005).
Laske, D. W. et al., "Intraventricular Immunotoxin Therapy for Leptomeningeal Neoplasia," Neurosurgery, 41(5):1039-1051 (1997).
Law, C. L. et al., "Efficient Elimination of B-Lineage Lymphomas by Anti-CD20-Auristatin Conjugates," Clinical Cancer Research, 10(23):7842-7851 (2004).
Lazar, E. et al., "Transforming Growth Factor alpha: Mutation of Aspartic Acid 47 and Leucine 48 Results in Different Biological Activities," Molecular and Cellular Biology, 8(3):247-1252 (1988).
Lea, N. et al., "Proteolytic cleavage of the A subunit is essential for maximal cytotoxicity of *Escherichia coli* O157:h7 Shiga-like toxin-1," Microbiology, 145(5):999-1004 (1999).
Lee, J. E. et al.,"Phylogenetic analysis of Shiga toxin 1 and Shiga toxin 2 genes associated with disease outbreaks," BMC Microbiology, 7(1):109 (2007), 12 pages; doi.org/10.1186/1471-2180-7-109.
Lee, H. T. et al., "Molecular mechanism of PD-1/PD-L1 blockade via anti-PD-L1 antibodies atezolizumab and durvalumab," Scientific Reports, 7(1):5532 (2017), 12 pages; doi:10.1038/s41598-017-06002-8.
Lee, R. S. et al., "Major histocompatibility complex class I presentation of exogenous soluble tumor antigen fused to the B-fragment of Shiga toxin," European Journal of Immunology, 28: 2726-2737 (1998).
Lehmann, C. H. K. et al., "Direct Delivery of Antigens to Dendritic Cells via Antibodies Specific for Endocytic Receptors as a Promising Strategy for Future Therapies," Vaccines, 4(2):1-32 (2016).
Lev, A. et al., "Tumor-specific Ab-mediated targeting of MHC-peptide complexes induces regression of human tumor xenografts in vivo," PNAS, 101(24):9051-9056 (2004).
Li, H. et al., "The CD20 Calcium Channel is Localized to Microvilli and Constitutively Associated with Membrane Rafts: Antibody binding increases the affinity of the association through an epitope-dependent cross-linking-independent mechanism," Journal of Biological Chemistry, 279(19):19893-19901 (2004).
Li, B. et al., "Development of Novel Tetravalent Anti-CD20 Antibodies with Potent Antitumor Activity," Cancer Research, 68(7):2400-2408 (2008).
Li, M. et al., "Clinical targeting recombinant immunotoxins for cancer therapy," Onco Targets and Therapy, 10:3645-3665 (2017).
Li, Y. et al., "Correction to: Discovery and preclinical characterization of the antagonist anti-PD-L1 monoclonal antibody LY3300054," Journal for Immuno Therapy of Cancer, vol. 6, No. 1, Jun. 2018, p. 1.
Lim, S. H. et al., "Fc gamma receptor IIb on target B cells promotes ritumixab internalization and reduces clinical efficacy," Blood, 118(9):2530-2540 (2011).
Ling, H. et al., "Structure of the Shiga-like Toxin I B-Pentameter complexed with an Analogue of Its Receptor Gb3," Biochemistry, 37(7):1777-1788 (1998).
Luqman, M. et al., "The antileukemia activity of a human antiCD40 antagonist antibody, HCD122, on human chronic lymphocytic leukemia cells," Blood, 112(3):711-720 (2008).
Lyu, M.-A et al., "Cell-targeting fusion constructs containing recombinant gelonin," Methods in Enzymology, 502:167-214 (2012).
Maak, M. et al., "Tumor-Specific Targeting of Pancreatic Cancer with Shiga Toxin B-Subunit," Molecular Cancer Therapeutics, 10(10):1918-1928 (2011).
Mallard, F. et al., "Direct Pathway from Early/Recycling Endosomes to the Golgi Apparatus Revealed through the Study of Shiga Toxin B-fragment Transport," The Journal of Cell Biology, 143(4):973-990 (1998).
Mascarell, L. et al., "Induction of Neutralizing Antibodies and Th1-Polarized and CD4-Independent CD8+ T-Cell Responses following Delivery of Human Immunodeficiency Virus Type 1 Tat Protein by Recombinant Adenylate Cyclase of Bordetella pertussis," Journal of Virology, 79(15):9872-9884 (2005).
Mazor, Y. et al., "ChFRP5-ZZ-PE38, a large IgG-toxin immunoconjugate outperforms the corresponding smaller FRP5(Fv)-ETA immunotoxin in eradicating ErbB2-expressing tumor xenografts," Cancer Letters, 257(1):124-135 (2007).
Mazor, R. et al., "Identification and elimination of an immunodominant T-cell epitope in recombinant immunotoxins based on Pseudomonas exotoxin A," Proceedings of the National Academy of Sciences U.S.A., 109(51):E3597-E3603 (2012).
McCluskey, A. J. et al., "The Catalytic Subunit of Shiga-like Toxin 1 Interacts with Ribosomal Stalk Proteins and is Inhibited by Their Conserved C-Terminal Domain," Journal of Molecular Biology, 378(2):375-386 (2008).
McCluskey et al., "Shiga-like Toxin 1: Molecular Mechanism of Toxicity and Discovery of Inhibitors", Thesis University of Toronto (2010); retrieved from the Internet: http:/hdl.handle.net/1807/32046.
McCluskey et al., "Charged and hydrophobic Surfaces on the A chain of Shiga-like Toxin 1 recognize the C-terminal Domain of Ribosomal Stalk Proteins," PLoS One 7(2):e31191 (2012).
McKenzie, J, et al., "Passage through the Golgi is necessary for Shiga toxin B subunit to reach the endoplasmic reticulum," The FEBS Journal, 276(6):1581-1595, 2008.
Meeting Abstracts, "33rd Annual Meeting & Pre-Conference Programs of the Society for Immunotherapy of Cancer (SITC 2018)," Washington, D.C., USA, Nov. 7-11, 2018, Journal for Immuno Therapy of Cancer, vol. 6, Supplement No. 1, Nov. 2018, pp. 1-205.
Meeting Abstracts, "34th Annual Meeting & Pre-Conference Programs of the Society for Immunotherapy of Cancer (SITC 2019): Part 2: National Harbor, MD, USA, Nov. 10, 2019," Journal for Immuno Therapy of Cancer, vol. 7, Supplement No. 1, Nov. 2019, pp. 1-237, Abstract P804.
Michel, R. B. et al., "Intracellular Accumulation of the Anti-CD20 Antibody 1F5 in B-Lymphoma Cells," Clinical Cancer Research, 8(8):2701-2713 (2002).
Miller, R. B. et al., "Design, Construction, and In-Vitro analyses of Multivalent Antibodies," Journal of Immunology, 170(9):4854-4861 (2003).

(56) References Cited

OTHER PUBLICATIONS

Moise, L. et al., "T cell epitope engineering: an avian H7N9 influenza vaccine strategy for pandemic preparedness and response," Human Vaccines & Immunotherapeutics, 14(9):2203-2207 (2018).
Molecular Templates, Molecular Templates Provides Corporate Update and Outlines 2020 Milestones, Jan. 8, 2020, 2 pages.
Molecular Templates, Inc., R&D Day, Conference Call Transcript, Nov. 15, 2019, Fair Disclosure Wire, pp. 1-17; retrieved on Jan. 15, 2021 from https://dialog.proquest.com/professional/docview/2320577373.
Molecular Templates Corporate Presentation, Nov. 2019, 26 pages.
Muzard, J. et al., "Grafting of protein L-binding activity onto recombinant antibody fragments," Analytical Biochemistry, 388(2):331-338 (2009).
Newland, J. W. et al., "Cloning of Genes for Production of *Escherichia coli* Shiga-Like Toxin Type II," Infection and Immunity, 55(11):2675-2680 (1987).
Nilson, B. H. K. et al., "Protein L from Peptostreptococcus magnus binds to the kappa light chain variable domain," Journal of Biological Chemistry, 267(4):2234-2239 (1992).
Nilson, B. H. K. et al., "Purification of antibodies using protein L-binding framework structures in the light chain variable domain," Journal of Immunological Methods, 164(1):33-40 (1993).
Ninkovic, T. et al., "Identification of O-glycosylated decapeptides within the MUC1 repeat domain as potential MHC class I (A2) binding epitopes," Molecular Immunology 47(1):131-140 (2009).
Noakes, K. L. et al., "Exploiting retrograde transport of Shiga-like Toxin 1 for the delivery of exogenous antigens into the MHC class I presentation pathway," FEBS Letters, 453(1-2):95-99 (1999).
Ogishi, M. & Yotsuyanagi, H., "Quantitative Prediction of the Landscape of T Cell Epitope Immunogenicity in Sequence Space," Frontiers in Immunology, vol. 10, Article 827, pp. 1-20 (2019).
Ohmura, M. et al., "Characterization of non-toxic mutant toxins of Vero toxin I that were constructed by replacing amino acids in the A subunit," Microbial Pathogenesis, 15(3):169-176 (1993).
Olafsen, T. et al., "Recombinant Anti-CD20 Antibody fragments for Small-Animal PET Imaging of B-Cell Lymphomas," Journal of Nuclear Medicine, 50(9):1500-1508 (2009).
Olafsen, T. et al., "ImmunoPET imaging of B-cell lymphoma using anti-CD20 scFv dimers (diabodies)," Protein Engineering, Design & Selection, 23(4):243-249 (2010).
Oloomi, M. et al., "In vivo characterization of Fusion Protein Comprising of A1 Subunit of Shiga Toxin and Human GM-CSF: Assessment of Its immunogenicity and Toxicity," Iranian Biomedical Journal, 14(4):136-141 (2010).
Onda, M. et al., "An immunotoxin with greatly reduced immunogenicity by identification and removal of B cell epitopes," Proceedings of the National Academy of Sciences U.S.A., 105(32):11311-11316 (2008).
Osicka, R. et al., "Delivery of CD8+ T-cell epitopes into major histocompatibility complex class I antigen presentation," Infection and Immunity, 68(1):247-256 (2000).
Pai-Scherf, L. H. et al., "Hepatotoxicity in Cancer Patients Receiving erb-38, a Recombinant Immunotoxin that Targets the erbB2 Receptor," Clinical Cancer Research, 5(9):2311-2315 (1999).
Passeri, D. & Spiegel, J., "Immunoconjugates: Magic Bullets for Cancer Therapy?" 1993; web page; retrieved Mar. 9, 2022 from https://ntrs.nasa.gov/api/citations/19930016378/downloads/19930016378.pdf, 1 page.
Passeri, D. & Spiegel, J., "Immunoconjugates: Magic Bullets for Cancer Therapy?" 1993; retrieved Mar. 23, 2022 from https://ntrs.nasa.gov/api/citations/19930016378/downloads/19930016378.pdf, 6 pages.
Pastan, I. et al., "Immunotoxin Treatment of Cancer," Annual Review of Medicine, 58:221-237 (2007).
Paul, W. E. (Ed.) "Fundamental Immunology" 3rd Edition, Raven Press, 292-295 (1993).
Peng, K. W. et al., "Oncolytic measles viruses displaying a single-chain antibody against CD38, a myeloma cell marker," Blood, 101(7):2557-2562 (2003).
Perampalam, S. et al., "Designing combinatorial protein libraries based on a protein toxin template," Molecular & Cellular Proteomics, American Society for Biochemistry and Molecular Biology, Inc., US, vol. 2, No. 9, Jan. 11, 2003, p. 868.
Perampalam, S. et al., "Designing combinatorial protein libraries based on a protein toxin template," HUPO 2nd Annual & IUBMB IXI World Congress, Oct. 8-11, Montreal, Poster Session 28 Proteomics & Biotechnology, 80.16 (Oct. 2003).
Perampalam, S. et al., "Cell-targeted Ribosome-Inactivating Proteins derived from Protein Combinatorial Libraries," Thesis-University of Toronto (2008), 172 pages.
Peterson, J. K. et al., "Integrating pharmacology and in vivo cancer models in preclinical and clinical drug development," European Journal of Cancer, 40(6):837-844 (2004).
Pirie, C. M. et al., "Convergent Potency of Internalized Gelonin Immunotoxins across Varied Cell Lines, Antigens, and Targeting Moieties," Journal of Biological Chemistry, 286(6):4165-4172 (2011).
Pisarev, V. M. et al., "T cells recognize PD(N/T)R motif common in a variable number of tandem repeat and degenerate repeat sequences of MUC1," International Immunopharmacology, 5(2):315-330 (2005).
Polito, L. et al., "The Conjugate Rituximab/saporin-S6 completely inhibits clonogenic growth of CD20-expressing cells and produces a synergistic toxic effect with Fludarabine," Leukemia 18(7):1215-1222 (2004).
Polito, L. et al., "Saporin-S6: A Useful Tool in Cancer Therapy," Toxins, 5:1698-1722 (2013).
Polson, A. G. et al., "Antibody-Drug Conjugates for the Treatment of Non-Hodgkin's Lymphoma: Target and Linker-Drug Selection," Cancer Research, 69(6):2358-2364 (2009).
Press, O. W. et al., "Endocytosis and Degradation of Monoclonal Antibodies Targeting Human B-Cell Malignancies," Cancer Research, 49(17):4906-4912 (1989).
Press, O. et al., "Retention of B-Cell Specific Monoclonal Antibodies by Human Lymphoma Cells," Blood, 83(5):1390-1397 (1994).
Preville, X, et al., "Eradication of Established Tumors by Vaccination With Recombinant Bordetella pertussis Adenylate Cyclase Carrying the Human Papillomavirus 16 E7 Oncoprotein," Cancer Research, 65(2):641-649 (2005).
Protein ID ABM97743, European Molecular Biology Laboratory (EMBL), Oloomi, M, et al., "synthetic construct partial A1-GMCSF chimeric protein", Sep. 10, 2007.
Promega Technical Reference, Amino Acids, 2018.
Rajagopalan, S. et al., "CD-20 Specific Engineered Toxin Body Demonstrates Direct Cell Kill of Multiple B-Cell Non-Hodgkin's Lymphoma Types," Blood, 122(21):5152 (2013).
Rajagopalan, S. et al., "CD20-specific Engineered Toxin Body demonstrates direct cell kill of multiple B-cell Non-Hodgkin's lymphoma types," The Journal of Cancer Research, 74(19 Suppl): Abstract # 647, (Oct. 1, 2014); Proceedings: AACR Annual Meeting 2014 (Apr. 5-9, 2014).
Rajagopalan, S, et al., "CD38-specific engineered toxin body: Therapeutic potential for multiple myeloma", The Journal of Cancer Research, 74(19 Suppl): Abstract #671, (Oct. 1, 2014) from American Association for Cancer Research (AACR) Annual Meeting 2014, (Apr. 5-9, 2014).
Rajagopalan, S. et al., "CD38-specific engineered toxin body: Therapeutic potential for multiple myeloma," The Journal of Cancer Research, 74(19 Suppl): Abstract nr 671 (Oct. 1, 2014).
Rajagopalan, S. et al., "HER2-targeted engineered toxin body demonstrates selective binding and cell kill of HER2-overexpressing breast cancer," The Journal of Cancer Research, 73(8 Suppl): Abstract #868 (Apr. 15, 2013).
Rajagopalan, S. et al., "HER2-targeted engineered toxin body demonstrates selective binding and cell kill of HER2-overexpressing breast cancer," Proceedings: American Association for Cancer Research (AACR) Annual Meeting 2013, Abstract # 868 (Apr. 6-10, 2013).
Rajagopalan, S. et al., "Next-generation engineered toxin bodies: CD38, PD-L1 and HER2 targeted ETBs," American Association for Cancer Research (AACR) Annual Meeting, 2016, Abstract #595 (Apr. 16-20, 2016).

(56) References Cited

OTHER PUBLICATIONS

Rajagopalan, S. et al., "Next-generation engineered toxin bodies: CD38, PD-L1 and HER2 targeted ETBs," The Journal of Cancer Research, 76(14 Suppl) (Jul. 15, 2016), Abstract nr 595.
Rajagopalan, S. et al., "A novel targeted engineered toxin body for treatment of HER2 positive breast cancer," Thirty-Seventh Annual CTRC-AACR San Antonio Breast Cancer Symposium, nr P4-15-17 (Dec. 9-13, 2014).
Ramakrishnan, S. & Houston, L., "Comparison of the Selective Cytotoxic Effects of Immunotoxins Containing Ricin A Chain or Pokeweed Antiviral Protein and Anti-Thy 1.1 Monoclonal Antibodies," Cancer Research, 44(1):201-208 (1984).
Ramos, H. J. et al., Abstract 3900, "The safety and efficacy profile of a PD-L1 directed, Engineered Toxin Body, as a novel targeted direct-cell kill approach for the treatment of PD-L1 expressing cancers," Molecular Templates, AACR Annual Meeting 2019; Mar. 29-Apr. 3, 2019; Atlanta, GA, AACR 2019, 2 pages.
Robinson, G. L. et al., "In vivo efficacy of a CD38-specific engineered toxin body," Clinical Cancer Research, 21(17 Suppl) (Sep. 21, 2015), Abstract A15.
Robinson, G. L. et al., "In vivo efficacy of a CD38-specific engineered toxin body," Proceedings: American Association for Cancer Research (AACR) Special Conference on Hematologic Malignancies: Translating Discoveries to Novel Therapies, Poster A15 (Sep. 21, 2015).
Robinson, G. L. et al., "MT-3724, an engineered toxin body targeting CD20 for non-Hodgkin's lymphoma," Proceedings: American Association for Cancer Research (AACR) 107th Annual Meeting 2016, Abstract #1483 (Apr. 6-10, 2016).
Robinson, G. L. et al., "MT-4019: a de-immunized engineered toxin body targeting CD38 for multiple myeloma," Proceedings: American Association for Cancer Research (AACR) Annual Meeting 2017, Poster, Abstract 2659 (Apr. 1-5, 2017).
Robinson, G. L. et al., "MT-3724, an engineered toxin body targeting CD20 for non-Hodgkin's lymphoma," Proceedings of the 107th Annual Meeting of the American Association for Cancer Research, Cancer Research, Jul. 15, 2016, 76(14 Suppl), Abstract 1483.
Romaniuk, S. I. et al., "Recombinant Diphtheria toxin derivatives: Perspectives of application," Russian Journal of Bioorganic Chemistry, 38(6):565-577 (2012).
Rosenthal, A. et al., "A phase 2 study of lenalidomide, rituximab, cyclophosphamide, and dexamethasone (LR-CD) for untreated low-grade non-Hodgkin lymphoma requiring therapy," Am J Hematol., 92(5):467-472 (2017).
Rossi, E. A. et al., "Novel Designs of Multivalent Anti-CD20 Humanized Antibodies as Improved Lymphoma Therapeutics," Cancer Research, 68(20):8384-8392 (2008).
Roudkenar, M. H. et al., "Selective cytotoxicity of recombinant STXA1-GM-CSF protein in hematopoietic cancer cells," Cell Biology and Toxicology, 22(3):213-219 (2006).
Rudikoff, S. et al., "Single amino acid substitution altering antigen-binding specificity," Proceedings of the National Academy of Sciences of the USA, 79(6):1979-1983 (1982).
Saijo, N. "What are the reasons for negative phase III trials of molecular-target-based drugs?" Cancer Science 95(10):772-776 (2004).
Sandvig, K. et al., "Protein toxins: mode of action and cell entry," Biochemical Society Transactions, 20(4):724-727 (1993).
Sandvig, K. et al., "Entry of Shiga Toxin into Cells," Zentralblatt für Bakteriologie, 278(2-3):296-305 (1993).
Saron, M. F. et al., "Anti-viral protection conferred by recombinant adenylate cyclase toxins from Bordetella pertussis carrying a CD8+ T cell epitope from lymphocytic choriomeningitis virus," Proceedings of the National Academy of Sciences U.S.A., 94(7):3314-3319 (1997).
Schindler, J. et al., "A Phase I Study of a Combination of anti-CD19 and anti-CD22 Immunotoxins (Combotox) in Adult Patients with Refractory B-Lineage Acute Lymphoblastic Leukemia," British Journal of Haematology, 154(4):1-11 (2011).

Schlecht, G. et al., "Antigen Targeting to CD11b Allows Efficient Presentation of CD4+ and CD8+ T Cell Epitopes and In Vivo Th1-Polarized T Cell Priming," The Journal of Immunology, 173(10):6089-6097 (2004).
Schuh, J. C., "Trials, Tribulations, and Trends in Tumor Modeling in Mice," Toxicologic Pathology, 32(Suppl. 1):53-66 (2004).
Schultz, J. C. et al., "A Tetravalent Single-chain Antibody-Streptavidin Fusion Protein for Pretargeted Lymphoma Therapy," Cancer Research, 60(23):6663-6669 (2000).
Schumacher, F.-R. et al., "Building proteomic tool boxes to monitor MHC class I and class II peptides," Proteomics, 17(1-2) (2017), 16 pages; doi:10.1002/pmic.201600061.
Sebo, P. et al., "Cell-Invasive Activity of Epitope-Tagged Adenylate Cyclase of Bordetella pertussis allows In Vitro Presentation of a Foreign Epitope to CD8+ Cytotoxic T Cells," Infection and Immunity, 63(10):3851-3857 (1995).
Sebo, P. et al., "In vivo induction of CTL responses by recombinant adenylate cyclase of Bordetella pertussis carrying multiple copies of a viral CD8+ T-cell epitope," FEMS Immunology & Medical Microbiology, 26(2):167-173 (1999).
Shan, D. et al., "Characterization of scFV-Ig Constructs Generated from the Anti-CD20 mAb 1F5 Using Linker Peptides of Varying Lengths," Journal of Immunology, 162(11):6589-6595 (1999).
Shaw, C. A. et al., "Stimulation of CD8+ T Cells following Diphtheria Toxin-Mediated Antigen Delivery into Dendritic Cells," Infection and Immunity, 74(2):1001-1008 (2006).
Shen, G. L. et al., "Evaluation of four CD22 antibodies as ricin A chain-containing immunotoxins for the in vivo therapy of human B-cell leukemias and lymphomas," International Journal of Cancer, 42(5):792-797 (1988).
Shete, V., "Generation and characterization of random site-directed mutants of Shiga-like toxin 1A by *Escherichia coli* O157:H7 in *Saccharomyces cerevisiae*," Thesis, Rutgers, The State University of New Jersey, New Brunswick (2009), retrieved from http://dx.doi.org/doi:10.7282/T300029Z.
Shiba, Y. et al., "AGAP2 regulates retrograde transport between early endosomes and the TGN," Journal of Cell Science, 123(Pt 14):2381-2390 (2010).
Sieber, T. et al., "Selective internalization of monoclonal antibodies by B-cell chronic lymphocytic leukemia cells," 121(3):458-461 (2003).
Simsova, M. et al., "The adenylate cyclase toxin from Bordetella pertussis—a novel promising vehicle for antigen delivery to dendritic cells," International Journal of Medical Microbiology, 239:571-576 (2004).
Singh, N. K. et al., "Emerging Concepts in TCR Specificity: Rationalizing and (Maybe) Predicting Outcomes," J Immunol, 199:2203-2213 (2017).
Sivam, G. et al., "Immunotoxin to a Human Melanoma-associated Antigen: Comparison of Gelonin with Ricin and Other A Chain Conjugates," Cancer Research, 47(12):3169-3173 (1987).
Skinner, L. M. & Jackson, M. P., "Investigation of ribosome binding by the Shiga Toxin A1 subunit, using competition and site-directed mutagenesis," Journal of Bacteriology, 179(4): 1368-1374 (1997).
Skinner, L. M. & Jackson, M. P., "Inhibition of prokaryotic translation by the Shiga toxin enzymatic subunit," Microbial Pathogenesis, 24(2):117-122 (1998).
Smith, D. C. et al., "Exogenous Peptides Delivered by Ricin Require Processing by Signal Peptidase for Transporter Associated with Antigen Processing-Independent MHC Class I-Restricted Presentation," The Journal of Immunology, 169(1):99-107 (2002).
Stenmark, H. et al., "Peptides fused to the amino-terminal end of Diphtheria toxin are translocated to the cytosol," The Journal of Cell Biology, 113(5):1025-1032 (1991).
Stepanov, A. et al., "Design of Targeted B Cell Killing Agents," PLoS One, 6(6):e20991 (2011); doi:10.1371/journal.pone.0020991, 10 pages.
Strop, P. et al., "Location Matters: Site of Conjugation Modulates Stability and Pharmacokinetics of Antibody Drug Conjugates," Chemistry & Biology, 20:161-167 (2013).
Su, H. et al., "Clinical grade production and characterization of a fusion protein comprised of the chemokine CCL2-ligand geneti-

(56) References Cited

OTHER PUBLICATIONS cally fused to a mutated and truncated form of the Shiga A1 subunit," Protein Expression and Purification, 66(2):149-157 (2009).
Suh, J. K. et al., "Shiga Toxin Attacks Bacterial Ribosomes as Effectively as Eucaryotic Ribosomes," Biochemistry, 37(26):9394-9398 (1998).
Suhan, M. L. et al., "Disruption of an Internal Membrane-Spanning Region in Shiga Toxin I Reduces Cytotoxicity," Infection and Immunity, 66(11):5252-5259 (1998).
Tacken, P. J. et al., "Effective induction of naive and recall T-cell responses by targeting antigen to human dendritic cells via a humanized anti-DC-SIGN antibody," Blood, 106(4): 1278-85 (2005).
Tesh, V. L. et al., "Comparison of the Relative Toxicities of Shiga-Like Toxins Type I and Type II for Mice," Infection and Immunity, 61(8):3392-3402 (1993).
Thompson, J. et al., "Improved binding of a bivalent single-chain immunotoxin results in increased efficacy for in vivo T-cell depletion," Protein Engineering, 14(12):1035-1041 (2001).
Thorpe, P. E. et al., "Cytotoxicity Acquired by Conjugation of an Anti-Thy1.1 Monoclonal Antibody and the Ribosome-Inactivating Protein, Gelonin," European Journal of Biochemistry, 116(3):447-454 (1981).
Torgersen, M. L. et al., "The A-subunit of surface-bound Shiga toxin stimulates clathrin-dependent uptake of the toxin," The FEBS Journal, 272(16):4103-4013 (2005).
Tosatto, C. E. et al., "Large-Scale Prediction of Protein Structure and Function from Sequence," Current Pharmaceutical Design, 12(17):2067-2086 (2006).
Vallera, D. A. et al., "Bioengineering a unique deimmunized bispecific targeted toxin that simultaneously recognizes human CD22 and CD19 Receptors in a mouse model of B-Cell metastases," Molecular Cancer Therapeutics, 9(6):1872-1883 (2010).
Varner, C. T. et al., "Recent Advances in Engineering Polyvalent Biological Interactions," Biomacromolecules, 16(1):43-55 (2014).
Vernet, E. et al., "Affinity-based entrapment of the HER2 receptor in the endoplasmic reticulum using an affibody molecule," Journal of Immunological Methods, 338:1-6 (2008).
Vervoordeldonk, S. F. et al., "Preclinical studies with radiolabeled monoclonal antibodies for treatment of patients with B-cell malignancies," Cancer, 73(3):1006-1011 (1994).
Vingert, B. et al., "The Shiga toxin B-subunit targets antigen in vivo to dendritic cells and elicits anti-tumor immunity," European Journal of Immunology, 36(5):1124-1135 (2006).
Von Minckwitz, G. et al., "Phase I clinical study of the recombinant antibody toxin scFv(FRP5)-ETA specific for the ErbB2/HER2 receptor in patients with advanced solid malignomas," Breast Cancer Research, 7(5):R617-R626 (2005).
Voskoglou-Nomikos, T. et al., "Clinical Predictive Value of the In Vitro Cell Line, Human Xenograft, and Mouse Allograft Preclinical Cancer Models," Clinical Cancer Research, 9(11): 4227-4239 (2003).
Wales, R. et al., "Addition of an endoplasmic reticulum retrieval sequence to ricin A chain significantly increases its cytotoxicity to mammalian cells," Journal of Biological Chemistry, 268(32):23986-23990 (1993).
Wang, E. et al., "T-cell-directed cancer vaccines: the melanoma model," Expert Opinion on Biological Therapy, 1(2):277-290 (2001).
Wargalla, U. D. & Reisfeld, R. A., "Rate of internalization of an immunotoxin correlates with cytotoxic activity against human tumor cells," PNAS USA, 86(13):5146-5150 (1989).
Weinstein, D. et al., "In vivo formation of hybrid toxins comprising Shiga toxin and the Shiga-like toxins and role of the B subunit in localization and cytotoxic activity," Infection and Immunity, 57(12):3743-3750 (1989).
Weldon, J. E. & Pastan, I., "A guide to taming a toxin: recombinant immunotoxins constructed from Pseudomonas exotoxin A for the treatment of cancer," FEBS Journal, 278(23):4683-4700 (2011).
Wels, W. et al., "Selective Inhibition of Tumor Cell Growth by a Recombinant Single-Chain Antibody-Toxin Specific for the erbB-2 Receptor," Cancer Research, 52:6310-6317 (1992).
Willert, E. K. et al., "Engineered toxin bodies: A next-generation immunotoxin scaffold with novel immuno-oncology functionality," Proceedings: American Association for Cancer Research (AACR) Annual Meeting 2015, Abstract #2477 (Apr. 18-22, 2015).
Willert, E. K. et al., "A novel targeted engineered toxin body for treatment of HER2 positive breast cancer," The Journal of Cancer Research, 75(9 Suppl) Abstract nr P4-15-17 (May 1, 2015).
Willert, E. K. et al., "Engineered toxin bodies: A next-generation immunotoxin scaffold with novel immuno-oncology functionality," The Journal of Cancer Research, 75(15 Suppl): Abstract nr 2477, (Aug. 1, 2015).
Willert, E. K. et al., "TAK-169, an exceptionally potent CD38 targeted engineered toxin body, as a novel direct cell kill approach for the treatment of multiple myeloma," Proceedings: American Association for Cancer Research (AACR) Annual Meeting 2019, Poster #2384 (Apr. 1, 2019).
Windschiegl, B. et al., "Lipid Reorganization Induced by Shiga Toxin Clustering on Planar Membranes," PLoS One, 4(7):e6238 (2009).
Wirth, R. et al., "Engineered Toxin Body demonstrating CD20-specific binding and cell kill in B-Cell Non-Hodgkin lymphoma cells," Proceedings: American Association for Cancer Research (AACR) 104th Annual Meeting 2013, Abstract #5477 (Apr. 6-10, 2013).
Wirth, R. et al., "Engineered Toxin Body demonstrating CD20-specific binding and cell kill in B-Cell Non-Hodgkin lymphoma cells," [Abstract]. In: Proceedings of the 104th Annual Meeting of the American Association for Cancer Research, Cancer Research, Apr. 15, 2013, 73(8 Suppl) Abstract #5477.
Wu, A. M. et al., "Multimerization of a chimeric anti-CD20 single chain Fv-Fc fusion protein is mediated through variable domain exchange," Protein Engineering, 14(12):1025-1033 (2001).
Wu, H. et al., "Humanization of a murine monoclonal antibody by simultaneous optimization of framework and CDR residues," J. Mol. Biol., 294:151-162 (1999).
Yamasaki, S. et al., "Importance of arginine at position 170 of the A subunit of Vero toxin 1 produced by enterohemorrhagic *Escherichia coli* for toxin activity," Microbial Pathogenesis, 11(1):1-9 (1991).
Yu, L. et al., "Interaction between bevacizumab and murine VEGF-A: a reassessment," Investigative Ophthalmology & Visual Science, 49(2):522-527 (2008).
Zacny, V. et al., "Novel toxin library for the discovery of oncology therapeutics," Cancer Research, 70(8 Suppl), Abstract #5506 (Apr. 2010).
Zahid, M. et al., "Design and reshaping of an scFv directed against human platelet glycoprotein VI with diagnostic potential," Analytical Biochemistry, 417(2):274-282 (2011).
Zapata, G. et al., "Engineering linear F(ab')2 fragments for efficient production in *Escherichia coli* and enhanced antiproliferative activity," Protein Engineering, 8(10):1057-1062 (1995).
U.S. Appl. No. 17/030,657, filed Sep. 24, 2020.
U.S. Appl. No. 17/228,579, filed Apr. 12, 2021.
U.S. Appl. No. 16/467,737, filed Jun. 7, 2019.
U.S. Appl. No. 17/314,563, filed May 7, 2021.
U.S. Appl. No. 17/533,552, filed Nov. 23, 2021.
U.S. Appl. No. 17/231,526, filed Apr. 15, 2021.
U.S. Appl. No. 17/233,911, filed Apr. 19, 2021.
U.S. Appl. No. 17/345,576, filed Jun. 11, 2021.
U.S. Appl. No. 15/125,142, filed Sep. 9, 2016.
U.S. Appl. No. 17/459,133, filed Aug. 27, 2021.
Batisse, C. et al., "A new delivery system for auristatin in STxB-drug conjugate therapy," Eur J Med Chem May 5, 2015; 95:483-91. doi: 10.1016/j.ejmech.2015.03.047. Epub Mar. 28, 2015.
Ge, Y. et al., "Prokaryotic Expression, Renaturalization and Antigenic Identification of Shiga Toxin I A Subunit," J Med Bol Biol, 5(4):319-322 (2008). Abstract.
Kim, S. et al., "Shiga toxin A subunit mutant of *Escherichia coli* O157:H7 releases outer membrane vesicles containing the B-pentameric complex," FEMS Immunology & Medical Microbiology, vol. 58, Issue 3, Apr. 2010, pp. 412-420. https://doi.org/10.1111/j.1574-695X.2010.00654.x.

(56) References Cited

OTHER PUBLICATIONS

Kostova, V. et al., "Targeted Shiga toxin-drug conjugates prepared via Cu-free click chemistry," Bioorg Med Chem. Nov. 15, 2015; 23(22):7150-7. doi: 10.1016/j.bmc.2015.10.010. Epub Oct. 8, 2015.

MHC CLASS I EPITOPE DELIVERING POLYPEPTIDES

CROSS REFERENCE TO RELATED APPLICATIONS

This application is a divisional application of U.S. application Ser. No. 17/231,526, filed Apr. 15, 2021, now U.S. Pat. No. 11,312,751, which is a continuation of U.S. application Ser. No. 16/220,468, filed Dec. 14, 2018, which is a continuation of U.S. application Ser. No. 15/114,474, filed Jul. 27, 2016, which is a national stage entry of International Application No. PCT/US2015/012968, filed on Jan. 26, 2015, which claims priority to U.S. Provisional Application No. 62/049,325, filed Sep. 11, 2014 and U.S. Provisional Application No. 61/932,000 filed on Jan. 27, 2014, the contents of which are incorporated herein by reference in their entirety for all purposes.

INCORPORATION BY REFERENCE OF SEQUENCE LISTING

The content of the text file submitted electronically herewith is incorporated herein by reference in its entirety: A computer readable format copy of the Sequence Listing (filename: MTEM_007_05US_SeqList_ST25.txt, date recorded: Mar. 28, 2022, file size: about 189 kilobytes).

FIELD OF THE INVENTION

The present invention relates generally to methods of modifying polypeptides to introduce the ability of the polypeptide to deliver a heterologous T-cell epitope for MHC class I presentation by a chordate cell and the polypeptides made using these methods. More specifically, the invention relates to methods of modifying polypeptides comprising proteasome delivery effector functions into heterologous, T-cell epitope delivering polypeptides that differ in their immunogenic properties from their parent molecules by the addition of one or more T-cell epitope-peptides which can be recognized by a MHC class I molecule and be presented on a cell surface by the MHC class I system of a chordate cell. Certain methods of the present invention relate to methods of modifying polypeptides to reduce antigenicity and/or immunogenicity via the introduction of one or more T-cell epitopes. In another aspect, the present invention relates to polypeptides created using methods of the invention and cell-targeted molecules comprising polypeptides created using methods of the invention. The cell-targeted molecules of the present invention may be used for numerous applications such as, e.g., the diagnosis and treatment of a variety of diseases, disorders, and conditions, such as, e.g., cancers, tumors, other growth abnormalities, immune disorders, and microbial infections.

BACKGROUND

The immune systems of chordates, such as amphibians, birds, fish, mammals, reptiles, and sharks, constantly scan both the extracellular and intracellular environments for exogenous molecules in an attempt to identify the presence of particularly threatening foreign molecules, cells, and pathogens. The Major Histo-Compatibility (MHC) system functions in chordates as part of the adaptive immune system (Janeway's Immunobiology (Murphy K, ed., Garland Science, $8^{th}$ ed., 2011)). Within a chordate, extracellular antigens are presented by the MHC class II system, whereas intracellular antigens can be presented by the MHC class I system.

Generally, the administration of exogenous peptides, polypeptides, or proteins to a cell results in these molecules not entering the cell due to the physical barrier of the plasma membrane. In addition, these molecules are often degraded into smaller molecules by extracellular enzymatic activities on the surfaces of cells and/or in the extracellular milieu. Polypeptides and proteins that are internalized from the extracellular environment by endocytosis are commonly degraded by lysosomal proteolysis as part of an endocytotic pathway involving early endosomes, late endosomes, and lysosomes. Polypeptides and proteins that are internalized from the extracellular environment by phagocytosis are commonly degraded by a similar pathway ending with phagolysosomes The MHC class II pathway presents antigenic peptides derived from molecules in the extracellular space, commonly after phagocytosis and processing by specialized antigen presenting cells; these cells can be professional antigen presenting cells or other antigen presenting cells, such as, e.g., dendritic cells (DCs), mononuclear phagocytes (MNPCs), certain endothelial cells, and B-lymphocytes (B-cells). These antigen presenting cells display certain peptides complexed with MHC class II molecules on their cell surface for recognition by CD4 positive (CD4+) T-lymphocytes (T-cells). On the other hand, the MHC class I system functions in most cells in a chordate to present antigenic peptides from an intracellular space, commonly the cytosol, for recognition by CD8+ T-cells.

The MHC class I system plays an essential role in the immune system by providing antigen presentation of intracellular antigens (*Cellular and Molecular Immunology* (Abbas A, ed., Saunders, $8^{th}$ ed., 2014)). This process is thought to be an important part of the adaptive immune system which evolved in chordates primarily to protect against neoplastic cells and microbial infections involving intracellular pathogens; however, certain damaged cells can be removed by this process as well. The presentation of an antigenic peptide complexed with a MHC class I molecule sensitizes the presenting cells to targeted killing by cytotoxic T-cells (CTLs) via lysis, induced apoptosis, and/or necrosis. The presentation of specific peptide epitopes complexed with MHC class I molecules plays a major role in stimulating and maintaining immune responses to cancers, tumors, and intracellular pathogens.

The MHC class I system continually functions to process and display on the cell surface various intracellular epitopes, both self or non-self (foreign) and both peptide or lipid antigens. The MHC class I display of foreign antigens from intracellular pathogens or transformed cells signal to CD8+ effector T-cells to mount protective T-cell immune responses. In addition, the MHC class I system continually functions to present self peptide epitopes in order to establish and maintain immunological tolerance.

Peptide epitope presentation by the MHC class I system involves five main steps: 1) generation of cytoplasmic peptides, 2) transport of peptides to the lumen of the endoplasmic reticulum (ER), 3) stable complex formation of MHC class I molecules bound to certain peptides, 4) display of those stable peptide-MHC class I molecule complexes (peptide-MHC class I complexes) on the cell surface, and 5) recognition of certain antigenic, presented peptide-MHC class I complexes by specific CD8+ T-cells, including specific CTLs.

The recognition of a presented antigen-MHC class I complex by a CD8+ T-cell leads to CD8+ T-cell activation, clonal expansion, and differentiation into CD8+ effector cells, including CTLs which target for destruction cells presenting specific epitope-MHC class I complexes. This leads to the creation of a population of specific CD8+ effector cells, some of which can travel throughout the body to seek and destroy cells displaying a specific epitope-MHC class I complex.

The MHC class I system is initiated with a cytosolic peptide. The existence of peptides in the cytosol can occur in multiple ways. In general, peptides presented by MHC class I molecules are derived from the proteasomal degradation of intracellular proteins and polypeptides. The MHC class I pathway can begin with transporters associated with antigen processing proteins (TAPs) associated with the ER membrane. TAPs translocate peptides from the cytosol to the lumen of the ER, where they can then associate with empty MHC class I molecules. TAPs translocate peptides which most commonly are of sizes around 8-12 amino acid residues but also including 6-40 amino acid residues (Koopmann J et al., *Eur J Immunol* 26: 1720-8 (1996)).

The MHC class I pathway can also be initiated in the lumen of the ER by a pathway involving transport of a protein, polypeptide, or peptide into the cytosol for processing and then re-entry back into the ER via TAP-mediated translocation.

The peptides transported from the cytosol into the lumen of the ER by TAP are then available to be bound by different MHC class I molecules. In the lumen of the ER, a multi-component peptide loading machine, which involves TAPs, helps assemble stable peptide-MHC class I molecule complexes and further process peptides in some instances, especially by cleavage into optimal sized peptides in a process called trimming (see Mayerhofer P, Tampé R, *J Mol Biol* pii S0022-2835 (2014)). In the ER, different MHC class I molecules tightly bind using highly specific immunoglobulin-type, antigen-binding domains to only those specific peptides for which the MHC class I molecule has a stronger affinity. Then the peptide-MHC class I complex is transported via the secretory pathway to the plasma membrane for presentation to the extracellular environment and recognition by CD8+ T-cells.

Recognition by a CD8+ T-cell of an epitope-MHC class I complex initiates protective immune responses which ultimately ends in the death of the presenting cell due to the cytotoxic activity of one or more CTLs. CTLs express different T-cell receptors (TCRs) with differing specificities. The MHC alleles are highly variable, and the diversity conferred by these polymorphisms can influence recognition by T-cells in two ways: by affecting the binding of peptide antigens and by affecting the contact regions between the MHC molecule and TCRs. In response to antigen-MHC class I molecule complex recognition by a CTL via its particular cell surface TCR, the CTL will kill the antigen-MHC class I complex presenting cell primarily via cytolytic activities mediated by the delivery of perforin and/or granzyme into the presenting cell. In addition, the CTL will release immuno-stimulatory cytokines, such as, e.g., interferon gamma (IFN-gamma), tumor necrosis factor alpha (TNF), macrophage inflammatory protein-1 beta (MIP-1beta), and interleukins such as IL-17, IL-4, and IL-22. Furthermore, activated CTLs can indiscriminately kill proximal to epitope-MHC class I complex presenting cell which activated them regardless of the proximal cell's present peptide-MHC class I complex repertoire (Wiedemann A et al., *Proc Natl Acad Sci USA* 103: 10985-90 (2006)). These epitope-MHC class I complex induced immune responses could conceivably be harnessed by therapeutics to kill certain cell-types within a patient as well as sensitize the immune system to other proximal cells.

The MHC class I presentation pathway could be exploited by various therapeutics in order to induce desired immune responses; however, there are several barriers to developing such a technology, including, e.g., delivery through the cell plasma membrane; escaping the endocytotic pathway and destruction in the lysosome; and generally avoiding the sequestration, modification, and/or destruction of foreign polypeptides by the targeted cell (Sahay G et al., *J Control Release* 145: 182-195 (2010); Fuchs H et al., *Antibodies* 2: 209-35 (2013)).

In addition, the effectiveness of polypeptide-comprising therapeutics, e.g. polypeptide based biologics and biopharmaceuticals, is often curtailed by undesirable immune responses generated in recipients in response to the therapeutics. Virtually all polypeptide-based therapeutics induce some level of immune response after administration to a mammalian subject. Different levels of immune responses include the production of low-level, low-affinity and transient immunoglobulin-M antibodies to high-level, high-affinity immunoglobulin-G antibodies. The immunogenicity of a therapeutic might cause unwanted immune responses in recipients which reduce therapeutic efficacy, adversely alter pharmacokinetics, and/or result in hypersensitivity reactions, anaphylaxis, anaphylactoid reactions, or infusion reactions among other consequences (see Buttel I et al., *Biologicals* 39: 100-9 (2011)).

For example, a polypeptide-based therapeutic can cause a recipient to create antibodies against antigenic sites in the therapeutic (sometimes called neutralizing antibodies or anti-drug antibodies). Immune responses generating antibodies recognizing a therapeutic can result immunological resistance to the effect(s) of the therapeutic. In addition, cross-reactions between anti-therapeutic antibodies with endogenous factors can result in undesirable clinical outcomes.

Polypeptide-based therapeutics with polypeptide sequences derived from species distantly related to the recipient, such as when the recipient is a mammal and the polypeptide sequences are derived from a plant or microorganism, tend to be aggressively targeted by the recipient's immune system (see, Sauerborn M et al., *Trends Pharmacol Sci* 31: 53-9 (2010), for review). Vertebrate immune systems have adapted to recognize foreign polypeptide sequences with both innate and adaptive immune systems. Thud, the administration of a polypeptide to a vertebrate from the same species of vertebrate can be recognized as non-self and elicit an immune response, such as, e.g., administering to a human a polypeptide comprising a recombinant junction of two heterologous human polypeptide sequences.

Therefore, when designing polypeptide-containing therapeutics it is often desirable to attempt to minimize the immunogenicity of the therapeutic to prevent and/or reduce the occurrence of undesired immune responses in subjects undergoing therapeutic treatment. In particular, polypeptide regions in therapeutics likely to produce B-cell and/or T-cell antigenicity and/or immunogenicity are targeted for removal, suppression, and minimization.

Both B-cell and T-cell epitopes can be predicted in a given polypeptide sequence in silico using software (see, Bryson C et al., *BioDrugs* 24: 1-8 (2010), for review). For example, software called EpiMatrix (EpiVax, Inc., Providence, RI, U.S.) was successfully used to predict T-cell immunogenicity in recombinant proteins (De Groot A et al., *Dev Biol* (Basel) 122: 171-94 (2005); Koren E et al., *Clin Immunol* 124: 26-32 (2007)).

Many approaches, such as the elimination of antigenic and/or immunogenic epitopes by truncation or mutation, have been described for reducing the immunogenicity of polypeptide-containing therapeutics (Tangri S et al., *J Immunol* 174: 3187-96 (2005); Mazor R et al., *Proc Natl Acad Sci USA* 109: E3597-603 (2012); Yumura K et al., *Protein Sci* 22: 213-21 (2012)). Foreign polypeptides can be recognized with exquisite specificity by the adaptive immune system via immune epitopes often present at a small number of discrete sites on the surface of the polypeptide. However, antibody-binding affinity can be dominated by interactions with a small number of specific amino acids within an epitope. Thus, modifications of the crucial amino acids in a polypeptide which disrupt an immunogenic epitope can reduce immunogenicity (Laroche Y et al., *Blood* 96: 1425-32 (2000)). Modifications which disrupt epitope recognition include amino acid deletions, substitutions, and epitope masking with non-immunogenic conjugates.

For the development of polypeptide-based therapeutics, it is desirable to avoid inducing B-cell mediated immune responses and the production of neutralizing antibodies in patients because it reduces the effectiveness of the therapy, changes the dose-effect profile, and limits the number of doses a patient can receive (see Lui W et al., *Proc Natl Acad Sci USA* 109: 11782-7 (2012)).

Thus, it would be desirable to have methods of creating novel T-cell epitope delivering polypeptides which can deliver one or more T-cell epitopes to the MHC class I presentation pathway of a cell. It would also be desirable to have polypeptides which under physiological conditions can deliver a T-cell epitope to the interior of a target cell to initiate desirable T-cell mediated immune responses but do not induce undesirable immune responses while in extracellular spaces, such as, e.g., the creation of inhibitory antibodies. Thus, it would be desirable to have T-cell epitope delivering polypeptides in which one or more CD8+ T-cell epitopes are added and one or more B-cell and/or CD4+ T-cell epitopes are abolished.

It would also be desirable to have cell-targeted, CD8+ T-cell epitope delivering molecules for the targeted delivery of cytotoxicity to specific cell types, e.g., infected or malignant cells. In addition, it would be desirable to have cell-targeted, CD8+ T-cell epitope delivering molecules which exhibit reduced B-cell immunogenicity. Once the T-cell immunogenic peptide(s) delivered by the cell-targeted molecule are presented to the surface of a target cell, the T-cell epitope can signal for the destruction of the presenting cell by activating the recipient's own immune system to recruit CD8+ T-cells. In addition, CD8+ T-cells activated by the target cell's displayed T-cell epitope-MHC class I complex can stimulate a wider immune response and alter the microenvironment (e.g. by release cytokines in a tumor or infected tissue locus), such that other immune cells (e.g. effector T-cells) may be recruited to the local area.

In addition, it would be desirable to have methods of creating novel T-cell epitope delivering polypeptides which are derived from toxins yet preserving certain biological effector functions of the parental toxin polypeptide, such as promoting cellular internalization, directing subcellular routing, and/or toxin enzymatic activity. In addition, it is desirable to have methods of engineering toxin-derived polypeptides by replacing a B-cell epitope with a T-cell epitope as a means to both reduce the likelihood of the polypeptide producing an undesirable immune response and to increase the likelihood of inducing a desirable T-cell response directed to those targeted cells that internalize the toxin polypeptide comprising molecule.

SUMMARY OF THE INVENTION

The present invention provides various embodiments of T-cell epitope delivering polypeptides (referred to herein as "CD8+ T-cell hyper-immunized") which as components of certain cell-targeted molecules have the ability to deliver a T-cell epitope for presentation by a nucleated, target cell within a chordate. The present invention also provides various embodiments of de-immunized, CD8+ T-cell hyper-immunized polypeptides which have reduced antigenic and/or immunogenic potential in mammals regarding a B-cell and/or CD4+ T-cell epitope (referred to herein as "B-cell and/or CD4+ T-cell de-immunized"). The present invention also provides various embodiments of cell-targeted, CD8+ T-cell epitope delivering molecules for the targeted delivery of cytotoxicity to specific cell types, e.g., infected or malignant cells within a chordate.

In addition, the present invention provides embodiments of methods of generating novel polypeptides capable of delivering one or more heterologous T-cell epitopes to the MHC class I presentation pathway of a cell. The present invention also provides various embodiments of methods of generating variants of polypeptides by simultaneously reducing the probability of B-cell and/or CD4+ T-cell immunogenicity while increasing the probability of CD8+ T-cell immunogenicity. The present invention also provides certain embodiments of the methods of generating novel polypeptides capable of delivering one or more heterologous T-cell epitopes to the MHC class I presentation pathway of a cell, wherein the starting polypeptide comprises a toxin effector region and certain polypeptides produced by using the methods of the invention result in polypeptides which retain toxin effector functions, such as, e.g., enzymatic activity and cytotoxicity.

The polypeptides of the present invention may be either CD8+ T-cell hyper-immunized or de-immunized or both. The de-immunized polypeptides of the present invention may be either B-cell epitope de-immunized or T-cell de-immunized or both. The T-cell de-immunized polypeptides of the present invention may be either CD4+ T-cell de-immunized or CD8+ T-cell de-immunized or both. Certain embodiments of the polypeptides of the present invention comprise one or more heterologous T-cell epitopes. In certain further embodiments of the polypeptides of the present invention, the one or more heterologous T-cell epitopes are CD8+ T-cell epitopes.

In certain embodiments, a polypeptide of the present invention comprises an embedded or inserted heterologous T-cell epitope, wherein the polypeptide is capable of intracellular delivery of the T-cell epitope from an early endosomal compartment to a proteasome of a cell in which the polypeptide is present. In certain further embodiments, the polypeptide of the present invention further comprises a toxin-derived polypeptide capable of routing to a subcellular compartment of a cell in which the toxin-derived polypeptide is present selected from the group consisting of: cytosol, endoplasmic reticulum, and lysosome. In certain further embodiments, the polypeptide of the present invention comprises a heterologous T-cell epitope is embedded or inserted in a toxin-derived polypeptide.

In certain embodiments, a polypeptide of the present invention comprises a toxin-derived polypeptide comprising a toxin effector polypeptide capable of exhibiting one or more toxin effector functions. In certain further embodiments, the toxin effector polypeptide is derived from a toxin selected from the group consisting of: ABx toxin, ribosome inactivating protein toxin, abrin, anthrax toxin, Aspf1, bouganin, bryodin, cholix toxin, claudin, diphtheria toxin, gelonin, heat-labile enterotoxin, mitogillin, pertussis toxin, pokeweed antiviral protein, pulchellin, *Pseudomonas* exotoxin A, restrictocin, ricin, saporin, sarcin, Shiga toxin, and subtilase cytotoxin.

In certain embodiments, the polypeptide of the present invention comprises the toxin effector polypeptide derived from amino acids 75 to 251 of SEQ ID NO:1, SEQ ID NO:2, or SEQ ID NO:3, or amino acids 2 to 389 of SEQ ID NO:45. In certain further embodiments, the polypeptide of the present invention comprises the Shiga toxin effector polypeptide derived from amino acids 1 to 241 of SEQ ID NO:1, SEQ ID NO:2, or SEQ ID NO:3. In certain further embodiments, the Shiga toxin effector polypeptide is derived from amino acids 1 to 251 of SEQ ID NO:1, SEQ ID NO:2, or SEQ ID NO:3. In certain further embodiments, the Shiga toxin effector polypeptide is derived from amino acids 1 to 261 of SEQ ID NO:1, SEQ ID NO:2, or SEQ ID NO:3.

In certain embodiments, a polypeptide of the present invention comprises an embedded or inserted heterologous CD8+ T-cell epitope, wherein the polypeptide is capable of intracellular delivery of the T-cell epitope to a MHC class I molecule from an early endosomal compartment of a cell in which the polypeptide is present. In certain further embodiments, the polypeptide further comprises a toxin-derived polypeptide capable of routing to a subcellular compartment of a cell in which the polypeptide is present selected from the group consisting of: cytosol, endoplasmic reticulum, and lysosome. In certain further embodiments, the polypeptide of the present invention comprises the heterologous CD8+ T-cell epitope in the toxin-derived polypeptide. In certain further embodiments, the polypeptide of the present invention comprises the toxin-derived polypeptide comprising a toxin effector polypeptide capable of exhibiting one or more toxin effector functions. In certain further embodiments, the polypeptide of the present invention comprises the toxin effector polypeptide derived from a toxin selected from the group consisting of: ABx toxin, ribosome inactivating protein toxin, abrin, anthrax toxin, Aspf1, bouganin, bryodin, cholix toxin, claudin, diphtheria toxin, gelonin, heat-labile enterotoxin, mitogillin, pertussis toxin, pokeweed antiviral protein, pulchellin, *Pseudomonas* exotoxin A, restrictocin, ricin, saporin, sarcin, Shiga toxin, and subtilase cytotoxin. In certain embodiments, the polypeptide of the present invention comprises the toxin effector polypeptide derived from amino acids 75 to 251 of SEQ ID NO:1, SEQ ID NO:2, or SEQ ID NO:3, or amino acids 2 to 389 of SEQ ID NO:45. In certain further embodiments, the polypeptide of the present invention comprises the Shiga toxin effector polypeptide derived from amino acids 1 to 241 of SEQ ID NO:1, SEQ ID NO:2, or SEQ ID NO:3. In certain further embodiments, the Shiga toxin effector polypeptide is derived from amino acids 1 to 251 of SEQ ID NO:1, SEQ ID NO:2, or SEQ ID NO:3. In certain further embodiments, the Shiga toxin effector polypeptide is derived from amino acids 1 to 261 of SEQ ID NO:1, SEQ ID NO:2, or SEQ ID NO:3.

In certain embodiments, a polypeptide of the present invention comprises a heterologous CD8+ T-cell epitope, wherein the polypeptide is capable of intracellular delivery of the T-cell epitope for presentation by a MHC class I molecule on the surface of a cell in which the polypeptide is present. In certain further embodiments, the polypeptide of the present invention comprises a toxin-derived polypeptide capable of routing to a subcellular compartment of a cell in which the toxin-derived polypeptide is present selected from the group consisting of: cytosol, endoplasmic reticulum, and lysosome. In certain further embodiments, the polypeptide of the present invention comprises the heterologous CD8+ T-cell epitope in the toxin-derived polypeptide. In certain further embodiments, the polypeptide of the present invention comprises the toxin-derived polypeptide comprising a toxin effector polypeptide capable of exhibiting one or more toxin effector functions. In certain further embodiments, the polypeptide of the present invention comprises the toxin effector polypeptide derived from a toxin selected from the group consisting of: ABx toxin, ribosome inactivating protein toxin, abrin, anthrax toxin, Aspf1, bouganin, bryodin, cholix toxin, claudin, diphtheria toxin, gelonin, heat-labile enterotoxin, mitogillin, pertussis toxin, pokeweed antiviral protein, pulchellin, *Pseudomonas* exotoxin A, restrictocin, ricin, saporin, sarcin, Shiga toxin, and subtilase cytotoxin. In certain embodiments, the polypeptide of the present invention comprises the toxin effector polypeptide derived from amino acids 75 to 251 of SEQ ID NO:1, SEQ ID NO:2, or SEQ ID NO:3, or amino acids 2 to 389 of SEQ ID NO:45. In certain further embodiments, the polypeptide of the present invention comprises the Shiga toxin effector polypeptide derived from amino acids 1 to 241 of SEQ ID NO:1, SEQ ID NO:2, or SEQ ID NO:3. In certain further embodiments, the Shiga toxin effector polypeptide is derived from amino acids 1 to 251 of SEQ ID NO:1, SEQ ID NO:2, or SEQ ID NO:3. In certain further embodiments, the Shiga toxin effector polypeptide is derived from amino acids 1 to 261 of SEQ ID NO:1, SEQ ID NO:2, or SEQ ID NO:3.

In certain embodiments, a polypeptide of the present invention comprises a proteasome delivering effector polypeptide associated with a heterologous CD8+ T-cell epitope, and capable of intracellular delivery of the T-cell epitope for presentation by a MHC class I molecule on the surface of a cell in which the polypeptide is present. In certain further embodiments, the polypeptide of the present invention comprises a Shiga toxin effector polypeptide, wherein the heterologous CD8+ T-cell epitope is not fused directly to the amino-terminus of the Shiga toxin effector polypeptide. In certain further embodiments, the polypeptide of the present invention further comprises a second T-cell epitope embedded or inserted into a B-cell epitope. In certain further embodiments, the polypeptide of the present invention further comprises a toxin-derived polypeptide. In certain further embodiments, the polypeptide of the present invention further comprises the toxin-derived polypeptide comprising a toxin effector polypeptide comprising the proteasome delivering effector polypeptide and the second T-cell epitope. In certain further embodiments, a polypeptide of the present invention comprises the toxin-derived polypeptide comprising a toxin effector polypeptide capable of exhibiting one or more toxin effector functions. In certain further embodiments, the polypeptide of the present invention comprises the toxin effector polypeptide derived from a toxin selected from the group consisting of: ABx toxin, ribosome inactivating protein toxin, abrin, anthrax toxin, Aspf1, bouganin, bryodin, cholix toxin, claudin, diphtheria toxin, gelonin, heat-labile enterotoxin, mitogillin, pertussis toxin, pokeweed antiviral protein, pulchellin, *Pseudomonas* exotoxin A, restrictocin, ricin, saporin, sarcin, Shiga toxin, and subtilase cytotoxin. In certain embodiments, the polypeptide of the present invention comprises the toxin effector polypeptide derived from amino acids 75 to 251 of SEQ ID NO:1, SEQ ID NO:2, or SEQ ID NO:3, or amino acids 2 to 389 of SEQ ID NO:45. In certain further embodiments, the polypeptide of the present invention comprises the Shiga toxin effector polypeptide derived from amino acids 1 to 241 of SEQ ID NO:1, SEQ ID NO:2, or SEQ ID NO:3. In certain further embodiments, the Shiga toxin effector polypeptide is derived from amino acids 1 to 251 of SEQ ID NO:1, SEQ ID NO:2, or SEQ ID NO:3. In certain further embodiments, the Shiga toxin effector polypeptide is derived from amino acids 1 to 261 of SEQ ID NO:1, SEQ ID NO:2, or SEQ ID NO:3.

In certain embodiments of the methods of the present invention is a method of increasing CD8+ T-cell immunogenicity of a polypeptide capable of intracellular routing to a subcellular compartment of a cell in which the polypeptide is present selected from the group consisting of: cytosol, endoplasmic reticulum, and lysosome; the method comprising the step of: embedding or inserting a heterologous CD8+ T-cell epitope in the polypeptide. In certain further embodiments, the method comprises the embedding or inserting step wherein the embedding or inserting in an endogenous B-cell epitope, an endogenous CD4+ T-cell epitope, and/or a catalytic domain of the polypeptide. In certain further embodiments of the method, the polypeptide of the method is derived from a toxin. In certain further embodiments of the method, the polypeptide comprises a toxin effector polypeptide capable of intracellular delivery of a T-cell epitope from an early endosomal compartment to a proteasome of a cell in which the toxin effector polypeptide is present, and the method comprises embedding or inserting the heterologous T-cell epitope in the toxin effector polypeptide. In certain further embodiments of the method, the embedding or inserting step results in a toxin effector polypeptide capable of exhibiting one or more toxin effector functions in addition to intracellular delivery of a T-cell epitope from an early endosomal compartment to a MHC class I molecule of a cell in which the toxin effector polypeptide is present.

In certain embodiments of the methods of the present invention is a method of increasing CD8+ T-cell immunogenicity of a polypeptide capable of intracellular delivery of a T-cell epitope from an early endosomal compartment to a proteasome of a cell in which the polypeptide is present, the method comprising the step of: embedding or inserting a heterologous CD8+ T-cell epitope in the polypeptide. In certain further embodiments of the method, the polypeptide of the method is derived from a toxin. In certain further embodiments of the method, the polypeptide comprises a toxin effector polypeptide capable of intracellular delivery of a T-cell epitope from an early endosomal compartment to a proteasome of a cell in which the toxin effector polypeptide is present, and the method comprises embedding or inserting the heterologous T-cell epitope in the toxin effector polypeptide. In certain further embodiments of the method, the embedding or inserting step results in a toxin effector polypeptide capable of exhibiting one or more toxin effector functions in addition to intracellular delivery of a T-cell epitope from an early endosomal compartment to a MHC class I molecule of a cell in which the toxin effector polypeptide is present.

In certain embodiments of the methods of the present invention is a method of increasing CD8+ T-cell immunogenicity of a polypeptide capable of intracellular delivery of a T-cell epitope from an early endosomal compartment to a MHC class I molecule of a cell in which the polypeptide is present, the method comprising the step of embedding or inserting a heterologous CD8+ T-cell epitope in the polypeptide. In certain further embodiments of the method, the polypeptide of the method is derived from a toxin. In certain further embodiments of the method, the polypeptide comprises a toxin effector polypeptide capable of intracellular delivery of a T-cell epitope from an early endosomal compartment to a proteasome of a cell in which the toxin effector polypeptide is present, and the method comprises embedding or inserting the heterologous T-cell epitope in the toxin effector polypeptide. In certain further embodiments of the method, the embedding or inserting step results in a toxin effector polypeptide capable of exhibiting one or more toxin effector functions in addition to intracellular delivery of a T-cell epitope from an early endosomal compartment to a MHC class I molecule of a cell in which the toxin effector polypeptide is present.

In certain embodiments of the methods of the present invention is a method of creating a T-cell epitope delivery molecule capable of intracellular delivery of a T-cell epitope from an early endosomal compartment to the cytosol, endoplasmic reticulum, and/or lysosome of a cell in which the molecule is present, the method comprising the step of: associating a heterologous T-cell epitope with a polypeptide capable of routing to a subcellular compartment of a cell in which the polypeptide is present selected from the group consisting of: cytosol, endoplasmic reticulum, and lysosome. In certain further embodiments of the method, the associating consists of embedding or inserting the heterologous T-cell epitope in an endogenous B-cell epitope, an endogenous CD4+ T-cell epitope, and/or a catalytic domain of the molecule. In certain further embodiments of the method, the polypeptide of the method is derived from a toxin. In certain further embodiments of the method, the polypeptide comprises a toxin effector polypeptide capable of intracellular delivery of a T-cell epitope from an early endosomal compartment to the cytosol, endoplasmic reticulum, and/or lysosome of a cell in which the toxin effector polypeptide is present, and the method comprises embedding or inserting the heterologous T-cell epitope in the toxin effector polypeptide. In certain further embodiments of the method, the embedding or inserting step results in a toxin effector polypeptide capable of exhibiting one or more toxin effector functions in addition to intracellular delivery of a T-cell epitope from an early endosomal compartment to the cytosol, endoplasmic reticulum, and/or lysosome of a cell in which the toxin effector polypeptide is present.

In certain embodiments of the methods of the present invention is a method of creating a CD8+ T-cell epitope delivery molecule capable of intracellular delivery of a T-cell epitope from an early endosomal compartment to a proteasome of a cell in which the delivery molecule is present, the method comprising the step of: embedding or inserting a heterologous CD8+ T-cell epitope in a proteasome delivering effector polypeptide capable of intracellular delivery of a T-cell epitope from an early endosomal compartment to a proteasome of a cell in which the proteasome delivering effector polypeptide is present. In certain further embodiments of the method, the associating consists of embedding or inserting the heterologous T-cell epitope in an endogenous B-cell epitope, an endogenous CD4+ T-cell epitope, and/or a catalytic domain of the molecule. In certain further embodiments of the method, the polypeptide of the method is derived from a toxin. In certain further embodiments of the method, the polypeptide comprises a toxin effector polypeptide capable of exhibiting one or more toxin effector functions in addition to intracellular delivery of a T-cell epitope from an early endosomal compartment to a proteasome of a cell in which the toxin effector polypeptide is present.

In certain embodiments of the methods of the present invention is a method of creating a CD8+ T-cell epitope delivery molecule capable of intracellular delivery of a T-cell epitope from an early endosomal compartment to a MHC class I molecule of a cell in which the delivery molecule is present, the method comprising the step of: embedding or inserting a heterologous CD8+ T-cell epitope in a proteasome delivering effector polypeptide capable of intracellular delivery of a T-cell epitope from an early endosomal compartment to a MHC class I molecule of a cell in which the proteasome delivering effector polypeptide is present. In certain further embodiments of the method, the associating consists of embedding or inserting the heterologous T-cell epitope in an endogenous B-cell epitope, an endogenous CD4+ T-cell epitope, and/or a catalytic domain of the molecule. In certain further embodiments of the method, the polypeptide of the method is derived from a toxin. In certain further embodiments of the method, the polypeptide comprises a toxin effector polypeptide comprising the proteasome delivering effector polypeptide, and the method comprises embedding or inserting the heterologous T-cell epitope in the toxin effector polypeptide. In certain further embodiments of the method, the toxin effector polypeptide resulting from the is capable of exhibiting one or more toxin effector functions in addition to intracellular delivery of a T-cell epitope from an early endosomal compartment to a MHC class I molecule of a cell in which the toxin effector polypeptide is present.

In certain embodiments of the methods of the present invention is a method of creating a CD8+ T-cell epitope delivery molecule capable when present in a cell of delivering a T-cell epitope for presentation by a MHC class I molecule, the method comprising the step of: embedding or inserting a heterologous CD8+ T-cell epitope in a proteasome delivering effector polypeptide capable of intracellular delivery of a T-cell epitope from an early endosomal compartment to a proteasome of a cell in which the proteasome delivering effector polypeptide is present. In certain further embodiments of the method, the associating consists of embedding or inserting the heterologous T-cell epitope in an endogenous B-cell epitope, an endogenous CD4+ T-cell epitope, and/or a catalytic domain of the molecule. In certain further embodiments of the method, the polypeptide of the method is derived from a toxin. In certain further embodiments of the method, the polypeptide comprises a toxin effector polypeptide comprising the proteasome delivering effector polypeptide, and the method comprises embedding or inserting the heterologous T-cell epitope in the toxin effector polypeptide. In certain further embodiments of the method, the toxin effector polypeptide resulting from the is capable of exhibiting one or more toxin effector functions in addition to intracellular delivery of a T-cell epitope from an early endosomal compartment to a MHC class I molecule of a cell in which the toxin effector polypeptide is present.

In certain embodiments of the methods of the present invention is a method of creating a CD8+ T-cell epitope delivery molecule capable when present in a cell of delivering a T-cell epitope for presentation by a MHC class I molecule, the method comprising the step of: embedding or inserting a heterologous CD8+ T-cell epitope in a proteasome delivering effector polypeptide capable of intracellular delivery of a T-cell epitope from an early endosomal compartment to a MHC class I molecule of a cell in which the proteasome delivering effector polypeptide is present. In certain further embodiments of the method, the associating consists of embedding or inserting the heterologous T-cell epitope in an endogenous B-cell epitope, an endogenous CD4+ T-cell epitope, and/or a catalytic domain of the molecule. In certain further embodiments of the method, the polypeptide of the method is derived from a toxin. In certain further embodiments of the method, the polypeptide comprises a toxin effector polypeptide comprising the proteasome delivering effector polypeptide, and the method comprises embedding or inserting the heterologous T-cell epitope in the toxin effector polypeptide. In certain further embodiments of the method, the toxin effector polypeptide resulting from the is capable of exhibiting one or more toxin effector functions in addition to intracellular delivery of a T-cell epitope from an early endosomal compartment to a MHC class I molecule of a cell in which the toxin effector polypeptide is present.

In certain embodiments, a de-immunized polypeptide of the present invention comprises a heterologous T-cell epitope disrupting an endogenous B-cell epitope and/or CD4+ T-cell epitope. In certain further embodiments, the polypeptide of the present invention comprises a toxin-derived polypeptide. In certain further embodiments, the heterologous CD8+ T-cell epitope is in the toxin-derived polypeptide. In certain further embodiments, the toxin-derived polypeptide of the present invention comprises a toxin effector polypeptide. In certain further embodiments, the heterologous CD8+ T-cell epitope in the toxin effector polypeptide. In certain further embodiments, the toxin effector polypeptide is capable of exhibiting one or more toxin effector functions. In certain further embodiments, the polypeptide of the present invention comprises the toxin effector polypeptide derived from a toxin selected from the group consisting of: ABx toxin, ribosome inactivating protein toxin, abrin, anthrax toxin, Aspf1, bouganin, bryodin, cholix toxin, claudin, diphtheria toxin, gelonin, heat-labile enterotoxin, mitogillin, pertussis toxin, pokeweed antiviral protein, pulchellin, *Pseudomonas* exotoxin A, restrictocin, ricin, saporin, sarcin, Shiga toxin, and subtilase cytotoxin. In certain further embodiments, the toxin effector polypeptide is a diphtheria toxin effector polypeptide comprising an amino acid sequence derived from the A and B Subunits of at least one member of the diphtheria toxin family, wherein the diphtheria toxin effector polypeptide comprises a disruption of at least one B-cell epitope and/or CD4+ T-cell epitope region of the amino acid sequence selected from the group of natively positioned amino acids consisting of: 3-10 of SEQ ID NO:39, 33-43 of SEQ ID NO:39, 71-77 of SEQ ID NO:39, 125-131 of SEQ ID NO:39, 138-146 of SEQ ID NO:39, 165-175 of SEQ ID NO:39, and 185-191 of SEQ ID NO:39; and wherein the diphtheria toxin effector polypeptide is capable of routing to a cytosol compartment of a cell in which the diphtheria toxin effector polypeptide is present. In certain further embodiments, the polypeptide of the present invention comprises the diphtheria toxin effector polypeptide derived from amino acids 2 to 389 of SEQ ID NO:45. In certain further embodiment, the toxin effector polypeptide is a Shiga toxin effector polypeptide comprising an amino acid sequence derived from an A Subunit of at least one member of the Shiga toxin family, wherein the Shiga toxin effector polypeptide comprises a disruption of at least one B-cell epitope and/or CD4+ T-cell epitope region of the Shiga toxin A Subunit amino acid sequence selected from the group of natively positioned amino acids consisting of: the B-cell epitope regions 1-15 of SEQ ID NO:1 or SEQ ID NO:2; 3-14 of SEQ ID NO:3; 26-37 of SEQ ID NO:3; 27-37 of SEQ ID NO:1 or SEQ ID NO:2; 39-48 of SEQ ID NO:1 or SEQ ID NO:2; 42-48 of SEQ ID NO:3; 53-66 of SEQ ID NO:1, SEQ ID NO:2, or SEQ ID NO:3; 94-115 of SEQ ID NO: 1, SEQ ID NO:2, or SEQ ID NO:3; 141-153 of SEQ ID NO:1 or SEQ ID NO:2; 140-156 of SEQ ID NO:3; 179-190 of SEQ ID NO:1 or SEQ ID NO:2; 179-191 of SEQ ID NO:3; 204 of SEQ ID NO:3; 205 of SEQ ID NO:1 or SEQ ID NO:2; and 210-218 of SEQ ID NO:3; 240-260 of SEQ ID NO:3; 243-257 of SEQ ID NO:1 or SEQ ID NO:2; 254-268 of SEQ ID NO:1 or SEQ ID NO:2; 262-278 of SEQ ID NO:3; 281-297 of SEQ ID NO:3; and 285-293 of SEQ ID NO:1 or SEQ ID NO:2, and the CD4+ T-cell epitope regions 4-33 of SEQ ID NO:1 or SEQ ID NO:2, 34-78 of SEQ ID NO:1 or SEQ ID NO:2, 77-103 of SEQ ID NO:1 or SEQ ID NO:2, 128-168 of SEQ ID NO:1 or SEQ ID NO:2, 160-183 of SEQ ID NO:1 or SEQ ID NO:2, 236-258 of SEQ ID NO:1 or SEQ ID NO:2, and 274-293 of SEQ ID NO:1 or SEQ ID NO:2; and wherein the Shiga toxin effector polypeptide is capable of routing to a cytosol compartment of a cell in which the Shiga toxin effector polypeptide is present. In certain embodiments, the polypeptide of the present invention comprises the Shiga toxin effector polypeptide derived from amino acids 75 to 251 of SEQ ID NO: 1, SEQ ID NO:2, or SEQ ID NO:3. In certain further embodiments, the polypeptide of the present invention comprises the Shiga toxin effector polypeptide derived from amino acids 1 to 241 of SEQ ID NO:1, SEQ ID NO:2, or SEQ ID NO:3. In certain further embodiments, the Shiga toxin effector polypeptide is derived from amino acids 1 to 251 of SEQ ID NO:1, SEQ ID NO:2, or SEQ ID NO:3. In certain further embodiments, the Shiga toxin effector polypeptide is derived from amino acids 1 to 261 of SEQ ID NO:1, SEQ ID NO:2, or SEQ ID NO:3.

In certain embodiments, a polypeptide of the present invention comprises a heterologous CD8+ T-cell epitope disrupting an endogenous B-cell epitope and/or an endogenous CD4+ T-cell epitope, wherein the polypeptide is capable of intracellular delivery of the CD8+ T-cell epitope from an early endosomal compartment to a proteasome of a cell in which the polypeptide is present. In certain further embodiments, the polypeptide of the present invention comprises a toxin-derived polypeptide. In certain further embodiments, the heterologous CD8+ T-cell epitope is in the toxin-derived polypeptide. In certain further embodiments, the toxin-derived polypeptide of the present invention comprises a toxin effector polypeptide. In certain further embodiments, the heterologous CD8+ T-cell epitope is in the toxin effector polypeptide. In certain further embodiments, the toxin effector polypeptide is capable of exhibiting one or more toxin effector functions. In certain further embodiments, the polypeptide of the present invention comprises the toxin effector polypeptide derived from a toxin selected from the group consisting of: ABx toxin, ribosome inactivating protein toxin, abrin, anthrax toxin, Aspf1, bouganin, bryodin, cholix toxin, claudin, diphtheria toxin, gelonin, heat-labile enterotoxin, mitogillin, pertussis toxin, pokeweed antiviral protein, pulchellin, *Pseudomonas* exotoxin A, restrictocin, ricin, saporin, sarcin, Shiga toxin, and subtilase cytotoxin. In certain further embodiments, the toxin effector polypeptide is a diphtheria toxin effector polypeptide comprising an amino acid sequence derived from the A and B Subunits of at least one member of the diphtheria toxin family, wherein the diphtheria toxin effector polypeptide comprises a disruption of at least one B-cell epitope and/or CD4+ T-cell epitope region of the amino acid sequence selected from the group of natively positioned amino acids consisting of: 3-10 of SEQ ID NO:39, 33-43 of SEQ ID NO:39, 71-77 of SEQ ID NO:39, 125-131 of SEQ ID NO:39, 138-146 of SEQ ID NO:39, 165-175 of SEQ ID NO:39, and 185-191 of SEQ ID NO:39; and wherein the diphtheria toxin effector polypeptide is capable of routing to a cytosol compartment of a cell in which the diphtheria toxin effector polypeptide is present. In certain further embodiments, the polypeptide of the present invention comprises the diphtheria toxin effector polypeptide derived from amino acids 2 to 389 of SEQ ID NO:45. In certain further embodiment, the toxin effector polypeptide is a Shiga toxin effector polypeptide comprising an amino acid sequence derived from an A Subunit of at least one member of the Shiga toxin family, wherein the Shiga toxin effector polypeptide comprises a disruption of at least one B-cell epitope and/or CD4+ T-cell epitope region of the Shiga toxin A Subunit amino acid sequence selected from the group of natively positioned amino acids consisting of: the B-cell epitope regions 1-15 of SEQ ID NO:1 or SEQ ID NO:2; 3-14 of SEQ ID NO:3; 26-37 of SEQ ID NO:3; 27-37 of SEQ ID NO:1 or SEQ ID NO:2; 39-48 of SEQ ID NO:1 or SEQ ID NO:2; 42-48 of SEQ ID NO:3; 53-66 of SEQ ID NO:1, SEQ ID NO:2, or SEQ ID NO:3; 94-115 of SEQ ID NO:1, SEQ ID NO:2, or SEQ ID NO:3; 141-153 of SEQ ID NO:1 or SEQ ID NO:2; 140-156 of SEQ ID NO:3; 179-190 of SEQ ID NO:1 or SEQ ID NO:2; 179-191 of SEQ ID NO:3; 204 of SEQ ID NO:3; 205 of SEQ ID NO:1 or SEQ ID NO:2; and 210-218 of SEQ ID NO:3; 240-260 of SEQ ID NO:3; 243-257 of SEQ ID NO:1 or SEQ ID NO:2; 254-268 of SEQ ID NO:1 or SEQ ID NO:2; 262-278 of SEQ ID NO:3; 281-297 of SEQ ID NO:3; and 285-293 of SEQ ID NO:1 or SEQ ID NO:2, and the CD4+ T-cell epitope regions 4-33 of SEQ ID NO:1 or SEQ ID NO:2, 34-78 of SEQ ID NO:1 or SEQ ID NO:2, 77-103 of SEQ ID NO:1 or SEQ ID NO:2, 128-168 of SEQ ID NO:1 or SEQ ID NO:2, 160-183 of SEQ ID NO:1 or SEQ ID NO:2, 236-258 of SEQ ID NO:1 or SEQ ID NO:2, and 274-293 of SEQ ID NO:1 or SEQ ID NO:2; and wherein the Shiga toxin effector polypeptide is capable of routing to a cytosol compartment of a cell in which the Shiga toxin effector polypeptide is present. In certain embodiments, the polypeptide of the present invention comprises the Shiga toxin effector polypeptide derived from amino acids 75 to 251 of SEQ ID NO:1, SEQ ID NO:2, or SEQ ID NO:3. In certain further embodiments, the polypeptide of the present invention comprises the Shiga toxin effector polypeptide derived from amino acids 1 to 241 of SEQ ID NO:1, SEQ ID NO:2, or SEQ ID NO:3. In certain further embodiments, the Shiga toxin effector polypeptide is derived from amino acids 1 to 251 of SEQ ID NO:1, SEQ ID NO:2, or SEQ ID NO:3. In certain further embodiments, the Shiga toxin effector polypeptide is derived from amino acids 1 to 261 of SEQ ID NO:1, SEQ ID NO:2, or SEQ ID NO:3.

In certain embodiments, a de-immunized polypeptide of the present invention comprises a heterologous CD8+ T-cell epitope disrupting an endogenous B-cell epitope and/or CD4+ T-cell epitope, wherein the polypeptide is capable of intracellular delivery of the CD8+ T-cell epitope to a MHC class I molecule from an early endosomal compartment of a cell in which the polypeptide is present. In certain further embodiments, the polypeptide of the present invention comprises a toxin-derived polypeptide. In certain further embodiments, the heterologous CD8+ T-cell epitope is in the toxin-derived polypeptide. In certain further embodiments, the toxin-derived polypeptide of the present invention comprises a toxin effector polypeptide. In certain further embodiments, the heterologous CD8+ T-cell epitope in the toxin effector polypeptide. In certain further embodiments, the toxin effector polypeptide is capable of exhibiting one or more toxin effector functions. In certain further embodiments, the polypeptide of the present invention comprises the toxin effector polypeptide derived from a toxin selected from the group consisting of: ABx toxin, ribosome inactivating protein toxin, abrin, anthrax toxin, Aspf1, bouganin, bryodin, cholix toxin, claudin, diphtheria toxin, gelonin, heat-labile enterotoxin, mitogillin, pertussis toxin, pokeweed antiviral protein, pulchellin, *Pseudomonas* exotoxin A, restrictocin, ricin, saporin, sarcin, Shiga toxin, and subtilase cytotoxin. In certain further embodiments, the toxin effector polypeptide is a diphtheria toxin effector polypeptide comprising an amino acid sequence derived from the A and B Subunits of at least one member of the diphtheria toxin family, wherein the diphtheria toxin effector polypeptide comprises a disruption of at least one B-cell epitope and/or CD4+ T-cell epitope region of the amino acid sequence selected from the group of natively positioned amino acids consisting of: 3-10 of SEQ ID NO:39, 33-43 of SEQ ID NO:39, 71-77 of SEQ ID NO:39, 125-131 of SEQ ID NO:39, 138-146 of SEQ ID NO:39, 165-175 of SEQ ID NO:39, and 185-191 of SEQ ID NO:39; and wherein the diphtheria toxin effector polypeptide is capable of routing to a cytosol compartment of a cell in which the diphtheria toxin effector polypeptide is present. In certain further embodiments, the polypeptide of the present invention comprises the diphtheria toxin effector polypeptide derived from amino acids 2 to 389 of SEQ ID NO:45. In certain further embodiment, the toxin effector polypeptide is a Shiga toxin effector polypeptide comprising an amino acid sequence derived from an A Subunit of at least one member of the Shiga toxin family, wherein the Shiga toxin effector polypeptide comprises a disruption of at least one B-cell epitope and/or CD4+ T-cell epitope region of the Shiga toxin A Subunit amino acid sequence selected from the group of natively positioned amino acids consisting of: the B-cell epitope regions 1-15 of SEQ ID NO:1 or SEQ ID NO:2; 3-14 of SEQ ID NO:3; 26-37 of SEQ ID NO:3; 27-37 of SEQ ID NO:1 or SEQ ID NO:2; 39-48 of SEQ ID NO:1 or SEQ ID NO:2; 42-48 of SEQ ID NO:3; 53-66 of SEQ ID NO:1, SEQ ID NO:2, or SEQ ID NO:3; 94-115 of SEQ ID NO:1, SEQ ID NO:2, or SEQ ID NO:3; 141-153 of SEQ ID NO:1 or SEQ ID NO:2; 140-156 of SEQ ID NO:3; 179-190 of SEQ ID NO:1 or SEQ ID NO:2; 179-191 of SEQ ID NO:3; 204 of SEQ ID NO:3; 205 of SEQ ID NO:1 or SEQ ID NO:2; and 210-218 of SEQ ID NO:3; 240-260 of SEQ ID NO:3; 243-257 of SEQ ID NO:1 or SEQ ID NO:2; 254-268 of SEQ ID NO:1 or SEQ ID NO:2; 262-278 of SEQ ID NO:3; 281-297 of SEQ ID NO:3; and 285-293 of SEQ ID NO:1 or SEQ ID NO:2, and the CD4+ T-cell epitope regions 4-33 of SEQ ID NO:1 or SEQ ID NO:2, 34-78 of SEQ ID NO:1 or SEQ ID NO:2, 77-103 of SEQ ID NO:1 or SEQ ID NO:2, 128-168 of SEQ ID NO:1 or SEQ ID NO:2, 160-183 of SEQ ID NO:1 or SEQ ID NO:2, 236-258 of SEQ ID NO:1 or SEQ ID NO:2, and 274-293 of SEQ ID NO:1 or SEQ ID NO:2; and wherein the Shiga toxin effector polypeptide is capable of routing to a cytosol compartment of a cell in which the Shiga toxin effector polypeptide is present. In certain embodiments, the polypeptide of the present invention comprises the Shiga toxin effector polypeptide derived from amino acids 75 to 251 of SEQ ID NO:1, SEQ ID NO:2, or SEQ ID NO:3. In certain further embodiments, the polypeptide of the present invention comprises the Shiga toxin effector polypeptide derived from amino acids 1 to 241 of SEQ ID NO:1, SEQ ID NO:2, or SEQ ID NO:3. In certain further embodiments, the Shiga toxin effector polypeptide is derived from amino acids 1 to 251 of SEQ ID NO:1, SEQ ID NO:2, or SEQ ID NO:3. In certain further embodiments, the Shiga toxin effector polypeptide is derived from amino acids 1 to 261 of SEQ ID NO:1, SEQ ID NO:2, or SEQ ID NO:3.

In certain embodiments, a de-immunized polypeptide of the present invention comprises a heterologous CD8+ T-cell epitope disrupting an endogenous B-cell epitope and/or CD4+ T-cell epitope, wherein the polypeptide is capable of intracellular delivery of the CD8+ T-cell epitope for presentation by a MHC class I molecule on the surface of a cell in which the polypeptide is present. In certain further embodiments, the polypeptide of the present invention comprises a toxin-derived polypeptide. In certain further embodiments, the heterologous CD8+ T-cell epitope is in the toxin-derived polypeptide. In certain further embodiments, the toxin-derived polypeptide of the present invention comprises a toxin effector polypeptide. In certain further embodiments, the heterologous CD8+ T-cell epitope in the toxin effector polypeptide. In certain further embodiments, the toxin effector polypeptide is capable of exhibiting one or more toxin effector functions. In certain further embodiments, the polypeptide of the present invention comprises the toxin effector polypeptide derived from a toxin selected from the group consisting of: ABx toxin, ribosome inactivating protein toxin, abrin, anthrax toxin, Aspf1, bouganin, bryodin, cholix toxin, claudin, diphtheria toxin, gelonin, heat-labile enterotoxin, mitogillin, pertussis toxin, pokeweed antiviral protein, pulchellin, *Pseudomonas* exotoxin A, restrictocin, ricin, saporin, sarcin, Shiga toxin, and subtilase cytotoxin. In certain further embodiments, the toxin effector polypeptide is a diphtheria toxin effector polypeptide comprising an amino acid sequence derived from the A and B Subunits of at least one member of the diphtheria toxin family, wherein the diphtheria toxin effector polypeptide comprises a disruption of at least one B-cell epitope and/or CD4+ T-cell epitope region of the amino acid sequence selected from the group of natively positioned amino acids consisting of: 3-10 of SEQ ID NO:39, 33-43 of SEQ ID NO:39, 71-77 of SEQ ID NO:39, 125-131 of SEQ ID NO:39, 138-146 of SEQ ID NO:39, 165-175 of SEQ ID NO:39, and 185-191 of SEQ ID NO:39; and wherein the diphtheria toxin effector polypeptide is capable of routing to a cytosol compartment of a cell in which the diphtheria toxin effector polypeptide is present. In certain further embodiments, the polypeptide of the present invention comprises the diphtheria toxin effector polypeptide derived from amino acids 2 to 389 of SEQ ID NO:45. In certain further embodiment, the toxin effector polypeptide is a Shiga toxin effector polypeptide comprising an amino acid sequence derived from an A Subunit of at least one member of the Shiga toxin family, wherein the Shiga toxin effector polypeptide comprises a disruption of at least one B-cell epitope and/or CD4+ T-cell epitope region of the Shiga toxin A Subunit amino acid sequence selected from the group of natively positioned amino acids consisting of: the B-cell epitope regions 1-15 of SEQ ID NO:1 or SEQ ID NO:2; 3-14 of SEQ ID NO:3; 26-37 of SEQ ID NO:3; 27-37 of SEQ ID NO:1 or SEQ ID NO:2; 39-48 of SEQ ID NO:1 or SEQ ID NO:2; 42-48 of SEQ ID NO:3; 53-66 of SEQ ID NO:1, SEQ ID NO:2, or SEQ ID NO:3; 94-115 of SEQ ID NO:1, SEQ ID NO:2, or SEQ ID NO:3; 141-153 of SEQ ID NO:1 or SEQ ID NO:2; 140-156 of SEQ ID NO:3; 179-190 of SEQ ID NO:1 or SEQ ID NO:2; 179-191 of SEQ ID NO:3; 204 of SEQ ID NO:3; 205 of SEQ ID NO:1 or SEQ ID NO:2; and 210-218 of SEQ ID NO:3; 240-260 of SEQ ID NO:3; 243-257 of SEQ ID NO:1 or SEQ ID NO:2; 254-268 of SEQ ID NO:1 or SEQ ID NO:2; 262-278 of SEQ ID NO:3; 281-297 of SEQ ID NO:3; and 285-293 of SEQ ID NO:1 or SEQ ID NO:2, and the CD4+ T-cell epitope regions 4-33 of SEQ ID NO:1 or SEQ ID NO:2, 34-78 of SEQ ID NO:1 or SEQ ID NO:2, 77-103 of SEQ ID NO:1 or SEQ ID NO:2, 128-168 of SEQ ID NO:1 or SEQ ID NO:2, 160-183 of SEQ ID NO:1 or SEQ ID NO:2, 236-258 of SEQ ID NO:1 or SEQ ID NO:2, and 274-293 of SEQ ID NO:1 or SEQ ID NO:2; and wherein the Shiga toxin effector polypeptide is capable of routing to a cytosol compartment of a cell in which the Shiga toxin effector polypeptide is present. In certain embodiments, the polypeptide of the present invention comprises the Shiga toxin effector polypeptide derived from amino acids 75 to 251 of SEQ ID NO:1, SEQ ID NO:2, or SEQ ID NO:3. In certain further embodiments, the polypeptide of the present invention comprises the Shiga toxin effector polypeptide derived from amino acids 1 to 241 of SEQ ID NO:1, SEQ ID NO:2, or SEQ ID NO:3. In certain further embodiments, the Shiga toxin effector polypeptide is derived from amino acids 1 to 251 of SEQ ID NO:1, SEQ ID NO:2, or SEQ ID NO:3. In certain further embodiments, the Shiga toxin effector polypeptide is derived from amino acids 1 to 261 of SEQ ID NO:1, SEQ ID NO:2, or SEQ ID NO:3.

In certain embodiments, a de-immunized polypeptide of the present invention comprises a proteasome delivering effector polypeptide comprising a first heterologous T-cell epitope disrupting an endogenous B-cell epitope and/or CD4+ T-cell epitope, wherein the proteasome delivering effector polypeptide is linked to a second CD8+ T-cell epitope; and the polypeptide is capable of intracellular delivery of the second CD8+ T-cell epitope for presentation by a MHC class I molecule on the surface of a cell in which the polypeptide is present. In certain further embodiments, the polypeptide of the present invention comprises a toxin-derived polypeptide. In certain further embodiments, the heterologous CD8+ T-cell epitope is in the toxin-derived polypeptide. In certain further embodiments, the toxin-derived polypeptide of the present invention comprises a toxin effector polypeptide. In certain further embodiments, the heterologous CD8+ T-cell epitope in the toxin effector polypeptide. In certain further embodiments, the toxin effector polypeptide is capable of exhibiting one or more toxin effector functions. In certain further embodiments, the polypeptide of the present invention comprises the toxin effector polypeptide derived from a toxin selected from the group consisting of: ABx toxin, ribosome inactivating protein toxin, abrin, anthrax toxin, Aspf1, bouganin, bryodin, cholix toxin, claudin, diphtheria toxin, gelonin, heat-labile enterotoxin, mitogillin, pertussis toxin, pokeweed antiviral protein, pulchellin, *Pseudomonas* exotoxin A, restrictocin, ricin, saporin, sarcin, Shiga toxin, and subtilase cytotoxin. In certain further embodiments, the toxin effector polypeptide is a diphtheria toxin effector polypeptide comprising an amino acid sequence derived from the A and B Subunits of at least one member of the diphtheria toxin family, wherein the diphtheria toxin effector polypeptide comprises a disruption of at least one B-cell epitope and/or CD4+ T-cell epitope region of the amino acid sequence selected from the group of natively positioned amino acids consisting of: 3-10 of SEQ ID NO:39, 33-43 of SEQ ID NO:39, 71-77 of SEQ ID NO:39, 125-131 of SEQ ID NO:39, 138-146 of SEQ ID NO:39, 165-175 of SEQ ID NO:39, and 185-191 of SEQ ID NO:39; and wherein the diphtheria toxin effector polypeptide is capable of routing to a cytosol compartment of a cell in which the diphtheria toxin effector polypeptide is present. In certain further embodiments, the polypeptide of the present invention comprises the diphtheria toxin effector polypeptide derived from amino acids 2 to 389 of SEQ ID NO:45. In certain further embodiment, the toxin effector polypeptide is a Shiga toxin effector polypeptide comprising an amino acid sequence derived from an A Subunit of at least one member of the Shiga toxin family, wherein the Shiga toxin effector polypeptide comprises a disruption of at least one B-cell epitope and/or CD4+ T-cell epitope region of the Shiga toxin A Subunit amino acid sequence selected from the group of natively positioned amino acids consisting of: the B-cell epitope regions 1-15 of SEQ ID NO:1 or SEQ ID NO:2; 3-14 of SEQ ID NO:3; 26-37 of SEQ ID NO:3; 27-37 of SEQ ID NO:1 or SEQ ID NO:2; 39-48 of SEQ ID NO:1 or SEQ ID NO:2; 42-48 of SEQ ID NO:3; 53-66 of SEQ ID NO:1, SEQ ID NO:2, or SEQ ID NO:3; 94-115 of SEQ ID NO: 1, SEQ ID NO:2, or SEQ ID NO:3; 141-153 of SEQ ID NO:1 or SEQ ID NO:2; 140-156 of SEQ ID NO:3; 179-190 of SEQ ID NO:1 or SEQ ID NO:2; 179-191 of SEQ ID NO:3; 204 of SEQ ID NO:3; 205 of SEQ ID NO:1 or SEQ ID NO:2; and 210-218 of SEQ ID NO:3; 240-260 of SEQ ID NO:3; 243-257 of SEQ ID NO:1 or SEQ ID NO:2; 254-268 of SEQ ID NO:1 or SEQ ID NO:2; 262-278 of SEQ ID NO:3; 281-297 of SEQ ID NO:3; and 285-293 of SEQ ID NO:1 or SEQ ID NO:2, and the CD4+ T-cell epitope regions 4-33 of SEQ ID NO:1 or SEQ ID NO:2, 34-78 of SEQ ID NO:1 or SEQ ID NO:2, 77-103 of SEQ ID NO:1 or SEQ ID NO:2, 128-168 of SEQ ID NO:1 or SEQ ID NO:2, 160-183 of SEQ ID NO:1 or SEQ ID NO:2, 236-258 of SEQ ID NO:1 or SEQ ID NO:2, and 274-293 of SEQ ID NO:1 or SEQ ID NO:2; and wherein the Shiga toxin effector polypeptide is capable of routing to a cytosol compartment of a cell in which the Shiga toxin effector polypeptide is present. In certain embodiments, the polypeptide of the present invention comprises the Shiga toxin effector polypeptide derived from amino acids 75 to 251 of SEQ ID NO:1, SEQ ID NO:2, or SEQ ID NO:3. In certain further embodiments, the polypeptide of the present invention comprises the Shiga toxin effector polypeptide derived from amino acids 1 to 241 of SEQ ID NO:1, SEQ ID NO:2, or SEQ ID NO:3. In certain further embodiments, the Shiga toxin effector polypeptide is derived from amino acids 1 to 251 of SEQ ID NO:1, SEQ ID NO:2, or SEQ ID NO:3. In certain further embodiments, the Shiga toxin effector polypeptide is derived from amino acids 1 to 261 of SEQ ID NO:1, SEQ ID NO:2, or SEQ ID NO:3.

In certain embodiments of the methods of the present invention is a method for reducing B-cell immunogenicity in a polypeptide, the method comprising the step of: disrupting a B-cell epitope with one or more amino acid residue(s) of a T-cell epitope added to the polypeptide. In certain further embodiments, the disrupting step further comprises the step or steps of making one or more amino acid substitutions in the B-cell epitope. In certain further embodiments, the disrupting step further comprises the step or steps of making one or more amino acid insertions in the B-cell epitope.

In certain embodiments of the methods of the present invention is a method for reducing B-cell immunogenicity in a polypeptide, the method comprising the steps of: identifying a B-cell epitope in a polypeptide; and disrupting the identified B-cell epitope with one or more amino acid residue(s) in a T-cell epitope added to polypeptide. In certain further embodiments, the disrupting step further comprises the step or steps of making one or more amino acid substitutions in the B-cell epitope. In certain further embodiments, the disrupting step further comprises the step or steps of making one or more amino acid insertions in the B-cell epitope.

In certain embodiments of the methods of the present invention is a method for reducing B-cell immunogenicity in a polypeptide while simultaneously increasing CD8+ T-cell immunogenicity of the polypeptide, the method comprising the step of: disrupting a B-cell epitope with one or more amino acid residue(s) in a heterologous CD8+ T-cell epitope added to the polypeptide. In certain further embodiments, the disrupting step further comprises the step or steps of making one or more amino acid substitutions in the B-cell epitope. In certain further embodiments, the disrupting step further comprises the step or steps of making one or more amino acid insertions in the B-cell epitope.

In certain embodiments of the methods of the present invention is a method for reducing B-cell immunogenicity in a polypeptide while simultaneously increasing CD8+ T-cell immunogenicity of the polypeptide, the method comprising the steps of: identifying a CD4+ T-cell epitope in a polypeptide; and disrupting the identified CD4+ T-cell epitope with one or more amino acid residue(s) in a CD8+ T-cell epitope added to the polypeptide. In certain further embodiments, the disrupting step further comprises the step or steps of making one or more amino acid substitutions in the B-cell epitope. In certain further embodiments, the disrupting step further comprises the step or steps of making one or more amino acid insertions in the B-cell epitope.

In certain embodiments of the methods of the present invention is method for reducing CD4+ T-cell immunogenicity in a polypeptide, the method comprising the step of: disrupting a CD4+ T-cell epitope with one or more amino acid residue(s) in a CD8+ T-cell epitope added to the polypeptide. In certain further embodiments, the disrupting step further comprises the step or steps of making one or more amino acid substitutions in the CD4+ T-cell epitope. In certain further embodiments, the disrupting step further comprises the step or steps of making one or more amino acid insertions in the CD4+ T-cell epitope.

In certain embodiments of the methods of the present invention is a method for reducing CD4+ T-cell immunogenicity in a polypeptide, the method comprising the steps of: identifying a CD4+ T-cell epitope in a polypeptide; and disrupting the identified CD4+ T-cell epitope with one or more amino acid residue(s) in a CD8+ T-cell epitope added to the polypeptide. In certain further embodiments, the disrupting step further comprises the step or steps of making one or more amino acid substitutions in the CD4+ T-cell epitope. In certain further embodiments, the disrupting step further comprises the step or steps of making one or more amino acid insertions in the CD4+ T-cell epitope.

In certain embodiments of the methods of the present invention is a method for reducing CD4+ T-cell immunogenicity in a polypeptide while simultaneously increasing CD8+ T-cell immunogenicity of the polypeptide, the method comprising the step of: disrupting a CD4+ T-cell epitope with one or more amino acid residue(s) in a heterologous CD8+ T-cell epitope added to the polypeptide. In certain further embodiments, the disrupting step further comprises the step or steps of making one or more amino acid substitutions in the CD4+ T-cell epitope. In certain further embodiments, the disrupting step further comprises the step or steps of making one or more amino acid insertions in the CD4+ T-cell epitope.

In certain embodiments of the methods of the present invention is a method for reducing CD4+ T-cell immunogenicity in a polypeptide while simultaneously increasing CD8+ T-cell immunogenicity of the polypeptide, the method comprising the steps of: identifying a CD4+ T-cell epitope in a polypeptide; and disrupting the identified CD4+ T-cell epitope with one or more amino acid residue(s) in a CD8+ T-cell epitope added to the polypeptide. In certain further embodiments, the disrupting step further comprises the step or steps of making one or more amino acid substitutions in the CD4+ T-cell epitope. In certain further embodiments, the disrupting step further comprises the step or steps of making one or more amino acid insertions in the CD4+ T-cell epitope.

Certain embodiments of the polypeptides of the present invention provide a polypeptide produced by any of the methods of the present invention.

In certain embodiments, the polypeptide of the present invention comprises or consists essentially of any one of SEQ ID NOs: 11-43 or 46-48.

In certain embodiments, a cell-targeted molecule of the present invention comprises a cell-targeting moiety or agent, and any polypeptide of the present invention. In certain further embodiments, the cell-targeted molecule further comprises a binding region comprising one or more polypeptides and capable of specifically binding at least one extracellular target biomolecule. In certain further embodiments, the binding region comprises a polypeptide selected from the group consisting of: a complementary determining region 3 (CDR3) fragment constrained FR3-CDR3-FR4 (FR3-CDR3-FR4) polypeptide, single-domain antibody fragment (sdAb), nanobody, heavy-chain antibody domain derived from a camelid (VHH fragment), heavy-chain antibody domain derived from a cartilaginous fish, immunoglobulin new antigen receptor (IgNAR), $V_{NAR}$ fragment, single-chain variable fragment (scFv), antibody variable fragment (Fv), antigen-binding fragment (Fab), Fd fragment, small modular immunopharmaceutical (SMIP) domain, fibronectin-derived $10^{th}$ fibronectin type III domain (10Fn3) (e.g. monobody), tenascin type III domain (e.g. TNfn3), ankyrin repeat motif domain (ARD), low-density-lipoprotein-receptor-derived A-domain (A domain of LDLR or LDLR-A), lipocalin (anticalin), Kunitz domain, Protein-A-derived Z domain, gamma-B crystallin-derived domain (Affilin), ubiquitin-derived domain, Sac7d-derived polypeptide, Fyn-derived SH2 domain (affitin), miniprotein, C-type lectin-like domain scaffold, engineered antibody mimic, and any genetically manipulated counterparts of any of the foregoing that retain binding functionality. In certain further embodiments of the cell-targeted molecule of the present invention, whereby upon administration of the cell-targeted molecule to a cell physically coupled with an extracellular target biomolecule of the binding region, the cell-targeted molecule is capable of causing death of the cell. In certain further embodiments of the cell-targeted molecule of the present invention, whereby upon administration of the cell-targeted molecule to a first population of cells whose members are physically coupled to extracellular target biomolecules of the binding region, and a second population of cells whose members are not physically coupled to any extracellular target biomolecule of said binding region, the cytotoxic effect of the cell-targeted molecule to members of said first population of cells relative to members of said second population of cells is at least 3-fold greater. In certain further embodiments of the cell-targeted molecules of the present invention, the binding region is capable of binding to an extracellular target biomolecule selected from the group consisting of: CD20, CD22, CD40, CD79, CD25, CD30, HER2/neu/ErbB2, EGFR, EpCAM, EphB2, prostate-specific membrane antigen, Cripto, endoglin, fibroblast activated protein, Lewis-Y, CD19, CD21, CS1/SLAMF7, CD33, CD52, EpCAM, CEA, gpA33, mucin, TAG-72, carbonic anhydrase IX, folate binding protein, ganglioside GD2, ganglioside GD3, ganglioside GM2, ganglioside Lewis-Y2, VEGFR, Alpha V beta3, Alpha5beta1, ErbB1/EGFR, Erb3, c-MET, IGFIR, EphA3, TRAIL-R1, TRAIL-R2, RANKL, FAP, tenascin, CD64, mesothelin, BRCA1, MART-1/MelanA, gp100, tyrosinase, TRP-1, TRP-2, MAGE-1, MAGE-3, GAGE-1/2, BAGE, RAGE, NY-ESO-1, CDK-4, beta-catenin, MUM-1, caspase-8, KIAA0205, HPVE6, SART-1, PRAME, carcinoembryonic antigen, prostate specific antigen, prostate stem cell antigen, human aspartyl (asparaginyl) beta-hydroxylase, EphA2, HER3/ErbB-3, MUC1, MART-1/MelanA, gp100, tyrosinase associated antigen, HPV-E7, Epstein-Barr virus antigen, Bcr-Abl, alpha-fetoprotein antigen, 17-A1, bladder tumor antigen, CD38, CD15, CD23, CD53, CD88, CD129, CD183, CD191, CD193, CD244, CD294, CD305, C3AR, FceRIa, galectin-9, mrp-14, siglec-8, siglec-10, CD49d, CD13, CD44, CD54, CD63, CD69, CD123, TLR4, FceRIa, IgE, CD107a, CD203c, CD14, CD68, CD80, CD86, CD105, CD115, F4/80, ILT-3, galectin-3, CD11a-c, GITRL, MHC Class II, CD284-TLR4, CD107-Mac3, CD195-CCR5, HLA-DR, CD16/32, CD282-TLR2, CD11c, and any immunogenic fragment of any of the foregoing. In certain further embodiments of the cell-targeted molecules of the present invention, the cell-targeted molecule further comprises a carboxy-terminal endoplasmic reticulum retention/retrieval signal motif of a member of the KDEL family. In certain further embodiments, the carboxy-terminal endoplasmic reticulum retention/retrieval signal motif selected from the group consisting of: KDEL (SEQ ID NO:61), HDEF (SEQ ID NO:62), HDEL (SEQ ID NO:63), RDEF (SEQ ID NO:64), RDEL (SEQ ID NO:65), WDEL (SEQ ID NO:66), YDEL (SEQ ID NO:67), HEEF (SEQ ID NO:68), HEEL (SEQ ID NO:69), KEEL (SEQ ID NO:70), REEL (SEQ ID NO:71), KAEL (SEQ ID NO:72), KCEL (SEQ ID NO:73), KFEL (SEQ ID NO:74), KGEL (SEQ ID NO:75), KHEL (SEQ ID NO:76), KLEL (SEQ ID NO:77), KNEL (SEQ ID NO:78), KQEL (SEQ ID NO:79), KREL (SEQ ID NO:80), KSEL (SEQ ID NO:81), KVEL (SEQ ID NO:82), KWEL (SEQ ID NO:83), KYEL (SEQ ID NO:84), KEDL (SEQ ID NO:85), KIEL (SEQ ID NO:86), DKEL (SEQ ID NO:87), FDEL (SEQ ID NO:88), KDEF (SEQ ID NO:89), KKEL (SEQ ID NO:90), HADL (SEQ ID NO:91), HAEL (SEQ ID NO:92), HIEL (SEQ ID NO:93), HNEL (SEQ ID NO:94), HTEL (SEQ ID NO:95), KTEL (SEQ ID NO:96), HVEL (SEQ ID NO:97), NDEL (SEQ ID NO:98), QDEL (SEQ ID NO:99), REDL (SEQ ID NO:100), RNEL (SEQ ID NO:101), RTDL (SEQ ID NO:102), RTEL (SEQ ID NO:103), SDEL (SEQ ID NO:104), TDEL (SEQ ID NO:105), and SKEL (SEQ ID NO:106).

In certain embodiments of the present invention, upon administration of the cell-targeted molecule of the present invention to a cell physically coupled with an extracellular target biomolecule of the cell-targeting moiety of the cytotoxic protein, the cytotoxic protein is capable of causing death of the cell.

In certain embodiments of the present invention, upon administration of the cell-targeted molecule of the present invention to two different populations of cell types with respect to the presence of an extracellular target biomolecule, the cell-targeted molecule is capable of causing cell death to the cell-types physically coupled with an extracellular target biomolecule of the cell-targeting moiety or agent's binding region at a $CD_{50}$ at least three times or less than the $CD_{50}$ to cell types which are not physically coupled with an extracellular target biomolecule of the cell-targeted molecule's cell-targeting moiety.

In certain embodiments, the cell-targeted molecule of the present invention comprises or consists essentially of a polypeptide of any one of the amino acid sequences of SEQ ID NOs: 49-60.

In certain further embodiments, the polypeptides of the present invention comprise a mutation which reduces or eliminates catalytic activity of a toxin-derived polypeptide but retains at least one other toxin effector function. In certain embodiments, the cell-targeted molecule of the present invention further comprises a toxin effector polypeptide, derived from a toxin effector polypeptide with enzymatic activity, which comprises a mutation relative to a naturally occurring toxin which changes the enzymatic activity of the toxin effector polypeptide. In certain further embodiments, the mutation is selected from at least one amino acid residue deletion, insertion, or substitution that reduces or eliminates cytotoxicity of the toxin effector polypeptide. In certain embodiments, the cell-targeted molecules of the invention comprise a Shiga toxin effector region which further comprises a mutation relative to a naturally occurring A Subunit of a member of the Diphtheria toxin family that changes the enzymatic activity of the diphtheria toxin effector region, the mutation selected from at least one amino acid residue deletion or substitution, such as, e.g. H21A, Y27A, W50A, Y54A, Y65A, E148A, and W153A. In certain embodiments, the cell-targeted molecules of the invention comprise a Shiga toxin effector region which further comprises a mutation relative to a naturally occurring A Subunit of a member of the Shiga toxin family that changes the enzymatic activity of the Shiga toxin effector region, the mutation selected from at least one amino acid residue deletion or substitution, such as, e.g., A231E, R75A, Y77S, Y114S, E167D, R170A, R176K and/or W203A in SEQ ID NO:1, SEQ ID NO:2, or SEQ ID NO:3.

The present invention also provides pharmaceutical compositions comprising a polypeptide and/or cell-targeted molecule of the invention and at least one pharmaceutically acceptable excipient or carrier; and the use of such a polypeptide, cell-targeted molecule, or a composition comprising the aforementioned polypeptide or cell-targeted molecule in methods of the invention as further described herein. Certain embodiments of the present invention are pharmaceutical compositions comprising any polypeptide of the present invention and/or any cell-targeted molecule of the present invention; and at least one pharmaceutically acceptable excipient or carrier.

Beyond the polypeptides, cell-targeted molecules, proteins, and compositions of the present invention, polynucleotides capable of encoding a polypeptide comprising a polypeptide or cell-targeted molecule or protein of the present invention comprising a polypeptide of the invention are within the scope of the present invention, as well as expression vectors which comprise a polynucleotide of the invention and host cells comprising an expression vector of the invention. Host cells comprising an expression vector may be used, e.g., in methods for producing a polypeptide and/or protein of the invention comprising it, or a polypeptide component or fragment thereof, by recombinant expression.

Additionally, the present invention provides methods of selectively killing cell(s) comprising the step of contacting a cell(s) with a cell-targeted molecule of the invention or a pharmaceutical composition comprising such a protein of the invention. In certain embodiments, the step of contacting the cell(s) occurs in vitro. In certain other embodiments, the step of contacting the cell(s) occurs in vivo.

The present invention further provides methods of treating diseases, disorders, and/or conditions in patients in need thereof comprising the step of administering to a patient in need thereof a therapeutically effective amount of a composition comprising a polypeptide of the invention, a polypeptide and/or protein comprising the aforementioned polypeptide, or a composition comprising any of the foregoing (e.g., a pharmaceutical composition). In certain embodiments, the disease, disorder, or condition to be treated using this method of the invention is selected from: a cancer, tumor, immune disorder, or microbial infection. In certain embodiments of this method, the cancer to be treated is selected from the group consisting of: bone cancer, breast cancer, central/peripheral nervous system cancer, gastrointestinal cancer, germ cell cancer, glandular cancer, head-neck cancer, hematological cancer, kidney-urinary tract cancer, liver cancer, lung/pleura cancer, prostate cancer, sarcoma, skin cancer, and uterine cancer. In certain embodiments of this method, the immune disorder to be treated is an immune disorder associated with a disease selected from the group consisting of: amyloidosis, ankylosing spondylitis, asthma, Crohn's disease, diabetes, graft rejection, graft-versus-host disease, Hashimoto's thyroiditis, hemolytic uremic syndrome, HIV-related diseases, lupus erythematosus, multiple sclerosis, polyarteritis, psoriasis, psoriatic arthritis, rheumatoid arthritis, scleroderma, septic shock, Sjorgren's syndrome, ulcerative colitis, and vasculitis.

Among certain embodiments of the present invention is a composition comprising a polypeptide of the invention, a polypeptide and/or cell-targeted molecule comprising the aforementioned polypeptide, or a composition comprising any of the foregoing, for the treatment or prevention of a cancer, tumor, immune disorder, or microbial infection. Among certain embodiments of the present invention is the use of a composition of matter of the invention in the manufacture of a medicament for the treatment or prevention of a cancer, tumor, immune disorder, or microbial infection.

Certain embodiments of the cell-targeted molecules of the present invention may be used to deliver one or more additional exogenous materials into a cell physically coupled with an extracellular target biomolecule of the protein of the present invention. Additionally, the present invention provides a method for delivering exogenous material to the inside of a cell(s) comprising contacting the cell(s), either in vitro or in vivo, with a cell-targeted molecule, pharmaceutical composition, and/or diagnostic composition of the present invention. The present invention further provides a method for delivering exogenous material to the inside of a cell(s) in a patient in need thereof, the method comprising the step of administering to the patient a cell-targeted molecule of the present invention, wherein the target cell(s) is physically coupled with an extracellular target biomolecule of the protein of the present invention.

Among certain embodiments of the present invention is the use of a compound (e.g. a polypeptide or a cell-targeted molecule) of the invention and/or composition (e.g. a pharmaceutical composition) of the invention in the diagnosis, prognosis, or characterization of a disease, disorder, or condition.

Among certain embodiments of the present invention is a diagnostic composition comprising a polypeptide of the invention and/or cell-targeted molecule comprising the aforementioned polypeptide, or a composition comprising any of the foregoing, and a detection promoting agent for the collection of information, such as diagnostically useful information about a cell type, tissue, organ, disease, disorder, condition, or patient.

Among certain embodiments of the present invention is the method of detecting a cell using a cell-targeted molecule and/or diagnostic composition of the invention comprising the steps of contacting a cell with said cell-targeted molecule and/or diagnostic composition and detecting the presence of said cell-targeted molecule and/or diagnostic composition. In certain embodiments, the step of contacting the cell(s) occurs in vitro. In certain embodiments, the step of contacting the cell(s) occurs in vivo. In certain embodiments, the step of detecting the cell(s) occurs in vitro. In certain embodiments, the step of detecting the cell(s) occurs in vivo.

For example, a diagnostic composition of the invention may be used to detect a cell in vivo by administering to a mammalian subject a composition comprising protein of the present invention which comprises a detection promoting agent and then detecting the presence of the protein of the present invention either in vitro or in vivo. The information collected may regard the presence of a cell physically coupled with an extracellular target of the binding region of the cell-targeted molecule of the present invention and may be useful in the diagnosis, prognosis, characterization, and/or treatment of a disease, disorder, or condition. Certain compounds (e.g. polypeptides and cell-targeted molecules) of the invention, compositions (e.g. pharmaceutical compositions and diagnostic compositions) of the invention, and methods of the invention may be used to determine if a patient belongs to a group that responds to a pharmaceutical composition of the invention.

Certain embodiments of the polypeptides of the present invention and the cell-targeted molecules of the present invention may be utilized as an immunogen or as a component of an immunogen for the immunization and/or vaccination of a chordate.

For certain embodiments, a method of the invention is for "seeding" a tissue locus within a chordate, the method comprising the step of: administering to the chordate a cell-targeted molecule of the invention, a pharmaceutical composition of the invention, or a diagnostic composition of the invention. In certain further embodiments, the methods of the invention for "seeding" a tissue locus are for "seeding" a tissue locus which comprises a malignant, diseased, or inflamed tissue. In certain further embodiments, the methods of the invention for "seeding" a tissue locus are for "seeding" a tissue locus which comprises the tissue selected from the group consisting of: diseased tissue, tumor mass, cancerous growth, tumor, infected tissue, or abnormal cellular mass. In certain further embodiments, the methods of the invention for "seeding" a tissue locus comprises administering to the chordate the cell-targeted molecule of the invention, the pharmaceutical composition of the invention, or the diagnostic composition of the invention comprising the heterologous T-cell epitope selected from the group consisting of: peptides not natively presented by the target cells of the cell-targeted molecule in MHC class I complexes, peptides not natively present within any protein expressed by the target cell, peptides not natively present within the proteome of the target cell, peptides not natively present in the extracellular microenvironment of the site to be seeded, and peptides not natively present in the tumor mass or infected tissue site to be targeted.

Among certain embodiments of the present invention are kits comprising a composition of matter of the present invention, and optionally, instructions for use, additional reagent(s), and/or pharmaceutical delivery device(s).

These and other features, aspects and advantages of the present invention will become better understood with regard to the following description, appended claims, and accompanying figures. The aforementioned elements of the invention may be individually combined or removed freely in order to make other embodiments of the invention, without any statement to object to such combination or removal hereinafter.

BRIEF DESCRIPTION OF THE FIGURES

FIG. 2 shows retention of ribosome inactivation, catalytic activity by T-cell hyper-immunized, toxin effector polypeptides. Embedding T cell epitopes into B-cell epitope regions of a toxin effector polypeptide did not significantly impair catalytic activity. Two exemplary Diphtheria toxin-derived polypeptides comprising a T-cell epitope embedded into a B-cell epitope region exhibited levels of ribosome inactivation comparable to a wild-type Diphtheria toxin.

FIG. 3 shows Western blot analyses of cell-targeted, cytotoxic proteins comprising T-cell hyper-immunized toxin effector polypeptides with a B-cell epitope region disrupted by different T-cell epitopes. Embedding or inserting T-cell epitopes into a B-cell epitope region disrupted epitope(s) recognized by various anti-SLT-1A antibodies by Western blot analysis. Lane 1 contains a cytotoxic protein with a WT Shiga toxin effector region; lane 2 contains a cytotoxic protein comprising 53-61-F2; lane 3 contains a cytotoxic protein comprising 53-61-F2-3; lane 4 contains a cytotoxic protein comprising 53-61-F2-2; and lane 5 contains a cytotoxic protein with a WT Shiga toxin effector region.

DETAILED DESCRIPTION

Figure 1:
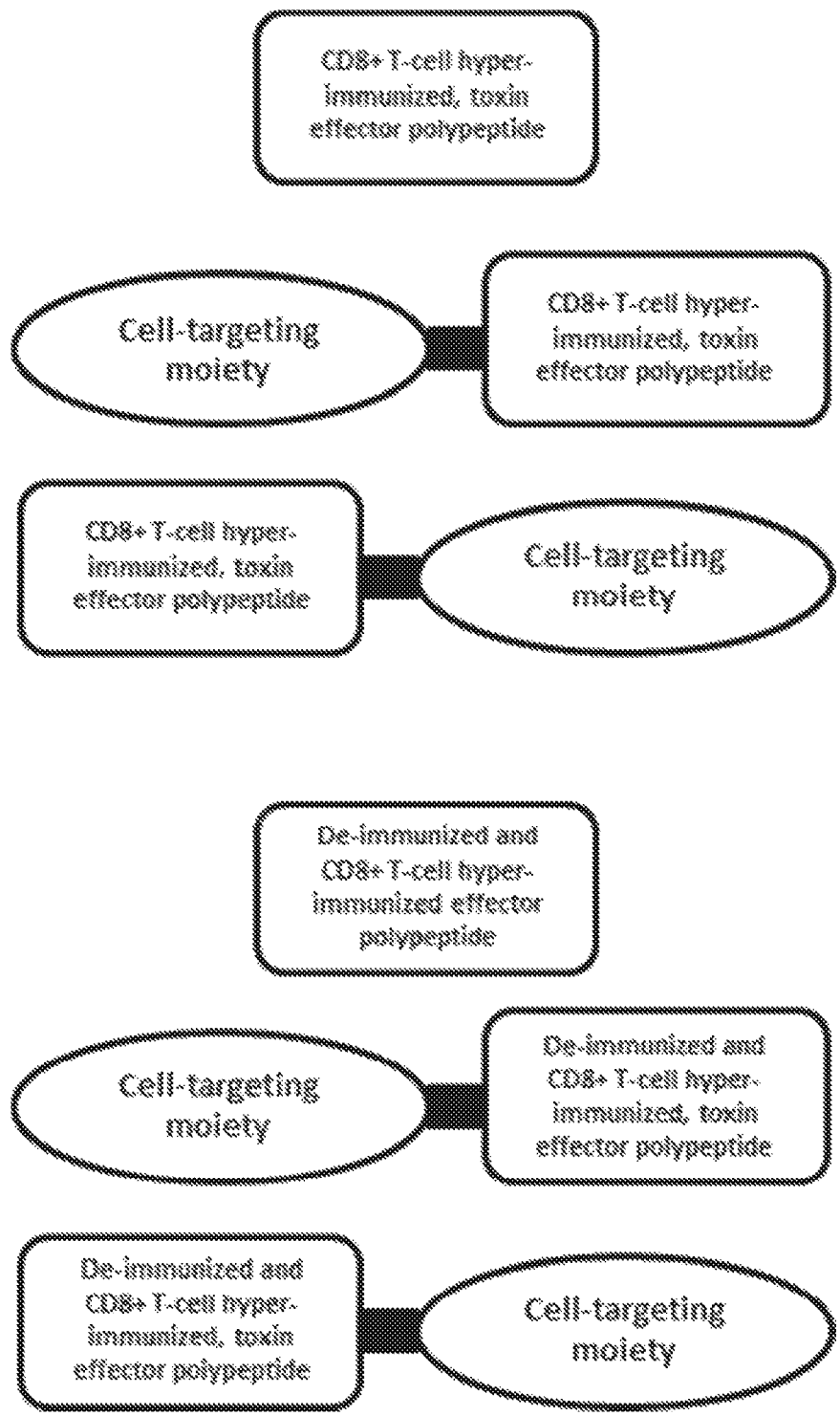
FIG. 1 shows schematic drawings of the general architecture of exemplary CD8+ T-cell hyper-immunized polypeptides and cell-targeted molecules of the invention and the general arrangement of exemplary T-cell epitope presenting effector polypeptides, including B-cell/CD4+ T-cell de-immunized variants, and cell-targeted proteins comprising the same.

The present invention is described more fully hereinafter using illustrative, non-limiting embodiments, and references to the accompanying figures. This invention may, however, be embodied in many different forms and should not be construed as to be limited to the embodiments set forth below. Rather, these embodiments are provided so that this disclosure is thorough and conveys the scope of the invention to those skilled in the art.

In order that the present invention may be more readily understood, certain terms are defined below. Additional definitions may be found within the detailed description of the invention.

As used in the specification and the appended claims, the terms "a," "an" and "the" include both singular and the plural referents unless the context clearly dictates otherwise.

As used in the specification and the appended claims, the term "and/or" when referring to two species, A and B, means at least one of A and B. As used in the specification and the appended claims, the term "and/or" when referring to greater than two species, such as A, B, and C, means at least one of A, B, or C, or at least one of any combination of A, B, or C (with each species in singular or multiple possibility).

Throughout this specification, the word "comprise" or variations such as "comprises" or "comprising" will be understood to imply the inclusion of a stated integer (or components) or group of integers (or components), but not the exclusion of any other integer (or components) or group of integers (or components).

Throughout this specification, the term "including" is used to mean "including but not limited to." "Including" and "including but not limited to" are used interchangeably.

The term "amino acid residue" or "amino acid" includes reference to an amino acid that is incorporated into a protein, polypeptide, or peptide. The term "polypeptide" includes any polymer of amino acids or amino acid residues. The term "polypeptide sequence" refers to a series of amino acids or amino acid residues which physically comprise a polypeptide. A "protein" is a macromolecule comprising one or more polypeptides or polypeptide "chains". A "peptide" is a small polypeptide of sizes less than a total of 15-20 amino acid residues. The term "amino acid sequence" refers to a series of amino acids or amino acid residues which physically comprise a peptide or polypeptide depending on the length. Unless otherwise indicated, polypeptide and protein sequences disclosed herein are written from left to right representing their order from an amino terminus to a carboxy terminus.

The terms "amino acid," "amino acid residue," "amino acid sequence," or "polypeptide sequence" include naturally occurring amino acids and, unless otherwise limited, also include known analogs of natural amino acids that can function in a similar manner as naturally occurring amino acids, such as selenocysteine, pyrrolysine, N-formylmethionine, gamma-carboxyglutamate, hydroxyprolinehypusine, pyroglutamic acid, and selenomethionine. The amino acids referred to herein are described by shorthand designations as follows in Table A:

TABLE A

Amino Acid Nomenclature

| Name | 3-letter | 1-letter |
|---|---|---|
| Alanine | Ala | A |
| Arginine | Arg | R |
| Asparagine | Asn | N |
| Aspartic Acid or Aspartate | Asp | D |
| Cysteine | Cys | C |
| Glutamic Acid or Glutamate | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |

TABLE A-continued

Amino Acid Nomenclature

| Name | 3-letter | 1-letter |
| --- | --- | --- |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The phrase "conservative substitution" with regard to a polypeptide, refers to a change in the amino acid composition of the polypeptide that does not substantially alter the function and structure of the overall polypeptide (see Creighton, *Proteins: Structures and Molecular Properties* (W. H. Freeman and Company, New York (2nd ed., 1992)).

As used herein, the term "expressed," "expressing," or "expresses" refers to translation of a polynucleotide or nucleic acid into a polypeptide or protein. The expressed polypeptide or proteins may remain intracellular, become a component of the cell surface membrane or be secreted into an extracellular space.

As used herein, the symbol "a" is shorthand for an immunoglobulin-type binding region capable of binding to the biomolecule following the symbol. The symbol "α" is used to refer to the functional characteristic of an immunoglobulin-type binding region based on its capability of binding to the biomolecule following the symbol.

The symbol "::" means the polypeptide regions before and after it are physically linked together to form a continuous polypeptide.

For purposes of the present invention, the phrase "derived from" means that the polypeptide region comprises amino acid sequences originally found in a protein and which may now comprise additions, deletions, truncations, or other alterations relative to the original sequence such that overall function and structure are substantially conserved.

For purposes of the present invention, the term "effector" means providing a biological activity, such as cytotoxicity, biological signaling, enzymatic catalysis, subcellular routing, and/or intermolecular binding resulting in the recruitment one or more factor(s), and/or allosteric effects.

As used herein, the terms "subunit" and "chain" with regard to multimeric toxins, such as, e.g., ABx toxins, are used interchangeably.

For purposes of the present invention, the phrase "CD8+ T-cell hyper-immunized" means that the molecule, when present inside a nucleated, chordate cell within a living chordate, has an increased antigenic and/or immunogenic potential regarding CD8+ T-cell antigenicity or immunogenicity. Commonly, CD8+ T-cell immunized molecules are capable of cellular internalization to an early endosomal compartment of a nucleated, chordate cell due either to an inherent feature(s) or as a component of a cell-targeted molecule.

For purposes of the present invention, the phrase "B-cell and/or CD4+ T-cell de-immunized" means that the molecule has a reduced antigenic and/or immunogenic potential after administration to a mammal regarding either B-cell antigenicity or immunogenicity and/or CD4+ T-cell antigenicity or immunogenicity.

For purposes of the present invention, the term "proteasome delivering effector" means a molecule that provides the biological activity of localizing within a cell to a subcellular compartment that is competent to result in the proteasomal degradation of the proteasome delivering effector molecule. Generally, this proteasome delivering biological activity can be determined from the initial sub-cellular location of the proteasome delivering effector molecule in an early endosomal compartment; however, it can also be determined earlier, e.g., from an extracellular starting location which involves passage into a cell and through an endosomal compartment of the cell, such as, e.g. after endocytotic entry into that cell. Alternatively, proteasome delivering effector biological activity may in certain embodiments not involve passage through any endosomal compartment of a cell before the proteasome delivering effector polypeptide is internalized and reaches a compartment competent to result in its proteasomal degradation. The ability of a given molecule to provide proteasome delivering effector function(s) may be assayed by the skilled worker using techniques known in the art.

The term "heterologous" with regard to T-cell epitope or T-cell epitope peptide component of a polypeptide of the present invention refers to an epitope or peptide sequence which did not initially occur in the polypeptide to be modified, but which has been added to the polypeptide using a method of the present invention, whether added via the processes of embedding, fusion, insertion, and/or amino acid substitution as described herein, or by any other engineering means. The result is a modified polypeptide comprising a T-cell epitope foreign to the original, unmodified polypeptide, i.e. the T-cell epitope was not present in the original polypeptide.

The term "endogenous" with regard to a B-cell epitope or CD4+ T-cell epitope in a polypeptide refers to an epitope already present in the polypeptide before being modified by a method of the present invention.

As used herein, the terms "disrupted", "disruption," or "disrupting," with regard to a polypeptide region or feature within a polypeptide refers to an alteration of at least one amino acid within the region or composing the feature. Amino acid alterations include various mutations, such as, e.g., a deletion, inversion, insertion, or substitution which alter the amino acid sequence of the polypeptide. Amino acid alterations also include chemical changes, such as, e.g., the alteration one or more atoms in an amino acid functional group or the addition of one or more atoms to an amino acid functional group.

The phrase "in association with" or "associated with" with regard to a T-cell epitope or T-cell epitope peptide component of a polypeptide of the present invention means the T-cell epitope and polypeptide are physically linked together, whether by covalent or non-covalent linkages, such as, e.g., embedded or inserted within the polypeptide, fused to the polypeptide, and/or chemically conjugated to the polypeptide.

The term "associating" with regard to the claimed invention means the act of making two molecules associated with each other or in association with each other.

The term "embedded" and grammatical variants thereof, with regard to a T-cell epitope or T-cell epitope peptide component of a polypeptide of the present invention refers to the internal replacement of one or more amino acids within a polypeptide region with different amino acids in order to generate a new polypeptide sequence sharing the same total number of amino acid residues. Thus, the term embedded does not include any external, terminal fusion of any additional amino acid, peptide, or polypeptide component to the starting polypeptide nor any additional internal insertion of any additional amino acid residues but rather only substitutions for existing amino acids. The internal replacement may be accomplished merely by amino acid residue substitution or by a series of substitutions, deletions, insertions, and/or inversions. If an insertion of one or more amino acids is used, then the equivalent number of proximal amino acids must be deleted next to the insertion to result in an embedded T-cell epitope. This is in contrast to use of the term "inserted" with regard to T-cell epitopes in the polypeptides of the present invention which instead refers to a polypeptide with an increased length equivalent to the length of the inserted T-cell epitope. Insertions include the previous even if other regions of the polypeptide not proximal to the insertion are deleted to then decrease the total length of the final polypeptide.

The term "fused" and grammatical variants thereof, with regard to a T-cell epitope or T-cell epitope peptide component of a polypeptide of the present invention refers to the external addition of four, five, six, or more amino acids to either the amino-terminus or carboxy terminus of a polypeptide in order to generate a new polypeptide which has a greater number of amino acid residues than the original. Fused T-cell epitopes include the addition of four, five, six, or more amino acids to either the amino-terminus or carboxy terminus even if other regions of the polypeptide are deleted to then decrease the total length of the final polypeptide as long as the new polypeptide retains an effector function of the original polypeptide, such as, e.g., proteasome delivering effector function.

As used herein, the term "toxin effector polypeptide" means a polypeptide that comprises a toxin-derived effector region that is sufficient to provide one or more biological activities present in the toxin from which the polypeptide was derived.

As used herein, the term "T-cell epitope delivering" means that a molecule provides the biological activity of localizing within a cell to a subcellular compartment that is competent to result in the proteasomal degradation of a T-cell epitope carrying polypeptide region. Generally, this proteasome delivering biological activity can be determined from the initial sub-cellular location of the T-cell epitope delivering molecule in an early endosomal compartment; however, it can also be determined earlier, e.g., from an extracellular starting location which involves passage into a cell and through an endosomal compartment of the cell, such as, e.g. after endocytotic entry into that cell. Alternatively, T-cell epitope delivering activity may in certain embodiments not involve passage through any endosomal compartment of a cell before the T-cell epitope delivering molecule is internalized and reaches a compartment competent to deliver a T-cell epitope to the proteasome for degradation into a T-cell epitope peptide. Effective T-cell epitope delivering function can be assayed by observing MHC presentation of the delivered T-cell epitope on a cell surface of a cell in which the T-cell epitope delivering molecule has internalized.

As used herein, a toxin effector function or activity may include, inter alia, promoting cellular internalization, promoting endosome escape, directing intracellular routing to a subcellular compartment, catalytic functions, substrate binding, inducing apoptosis of cell, causing cytostasis, and cytotoxicity.

As used herein, the retention of a toxin-derived polypeptide effector function refers to a level of toxin effector functional activity, as measured by an appropriate quantitative assay with reproducibility, comparable to a wild-type (WT) polypeptide control. For example, various assays know to the skilled worker may be used to measure the enzymatic activity and/or intracellular routing of a toxin effector polypeptide. The enzymatic polypeptide effector toxin function of a polypeptide of the present invention is retained if its enzymatic activity is comparable to a wild-type (WT) polypeptide in the same assay under the same conditions.

The term "selective cytotoxicity" with regard to the cytotoxic activity of a cytotoxic protein refers to the relative levels of cytotoxicity between a targeted cell population and a non-targeted bystander cell population, which can be expressed as a ratio of the half-maximal cytotoxic concentration ($CD_{50}$) for a targeted cell type over the $CD_{50}$ for an untargeted cell type to show preferentiality of cell killing of the targeted cell type.

Introduction

The present invention provides methods of generating polypeptides and cell-targeted molecules which are capable of delivering T-cell epitope peptides to the MHC class I system of a target cell for cell surface presentation. The present invention also provides exemplary T-cell epitope delivering polypeptides, made using the methods of the invention, which are capable of delivering heterologous T-cell epitopes to the MHC class I system of a target cell for cell surface presentation. The polypeptides created using the methods of the present invention, e.g. T-cell epitope delivering polypeptides and CD8+ T-cell hyper-immunized polypeptides, may be utilized as components of various molecules and compositions, e.g. cytotoxic therapeutics, therapeutic delivery agents, and diagnostic molecules.

In addition, the present invention provides methods of generating variants of polypeptides by simultaneously reducing the probability of B-cell antigenicity and/or immunogenicity while providing at an overlapping position within the polypeptide a heterologous T-cell epitope for increasing the probability of T-cell immunogenicity via MHC class I presentation. The present invention also provides exemplary B-cell epitope de-immunized, T-cell epitope delivering polypeptides made using the methods of the invention, which are capable of delivering heterologous T-cell epitopes to the MHC class I system of a target cell for cell surface presentation. The polypeptides created using the methods of the present invention, e.g. B-cell/CD4+ T-cell de-immunized T-cell epitope delivering polypeptides, CD8+ T-cell hyper-immunized and CD4+ T-cell de-immunized polypeptides, may be utilized as components of various molecules and compositions, e.g. cytotoxic therapeutics, therapeutic delivery agents, and diagnostic molecules.

I. The General Structure of a CD8+ T-Cell Hyper-Immunized Polypeptide

The present invention involves the engineering of polypeptides comprising various proteasome delivery effector polypeptide regions to comprise one or more heterologous T-cell epitopes; and where upon delivery of the polypeptide to an early endosomal compartment of a eukaryotic cell, the polypeptide is capable of localizing within the cell to a subcellular compartment sufficient for delivering the one or more heterologous T-cell epitopes to the proteasome for degradation and entry into the cell's MHC class I system. While the proteasome delivery effector polypeptides may come from any source, in certain embodiments, the polypeptides of the invention are derived from various proteasome delivery effector polypeptides derived from naturally occurring protein toxins.

A. Polypeptides Engineered to Comprise One or More Heterologous. T-Cell Epitopes and a Proteasome Delivery Effector Polypeptide The present invention contemplates the use of various polypeptides as a starting point for modification into a polypeptide of the present invention via the embedding, fusing, and/or inserting of one or more heterologous T-cell epitopes. These source polypeptides should exhibit, or be predicted, to exhibit a proteasome delivery effector capability.

The predominant source of peptide epitopes entering the MHC class I pathway are peptides resulting from proteasomal degradation of cytosolic molecules. However, ER-localized molecules, such as viral glycoproteins and transformed cell glycoproteins, can also be displayed by the MHC class I system by a different route. Although this alternative route to MHC class I presentation begins in the ER, the polypeptide or protein source of the peptide is transported to the cytosol for proteolytic processing by the proteasome before being transported by TAPs to the lumen of the ER for peptide loading onto MHC class I molecules. The exact mechanism underlying this alternative route is not clear but might involve an ER-associated degradation (ERAD)-type surveillance system to detect misfolded proteins, "defective ribosomal products," and structures mimicking the aforementioned. This ERAD-type system transports certain polypeptides and proteins to proteasomes in the cytosol for degradation, which can result in the production of cytosolic antigenic peptides. In addition, research on the intracellular routing of various toxins suggests that reaching either the cytosol or the endoplasmic reticulum is sufficient for delivery of a T-cell epitope into the MHC class I pathway.

Therefore, polypeptides and proteins known or discovered to localize to and/or direct their own intracellular transport to the cytosol and/or endoplasmic reticulum represent a class of molecules predicted to comprise one or more proteasome delivery effector polypeptide regions which exhibit a proteasome delivery function(s). Certain proteins and polypeptides, such as, e.g., certain toxins, exhibit the ability to escape from endosomal compartments into the cytosol, thereby avoiding lysosomal degradation. Thus, polypeptides and proteins known or discovered to escape endosomal compartments and reach the cytosol are included in the class of molecules mentioned above. The exact route the polypeptide or protein takes to the cytosol or ER is irrelevant as long as the polypeptide or protein eventually reaches a subcellular location that permits access to the proteasome.

In addition, certain molecules are able to reach the proteasome of a cell after being localized to a lysosome. For example, foreign proteins introduced directly into the cytosol of a cell, such as listeriolysin and other proteins secreted by *Listeria* monocytogernes, can enter the MHC class I pathway and be presented in MHC class I complexes for recognition by effector T-cells (Villanueva M et al., *J Immunol* 155: 5227-33 (1995)). In addition, lysosomal proteolysis, including phagolysosome proteolysis, can produce antigenic peptides that are translocated into the cytosol and enter the MHC class I pathway for cell surface presentation in a process called cross-presentation, which may have evolved from a canonical ERAD system (Gagnon E et al., *Cell* 110: 119-31 (2002)). Thus, certain polypeptides and proteins known or discovered to localize to lysosomes may be suitable sources for polypeptides with proteasome delivery effector regions which exhibit a proteasome delivery function(s).

The ability of a proteinaceous molecule to intracellularly route to the cytosol, ER, and/or lysosomal compartments of a cell from the starting position of an early endosomal compartment can be determined by the skilled worker using assays known in the art. Then, the proteasome delivery effector polypeptide regions of a source polypeptide or protein, such as, e.g., a toxin, can be mapped and isolated by the skilled worker using standard techniques known in the art.

1. Proteasome Delivery Effector Polypeptides Derived from Toxins

The present invention contemplates the use of various polypeptides derived from toxins as proteasome delivering effector regions. Many toxins represent optimal sources of proteasome delivering effector polypeptides because of the wealth of knowledge about their intracellular routing behaviors.

Many naturally occurring proteinaceous toxins have highly evolved structures optimized for directing intracellular routing in vertebrate host cells, including via endosomal escape and retrograde transport pathways.

Numerous toxins exhibit endosome escape properties, commonly via pore formation (Mandal M et al., *Biochim Biophys Acta* 1563: 7-17 (2002)). For example, diphtheria toxin and plant type II ribosome inactivating proteins like ricin can escape from endosomes (Murphy S et al., *Biochim Biophys Acta* 1824: 34-43 (2006); Slominska-Wojewodzka M, Sandvig K, *Antibodies* 2: 236-269 (2013); Walsh M et al., *Virulence* 4: 774-84 (2013)). Escape from endosomal compartments, including lysosomes, can be measured directly and quantitated using assays known in the art, such as, e.g., using reporter assays with horseradish peroxidase, bovine serum albumin, fluorophores like ALEXA FLUOR® 488, and toxin derived polypetides (see e.g. Bartz R et al., *Biochem J* 435: 475-87 (2011); Gilabert-Oriol R et al., *Toxins* 6: 1644-66 (2014)).

Many toxins direct their own intracellular routing in vertebrate host cells. For example, the intoxication pathways of many toxins can be described as a multi-step process involving 1) cellular internalization of the toxin into host cells, 2) intracellular routing of the toxin via one or more sub-cellular compartments, and 3) subsequent localization of a catalytic portion of the toxin to the cytosol where host factor substrates are enzymatically modified. For example, this process describes the intoxication pathway of anthrax lethal factors, cholera toxins, diphtheria toxins, pertussis toxins, *Pseudomonas* exotoxins, and type II ribosome inactivating proteins like ricin and Shiga toxins.

Similarly, recombinant toxins, modified toxin structures, and engineered polypeptides derived from toxins can preserve these same properties. For example, engineered recombinant polypeptides derived from diphtheria toxin (DT), anthrax lethal factor (LF) toxin, and *Pseudomonas* exotoxin A (PE) have been used as delivery vehicles for moving polypeptides from an extracellular space to the cytosol. Any protein toxin with the intrinsic ability to intracellularly route from an early endosomal compartment to either the cytosol or the ER represents a source for a proteasome delivery effector polypeptide which may be exploited for the purposes of the present invention, such as a starting component for modification or as a source for mapping a smaller proteasome delivery effector region therein.

For many toxins targeting eukaryotic cells, toxicity is the result of an enzymatic mechanism involving a substrate(s) in the cytosol (see Table I). These toxins have evolved toxin structures with the ability to deliver enzymatically active polypeptide regions of their holotoxins to the cytosol. The enzymatic regions of these toxins may be used as starting components for creating the polypeptides of the present invention.

TABLE I

Exemplary Protein Toxin Sources of Proteasome Delivering Effector Polypeptides

| Protein Toxin | Substrate - Subcellular Location |
| --- | --- |
| Abrins | sarcin-ricin loop - cytosol |
| Anthrax lethal factor | MAPKK - cytosol |
| Aspf1 | sarcin-ricin loop - cytosol |
| Bouganin | sarcin-ricin loop - cytosol |
| Bryodins | sarcin-ricin loop - cytosol |
| Cholix toxin | heterotrimeric G protein - cytosol |
| Cinnamomin | sarcin-ricin loop - cytosol |
| Claudin | sarcin-ricin loop - cytosol |
| Clavin | sarcin-ricin loop - cytosol |
| C. difficile TcdA | Ras GTPases - cytosol |
| C. difficile TcdA | Rho GTPases - cytosol |
| C. perfringens iota | Rho GTPases - cytosol |
| cytolethal distending | DNA - nucleus |
| Dianthins | sarcin-ricin loop - cytosol |
| Diphtheria toxins | elongation factor-2 (EF2) - cytosol |
| Ebulins | sarcin-ricin loop - cytosol |
| Gelonin | sarcin-ricin loop - cytosol |
| Gigantin | sarcin-ricin loop - cytosol |
| heat-labile enterotoxins | heterotrimeric G protein - cytosol |
| Maize RIPs | sarcin-ricin loop - cytosol |
| Mitogillin | sarcin-ricin loop - cytosol |
| Nigrins | sarcin-ricin loop - cytosol |
| Pertussis toxins | heterotrimeric G protein - cytosol |
| PD-Ls | sarcin-ricin loop - cytosol |
| PAPs | sarcin-ricin loop - cytosol |
| Pseudomonas toxins | elongation factor-2 (EF2) - cytosol |
| Pulchellin | sarcin-ricin loop - cytosol |
| Restrictocin | sarcin-ricin loop - cytosol |
| Ricins | sarcin-ricin loop - cytosol |
| Saporins | sarcin-ricin loop - cytosol |
| Sarcins | sarcin-ricin loop - cytosol |
| Shiga toxins | sarcin-ricin loop - cytosol |
| Subtilase cytotoxins | endoplasmic chaperon - ER |
| Trichosanthins | sarcin-ricin loop - cytosol |

The toxins in two toxin superfamilies, with overlapping members, are very amenable for use in the present invention: ABx toxins and ribotoxins.

ABx toxins are capable of entering eukaryotic cells and routing to the cytosol to attack their molecular targets. Similarly, ribotoxins are capable of entering eukaryotic cells and routing to the cytosol to inactivate ribosomes. Members of both the Abx toxin and ribotoxin superfamilies are appropriate sources for identifying toxin-derived polypeptides and proteasome delivery effector polypeptides for use in the present invention ABx toxins, which are also referred to as binary toxins, are found in bacteria, fungi, and plants. The ABx toxins form a superfamily of toxins that share the structural organization of two or more polypeptide chains with distinct functions, referred to as A and B subunits. The x represents the number of B subunits in the holotoxins of the members of the ABx family, such as, e.g., $AB_1$ for diphtheria toxin and $AB_5$ for Shiga toxin. The $AB_5$ toxin superfamily is comprised of 4 main families: cholix toxins (Ct or Ctx), pertussis toxins (Ptx), Shiga toxins (Stx), and Subtilase cytotoxins (SubAB). The cytotoxic mechanisms of $AB_5$ toxins involves subcellular routing of their A subunits within an intoxicated, eukaryotic, host cell to either the cytosol or the ER where the catalytic A subunits act upon their enzymatic substrates representing various host cell proteins (see Table I).

Diphtheria toxins disrupt proteins synthesis via the catalytic ADP-ribosylation of the eukaryotic elongation factor-2 (EF2). Diphtheria toxins consists of a catalytic A subunit and a B subunit, which contains a phospholipid bilayer translocation effector domain and a cell-targeting binding domain. During the diphtheria toxin intoxication process, diphtheria toxins can intracellularly route their catalytic domains to the cytosol of a eukaryotic cell, perhaps via endosomal escape (Murphy J, *Toxins* (Basel) 3: 294-308 (2011)). This endosomal escape mechanism may be shared with other toxins such as, e.g., anthrax lethal and edema factors, and the general ability of endosome escape is exhibited by many diverse toxins, including, e.g., certain *C. difficile* toxins, gelonin, lysteriolysin, PE, ricin, and saporin (see e.g. Varkouhi A et al., *J Control Release* 151: 220-8 (2010); Murphy J, *Toxins* (Basel) 3: 294-308 (2011)).

In particular, toxins which inactivate ribosomes in the cytosol are useful for identifying proteasome delivery effector polypeptides for use in the present invention. These toxins comprise polypeptide regions which simultaneously provide both cytosol targeting effector function(s) and cytotoxic ribotoxic toxin effector function(s).

With regard to the claimed invention, the phrase "ribotoxic toxin effector polypeptide" refers to a polypeptide derived from proteins, including naturally occurring ribotoxins and synthetic ribotoxins, which is capable of effectuating ribosome inactivation in vitro, protein synthesis inhibition in vitro and/or in vivo, cytotoxicity, and/or cytostasis. Commonly, ribotoxic toxin effector polypeptides are derived from naturally occurring protein toxins or toxin-like structures which are altered or engineered by human intervention. However, other polypeptides, such as, e.g., naturally occurring enzymatic domains not natively present in a toxin or synthetic polypeptide, are within the scope of that term as used herein (see e.g. Newton D et al., *Blood* 97: 528-35 (2001); De Lorenzo C et al., *FEBS Lett* 581: 296-300 (2007); De Lorenzo C, D'Alessio G, *Curr Pharm Biotechnol* 9: 210-4 (2008); Menzel C et al., *Blood* 111: 3830-7 (2008)). Thus, ribotoxic toxin effector polypeptides may be derived from synthetic or engineered protein constructs with increased or decreased ribotoxicity, and/or naturally occurring proteins that have been otherwise altered to have a non-native characteristic.

The ribotoxic toxin effector polypeptides may be derived from ribotoxic domains of proteins from diverse phyla, such as, e.g., algae, bacteria, fungi, plants, and animals. For example, polypeptides derived from various ribotoxins have been linked or fused to immunoglobulin domains or receptor ligands through chemical conjugation or recombinant protein engineering with the hope of creating cell-type-specific cytotoxic therapeutics (Pastan I et al., *Annu Rev Biochem* 61: 331-54 (1992); Foss F et al., *Curr Top Microbiol Immunol* 234: 63-81 (1998); Olsnes S, *Toxicon* 44: 361-70 (2004); Pastan I, et al., *Nat Rev Cancer* 6: 559-65 (2006); Lacadena J et al., *FEMS Microbiol Rev* 31: 212-37 (2007); de Virgilio M et al., *Toxins* 2: 2699-737 (2011); Walsh M, *Virulence* 4: 774-84 (2013); Weidle U et al., *Cancer Genomics Proteomics* 11: 25-38 (2014)).

Ribotoxic toxin effector polypeptides may be derived from the catalytic domains of members of the Ribosome Inactivating Protein (RIP) Superfamily of protein ribotoxins (de Virgilio M et al., *Toxins* 2: 2699-737 (2011); Lapadula W et al., *PLoS ONE* 8: e72825 (2013); Walsh M, *Virulence* 4: 774-84 (2013)). RIPs are ribotoxic proteins expressed in algae, bacteria, fungi, and plants which are often potent inhibitors of eukaryotic and prokaryotic protein synthesis at sub-stoichiometric concentrations (see Stirpe, F, *Biochem J* 202: 279-80 (1982)). Various RIPs are considered promising sources for toxin effector polypeptide sequences for use in therapeutics for treating cancers (see Pastan I, et al., *Nat Rev Cancer* 6: 559-65 (2006); Fracasso G et al., *Ribosome-inactivating protein-containing conjugates for therapeutic use*, Toxic Plant Proteins 18, pp. 225-63 (Eds. Lord J, Hartley, M. Berlin, Heidelberg: Springer-Verlag, 2010); de Virgilio M et al., *Toxins* 2: 2699-737 (2011); Puri M et al., *Drug Discov Today* 17: 774-83 (2012); Walsh M, *Virulence* 4: 774-84 (2013)).

The most commonly used ribotoxins in recombinant cytotoxic polypeptides include diphtheria toxin, *Pseudomonas* exotoxin A, ricin, α-sarcin, saporin, and gelonin (see Shapira A, Benhar I, *Toxins* 2: 2519-83 (2010); Yu C et al., *Cancer Res* 69: 8987-95 (2009); Fuenmayor J, Montafio R, *Cancers* 3: 3370-93 (2011); Weldon, *FEBS J* 278: 4683-700 (2011); Carreras-Sangrá N et al., *Protein Eng Des Sel* 25: 425-35 (2012); Lyu M at al., *Methods Enzymol* 502: 167-214 (2012); Antignani, *Toxins* 5: 1486-502 (2013); Lin H et al., *Anticancer Agents Med Chem* 13: 1259-66 (2013); Polito L et al., *Toxins* 5: 1698-722 (2013); Walsh M, *Virulence* 4: 774-84 (2013)). These ribotoxins are generally classified as ribosome inactivating proteins (RIPs) and share a general cytotoxic mechanism of inactivating eukaryotic ribosomes by attacking the sarcin-ricin loop (SRL) or proteins required for ribosome function which bind to the SRL.

The SRL structure is highly conserved between the three phylogenetic groups, Archea, Bacteria and Eukarya, such that both prokaryotic and eukaryotic ribosomes share a SRL ribosomal structure (Gutell R et al., *Nucleic Acids Res* 21: 3055-74 (1993); Szewczak A, Moore P, *J Mol Biol* 247: 81-98 (1995); Gluck A, Wool I, *J Mol Biol* 256: 838-48 (1996); Seggerson K, Moore P, *RNA* 4: 1203-15 (1998); Correll C et al., *J Mol Biol* 292: 275-87 (1999)). The SRL of various species from diverse phyla can be superimposed onto a crystal structure electron density map with high precision (Ban N et al., *Science* 11: 905-20 (2000); Gabashvili I et al., *Cell* 100: 537-49 (2000)). The SRL is the largest universally conserved ribosomal sequence which forms a conserved secondary structure vital to the ribosome function of translocation via the cooperation of elongation factors, such as EF-Tu, EF-G, EF1, and EF2 (Voorhees R et al., *Science* 330: 835-8 (2010); Shi X et al., *J Mol Biol* 419: 125-38 (2012); Chen K et al., *PLoS One* 8: e66446 (2013)). The SRL (sarcin-ricin loop) was named for being the shared target of the fungal ribotoxin sarcin and the plant type II RIP ricin.

The RIP Superfamily includes RIPs, fungal ribotoxins, and bacterial ribotoxins that interfere with ribosome translocation functions (see Table I; Brigotti M et al., *Biochem J* 257: 723-7 (1989)). Most RIPs, like abrin, gelonin, ricin, and saporin, irreversibly depurinate a specific adenine in the universally conserved sarcin/ricin loop (SRL) of the large rRNAs of ribosomes (e.g. A4324 in animals, A3027 in fungi, and A2660 in prokaryotes). Most fungal ribotoxins, like α-sarcin, irreversibly cleave a specific bond in the SRL (e.g. the bond between G4325 and A4326 in animals, G3028 and A3029 in fungi, and G2661 and A2662 in prokaryotes) to catalytically inhibit protein synthesis by damaging ribosomes (Martinez-Ruiz A et al., *Toxicon* 37: 1549-63 (1999); Lacadena J et al., *FEMS Microbiol Rev* 31: 212-37 (2007); Tan Q et al., *J Biotechnol* 139: 156-62 (2009)). The bacterial protein ribotoxins Ct, DT, and PE are classified in the RIP Superfamily because they can inhibit protein synthesis by catalytically damaging ribosome function and induce apoptosis efficiently with only a few toxin molecules.

RIPs are defined by one common feature, the ability to inhibit translation in vitro by damaging the ribosome via ribosomal RNA (rRNA) N-glycosidase activity. By 2013, over one hundred RIPs had been described (Walsh M, *Virulence* 4: 774-84 (2013)). Most RIPs depurinate a specific adenine residue in the universally conserved sarcin/ricin loop (SRL) of the large rRNA of both eukaryotic and prokaryotic ribosomes. The highest number of RIPs has been found in the following families: Caryophyllaceae, Sambucaceae, Cucurbitaceae, Euphorbiaceae, Phytolaccaceae, and Poaceae.

Members of the RIP family are categorized into at least three classes based on their structures. Type I RIPs, e.g. gelonin, luffins, PAP, saporins and trichosanthins, are monomeric proteins comprising an enzymatic domain and lacking an associated targeting domain. Type II RIPs, e.g. abrin, ricin, Shiga toxins, are multi-subunit, heteromeric proteins with an enzymatic A subunit and a targeting B subunit(s) typical of binary ABx toxins (Ho M, et al., *Proc Natl Acad Sci USA* 106: 20276-81 (2009)). Type III RIPs, e.g. barley JIP60 RIP and maize b-32 RIP, are synthesized as proenzymes that require extensive proteolytic processing for activation (Peumans W et al., *FASEB J* 15: 1493-1506 (2001); Mak A et al., *Nucleic Acids Res* 35: 6259-67 (2007)).

Although there is low sequence homology (<50% identity) between members of the RIP family, their catalytic domains share conserved tertiary structures which are superimposable such that key residues involved in the depurination of the ribosome are identifiable (de Virgilio M et al., *Toxins* 2: 2699-737 (2011); Walsh M, *Virulence* 4: 774-84 (2013)). For example, the catalytic domains of ricin and Shiga toxin are superimposable using crystallographic data despite the 18% sequence identity of their A-chain subunits (Fraser M et al., *Nat Struct Biol* 1: 59-64 (1994)).

Many enzymes and polypeptide effector regions have been used to create cytotoxic components of immunotoxins such as, e.g., gelonin, saporin, pokeweed antiviral protein (PAP), bryodin, bouganin, momordin, dianthin, momorcochin, trichokirin, luffin, restrictocin, mitogillin, alpha-sarcin, Onconase®, pancreatic ribonuclease, Bax, eosinophil-derived neurotoxin, and angiogenin. In particular, potently cytotoxic immunotoxins have been generated using polypeptides derived from the RIPs: ricin, gelonin, saporin, momordin, and PAPs (Pasqualucci L et al., *Haematologica* 80: 546-56 (1995)).

During their respective intoxication processes, cholera toxins, ricins, and Shiga toxins all subcellularly route to the ER where their catalytic domains are then released and translocated to the cytosol. These toxins may take advantage of the host cell's unfolded protein machinery and ERAD system to signal the host cell to export their catalytic domains into the cytosol (see Spooner R, Lord J, *Curr Top Microbiol Immunol* 357: 190-40 (2012)).

The ability of a given molecule to intracellularly route to specific sub-cellular compartments may be assayed by the skilled worker using techniques known in the art. This includes common techniques in the art that can localize a molecule of interest to any one of the following sub-cellular compartments: cytosol, ER, and lysosome.

With regard to the claimed invention, the phrase "cytosol targeting toxin effector polypeptide" refers to a polypeptide derived from proteins, including naturally occurring ribotoxins and synthetic ribotoxins, which are capable of routing intracellularly to the cytosol after cellular internalization. Commonly, cytosolic targeting toxin effector regions are derived from naturally occurring protein toxins or toxin-like structures which are altered or engineered by human intervention, however, other polypeptides, such as, e.g., computational designed polypeptides, are within the scope of the term as used herein (see e.g. Newton D et al., *Blood* 97:

528-35 (2001); De Lorenzo C et al., *FEBS Lett* 581: 296-300 (2007); De Lorenzo C, D'Alessio G, *Curr Pharm Biotechnol* 9: 210-4 (2008); Menzel C et al., *Blood* 111: 3830-7 (2008)). Thus, cytosolic targeting toxin effector regions may be derived from synthetic or engineered protein constructs with increased or decreased ribotoxicity, and/or naturally occurring proteins that have been otherwise altered to have a non-native characteristic. The ability of a given molecule to provide cytosol targeting toxin effector function(s) may be assayed by the skilled worker using techniques known in the art.

The cytosolic targeting toxin effector regions of the present invention may be derived from ribotoxic toxin effector polypeptides and often overlap or completely comprise a ribotoxic toxin effector polypeptide.

2. Proteasome Delivery Effector Polypeptides Derived from Other Polypeptide Regions or Non-Proteinaceous Materials There are numerous proteinaceous molecules, other than toxin-derived molecules, which have the intrinsic ability to localize within a cell and/or direct their own intracellular routing, to the cytosol, ER, or any other subcellular compartment suitable for delivery to a proteasome. Any of these polypeptides may be used directly or derivatized into proteasome delivery effector polypeptides for use in the present invention as long as the intrinsic subcellular localization effector function is preserved.

For example, numerous molecules are known to be able to escape from endosomal compartments after being endocytosed into a cell, including numerous naturally occurring proteins and polypeptides, via numerous mechanisms, including pore formation, lipid bilayer fusion, and proton sponge effects (see e.g. Varkouhi A et al., *J Control Release* 151: 220-8 (2010)). Non-limiting examples of non-toxin derived molecules with endosomal escape functions include: viral agents like hemagglutinin HA2; vertebrate derived polypeptides and peptides like human calcitonin derived peptides, bovine prion protein, and sweet arrow peptide; synthetic biomimetic peptides; and polymers with endosome disrupting abilities (see e.g. Varkouhi A et al., *J Control Release* 151: 220-8 (2010)). Escape from endosomal compartments, including lysosomes, can be measured directly and quantitated using assays known in the art, such as, e.g., using reporter assays with horseradish peroxidase, bovine serum albumin, fluorophores like ALEXA FLUOR® 488, and toxin derived polypetides (see e.g. Bartz R et al., *Biochem J* 435: 475-87 (2011); Gilabert-Oriol, R et al., *Toxins* 6: 1644-66 (2014)).

Other examples are molecules which localize to specific intracellular compartments. Most polypeptides comprising an endoplasmic retention/retrieval signal motif (e.g. KDEL (SEQ ID NO:61)) can localize to the ER of a eukaryotic cell from different compartments within the cell.

The ability of a polypeptide to intracellularly route to the cytosol, ER, and/or lysosomal compartments of a cell from the starting position of an early endosomal compartment can be determined by the skilled worker using assays known in the art. Then, the proteasome delivery effector polypeptide regions of a source polypeptide or protein, such as, e.g., a toxin, can be mapped and isolated by the skilled worker using standard techniques known in the art.

3. Polypeptides Engineered to Comprise One or More Heterologous, T-Cell Epitopes and a Proteasome Delivery Effector Polypeptide Once a proteasome delivery effector polypeptide is obtained, it can be engineered into a T-cell hyper-immunized and/or B-cell/CD4+ T-cell de-immunized polypeptide of the present invention using the methods of the present invention. Using the methods of the present invention, one or more T-cell epitopes are embedded, fused, or inserted into any proteasome delivery effector polypeptide, such as, e.g., a toxin effector polypeptide which routes to the cytosol (which may include a ribotoxic toxin effector polypeptide), in order to create polypeptides of the present invention, which starting from an early endosomal compartment are capable of delivering a T-cell epitope to the proteasome for entry into the MHC class I pathway and subsequent MHC class I presentation.

A given molecule's ability to deliver T-cell epitopes to the proteasome for entry into the MHC class I pathway of a cell may be assayed by the skilled worker using the methods described herein and/or techniques known in the art (see Examples, infra). Similarly, a given molecule's ability to deliver a T-cell epitope from an early endosome compartment to a proteasome may be assayed by the skilled worker using the methods described herein and/or techniques known in the art.

A given molecule's ability to deliver a T-cell epitope from an early endosome compartment to a MHC class I molecule for presentation on the surface of a cell may be assayed by the skilled worker using the methods described herein and/or techniques known in the art (see Examples, infra). Similarly, a given molecule's ability to deliver a T-cell epitope from an early endosome compartment to a MHC class I molecule may be assayed by the skilled worker using the methods described herein and/or techniques known in the art.

The proteasome delivery effector polypeptides modified using the methods of the present invention are not required to be capable of inducing or promoting cellular internalization either before or after modification by the methods of the present invention. In order to make cell-targeted molecules of the present invention, the polypeptides of the present invention may be linked, using standard techniques known in the art, with other components known to the skilled worker in order to provide cell-targeting and/or cellular internalization function(s) as needed.

B. Heterologous T-Cell Epitopes

The polypeptides and cell-targeted molecules of the present invention each comprise one or more heterologous T-cell epitopes. A T-cell epitope is a molecular structure which is comprised by an antigen and can be represented by a peptide or linear amino acid sequence. A heterologous T-cell epitope is an epitope not already present in the source polypeptide or starting proteasome delivery effector polypeptide that is modified using a method of the present invention in order to create a T-cell hyper-immunized and/or B-cell/CD4+ T-cell de-immunized polypeptide of the present invention.

The heterologous T-cell epitope peptide may be incorporated into the source polypeptide via numerous methods known to the skilled worker, including, e.g., the processes of creating one or more amino acid substitutions within the source polypeptide, fusing one or more amino acids to the source polypeptide, inserting one or more amino acids into the source polypeptide, linking a peptide to the source polypeptide, and/or a combination of the aforementioned processes. The result is a modified variant of the source polypeptide which comprises one or more heterologous T-cell epitopes.

Although any T-cell epitope is contemplated as being used as a heterologous T-cell epitope of the present invention, certain epitopes may be selected based on desirable properties. One objective is to create CD8+ T-cell hyper-immunized polypeptides, meaning that the heterologous T-cell epitope is highly immunogenic and can elicit robust immune responses in vivo when displayed complexed with a MHC class I molecule on the surface of a cell. In certain embodiments of the polypeptides of the present invention, the one or more heterologous T-cell epitopes are CD8+ T-cell epitopes.

T-cell epitopes may be derived from a number of sources, including peptide components of proteins and peptides derived from proteins already known or shown to be capable of eliciting a mammalian immune response. T-cell epitopes may be created or derived from various naturally occurring proteins. T-cell epitopes may be derived from various naturally occurring proteins foreign to mammals, such as, e.g., proteins of microorganisms. In particular, infectious microorganisms may contain numerous proteins with known antigenic and/or immunogenic properties or sub-regions or epitopes. T-cell epitopes may be derived from mutated human proteins and/or human proteins aberrantly expressed by malignant human cells.

T-cell epitopes may be chosen or derived from a number of source molecules already known to be capable of eliciting a mammalian immune response, including peptides, peptide components of proteins, and peptides derived from proteins. For example, the proteins of intracellular pathogens with mammalian hosts are sources for T-cell epitopes. There are numerous intracellular pathogens, such as viruses, bacteria, fungi, and single-cell eukaryotes, with well-studied antigenic proteins or peptides. T-cell epitopes can be selected or identified from human viruses or other intracellular pathogens, such as, e.g., bacteria like *Mycobacterium*, fungi like toxoplasmae, and protists like trypanosomes.

For example, there are many known immunogenic viral peptide components of viral proteins from human viruses. Numerous human T-cell epitopes have been mapped to peptides within proteins from influenza A viruses, such as peptides in the proteins HA glycoproteins FE17, S139/1, CH65, C05, hemagglutin 1 (HA1), hemagglutinin 2 (HA2), nonstructural protein 1 and 2 (NS1 and NS2), matrix protein 1 and 2 (M1 and M2), nucleoprotein (NP), neuraminidase (NA)), and many of these peptides have been shown to elicit human immune responses, such as by using ex vivo assay (see e.g. Assarsson E et al, *J Virol* 82: 12241-51 (2008); Alexander J et al., *Hum Immunol* 71: 468-74 (2010); Wang M et al., *PLoS One* 5: e10533 (2010); Wu J et al., Clin Infect Dis 51: 1184-91 (2010); Tan P et al., *Human Vaccin* 7: 402-9 (2011); Grant E et al., *Immunol Cell Biol* 91: 184-94 (2013); Terajima M et al., *Virol J* 10: 244 (2013)). Similarly, numerous human T-cell epitopes have been mapped to peptide components of proteins from human cytomegaloviruses (HCMV), such as peptides in the proteins pp65 (UL83), UL128-131, immediate-early 1 (IE-1; UL123), glycoprotein B, tegument proteins, and many of these peptides have been shown to elicit human immune responses, such as by using ex vivo assays (Schoppel K et al., *J Infect Dis* 175: 533-44 (1997); Elkington R et al, *J Virol* 77: 5226-40 (2003); Gibson L et al., *J Immunol* 172: 2256-64 (2004); Ryckman B et al., *J Virol* 82: 60-70 (2008); Sacre K et al., J Viral 82: 10143-52 (2008)).

While any T-cell epitope may be used in the compositions and methods of the present invention, certain T-cell epitopes may be preferred based on their known and/or empirically determined characteristics.

In many species, the MHC gene encodes multiple MHC-I molecular variants. Because MHC class I protein polymorphisms can affect antigen-MHC class I complex recognition by CD8+ T-cells, heterologous T-cell epitopes may be chosen using based on knowledge about certain MHC class I polymorphisms and/or the ability of certain antigen-MHC class I complexes to be recognized by T-cells of different genotypes.

There are well-defined peptide-epitopes that are known to be immunogenic, MHC class I restricted, and/or matched with a specific human leukocyte antigen (HLA) variant(s). For applications in humans or involving human target cells, HLA-Class I-restricted epitopes can be selected or identified by the skilled worker using standard techniques known in the art. The ability of peptides to bind to human MHC Class I molecules can be used to predict the immunogenic potential of putative T-cell epitopes. The ability of peptides to bind to human MHC class I molecules can be scored using software tools. T-cell epitopes may be chosen for use as a heterologous T-cell epitope component of the present invention based on the peptide selectivity of the HLA variants encoded by the alleles more prevalent in certain human populations. For example, the human population is polymorphic for the alpha chain of MHC class I molecules, and the variable alleles are encoded by the HLA genes. Certain T-cell epitopes may be more efficiently presented by a specific HLA molecule, such as, e.g., the commonly occurring HLA variants encoded by the HLA-A allele groups HLA-A2 and HLA-A3.

When choosing T-cell epitopes for use as a heterologous T-cell epitope component of the present invention, multiple factors in the process of epitope selection by MHC class I molecules may be considered that can influence epitope generation and transport to receptive MHC class I molecules, such as, e.g., the epitope specificity of the following factors in the target cell: proteasome, ERAAP/ERAP1, tapasin, and TAPs can (see e.g. Akram A, Inman R, *Clin Immunol* 143: 99-115 (2012)).

When choosing T-cell epitopes for use as a heterologous T-cell epitope component of the present invention, epitope-peptides may be selected which best match the MHC Class I molecules present in the cell-type or cell populations to be targeted. Different MHC class I molecules exhibit preferential binding to particular peptide sequences, and particular peptide-MHC class I variant complexes are specifically recognized by the TCRs of effector T-cells. The skilled worker can use knowledge about MHC class I molecule specificities and TCR specificities to optimize the selection of heterologous T-cell epitopes used in the present invention.

In addition, multiple immunogenic T-cell epitopes for MHC class I presentation may be embedded in the same polypeptide component(s) for use in the targeted delivery of a plurality of T-cell epitopes simultaneously.

C. Proteasome Delivery Effector Polypeptides which Comprise One or More Heterologous T-Cell Epitopes Embedded or Inserted to Disrupt an Endogenous B-Cell and/or CD4+ T-Cell Epitope Region Despite the attractiveness of using proteasome delivery effector polypeptides as components of therapeutics, many polypeptides are immunogenic in extracellular spaces when administered to vertebrates. Unwanted immunogenicity in protein therapeutics has resulted in reduced efficacy, unpredictable pharmacokinetics, and undesirable immune responses that limit dosages and repeat administrations. In efforts to de-immunize therapeutics, one main challenge is silencing or disrupting immunogenic epitopes within a polypeptide effector domain, e.g. its cytosolic targeting domain, while retaining the desired polypeptide effector function(s), such as, e.g., proteasome delivery. In addition, it is a significant challenge to disrupt immune epitopes by amino acid substitution in a polypeptide structure while preserving its function while simultaneously adding one or more T-cell epitopes that will not be recognized by the immune system until after cellular internalization, processing, and cell-surface presentation by a target cell. Solving this challenge enables the creation of polypeptides which exhibit desired CD8+ T-cell immunogenicity while reducing undesired B-cell and CD4+ T-cell immunogenicity—referred to herein as "CD8+ T-cell hyper-immunized and/or B-cell/CD4+ T-cell de-immunized" molecules or "T-cell epitope delivering and/or B-cell/CD4+ T-cell de-immunized" molecules.

II. The General Structure of Cell-Targeted Molecules Comprising T-Cell Epitope Delivering. CD8+ T-Cell Hyper-Immunized Polypeptides of the Invention The polypeptides of the present invention may be coupled to numerous other polypeptides, agents, and moieties to create cell-targeted molecules, such as, e.g. cytotoxic, cell-targeted proteins of the present invention. Cytotoxic polypeptides and proteins may be constructed using the T-cell epitope comprising proteasome delivering effector polypeptides of the invention and the addition of cell-targeting components, such as, e.g., a binding region capable of exhibiting high affinity binding to an extracellular target biomolecule physically-coupled to the surface of a specific cell type(s). In addition, the B-cell epitope de-immunized polypeptides of the present invention, whether toxic or non-toxic, may be used as components of numerous useful molecules for administration to mammals.

A. Cell-Targeted Molecules Comprising a Proteasome Effector Polypeptide Comprising a Heterologous T-Cell Epitope The present invention includes cell-targeted molecules, each comprising 1) a cell-targeting binding region and 2) a proteasome delivering effector polypeptide of the invention which comprises a heterologous T-cell epitope.

Cell-Targeting Moeities

Certain molecules of the present invention comprise a T-cell hyper-immunized proteasome delivering effector polypeptide of the present invention linked to a cell-targeting moiety comprising a binding region capable of specifically binding an extracellular target biomolecule. In certain embodiments, the molecules of the present invention comprise a single polypeptide or protein such that the T-cell hyper-immunized proteasome delivering effector polypeptide and cell-targeting binding region are fused together to form a continuous polypeptide chain or cell-targeting fusion protein.

Cell-targeting moieties of the cell-targeted molecules of the present invention comprise molecular structures, that when linked to a polypeptide of the present invention, are each capable of bringing the cell-targeted molecule within close proximity to specific cells based on molecular interactions on the surfaces of those specific cells. Cell-targeting moieties include ligand and polypeptides which bind to cell-surface targets.

One type of cell-targeting moiety is a proteinaceous binding region. Binding regions of the cell-targeted molecules of the present invention comprise one or more polypeptides capable of selectively and specifically binding an extracellular target biomolecule. Binding regions may comprise one or more various polypeptide moieties, such as ligands whether synthetic or naturally occurring ligands and derivatives thereof, immunoglobulin derived domains, synthetically engineered scaffolds as alternatives to immunoglobulin domains, and the like. The use of proteinaceous binding regions in cell-targeting molecules of the invention allows for the creation of cell-targeting molecules which are single-chain, cell-targeting proteins.

There are numerous binding regions known in the art that are useful for targeting polypeptides to specific cell-types via their binding characteristics, such as ligands, monoclonal antibodies, engineered antibody derivatives, and engineered alternatives to antibodies.

According to one specific, but non-limiting aspect, the binding region of the cell-targeted molecule of the present invention comprises a naturally occurring ligand or derivative thereof that retains binding functionality to an extracellular target biomolecule, commonly a cell surface receptor. For example, various cytokines, growth factors, and hormones known in the art may be used to target the cell-targeted molecules of the present invention to the cell-surface of specific cell types expressing a cognate cytokine receptor, growth factor receptor, or hormone receptor. Certain non-limiting examples of ligands include (alternative names are indicated in parentheses) B-cell activating factors (BAFFs, APRIL), colony stimulating factors (CSFs), epidermal growth factors (EGFs), fibroblast growth factors (FGFs), vascular endothelial growth factors (VEGFs), insulin-like growth factors (IGFs), interferons, interleukins (such as IL-2, IL-6, and IL-23), nerve growth factors (NGFs), platelet derived growth factors, transforming growth factors (TGFs), and tumor necrosis factors (TNFs).

According to certain other embodiments, the binding region comprises a synthetic ligand capable of binding an extracellular target biomolecule. One non-limiting example is antagonists to cytotoxic T-lymphocyte antigen 4 (CTLA-4).

According to one specific, but non-limiting aspect, the binding region may comprise an immunoglobulin-type binding region. The term "immunoglobulin-type binding region" as used herein refers to a polypeptide region capable of binding one or more target biomolecules, such as an antigen or epitope. Binding regions may be functionally defined by their ability to bind to target molecules. Immunoglobulin-type binding regions are commonly derived from antibody or antibody-like structures; however, alternative scaffolds from other sources are contemplated within the scope of the term.

Immunoglobulin (Ig) proteins have a structural domain known as an Ig domain. Ig domains range in length from about 70-110 amino acid residues and possess a characteristic Ig-fold, in which typically 7 to 9 antiparallel beta strands arrange into two beta sheets which form a sandwich-like structure. The Ig fold is stabilized by hydrophobic amino acid interactions on inner surfaces of the sandwich and highly conserved disulfide bonds between cysteine residues in the strands. Ig domains may be variable (IgV or V-set), constant (IgC or C-set) or intermediate (IgI or I-set). Some Ig domains may be associated with a complementarity determining region (CDR) which is important for the specificity of antibodies binding to their epitopes. Ig-like domains are also found in non-immunoglobulin proteins and are classified on that basis as members of the Ig superfamily of proteins. The HUGO Gene Nomenclature Committee (HGNC) provides a list of members of the Ig-like domain containing family.

An immunoglobulin-type binding region may be a polypeptide sequence of an antibody or antigen-binding fragment thereof wherein the amino acid sequence has been varied from that of a native antibody or an Ig-like domain of a non-immunoglobulin protein, for example by molecular engineering or selection by library screening. Because of the relevance of recombinant DNA techniques and in vitro library screening in the generation of immunoglobulin-type binding regions, antibodies can be redesigned to obtain desired characteristics, such as smaller size, cell entry, or other therapeutic improvements. The possible variations are many and may range from the changing of just one amino acid to the complete redesign of, for example, a variable region. Typically, changes in the variable region will be made in order to improve the antigen-binding characteristics, improve variable region stability, or reduce the potential for immunogenic responses.

There are numerous immunoglobulin-type binding regions contemplated as components of the present invention. In certain embodiments, the immunoglobulin-type binding region is derived from an immunoglobulin binding region, such as an antibody paratope capable of binding an extracellular target biomolecule. In certain other embodiments, the immunoglobulin-type binding region comprises an engineered polypeptide not derived from any immunoglobulin domain but which functions like an immunoglobulin binding region by providing high-affinity binding to an extracellular target biomolecule. This engineered polypeptide may optionally include polypeptide scaffolds comprising or consisting essentially of complementary determining regions from immunoglobulins as described herein.

There are also numerous binding regions in the prior art that are useful for targeting polypeptides to specific cell-types via their high-affinity binding characteristics. In certain embodiments, the binding region of the present proteins is selected from the group which includes single-domain antibody domains (sdAbs), nanobodies, heavy-chain antibody domains derived from camelids ($V_HH$ fragments), bivalent nanobodies, heavy-chain antibody domains derived from cartilaginous fishes, immunoglobulin new antigen receptors (IgNARs), $V_{NAR}$ fragments, single-chain variable (scFv) fragments, multimerizing scFv fragments (diabodies, triabodies, tetrabodies), bispecific tandem scFv fragments, disulfide stabilized antibody variable (Fv) fragments, disulfide stabilized antigen-binding (Fab) fragments consisting of the $V_L$, $V_H$, $C_L$ and $C_H1$ domains, divalent F(ab')2 fragments, Fd fragments consisting of the heavy chain and $C_H1$ domains, single chain Fv-$C_H3$ minibodies, bispecific minibodies, dimeric $C_H2$ domain fragments ($C_H2D$), Fc antigen binding domains (Fcabs), isolated complementary determining region 3 (CDR3) fragments, constrained framework region 3, CDR3, framework region 4 (FR3-CDR3-FR4) polypeptides, small modular immunopharmaceutical (SMIP) domains, and any genetically manipulated counterparts of the foregoing that retain its paratope and binding function (see Saerens D et al., *Curr. Opin. Pharmacol* 8: 600-8 (2008); Dimitrov D, *MAbs* 1: 26-8 (2009); Weiner L, *Cell* 148: 1081-4 (2012); Ahmad Z et al., (*Clin Dev Immunol* 2012: 980250 (2012)).

In accordance with certain other embodiments, the binding region includes engineered, alternative scaffolds to immunoglobulin domains that exhibit similar functional characteristics, such as high-affinity and specific binding of target biomolecules, and enables the engineering of improved characteristics, such as greater stability or reduced immunogenicity. For certain embodiments of the cell-targeted proteins of the present invention, the binding region is selected from the group which includes engineered, fibronectin-derived, $10^{th}$ fibronectin type III (10Fn3) domain (monobodies, AdNectins™, or AdNexins™); engineered, tenascin-derived, tenascin type III domain (Centryns™); engineered, ankyrin repeat motif containing polypeptide (DARPins™); engineered, low-density-lipoprotein-receptor-derived, A domain (LDLR-A) (Avimers™); lipocalin (anticalins); engineered, protease inhibitor-derived, Kunitz domain; engineered, Protein-A-derived, Z domain (Affibodies™); engineered, gamma-B crystallin-derived scaffold or engineered, ubiquitin-derived scaffold (Affilins); Sac7d-derived polypeptides (Nanofitins® or affitins); engineered, Fyn-derived, SH2 domain (Fynomers®); miniproteins; C-type lectin-like domain scaffolds; engineered antibody mimics; and any genetically manipulated counterparts of the foregoing that retains its binding functionality (Worn A, Plückthun A, *J Mol Biol* 305: 989-1010 (2001); Xu L et al., Chem Biol 9: 933-42 (2002); Wikman M et al., *Protein Eng Des Sel* 17: 455-62 (2004); Binz H et al., *Nat Biotechnol* 23: 1257-68 (2005); Hey T et al., *Trends Biotechnol* 23:514-522 (2005); Holliger P, Hudson P, *Nat Biotechnol* 23: 1126-36 (2005); Gill D, Damle N, *Curr Opin Biotech* 17: 653-8 (2006); Koide A, Koide S, *Methods Mol Biol* 352: 95-109 (2007); Byla P et al., *J Biol Chem* 285: 12096 (2010); Zoller F et al., *Molecules* 16: 2467-85 (2011)).

Any of the above binding regions may be used as a component of the present invention as long as the binding region component has a dissociation constant of $10^{-5}$ to $10^{-12}$ moles per liter, preferably less than 200 nanomolar (nM), towards an extracellular target biomolecule.

Certain cell-targeted molecules of the present invention comprise a polypeptide of the present invention linked to an extracellular target biomolecule specific binding region comprising one or more polypeptides capable of selectively and specifically binding an extracellular target biomolecule. Extracellular target biomolecules may be selected based on numerous criteria.

Extracellular Target Biomolecules of the Cell-Targeting Moieties

Certain binding regions of the cell-targeted molecules of the present invention comprise a polypeptide region capable of binding specifically to an extracellular target biomolecule, preferably which is physically-coupled to the surface of a cell type of interest, such as a cancer cell, tumor cell, plasma cell, infected cell, or host cell harboring an intracellular pathogen.

The term "target biomolecule" refers to a biological molecule, commonly a protein or a protein modified by post-translational modifications, such as glycosylation, which is capable of being bound by a binding region to target a protein to a specific cell-type or location within an organism. Extracellular target biomolecules may include various epitopes, including unmodified polypeptides, polypeptides modified by the addition of biochemical functional groups, and glycolipids (see e.g. U.S. Pat. No. 5,091,178; EP 2431743). It is desirable that an extracellular target biomolecule be endogenously internalized or be readily forced to internalize upon interaction with a cell-targeted molecule of the present invention.

For purposes of the present invention, the term "extracellular" with regard to modifying a target biomolecule refers to a biomolecule that has at least a portion of its structure exposed to the extracellular environment. Extracellular target biomolecules include cell membrane components, transmembrane spanning proteins, cell membrane-anchored biomolecules, cell-surface-bound biomolecules, and secreted biomolecules.

With regard to the present invention, the phrase "physically coupled" when used to describe a target biomolecule means both covalent and/or non-covalent intermolecular interactions that couple the target biomolecule, or a portion thereof, to the outside of a cell, such as a plurality of non-covalent interactions between the target biomolecule and the cell where the energy of each single interaction is on the order of about 1-5 kiloCalories (e.g. electrostatic bonds, hydrogen bonds, Van der Walls interactions, hydrophobic forces, etc.). All integral membrane proteins can be found physically coupled to a cell membrane, as well as peripheral membrane proteins. For example, an extracellular target biomolecule might comprise a transmembrane spanning region, a lipid anchor, a glycolipid anchor, and/or be non-covalently associated (e.g. via non-specific hydrophobic interactions and/or lipid binding interactions) with a factor comprising any one of the foregoing.

The binding regions of the cell-targeted molecules of the present invention may be designed or selected based on numerous criteria, such as the cell-type specific expression of their target biomolecules and/or the physical localization of their target biomolecules with regard to specific cell types. For example, certain cytotoxic proteins of the present invention comprise binding domains capable of binding cell-surface targets which are expressed exclusively by only one cell-type to the cell surface.

All nucleated vertebrate cells are believed to be capable of presenting intracellular peptide epitopes using the MHC class I system. Thus, extracellular target biomolecules of the cell-targeted molecules of the invention may in principle target any nucleated vertebrate cell for T-cell epitope delivery into the MHC class I presentation pathway.

Extracellular target biomolecules of the binding region of the cell-targeted molecules of the present invention may include biomarkers over-proportionately or exclusively present on cancer cells, immune cells, and cells infected with intracellular pathogens, such as viruses, bacteria, fungi, prions, or protozoans.

The skilled worker, using techniques known in the art, can link the T-cell hyper-immunized and/or B-cell/CD4+ T-cell de-immunized polypeptides of the present invention to various other molecules to target specific extracellular target biomolecules physically coupled to cells and promote target cell internalization. For example, a polypeptide of the invention may be linked to cell-surface receptor targeting molecule which is more readily endocytosed, such as, e.g., via receptor mediated endocytosis, or to a molecule which promotes cellular internalization via mechanisms at the cell surface, such as, e.g. promoting clathrin coated pit assembly, phospholipid layer deformation, and/or tubular invagination. The ability of a cell-targeting moiety to facilitate cellular internalization after target binding may be determined using assays known to the skilled worker.

Endoplasmic Reticulum Retention/Retrieval Signal Motif of a Member of the KDEL Family For purposes of the present invention, the phrase "endoplasmic reticulum retention/retrieval signal motif," KDEL-type signal motif ("KDEL" disclosed as SEQ ID NO:61), or signal motif refers to any member of the KDEL family capable of functioning within a eukaryotic cell to promote subcellular localization of a protein to the endoplasmic reticulum via KDEL receptors.

The carboxy-terminal lysine-asparagine-glutamate-leucine (KDEL (SEQ ID NO:61)) sequence is a canonical, endoplasmic reticulum retention and retrieval signal motif for soluble proteins in eukaryotic cells and is recognized by the KDEL receptors (see, Capitani M, Sallese M, *FEBS Lett* 583: 3863-71 (2009), for review). The KDEL family of signal motifs includes many KDEL-like motifs, such as HDEL (SEQ ID NO:63), RDEL (SEQ ID NO:65), WDEL (SEQ ID NO:66), YDEL (SEQ ID NO:67), HEEL (SEQ ID NO:69), KEEL (SEQ ID NO:70), REEL (SEQ ID NO:71), KFEL (SEQ ID NO:74), KIEL (SEQ ID NO:86), DKEL (SEQ ID NO:87), KKEL (SEQ ID NO:90), HNEL (SEQ ID NO:94), HTEL (SEQ ID NO:95), KTEL (SEQ ID NO:96), and HVEL (SEQ ID NO:97), all of which are found at the carboxy-terminals of proteins which are known to be residents of the lumen of the endoplasmic reticulum of throughout multiple phylogenetic kingdoms (Munro S, Pelham H, *Cell* 48: 899-907 (1987); Raykhel I et al., *J Cell Biol* 179: 1193-204 (2007)). The KDEL signal motif family includes at least 46 polypeptide variants shown using synthetic constructs (Raykhel, *J Cell Biol* 179: 1193-204 (2007)). Additional KDEL signal motifs include ALEDEL (SEQ ID NO:107), HAEDEL (SEQ ID NO:108), HLEDEL (SEQ ID NO:109), KLEDEL (SEQ ID NO:110), IRSDEL (SEQ ID NO:111), ERSTEL (SEQ ID NO:112), and RPSTEL (SEQ ID NO:113) (Alanen H et al., *J Mol Biol* 409: 291-7 (2011)). A generalized consensus motif representing the majority of KDEL signal motifs has been described as [KRHQSA]-[DENQ]-E-L (Hulo N et al., *Nucleic Acids Res* 34: D227-30 (2006)).

Proteins containing KDEL family signal motifs are bound by KDEL receptors distributed throughout the Golgi complex and transported to the endoplasmic reticulum by a microtubule-dependent mechanism for release into the lumen of the endoplasmic reticulum (Griffiths G et al., *J Cell Biol* 127: 1557-74 (1994); Miesenbock G, Rothman J, *J Cell Biol* 129: 309-19 (1995)). KDEL receptors dynamically cycle between the Golgi complex and endoplasmic reticulum (Jackson M et al., *EMBO J.* 9: 3153-62 (1990); Schutze M et al., *EMBO J.* 13: 1696-1705 (1994)).

For purposes of the present invention, the members of the KDEL family include synthetic signal motifs able to function within a eukaryotic cell to promote subcellular localization of a protein to the endoplasmic reticulum via KDEL receptors. In other words, some members of the KDEL family might not occur in nature or have yet to be observed in nature but have or may be constructed and empirically verified using methods known in the art; see e.g., Raykhel I et al., *J Cell Biol* 179: 1193-204 (2007).

As a component of certain embodiments of the polypeptides and cell-targeted molecules of the present invention, the KDEL-type signal motif is physically located, oriented, or arranged within the polypeptide or cell-targeted protein such that it is on a carboxy-terminal.

For the purposes of the present invention, the specific order or orientation is not fixed for the T-cell hyper-immunized and/or B-cell/CD4+ T-cell de-immunized polypeptide and the cell-targeting binding region in relation to each other or the entire, cell-targeted, fusion protein's N-terminal(s) and C-terminal(s) (see e.g. FIG. 1).

The general structure of the cell-targeted molecules of the present invention is modular, in that various, diverse cell-targeting binding regions may be used with various CD8+ T-cell hyper-immunized and/or B-cell/CD4+ T-cell de-immunized polypeptides to provide for diverse targeting of various extracellular target biomolecules and thus targeting of cytotoxicity, cytostasis, and/or exogenous material delivery to various diverse cell types. CD8+ T-cell hyper-immunized and B-cell/CD4+ T-cell de-immunized polypeptides which do not result in T-cell epitope presentation and/or are not cytotoxic due to improper subcellular routing may still be useful as components of cell targeted molecules for delivering exogenous materials into cells, such as, e.g., a T-cell epitope or antigen.

III. Linkages Connecting Polypeptide Components of the Invention and/or their Subcomponents Individual cell-targeting moiety, polypeptide, and/or protein components of the present invention, e.g. the cell-targeting binding regions and CD8+ T-cell hyper-immunized and/or B-cell/CD4+ T-cell de-immunized polypeptides, may be suitably linked to each other via one or more linkers well known in the art and/or described herein. Individual polypeptide subcomponents of the binding regions, e.g. heavy chain variable regions ($V_H$), light chain variable regions ($V_L$), CDR, and/or ABR regions, may be suitably linked to each other via one or more linkers well known in the art and/or described herein (see e.g. Weisser N, Hall J, *Biotechnol Adv* 27: 502-20 (2009); Chen X et al., *Adv Drug Deliv Rev* 65: 1357-69 (2013)). Protein components of the invention, e.g., multi-chain binding regions, may be suitably linked to each other or other polypeptide components of the invention via one or more linkers well known in the art. Peptide components of the invention, e.g., KDEL family endoplasmic reticulum retention/retrieval signal motifs, may be suitably linked to another component of the invention via one or more linkers, such as a proteinaceous linker, which are well known in the art.

Suitable linkers are generally those which allow each polypeptide component of the present invention to fold with a three-dimensional structure very similar to the polypeptide components produced individually without any linker or other component. Suitable linkers include single amino acids, peptides, polypeptides, and linkers lacking any of the aforementioned such as various non-proteinaceous carbon chains, whether branched or cyclic (see e.g. Chen X et al., *Adv Drug Deliv Rev* 65: 1357-69 (2013)).

Suitable linkers may be proteinaceous and comprise one or more amino acids, peptides, and/or polypeptides. Proteinaceous linkers are suitable for both recombinant fusion proteins and chemically linked conjugates. A proteinaceous linker typically has from about 2 to about 50 amino acid residues, such as, e.g., from about 5 to about 30 or from about 6 to about 25 amino acid residues. The length of the linker selected will depend upon a variety of factors, such as, e.g., the desired property or properties for which the linker is being selected (see e.g. Chen X et al., *Adv Drug Deliv Rev* 65: 1357-69 (2013)).

Suitable linkers may be non-proteinaceous, such as, e.g. chemical linkers (see e.g. Dosio F et al., *Toxins* 3: 848-83 (2011); Feld J et al., *Oncotarget* 4: 397-412 (2013)). Various non-proteinaceous linkers known in the art may be used to link cell-targeting moieties to the CD8+ T-cell hyper-immunized and/or B-cell/CD4+ T-cell de-immunized polypeptide components, such as linkers commonly used to conjugate immunoglobulin-derived polypeptides to heterologous polypeptides. For example, polypeptide regions may be linked using the functional side chains of their amino acid residues and carbohydrate moieties such as, e.g., a carboxy, amine, sulfhydryl, carboxylic acid, carbonyl, hydroxyl, and/or cyclic ring group. For example, disulfide bonds and thioether bonds may be used to link two or more polypeptides (see e.g. Fitzgerald D et al., *Bioconjugate Chem* 1: 264-8 (1990); Pasqualucci L et al., *Haematologica* 80: 546-56 (1995)). In addition, non-natural amino acid residues may be used with other functional side chains, such as ketone groups (see e.g. Sun S et al., *Chembiochem* Jul. 18 2014; Tian F et al., *Proc Natl Acad Sci USA* 111: 1766-71 (2014)). Examples of non-proteinaceous chemical linkers include but are not limited to N-succinimidyl (4-iodoacetyl)-aminobenzoate, S—(N-succinimidyl) thioacetate (SATA), N-succinimidyl-oxycarbonyl-α-methyl-α-(2-pyridyldithio) toluene (SMPT), N-succinimidyl 4-(2-pyridyldithio)-pentanoate (SPP), succinimidyl 4-(N-maleimidomethyl) cyclohexane carboxylate (SMCC or MCC), sulfosuccinimidyl (4-iodoacetyl)-aminobenzoate, 4-succinimidyl-oxycarbonyl-α-(2-pyridyldithio) toluene, sulfosuccinimidyl-6-(α-methyl-α-(pyridyldithiol)-toluamido) hexanoate, N-succinimidyl-3-(-2-pyridyldithio)-proprionate (SPDP), succinimidyl 6(3(-(-2-pyridyldithio)-proprionamido) hexanoate, sulfosuccinimidyl 6(3(-(-2-pyridyldithio)-propionamido) hexanoate, maleimidocaproyl (MC), maleimidocaproyl-valine-citrulline-p-aminobenzyloxycarbonyl (MC-vc-PAB), 3-maleimidobenzoic acid N-hydroxysuccinimide ester (MBS), alpha-alkyl derivatives, sulfoNHS-ATMBA (sulfosuccinimidyl N-[3-(acetylthio)-3-methylbutyryl-beta-alanine]), sulfodicholorphenol, 2-iminothiolane, 3-(2-pyridyldithio)-propionyl hydrazide, Ellman's reagent, dichlorotriazinic acid, and S-(2-thiopyridyl)-L-cysteine (see e.g. Thorpe P et al., *Eur J Biochem* 147: 197-206 (1985); Thorpe P et al., *Cancer Res* 47: 5924-31 (1987); Thorpe P et al., *Cancer Res* 48: 6396-403 (1988); Grossbard M et al., *Blood* 79: 576-85 (1992); Lui C et al., *Proc Natl Acad Sci USA* 93: 8618-23 (1996); Doronina S et al., *Nat Biotechnol* 21: 778-84 (2003); Feld J et al., *Oncotarget* 4: 397-412 (2013)).

Suitable linkers, whether proteinaceous or non-proteinaceous, may include, e.g., protease sensitive, environmental redox potential sensitive, pH sensitive, acid cleavable, photocleavable, and/or heat sensitive linkers (see e.g. Dosio F et al., *Toxins* 3: 848-83 (2011); Chen X et al., *Adv Drug Deliv Rev* 65: 1357-69 (2013); Feld J et al., *Oncotarget* 4: 397-412 (2013)).

Proteinaceous linkers may be chosen for incorporation into recombinant fusion cell-targeted molecules of the present invention. For recombinant fusion cell-targeted proteins of the invention, linkers typically comprise about 2 to 50 amino acid residues, preferably about 5 to 30 amino acid residues (Argos P, *J Mol Biol* 211: 943-58 (1990); Williamson M, *Biochem J* 297: 240-60 (1994); George R, Heringa J, *Protein Eng* 15: 871-9 (2002); Kreitman R, *AAPS J* 8: E532-51 (2006)). Commonly, proteinaceous linkers comprise a majority of amino acid residues with polar, uncharged, and/or charged residues, such as, e.g., threonine, proline, glutamine, glycine, and alanine (see e.g. Huston J et al. *Proc Natl Acad Sci U.S.A.* 85: 5879-83 (1988); Pastan I et al., *Annu Rev Med* 58: 221-37 (2007); Li J et al., *Cell Immunol* 118: 85-99 (1989); Cumber A et al. *Bioconj Chem* 3: 397-401 (1992); Friedman P et al., *Cancer Res* 53: 334-9 (1993); Whitlow M et al., *Protein Engineering* 6: 989-95 (1993); Siegall C et al., *J Immunol* 152: 2377-84 (1994); Newton et al. *Biochemistry* 35: 545-53 (1996); Ladurner et al. *J Mol Biol* 273: 330-7 (1997); Kreitman R et al., *Leuk Lymphoma* 52: 82-6 (2011); U.S. Pat. No. 4,894,443). Non-limiting examples of proteinaceous linkers include alanine-serine-glycine-glycine-proline-glutamate (ASGGPE) (SEQ ID NO:114), valine-methionine (VM), alanine-methionine (AM), AM($G_{2\ to\ 4}$S)$_x$AM where G is glycine, S is serine, and x is an integer from 1 to 10 (SEQ ID NO: 115).

Proteinaceous linkers may be selected based upon the properties desired. Proteinaceous linkers may be chosen by the skilled worker with specific features in mind, such as to optimize one or more of the fusion molecule's folding, stability, expression, solubility, pharmacokinetic properties, pharmacodynamic properties, and/or the activity of the fused domains in the context of a fusion construct as compared to the activity of the same domain by itself. For example, proteinaceous linkers may be selected based on flexibility, rigidity, and/or cleavability (see e.g. Chen X et al., *Adv Drug Deliv Rev* 65: 1357-69 (2013)). The skilled worker may use databases and linker design software tools when choosing linkers. Certain linkers may be chosen to optimize expression (see e.g. Turner D et al., *J Immunol Methods* 205: 43-54 (1997)). Certain linkers may be chosen to promote intermolecular interactions between identical polypeptides or proteins to form homomultimers or different polypeptides or proteins to form heteromultimers. For example, proteinaceous linkers may be selected which allow for desired non-covalent interactions between polypeptide components of the cell-targeted proteins of the invention, such as, e.g., interactions related to the formation dimers and other higher order multimers (see e.g. U.S. Pat. No. 4,946, 778).

Flexible proteinaceous linkers are often greater than 12 amino acid residues long and rich in small, non-polar amino acid residues, polar amino acid residues, and/or hydrophilic amino acid residues, such as, e.g., glycines, serines, and threonines (see e.g. Bird R et al., *Science* 242: 423-6 (1988); Friedman P et al., *Cancer Res* 53: 334-9 (1993); Siegall C et al., *J Immunol* 152: 2377-84 (1994)). Flexible proteinaceous linkers may be chosen to increase the spatial separation between components and/or to allow for intramolecular interactions between components. For example, various "GS" linkers are known to the skilled worker and are composed of multiple glycines and/or one or more serines, sometimes in repeating units, such as, e.g., $(G_xS)_n$, (SEQ ID NO: 116), $(S_xG)_n$ (SEQ ID NO: 117), $(GGGGS)_n$ (SEQ ID NO:118), and $(G)_n$ (SEQ ID NO:119). in which x is 1 to 6 and n is 1 to 30 (see e.g. WO 96/06641). Non-limiting examples of flexible proteinaceous linkers include GKSSGSGSESKS (SEQ ID NO:120), GST-SGSGKSSEGKG (SEQ ID NO:121), GST-SGSGKSSEGSGSTKG (SEQ ID NO:122), GST-SGSGKPGSGEGSTKG (SEQ ID NO:123), EGKSSGSGSESKEF (SEQ ID NO:124), SRSSG (SEQ ID NO:125), and SGSSC (SEQ ID NO:126).

Rigid proteinaceous linkers are often stiff alpha-helical structures and rich in proline residues and/or one or more strategically placed prolines (see Chen X et al., *Adv Drug Deliv Rev* 65: 1357-69 (2013)). Rigid linkers may be chosen to prevent intramolecular interactions between linked components.

Suitable linkers may be chosen to allow for in vivo separation of components, such as, e.g., due to cleavage and/or environment-specific instability (see Dosio F et al., *Toxins* 3: 848-83 (2011); Chen X et al., *Adv Drug Deliv Rev* 65: 1357-69 (2013)). In vivo cleavable proteinaceous linkers are capable of unlinking by proteolytic processing and/or reducing environments often at a specific site within an organism or inside a certain cell type (see e.g. Doronina S et al., *Bioconjug Chem* 17: 144-24 (2006); Erickson H et al., *Cancer Res* 66: 4426-33 (2006)). In vivo cleavable proteinaceous linkers often comprise protease sensitive motifs and/or disulfide bonds formed by one or more cysteine pairs (see e.g. Pietersz G et al., *Cancer Res* 48: 4469-76 (1998); The J et al., *J Immunol Methods* 110: 101-9 (1998); see Chen X et al., *Adv Drug Deliv Rev* 65: 1357-69 (2013)). In vivo cleavable proteinaceous linkers may be designed to be sensitive to proteases that exist only at certain locations in an organism, compartments within a cell, and/or become active only under certain physiological or pathological conditions (such as, e.g., proteases with abnormally high levels, proteases overexpressed at certain disease sites, and proteases specifically expressed by a pathogenic microorganism). For example, there are proteinaceous linkers known in the art which are cleaved by proteases present only intracellularly, proteases present only within specific cell types, and proteases present only under pathological conditions like cancer or inflammation, such as, e.g., R-x-x-R motif and AMGRSGGGCAGNRVGSSLSCGGLNLQAM (SEQ ID NO:127).

In certain embodiments of the cell-targeted molecules of the present invention, a linker may be used which comprises one or more protease sensitive sites to provide for cleavage by a protease present within a target cell. In certain embodiments of the cell-targeted molecules of the invention, a linker may be used which is not cleavable to reduce unwanted toxicity after administration to a vertebrate organism.

Suitable linkers may include, e.g., protease sensitive, environmental redox potential sensitive, pH sensitive, acid cleavable, photocleavable, and/or heat sensitive linkers, whether proteinaceous or non-proteinaceous (see Chen X et al., *Adv Drug Deliv Rev* 65: 1357-69 (2013)).

Suitable cleavable linkers may include linkers comprising cleavable groups which are known in the art such as, e.g., Zarling D et al., *J Immunol* 124: 913-20 (1980); Jung S, Moroi M, *Biochem Biophys Acta* 761: 152-62 (1983); Bouizar Z et al., *Eur J Biochem* 155: 141-7 (1986); Park L et al., *J Biol Chem* 261: 205-10 (1986); Browning J, Ribolini A, *J Immunol* 143: 1859-67 (1989); Joshi S, Burrows R, *J Biol Chem* 265: 14518-25 (1990)).

Suitable linkers may include pH sensitive linkers. For example, certain suitable linkers may be chosen for their instability in lower pH environments to provide for dissociation inside a subcellular compartment of a target cell. For example, linkers that comprise one or more trityl groups, derivatized trityl groups, bismaleimideothoxy propane groups, adipic acid dihydrazide groups, and/or acid labile transferrin groups, may provide for release of components of the cell-targeted molecules of the invention, e.g. a polypeptide component, in environments with specific pH ranges (see e.g. Welhöner H et al., *J Biol Chem* 266: 4309-14 (1991); Fattom A et al., *Infect Immun* 60: 584-9 (1992)). Certain linkers may be chosen which are cleaved in pH ranges corresponding to physiological pH differences between tissues, such as, e.g., the pH of tumor tissue is lower than in healthy tissues (see e.g. U.S. Pat. No. 5,612,474).

Photocleavable linkers are linkers that are cleaved upon exposure to electromagnetic radiation of certain wavelength ranges, such as light in the visible range (see e.g. Goldmacher V et al., *Bioconj Chem* 3: 104-7 (1992)). Photocleavable linkers may be used to release a component of a cell-targeted molecule of the invention, e.g. a polypeptide component, upon exposure to light of certain wavelengths. Non-limiting examples of photocleavable linkers include a nitrobenzyl group as a photocleavable protective group for cysteine, nitrobenzyloxycarbonyl chloride cross-linkers, hydroxypropylmethacrylamide copolymer, glycine copolymer, fluorescein copolymer, and methylrhodamine copolymer (Hazum E et al., *Pept Proc Eur Pept Symp*, 16th, Brunfeldt K, ed., 105-110 (1981); Senter et al., *Photochem Photobiol* 42: 231-7 (1985); Yen et al., *Makromol Chem* 190: 69-82 (1989); Goldmacher V et al., *Bioconj Chem* 3: 104-7 (1992)). Photocleavable linkers may have particular uses in linking components to form cell-targeted molecules of the invention designed for treating diseases, disorders, and conditions that can be exposed to light using fiber optics.

In certain embodiments of the cell-targeted molecules of the present invention, a cell-targeting binding region is linked to a CD8+ T-cell hyper-immunized and/or B-cell/CD4+ T-cell de-immunized polypeptide using any number of means known to the skilled worker, including both covalent and noncovalent linkages (see e.g. Chen X et al., *Adv Drug Deliv Rev* 65: 1357-69 (2013); Behrens C, Liu B, *MAbs* 6: 46-53 (2014).

In certain embodiments of the cell-targeted proteins of the present invention, the protein comprises a binding region which is a scFv with a linker connecting a heavy chain variable (V$_H$) domain and a light chain variable (V$_L$) domain. There are numerous linkers known in the art suitable for this purpose, such as, e.g., the 15-residue (Gly4Ser)$_3$ peptide (SEQ ID NO:128). Suitable scFv linkers which may be used in forming non-covalent multivalent structures include GGS, GGGS (SEQ ID NO:129), GGGGS (SEQ ID NO:130), GGGGSGGG (SEQ ID NO:131), GGSGGGG (SEQ ID NO:132), GST-SGGGSGGGSGGGGSS (SEQ ID NO:133), and GST-SGSGKPGSSEGSTKG (SEQ ID NO:134) (Plückthun A, Pack P, *Immunotechnology* 3: 83-105 (1997); Atwell J et al., *Protein Eng* 12: 597-604 (1999); Wu A et al., *Protein Eng* 14: 1025-33 (2001); Yazaki P et al., *J Immunol Methods* 253: 195-208 (2001); Carmichael J et al., *J Mol Biol* 326: 341-51 (2003); Arndt M et al., *FEBS Lett* 578: 257-61 (2004); Bie C et al., *World J Hepatol* 2: 185-91(2010)).

Suitable methods for linkage of the components of the cell-targeted molecules of the present invention may be by any method presently known in the art for accomplishing such, as long as the attachment does not substantially impede the binding capability of the cell-targeting moiety, the cellular internalization of the CD8+ T-cell hyper-immunized and/or B-cell/CD4+ T-cell de-immunized polypeptide component, and/or when appropriate the desired toxin effector function(s) as measured by an appropriate assay, including assays described herein.

For the purposes of the cell-targeted molecules of the present invention, the specific order or orientation is not fixed for the cell-targeting binding region and CD8+ T-cell hyper-immunized and/or B-cell/CD4+ T-cell de-immunized polypeptide region in relation to each other or the entire cell-targeted molecule (see e.g. FIG. 1). The components of the polypeptides and cell-targeted molecules of the present invention may be arranged in any order provided that the desired activities of the cell-targeting moiety and the T-cell hyper-immunized and/or B-cell/CD4+ T-cell de-immunized effector polypeptide region are not eliminated. In certain embodiments of the cell-targeted molecules of the present invention, the cell-targeting moiety, CD8+ T-cell hyper-immunized and/or B-cell/CD4+ T-cell de-immunized polypeptide, and/or endoplasmic reticulum retention/retrieval signal motif may be directly linked to each other and/or suitably linked to each other via one or more intervening polypeptide sequences, such as with one or more linkers well known in the art and/or described herein.

IV. Examples of Specific Structural Variations of T-Cell Epitope Delivering. CD8+ T-Cell Hyper-Immunized Polypeptides and Cell-Targeted Fusion Proteins Comprising the Same A T-cell hyper-immunized polypeptide with the capability of delivering a T-cell epitope for MHC class I presentation by a target cell may be created, in principle, by adding a T-cell epitope to any proteasome delivering effector polypeptide. A B-cell/CD4+ T-cell de-immunized sub-variant of the T-cell hyper-immunized polypeptide of the present invention may be created by replacing one or more amino acid residues in any B-cell and/or CD4+ T-cell epitope region within a proteasome delivering effector polypeptide with an overlapping heterologous T-cell epitope. A cell-targeted molecule with the ability to deliver a CD8+ T-cell epitope for MHC class I presentation by a target cell may be created, in principle, by linking any CD8+ T-cell hyper-immunized and/or B-cell/CD4+ T-cell de-immunized polypeptide of the invention to a cell-targeting moiety as long as the resulting molecule has a cellular internalization capability provided by at least the polypeptide of the invention, the cell-targeting moiety, or the structural combination of them together.

A CD8+ T-cell hyper-immunized polypeptide with the capability of delivering a CD8+ T-cell epitope for MHC class I presentation by a target cell may be created by using a toxin-derived, proteasome delivering effector polypeptide. Similarly, a B-cell/CD4+ T-cell de-immunized, CD8+ T-cell hyper-immunized polypeptide of the present invention may be created by replacing one or more amino acid residues in any B-cell epitope region in a toxin-derived, proteasome-delivering effector polypeptide with an overlapping heterologous CD8+ T-cell epitope.

Certain T-cell hyper-immunized and B-cell/CD4+ T-cell de-immunized polypeptides of the present invention comprise a disruption of at least one putative B-cell epitope region by the addition of a heterologous T-cell epitope in order to reduce the antigenic and/or immunogenic potential of the polypeptides after administration to a mammal. The terms "disrupted" or "disruption" or "disrupting" as used herein with regard to a B-cell epitope region refers to the deletion of at least one amino acid in a B-cell epitope region, inversion of two or more amino acids where at least one of the inverted amino acids is in a B-cell epitope region, insertion of at least one amino acid in a B-cell epitope region, or mutation of at least one amino acid in a B-cell epitope region. A B-cell epitope region disruption by mutation includes amino acid substitutions with non-standard amino acids and/or non-natural amino acids. The number of amino acid residues in the region affected by the disruption is preferably two or more, three or more, four or more, five or more, six or more, seven or more and so forth up to 8, 9, 10, 11, 12, or more amino acid residues.

Certain B-cell epitope regions and disruptions are indicated herein by reference to specific amino acid positions of native Shiga toxin A Subunits or a prototypical Diphtheria toxin A Subunit provided in the Sequence Listing, noting that naturally occurring toxin A Subunits may comprise precursor forms containing signal sequences of about 22 amino acids at their amino-terminals which are removed to produce mature toxin A Subunits and are recognizable to the skilled worker.

Certain T-cell hyper-immunized and B-cell/CD4+ T-cell de-immunized polypeptides of the present invention comprise a disruption of at least one putative CD4+ T-cell epitope region by the addition of a heterologous T-cell epitope in order to reduce the CD4+ T-cell antigenic and/or immunogenic potential of the polypeptides after administration to a mammal. The terms "disrupted" or "disruption" or "disrupting" as used herein with regard to a CD4+ T-cell epitope region refers to the deletion of at least one amino acid in a CD4+ T-cell epitope region, inversion of two or more amino acids where at least one of the inverted amino acids is in a CD4+ T-cell epitope, insertion of at least one amino acid in a CD4+ T-cell epitope region, or mutation of at least one amino acid in a CD4+ T-cell epitope region. A CD4+ T-cell epitope region disruption by mutation includes amino acid substitutions with non-standard amino acids and/or non-natural amino acids. The number of amino acid residues in the region affected by the disruption is preferably two or more, three or more, four or more, five or more, six or more, seven or more and so forth up to 8, 9, 10, 11, 12, or more amino acid residues.

Certain CD4+ T-cell epitope regions and disruptions are indicated herein by reference to specific amino acid positions of native Shiga toxin A Subunits or a prototypical Diphtheria toxin A Subunit provided in the Sequence Listing, noting that naturally occurring toxin A Subunits may comprise precursor forms containing signal sequences of about 22 amino acids at their amino-terminals which are removed to produce mature toxin A Subunits and are recognizable to the skilled worker.

1. Shiga Toxin Derived, CD8+ T-Cell Epitope Presenting, and B-Cell/CD4+ T-Cell De-Immunized Polypeptides The Shiga toxin family of protein toxins is composed of various naturally occurring toxins which are structurally and functionally related, e.g., Shiga toxin, Shiga-like toxin 1, and Shiga-like toxin 2 (Johannes L, Römer W, *Nat Rev Microbiol* 8: 105-16 (2010)). Members of the Shiga toxin family share the same overall structure and mechanism of action (Engedal, N et al., *Microbial Biotech* 4: 32-46 (2011)). For example, Stx, SLT-1 and SLT-2 display indistinguishable enzymatic activity in cell free systems (Head S et al., *J Biol Chem* 266: 3617-21 (1991); Tesh V et al., *Infect Immun* 61: 3392-402 (1993); Brigotti M et al., *Toxicon* 35:1431-1437 (1997)).

The Shiga toxin family encompasses true Shiga toxin (Stx) isolated from *S. dysenteriae* serotype 1, Shiga-like toxin 1 variants (SLT1 or Stx1 or SLT-1 or Sit-I) isolated from serotypes of enterohemorrhagic *E. coli*, and Shiga-like toxin 2 variants (SLT2 or Stx2 or SLT-2) isolated from serotypes of enterohemorrhagic *E. coli*. SLT1 differs by only one residue from Stx, and both have been referred to as Verocytotoxins or Verotoxins (VTs) (O'Brien, *Curr Top Microbiol Immunol* 180: 65-94 (1992)). Although SLT1 and SLT2 variants are only about 53-60% similar to each other at the amino acid sequence level, they share mechanisms of enzymatic activity and cytotoxicity common to the members of the Shiga toxin family (Johannes, *Nat Rev Microbiol* 8: 105-16 (2010)). Over 39 different Shiga toxins have been described, such as the defined subtypes Stx1a, Stx1c, Stx1d, and Stx2a-g (Scheutz F et al., *J Clin Microbiol* 50: 2951-63 (2012)). Members of the Shiga toxin family are not naturally restricted to any bacterial species because Shiga-toxin-encoding genes can spread among bacterial species via horizontal gene transfer (Strauch E et al., *Infect Immun* 69: 7588-95 (2001); Zhaxybayeva O, Doolittle W, *Curr Biol* 21: R242-6 (2011)). As an example of interspecies transfer, a Shiga toxin was discovered in a strain of *A. haemolyticus* isolated from a patient (Grotiuz G et al., *J Clin Microbiol* 44: 3838-41 (2006)). Once a Shiga toxin encoding polynucleotide enters a new subspecies or species, the Shiga toxin amino acid sequence is presumed to be capable of developing slight sequence variations due to genetic drift and/or selective pressure while still maintaining a mechanism of cytotoxicity common to members of the Shiga toxin family (see Scheutz, *J Clin Microbiol* 50: 2951-63 (2012)).

For purposes of the present invention, the phrase "Shiga toxin effector region" refers to a polypeptide region derived from a Shiga toxin A Subunit of a member of the Shiga toxin family that is capable of exhibiting at least one Shiga toxin function. Shiga toxin functions include, e.g., cell entry, lipid membrane deformation, directing subcellular routing, catalytically inactivating ribosomes, effectuating cytotoxicity, and effectuating cytostatic effects.

For purposes of the present invention, a Shiga toxin effector function is a biological activity conferred by a polypeptide region derived from a Shiga toxin A Subunit. Non-limiting examples of Shiga toxin effector functions include cellular internalization, subcellular routing, catalytic activity, and cytotoxicity. Non-limiting examples of Shiga toxin catalytic activities include ribosome inactivation, protein synthesis inhibition, N-glycosidase activity, polynucleotide:adenosine glycosidase activity, RNAase activity, and DNAase activity. RIPs can depurinate nucleic acids, polynucleosides, polynucleotides, rRNA, ssDNA, dsDNA, mRNA (and polyA), and viral nucleic acids (Barbieri L et al., *Biochem J* 286: 1-4 (1992); Barbieri L et al., *Nature* 372: 624 (1994); Ling J et al., *FEBS Lett* 345: 143-6 (1994); Barbieri L et al., *Biochem J* 319: 507-13 (1996); Roncuzzi L, Gasperi-Campani A, *FEBS Lett* 392: 16-20 (1996); Stirpe F et al., *FEBS Lett* 382: 309-12 (1996); Barbieri L et al., *Nucleic Acids Res* 25: 518-22 (1997); Wang P, Tumer N, *Nucleic Acids Res* 27: 1900-5 (1999); Barbieri L et al., *Biochim Biophys Acta* 1480: 258-66 (2000); Barbieri L et al., *J Biochem* 128: 883-9 (2000); Bagga S et al., *J Biol Chem* 278: 4813-20 (2003); Picard D et al., *J Biol Chem* 280: 20069-75 (2005)). Some RIPs show antiviral activity and superoxide dismutase activity (Erice A et al., *Antimicrob Agents Chemother* 37: 835-8 (1993): Au T et al., *FEBS Lett* 471: 169-72 (2000); Parikh B, Tumer N, *Mini Rev Med Chem* 4: 523-43 (2004); Sharma N et al., *Plant Physiol* 134: 171-81 (2004)). Shiga toxin catalytic activities have been observed both in vitro and in vivo. Assays for Shiga toxin effector activity can measure various activities, such as, e.g., protein synthesis inhibitory activity, depurination activity, inhibition of cell growth, cytotoxicity, supercoiled DNA relaxation activity, and/or nuclease activity.

As used herein, the retention of Shiga toxin effector function refers to a level of Shiga toxin functional activity, as measured by an appropriate quantitative assay with reproducibility comparable to a wild-type Shiga toxin effector polypeptide control. For ribosome inhibition, Shiga toxin effector function is exhibiting an $IC_{50}$ of 10,000 pM or less. For cytotoxicity in a target positive cell kill assay, Shiga toxin effector function is exhibiting a $CD_{50}$ of 1,000 nM or less, depending on the cell type and its expression of the appropriate extracellular target biomolecule.

As used herein, the retention of "significant" Shiga toxin effector function refers to a level of Shiga toxin functional activity, as measured by an appropriate quantitative assay with reproducibility comparable to a wild-type Shiga toxin effector polypeptide control. For in vitro ribosome inhibition, significant Shiga toxin effector function is exhibiting an $IC_{50}$ of 300 pM or less depending on the source of the ribosomes (e.g. bacteria, archaea, or eukaryote (algae, fungi, plants, or animals)). This is significantly greater inhibition as compared to the approximate $IC_{50}$ of 100,000 pM for the catalytically inactive SLT-1A 1-251 double mutant (Y77S, E167D). For cytotoxicity in a target positive cell kill assay in laboratory cell culture, significant Shiga toxin effector function is exhibiting a $CD_{50}$ of 100, 50, or 30 nM or less, depending on the cell line and its expression of the appropriate extracellular target biomolecule. This is significantly greater cytotoxicity to the appropriate target cell line as compared to the SLT-1A component alone, without a cell-targeting binding region, which has a $CD_{50}$ of 100-10,000 nM, depending on the cell line.

For some samples, accurate values for either $IC_{50}$ or $CD_{50}$ might be unobtainable due to the inability to collect the required data points for an accurate curve fit. Inaccurate $IC_{50}$ and/or $CD_{50}$ values should not be considered when determining significant Shiga toxin effector function activity. Data insufficient to accurately fit a curve as described in the analysis of the data from exemplary Shiga toxin effector function assays, such as, e.g., assays described in the Examples, should not be considered as representative of actual Shiga toxin effector function. For example, theoretically neither an $IC_{50}$ nor $CD_{50}$ can be determined if greater than 50% ribosome inhibition or cell death, respectively, does not occur in a concentration series for a given sample.

The failure to detect activity in Shiga toxin effector function may be due to improper expression, polypeptide folding, and/or polypeptide stability rather than a lack of cell entry, subcellular routing, and/or enzymatic activity. Assays for Shiga toxin effector functions may not require much polypeptide of the invention to measure significant amounts of Shiga toxin effector function activity. To the extent that an underlying cause of low or no effector function is determined empirically to relate to protein expression or stability, one of skill in the art may be able to compensate for such factors using protein chemistry and molecular engineering techniques known in the art, such that a Shiga toxin functional effector activity may be restored and measured. As examples, improper cell-based expression may be compensated for by using different expression control sequences; improper polypeptide folding and/or stability may benefit from stabilizing terminal sequences, or compensatory mutations in non-effector regions which stabilize the three-dimensional structure of the protein, etc. When new assays for individual Shiga toxin functions become available, CD8+ T-cell hyper-immunized and/or B-cell/CD4+ T-cell de-immunized Shiga toxin effector polypeptides may be analyzed for any level of those Shiga toxin effector functions, such as a being within 1000-fold or 100-fold or less the activity of a wild-type Shiga toxin effector polypeptide or exhibiting 3-fold to 30-fold or greater activity as compared to a functional knockout Shiga toxin effector polypeptide.

Sufficient subcellular routing may be merely deduced by observing cytotoxicity in cytotoxicity assays, such as, e.g., cytotoxicity assays based on T-cell epitope presentation or based on a toxin effector function involving a cytosolic and/or ER target substrate.

It should be noted that even if the cytotoxicity of a Shiga toxin effector polypeptide is reduced relative to wild-type, in practice, applications using attenuated CD8+ T-cell hyper-immunized and/or B-cell/CD4+ T-cell de-immunized Shiga toxin effector polypeptides may be equally or more effective than those using wild-type Shiga toxin effector polypeptides because the reduced antigenicity and/or immunogenicity might offset the reduced cytotoxicity, such as, e.g., by allowing higher dosages, more repeated administrations, or chronic administration. Wild-type Shiga toxin effector polypeptides are very potent, being able to kill with only one molecule reaching the cytosol or perhaps 40 molecules being internalized. CD8+ T-cell hyper-immunized and/or B-cell/CD4+ T-cell de-immunized Shiga toxin effector polypeptides with even considerably reduced Shiga toxin effector functions, such as, e.g., subcellular routing or cytotoxicity, as compared to wild-type Shiga toxin effector polypeptides may still be potent enough for applications based on targeted cell killing and/or specific cell detection.

Certain embodiments of the present invention provide polypeptides comprising a Shiga toxin effector polypeptide comprising an amino acid sequence derived from an A Subunit of a member of the Shiga toxin Family, the Shiga toxin effector region comprising a disruption of at least one natively positioned B-cell epitope region provided herein (see e.g. Tables 2, 3, and 4). In certain embodiments, a CD8+ T-cell hyper-immunized and B-cell/CD4+ T-cell de-immunized Shiga toxin effector polypeptide of the invention may comprise or consist essentially of full-length Shiga toxin A Subunit (e.g. SLT-1A (SEQ ID NO:1), StxA (SEQ ID NO:2), or SLT-2A (SEQ ID NO:3)) comprising at least one disruption of the amino acid sequence selected from the group of natively positioned amino acids consisting of: the B-cell epitope regions 1-15 of SEQ ID NO:1 or SEQ ID NO:2; 3-14 of SEQ ID NO:3; 26-37 of SEQ ID NO:3; 27-37 of SEQ ID NO:1 or SEQ ID NO:2; 39-48 of SEQ ID NO:1 or SEQ ID NO:2; 42-48 of SEQ ID NO:3; 53-66 of SEQ ID NO:1, SEQ ID NO:2, or SEQ ID NO:3; 94-115 of SEQ ID NO:1, SEQ ID NO:2, or SEQ ID NO:3; 141-153 of SEQ ID NO:1 or SEQ ID NO:2; 140-156 of SEQ ID NO:3; 179-190 of SEQ ID NO:1 or SEQ ID NO:2; 179-191 of SEQ ID NO:3, 204 of SEQ ID NO:3; 205 of SEQ ID NO:1 or SEQ ID NO:2; and 210-218 of SEQ ID NO:3; 240-260 of SEQ ID NO:3; 243-257 of SEQ ID NO:1 or SEQ ID NO:2; 254-268 of SEQ ID NO:1 or SEQ ID NO:2; 262-278 of SEQ ID NO:3; 281-297 of SEQ ID NO:3; and 285-293 of SEQ ID NO:1 or SEQ ID NO:2, and the CD4+ T-cell epitope regions 4-33 of SEQ ID NO:1 or SEQ ID NO:2, 34-78 of SEQ ID NO:1 or SEQ ID NO:2, 77-103 of SEQ ID NO:1 or SEQ ID NO:2, 128-168 of SEQ ID NO:1 or SEQ ID NO:2, 160-183 of SEQ ID NO:1 or SEQ ID NO:2, 236-258 of SEQ ID NO:1 or SEQ ID NO:2, and 274-293 of SEQ ID NO:1 or SEQ ID NO:2; or the equivalent position in a conserved Shiga toxin effector polypeptide and/or non-native Shiga toxin effector polypeptide sequence.

Certain embodiments of the present invention provide polypeptides comprising a Shiga toxin effector polypeptide comprising an amino acid sequence derived from an A Subunit of a member of the Shiga toxin Family, the Shiga toxin effector region comprising a disruption of at least one natively positioned CD4+ T-cell epitope region provided herein (see e.g. Tables 2, 3, and 4). In certain embodiments, a CD8+ T-cell hyper-immunized and B-cell/CD4+ T-cell de-immunized Shiga toxin effector polypeptide of the invention may comprise or consist essentially of full-length Shiga toxin A Subunit (e.g. SLT-1A (SEQ ID NO:1), StxA (SEQ ID NO:2), or SLT-2A (SEQ ID NO:3)) comprising at least one disruption of the amino acid sequence selected from the group of natively positioned amino acids consisting of: 4-33, 34-78, 77-103, 128-168, 160-183, 236-258, and 274-293; or the equivalent position in a conserved Shiga toxin effector polypeptide and/or non-native Shiga toxin effector polypeptide sequence.

In certain embodiments, a Shiga toxin effector polypeptide of the present invention may comprise or consist essentially of a truncated Shiga toxin A Subunit. Truncations of Shiga toxin A Subunits might result in the deletion of entire B-cell epitope regions without affecting toxin effector catalytic activity and cytotoxicity. The smallest Shiga toxin A Subunit fragment exhibiting significant enzymatic activity is a polypeptide composed of residues 75-247 of StxA (Al-Jaufy, *Infect Immun* 62: 956-60 (1994)). Truncating the carboxy-terminus of SLT-1A, StxA, or SLT-2A to amino acids 1-251 removes two predicted B-cell epitope regions, two predicted CD4 positive (CD4+) T-cell epitopes, and a predicted discontinuous B-cell epitope. Truncating the amino-terminus of SLT-1A, StxA, or SLT-2A to 75-293 removes at least three predicted B-cell epitope regions and three predicted CD4+ T-cell epitopes. Truncating both amino- and carboxy-terminals of SLT-1A, StxA, or SLT-2A to 75-251 deletes at least five predicted B-cell epitope regions, four putative CD4+ T-cell epitopes, and one predicted discontinuous B-cell epitope.

In certain embodiments, a Shiga toxin effector polypeptide of the present invention may comprise or consist essentially of a full-length or truncated Shiga toxin A Subunit with at least one mutation, e.g. deletion, insertion, inversion, or substitution, in a provided B-cell and/or CD4+ T-cell epitope region. In certain further embodiments, the polypeptides comprise a disruption which comprises a deletion of at least one amino acid within the B-cell and/or CD4+ T-cell epitope region. In certain further embodiments, the polypeptides comprise a disruption which comprises an insertion of at least one amino acid within the B-cell and/or CD4+ T-cell epitope region. In certain further embodiments, the polypeptides comprise a disruption which comprises an inversion of amino acids, wherein at least one inverted amino acid is within the B-cell and/or CD4+ T-cell epitope region. In certain further embodiments, the polypeptides comprise a disruption which comprises a mutation, such as an amino acid substitution to a non-standard amino acid or an amino acid with a chemically modified side chain. Numerous examples of amino acid substitutions are provided in the Examples.

In other embodiments, the Shiga toxin effector polypeptides of the present invention comprises or consists essentially of a truncated Shiga toxin A Subunit which is shorter than a full-length Shiga toxin A Subunit wherein at least one amino acid is disrupted in a natively positioned B-cell and/or CD4+ T-cell epitope region provided in the Examples (see Tables 2, 3, and/or 4).

The CD8+ T-cell hyper-immunized and/or B-cell CD4+ T-cell de-immunized Shiga toxin effector polypeptides of the invention may be smaller than the full length A subunit, such as, e.g., consisting of the polypeptide region from amino acid position 77 to 239 (SLT-1A (SEQ ID NO:1) or StxA (SEQ ID NO:2)) or the equivalent in other A Subunits of members of the Shiga toxin family (e.g. 77 to 238 of (SEQ ID NO:3)). For example, in certain embodiments of the present invention, the Shiga toxin effector polypeptides derived from SLT-1A may be derived from amino acids 75 to 251 of SEQ ID NO:1, 1 to 241 of SEQ ID NO:1, 1 to 251 of SEQ ID NO:1, or amino acids 1 to 261 of SEQ ID NO:1 wherein at least one amino acid is disrupted in an endogenous B-cell and/or CD4+ T-cell epitope region provided in the Examples (Tables 2, 3, and/or 4). Similarly, CD8+ T-cell hyper-immunized and/or B-cell/CD4+ T-cell de-immunized Shiga toxin effector regions derived from StxA may comprise or consist essentially of amino acids 75 to 251 of SEQ ID NO:2, 1 to 241 of SEQ ID NO:2, 1 to 251 of SEQ ID NO:2, or amino acids 1 to 261 of SEQ ID NO:2 wherein at least one amino acid is disrupted in at least one endogenous B-cell and/or CD4+ T-cell epitope region provided in the Examples (Tables 2, 3, and/or 4). Additionally, the Shiga toxin effector regions derived from SLT-2 may comprise or consist essentially of amino acids 75 to 251 of SEQ ID NO:3, 1 to 241 of SEQ ID NO:3, 1 to 251 of SEQ ID NO:3, or amino acids 1 to 261 of SEQ ID NO:3 wherein at least one amino acid is disrupted in at least one B-cell and/or CD4+ T-cell epitope region provided in the Examples (Tables 2, 3, and/or 4).

Certain embodiments of the cell-targeted molecules of the present invention each comprise a CD8+ T-cell hyper-immunized and/or B-cell/CD4+ T-cell de-immunized Shiga toxin effector polypeptide which retains a Shiga toxin effector function but which may be engineered from a cytotoxic parental molecule to a polypeptide with diminished or abolished cytotoxicity for non-cytotoxic functions, e.g., effectuating cytostasis, delivery of exogenous materials, and/or detection of cell types, by mutating one or more key residues for enzymatic activity.

For certain embodiments, the polypeptides of the present invention comprise Shiga toxin effector polypeptides. For certain embodiments, the polypeptides of the present invention comprise or consist essentially of one of the polypeptides of SEQ ID NOs: 11-43.

For certain embodiments, the cell-targeted molecules of the present invention are cytotoxic proteins comprising Shiga toxin effector polypeptides. For certain embodiments, the cell-targeted molecules of the present invention comprise or consist essentially of one of the polypeptides of SEQ ID NOs: 49-54.

2. Diphtheria Toxin Derived. CD8+ T-Cell Hyper-Immunized and/or B-Cell/CD4+ T-Cell De-Immunized Polypeptides For purposes of the present invention, the phrase "diphtheria toxin effector region" refers to a polypeptide region derived from a diphtheria toxin of a member of the Diphtheria toxin family that is capable of exhibiting at least one diphtheria toxin function. Diphtheria toxin functions include, e.g., cell entry, endosome escape, directing subcellular routing, catalytically inactivating ribosomes, effectuating cytotoxicity, and effectuating cytostatic effects.

For purposes of the present invention, a diphtheria toxin effector function is a biological activity conferred by a polypeptide region derived from a diphtheria toxin. Non-limiting examples of diphtheria toxin effector functions include cellular internalization, subcellular routing, catalytic activity, and cytotoxicity. Non-limiting examples of diphtheria toxin catalytic activities include ribosome inactivation, protein synthesis inhibition, and ADP-ribosylation. Diphtheria toxin catalytic activities have been observed both in vitro and in vivo. Assays for diphtheria toxin effector activity can measure various activities, such as, e.g., protein synthesis inhibitory activity, ADP-ribosylation, inhibition of cell growth, and/or cytotoxicity. Sufficient subcellular routing may be merely deduced by observing cytotoxicity in cytotoxicity assays, such as, e.g., cytotoxicity assays based on T-cell epitope presentation or based on a toxin effector function involving a cytosolic and/or ER target substrate.

It should be noted that even if a toxin effector activity of a diphtheria toxin effector polypeptide is reduced relative to wild-type, in practice, applications using attenuated CD8+ T-cell hyper-immunized and/or B-cell/CD4+ T-cell de-immunized diphtheria toxin effector polypeptides may be equally or more effective than those using diphtheria toxin effector polypeptides with wild-type levels of activity because the reduced antigenicity and/or immunogenicity might offset the reduced cytotoxicity, such as, e.g., by allowing higher dosages, more repeated administrations, or chronic administration. Diphtheria toxin effector polypeptides exhibiting only the effector activity of subcellular routing are appropriate for use in applications based on targeted cell CD8+ T-cell epitope delivery.

Certain embodiments of the present invention provide polypeptides comprising a diphtheria toxin effector polypeptide comprising an amino acid sequence derived from an A Subunit of a member of the Diphtheria toxin Family, the diphtheria toxin effector region comprising a disruption of at least one natively positioned B-cell and/or CD4+ T-cell epitope region provided herein (see e.g. Table 5). In certain embodiments, a CD8+ T-cell hyper-immunized and B-cell/CD4+ T-cell de-immunized diphtheria toxin effector polypeptide of the invention may comprise or consist essentially of the polypeptide of amino acids 2-389 of SEQ ID NO:45 comprising at least one disruption of the amino acid sequence selected from the group of natively positioned amino acids consisting of: 3-10 of SEQ ID NO:44, 15-31 of SEQ ID NO:44, 32-54 of SEQ ID NO:44; 33-43 of SEQ ID NO:44, 71-77 of SEQ ID NO:44, 93-113 of SEQ ID NO:44, 125-131 of SEQ ID NO:44, 138-146 of SEQ ID NO:44, 141-167 of SEQ ID NO:44, 165-175 of SEQ ID NO:44, 182-201 of SEQ ID NO:45, 185-191 of SEQ ID NO:44, and 225-238 of SEQ ID NO:45; or the equivalent position in a conserved diphtheria toxin effector polypeptide and/or non-native diphtheria toxin effector polypeptide sequence.

Optionally, the diphtheria toxin effector polypeptide of the invention may comprise one or more mutations (e.g. substitutions, deletions, insertions or inversions) as compared to wild-type as long as at least one amino acid is disrupted in at least one natively positioned B-cell and/or CD4+ T-cell epitope region provided in the Examples (see Table 5). In certain embodiments of the invention, the CD8+ T-cell hyper-immunized and/or B-cell/CD4+ T-cell de-immunized diphtheria toxin effector polypeptides have sufficient sequence identity to a naturally occurring diphtheria toxin A Subunit to retain cytotoxicity after entry into a cell, either by well-known methods of host cell transformation, transfection, infection or induction, or by internalization mediated by a cell-targeting binding region linked with the diphtheria toxin effector polypeptide.

The most critical residues for enzymatic activity and/or cytotoxicity in the diphtheria toxin A Subunits have been mapped to the following residue-positions: histidine-21, tyrosine-27, glycine-52, tryptophan-50, tyrosine-54, tyrosine-65, glutamate-148, and tryptophan-153 (Tweten R et al., *J Biol Chem* 260: 10392-4 (1985); Wilson B et al., *J Biol Chem* 269: 23296-301 (1994); Bell C, Eisenberg D, *Biochemistry* 36: 481-8 (1997); Cummings M et al., *Proteins* 31: 282-98 (1998); Keyvani K et al., *Life Sci* 64: 1719-24 (1999); Dolan K et al., *Biochemistry* 39: 8266-75 (2000); Zdanovskaia M et al., *Res Micrbiol* 151: 557-62 (2000); Kahn K, Bruice T, *J Am Chem Soc* 123: 11960-9 (2001); Malito E et al., *Proc Natl Acad Sci USA* 109: 5229-34 (2012)). The capacity of a cytotoxic, cell-targeted molecule of the invention to cause cell death, e.g. its cytotoxicity, may be measured using any one or more of a number of assays well known in the art.

Among certain embodiments of the present invention, the polypeptides comprise the CD8+ T-cell hyper-immunized and B-cell/CD4+ T-cell de-immunized diptheria toxin effector comprising or consisting essentially of amino acids 2 or amino acids 2-389 of SEQ ID NO:45 wherein at least one amino acid is disrupted in the natively positioned B-cell epitope and/or CD4+ T-cell epitope regions provided in the Examples (Table 5).

For certain embodiments, the polypeptides of the present invention comprise diphtheria toxin effector polypeptides. For certain embodiments, the polypeptides of the present invention comprise or consist essentially of one of the polypeptides of SEQ ID NOs: 46-48.

For certain embodiments, the cell-targeted molecules of the present invention are cytotoxic proteins comprising diphtheria toxin effector polypeptides. For certain embodiments, the cell-targeted molecules of the present invention comprise or consist essentially of one of the polypeptides of SEQ ID NOs: 55-60.

For certain embodiments, the polypeptide of the present invention comprises or consists essentially of any one of the polypeptides of SEQ ID NOs: 11-43 or 46-48.

Cell-targeted molecules of the present invention each comprise at least one T-cell hyper-immunized and/or B-cell/CD4+ T-cell de-immunized polypeptide linked to a cell-targeting moiety which can bind specifically to at least one extracellular target biomolecule in physical association with a cell, such as a target biomolecule expressed on the surface of a cell. This general structure is modular in that any number of diverse cell-targeting moieties may be linked to the CD8+ T-cell hyper-immunized and/or B-cell/CD4+ T-cell de-immunized polypeptides of the present invention.

It is within the scope of the invention to use fragments, variants, and/or derivatives of the polypeptides and cell-targeted molecules of the present invention which contain a functional binding site to any extracellular part of a target biomolecule, and even more preferably capable of binding a target biomolecule with high affinity (e.g. as shown by $K_D$). Any cell-targeting moiety which binds an extracellular part of a target biomolecule with a dissociation constant ($K_D$) of $10^{-5}$ to $10^{-12}$ moles/liter, preferably less than 200 nM, may be substituted for use in making cell-targeted molecules of the invention and methods of the invention.

VI. Variations in the Polypeptide Sequence of the T-Cell Hyper-Immunized and/or B-Cell/CD4+ T-Cell De-Immunized Polypeptides of the Invention and Cell-Targeted Molecules Comprising the Same The skilled worker will recognize that variations may be made to T-cell hyper-immunized and/or B-cell/CD4+ T-cell de-immunized polypeptides and cell-targeted molecules of the present invention, and polynucleotides encoding any of the former, without diminishing their biological activities, e.g., by maintaining the overall structure and function of the toxin effector region in conjunction with one or more epitope disruptions which reduce antigenic and/or immunogenic potential. For example, some modifications may facilitate expression, purification, and/or pharmacokinetic properties, and/or immunogenicity. Such modifications are well known to the skilled worker and include, for example, a methionine added at the amino terminus to provide an initiation site, additional amino acids placed on either terminus to create conveniently located restriction sites or termination codons, and biochemical affinity tags fused to either terminus to provide for convenient detection and/or purification.

Also contemplated herein is the inclusion of additional amino acid residues at the amino and/or carboxy termini, such as sequences for epitope tags or other moieties. The additional amino acid residues may be used for various purposes including, e.g., facilitating cloning, facilitating expression, post-translational modification, facilitating synthesis, purification, facilitating detection, and administration. Non-limiting examples of epitope tags and moieties are chitin binding protein domains, enteropeptidase cleavage sites, Factor Xa cleavage sites, FlAsH tags, FLAG tags, green fluorescent proteins (GFP), glutathione-S-transferase moieties, HA tags, maltose binding protein domains, myc tags, polyhistidine tags, ReAsH tags, strep-tags, strep-tag 11, TEV protease sites, thioredoxin domains, thrombin cleavage site, and V5 epitope tags.

In certain of the above embodiments, the polypeptide sequence of the CD8+ T-cell hyper-immunized and/or B-cell/CD4+ T-cell de-immunized polypeptides and/or cell-targeted proteins of the invention are varied by one or more conservative amino acid substitutions introduced into the polypeptide region(s) as long as at least one amino acid is disrupted in at least one natively positioned B-cell epitope region provided herein. As used herein, the term "conservative substitution" denotes that one or more amino acids are replaced by another, biologically similar amino acid residue. Examples include substitution of amino acid residues with similar characteristics, e.g. small amino acids, acidic amino acids, polar amino acids, basic amino acids, hydrophobic amino acids and aromatic amino acids (see, for example, Table C, infra). An example of a conservative substitution with a residue normally not found in endogenous, mammalian peptides and proteins is the conservative substitution of an arginine or lysine residue with, for example, ornithine, canavanine, aminoethylcysteine, or another basic amino acid. For further information concerning phenotypically silent substitutions in peptides and proteins see, e.g., Bowie J et al., *Science* 247: 1306-10 (1990).

TABLE C

Examples of Conservative Amino Acid Substitutions

| I | II | III | IV | V | VI | VII | VIII | IX | X | XI | XII | XIII | XIV |
|---|----|-----|----|---|----|----|------|----|---|----|-----|------|-----|
| A | D | H | C | F | N | A | C | F | A | C | A | A | D |
| G | E | K | I | W | Q | G | M | H | C | D | C | C | E |
| P | Q | R | L | Y | S | I | P | W | F | E | D | D | G |
| S | N |   | M |   | T | L |   |   | Y | G | H | G | E |
| T |   |   | V |   |   | V |   |   | H | K | N | G | P |
|   |   |   |   |   |   |   |   |   | I | N | P | H | Q |
|   |   |   |   |   |   |   |   |   | L | Q | S | K | R |
|   |   |   |   |   |   |   |   |   | M | R | T | N | S |
|   |   |   |   |   |   |   |   |   | R | S | V | Q | T |
|   |   |   |   |   |   |   |   |   | T | T |   | R |   |
|   |   |   |   |   |   |   |   |   | V |   |   | S |   |
|   |   |   |   |   |   |   |   |   | W |   |   | P |   |
|   |   |   |   |   |   |   |   |   | Y |   |   | T |   |

In the conservative substitution scheme in Table C, exemplary conservative substitutions of amino acids are grouped by physicochemical properties—I: neutral, hydrophilic; II: acids and amides; III: basic; IV: hydrophobic; V: aromatic, bulky amino acids, VI hydrophilic uncharged, VII aliphatic uncharged, VIII non-polar uncharged, IX cycloalkenyl-associated, X hydrophobic, XI polar, XII small, XIII turn-permitting, and XIV flexible. For example, conservative amino acid substitutions include the following: 1) S may be substituted for C; 2) M or L may be substituted for F; 3) Y may be substituted for M; 4) Q or E may be substituted for K; 5) N or Q may be substituted for H; and 6) H may be substituted for N.

Additional conservative amino acid substitutions include the following: 1) S may be substituted for C; 2) M or L may be substituted for F; 3) Y may be substituted for M; 4) Q or E may be substituted for K; 5) N or Q may be substituted for H; and 6) H may be substituted for N.

In certain embodiments, the CD8+ T-cell hyper-immunized and/or B-cell/CD4+ T-cell de-immunized polypeptides and/or cell-targeted molecules (e.g. cell-targeted proteins) of the present invention may comprise functional fragments or variants of a polypeptide region of the invention that have, at most, 20, 15, 10, 9, 8, 7, 6, 5, 4, 3, 2, or 1 amino acid substitutions.

In certain embodiments, the CD8+ T-cell hyper-immunized and/or B-cell/CD4+ T-cell de-immunized polypeptides and/or cell-targeted molecules of the present invention may comprise functional fragments or variants of a polypeptide region of the invention that have, at most, 20, 15, 10, 9, 8, 7, 6, 5, 4, 3, 2, or 1 amino acid substitutions compared to a polypeptide sequence recited herein, as long as it retains a disruption of at least one amino acid in a natively positioned B-cell and/or CD4+ T-cell epitope region provided in the Examples (Tables 2, 3, 4, and/or 5) and as long as the polypeptides or proteins retain a T-cell epitope delivery functionality alone and/or as a component of a therapeutic and/or diagnostic composition. Variants of the CD8+ T-cell hyper-immunized and/or B-cell/CD4+ T-cell de-immunized Shiga toxin effector polypeptides and/or cell-targeted proteins of the invention are within the scope of the invention as a result of changing a polypeptide of the cell-targeted protein of the invention by altering one or more amino acids or deleting or inserting one or more amino acids, such as within the binding region or the CD8+ T-cell hyper-immunized and/or B-cell/CD4+ T-cell de-immunized polypeptide region, in order to achieve desired properties, such as changed cytotoxicity, changed cytostatic effects, changed immunogenicity, and/or changed serum half-life. A B-cell epitope de-immunized and CD8+ T-cell hyper-immunized polypeptide and/or a cell-targeted protein of the invention may further be with or without a signal sequence.

Accordingly, in certain embodiments, the Shiga toxin effector or diphtheria toxin effector polypeptides of the present invention comprise or consists essentially of amino acid sequences having at least 55%, 60%, 65%, 70%, 75%, 80%, 85%, 90%, 95%, 97%, 98%, 990%, 99.5% or 99.7% overall sequence identity to a naturally occurring toxin, such as, e.g., Shiga toxin A Subunit, such as SLT-1A (SEQ ID NO:1), StxA (SEQ ID NO:2), and/or SLT-2A (SEQ ID NO:3), or a diphtheria toxin catalytic domain (SEQ ID NO:44). In certain embodiments, the de-immunized Shiga toxin effector or diphtheria toxin effector polypeptides of the present invention comprise or consists essentially of amino acid sequences having at least 55%, 60%, 65%, 70%, 75%, 80%, 85%, 90%, 95%, 97%, 98%, 99%, 99.5% or 99.7% overall sequence identity to a naturally occurring toxin wherein at least one amino acid is disrupted in at least one natively positioned B-cell and/or CD4+ T-cell epitope region provided in the Examples (Tables 2, 3, 4, and/or 5).

In certain embodiments of the cell-targeted molecules of the present invention, one or more amino acid residues may be mutated, inserted, or deleted in order to increase the enzymatic activity of the CD8+ T-cell hyper-immunized and/or B-cell/CD4+ T-cell de-immunized toxin effector polypeptide region. For example, mutating residue-position alanine-231 in Stx1A to glutamate increased its enzymatic activity in vitro (Suhan M, Hovde C, *Infect Immun* 66: 5252-9 (1998)).

In certain embodiments of the cell-targeted molecules of the present invention, one or more amino acid residues may be mutated or deleted in order to reduce or eliminate catalytic and/or cytotoxic activity of the CD8+ T-cell hyper-immunized and/or B-cell/CD4+ T-cell de-immunized toxin effector polypeptide region. For example, the catalytic and/or cytotoxic activity of the A Subunits of members of the Shiga toxin family or Diphtheria toxin family may be diminished or eliminated by mutation or truncation.

In certain embodiments of the present invention, the ribotoxin effector region has been altered such that it no longer supports catalytic inactivation of a ribosome in vitro. However, other means of modifying a ribotoxic effector region to reduce or eliminate ribotoxicity are also envisioned within the scope of the present invention. For example, certain mutations can render a ribotoxic effector region unable to bind its ribosome substrate despite maintaining catalytic ability observable by an in vitro assay whereas other mutations can render a ribotoxic region unable to target a specific ribonucleic acid sequence within in the ribosome despite maintaining catalytic ability towards naked nucleic acids in vitro (see e.g. Alford S et al., *BMC Biochem* 10: 9 (2009); Alvarez-Garcia E et al., *Biochim Biophys Act* 1814: 1377-82 (2011); Wong Y et al., *PLoS One* 7: e49608 (2012)).

In DT, there are several amino acid residues known to be important for catalytic activity, such as, e.g., histidine-21, tyrosine-27, glycine-52, tryptophan-50, tyrosine-54, tyrosine-65, glutamate-148, and tryptophan-153 (Tweten R et al., *J Biol Chem* 260: 10392-4 (1985); Wilson B et al., *J Biol Chem* 269: 23296-301 (1994); Bell C, Eisenberg D, *Biochemistry* 36: 481-8 (1997): Cummings M et al., *Proteins* 31: 282-98 (1998); Keyvani K et al., *Life Sci* 64: 1719-24 (1999); Dolan K et al., *Biochemistry* 39: 8266-75 (2000); Zdanovskaia M et al., *Res Micrbiol* 151: 557-62 (2000); Kahn K, Bruice T, *J Am Chem Soc* 123: 11960-9 (2001); Malito E et al., *Proc Natl Acad Sci USA* 109: 5229-34 (2012)). Glutamate-581 in cholix toxin is conserved with glutamate-148 in DT (Jorgensen R et al., *EMBO Rep* 9: 802-9 (2008)), and thus, mutations of glutamate-581 in cholix toxin are predicted to reduce the enzymatic activity of cholix toxin.

In PE, there are several amino acid residues known to be important for catalytic activity, such as, e.g., tryptophan-417, histidine-426, histidine-440, glycine-441, arginine-485, tryptophan-458, tryptophan-466, tyrosine-470, tyrosine-481, glutamate-546, arginine-551, glutamate-553, and tryptophan-558 (Douglas C, Collier R, *J Bacteriol* 169: 4967-71 (1987); Wilson B, Colliver R, *Curr Top Microbiol Immunol* 175: 27-41 (1992)); Beattie B et al., *Biochemistry* 35: 15134-42 (1996); Roberts T, Merrill A, *Biochem J* 367: 601-8 (2002); Yates S et al., *Biochem J* 385: 667-75 (2005); Jorgensen R et al., *EMBO Rep* 9: 802-9 (2008)). Glutamate-574 and glutamate-581 in cholix toxin is conserved with glutamate-546 and glutamate-553 in PE respectively (Jorgensen R et al., *EMBO Rep* 9: 802-9 (2008)), and thus, mutations of glutamate-574 and/or glutamate-581 in cholix toxin are predicted to reduce the enzymatic activity of cholix toxin.

Because the catalytic domains of cholix toxin, DT, PE, and other related enzymes are superimposable (Jorgensen R, et al., *J Biol Chem* 283: 10671-8 (2008)), amino acid residues required for catalytic activity may be predicted in related polypeptide sequences by sequence alignment methods known to the skilled worker.

Several members of the RIP family have been well studied with regard to catalytic residues. For example, most RIP family members share five key amino acid residues for catalysis, such as e.g., two tyrosines near the amino terminus of the catalytic domain, a glutamate and arginine near the center of the catalytic domain, and a tryptophan near the carboxy terminus of the catalytic domain (Lebeda F, Olson M, *Int J Biol Macromol* 24: 19-26 (1999); Mlsna D et al., *Protein Sci* 2: 429-35 (1993); de Virgilio M et al., *Toxins* 2: 2699-737 (2011); Walsh M, *Virulence* 4: 774-84 (2013))). Because the catalytic domains of members of the RIP family are superimposable, amino acid residues required for catalytic activity may be predicted in unstudied and/or new members of the RIP family by sequence alignment methods known to the skilled worker (see e.g. Husain J et al., *FEBS Lett* 342: 154-8 (1994); Ren J et al., *Structure* 2: 7-16 (1994); Lebeda F, Olson M, *Int J Biol Macromol* 24: 19-26 (1999); Ma Q et al., *Acta Crystallogr D Biol Crystallogr* 56: 185-6 (2000); Savino C et al., *FEBS Lett* 470: 239-43 (2000); Robertus J, Monzingo A, *Mini Rev Med Chem* 4: 477-86 (2004); Mishra V et al., *J Biol Chem* 280: 20712-21 (2005); Zhou C et al., *Bioinformatics* 21: 3089-96 (2005); Lubelli C et al., *Anal Biochem* 355: 102-9 (2006); Touloupakis E et al., *FEBS J* 273: 2684-92 (2006); Hou X et al., *BMC Struct Biol* 7: 29 (2007); Meyer A et al., *Biochem Biophys Res Commun* 364: 195-200 (2007); Ruggiero A et al., *Protein Pept Lett* 14: 97-100 (2007); Wang T et al., *Amino Acids* 34: 239-43 (2008)).

In the A Subunit of abrin, there are several amino acid residues important for catalytic activity, such as, e.g., tyrosine-74, tyrosine-113, glutamate-164, arginine-167, and tryptophan-198 (Hung C et al., *Eur J Biochem* 219: 83-7 (1994); Chen J et al., *Protein Eng* 10: 827-33 (1997); Xie L et al., *Eur J Biochem* 268: 5723-33 (2001)).

In charybdin, there are several amino acid residues important for catalytic activity, such as, e.g., valine-79, tyrosine-117, glutamate-167, and arginine-170 (Touloupakis E et al., *FEBS J* 273: 2684-92 (2006)).

In the A Subunit of cinnamomin, there are several amino acid residues important for catalytic activity, such as, e.g., tyrosine-75, tyrosine-115, glutamate-167, arginine-170, and tryptophan-201 (Hung C et al., *Eur. J Biochem* 219: 83-7 (1994); Chen J et al., *Protein Eng* 10: 827-33 (1997)).

In luffaculin, there are several amino acid residues important for catalytic activity, such as, e.g., tyrosine-70, glutamate-85, tyrosine-110, glutamate-159, and arginine-162 (Hou X et al., *BMC Struct Biol* 7: 29 (2007)).

In luffins, there are several amino acid residues important for catalytic activity, such as, e.g., tyrosine-71, glutamate-86, tyrosine-111, glutamate-160, and arginine-163 (Ma Q et al., *Acta Crystallogr D Biol Crystallogr* 56: 185-6 (2000))

In maize RIPs, there are several amino acid residues important for catalytic activity, such as, e.g., tyrosine-79, tyrosine-115, glutamate-167, arginine-170, and tryptophan-201 (Robertus J, Monzingo A, *Mini Rev Med Chem* 4: 477-86 (2004); Yang Y et al., *J Mol Biol* 395: 897-907 (2009)).

In the PD-Ls, there are several amino acid residues important for catalytic activity, such as, e.g., tyrosine-72, tyrosine-122, glutamate-175, arginine-178, and tryptophan-207 in PDL-1 (Ruggiero A et al., *Biopolymers* 91: 1135-42 (2009)).

In the A Subunit of the mistletoe RIP, there are several amino acid residues important for catalytic activity, such as, e.g., tyrosine-66, phenylalanine-75, tyrosine-110, glutamate-159, arginine-162, glutamate-166, arginine-169, and tryptophan-193 (Langer M et al., *Biochem Biophys Res Commun* 264: 944-8 (1999); Mishra V et al., *Act Crystallogr D Biol Crystallogr* 60: 2295-2304 (2004); Mishra V et al., *J Biol Chem* 280: 20712-21 (2005); Wacker R et al., *J Pept Sci* 11: 289-302 (2005)).

In pokeweed antiviral protein (PAP), there are several amino acid residues important for catalytic activity, such as, e.g., lysine-48, tyrosine-49, arginine-67, arginine-68, asparagine-69, asparagine-70, tyrosine-72, phenylalanine-90, asparagine-91, aspartate-92, arginine-122, tyrosine-123, glutamate-176, arginine-179, tryptophan-208, and lysine-210 (Rajamohan F et al., *J Biol Chem* 275: 3382-90 (2000); Rajamohan F et al., *Biochemistry* 40: 9104-14 (2001)).

In the A chain of ricin, there are several amino acid residues known to be important for catalytic activity, such as, e.g., arginine-48, tyrosine-80, asparagine-122, tyrosine-123, glutamate-177, arginine-180, serine-203, asparagine-209, tryptophan-211, glycine-212, arginine-213, serine-215, and isoleucine-252 (Frankel A et al., *Mol Cell Biol* 9: 415-20 (1989); Schlossman D et al., *Mol Cell Biol* 9: 5012-21 (1989); Gould J et al., *Mol Gen Genet* 230: 91-90 (1991); Ready M et al., *Proteins* 10: 270-8 (1991); Rutenber E et al., *Proteins* 10: 240-50 (1991); Monzingo A, Robertus, J, *J Mol Biol* 227: 1136-45 (1992); Day P et al., *Biochemistry* 35: 11098-103 (1996); Marsden C et al., *Eur J Biochem* 27: 153-62 (2004); Pang Y et al., *PLoS One* 6: e17883 (2011)). In ricin, there are several amino acid residues which when deleted are known to impair the catalytic activity of ricin such as, e.g., N24, F25, A28, V29, Y81, V82, V83, G84, E146, E147, A148, I149, S168, F169, I170, I171, C172, I173, Q174, M175, I176, S177, E178, A179, A180, R181, F182, Q183, Y184, D202, P203, I206, T207, N210, S211, W212, and G213 (Munishkin A, Wool I, *J Biol Chem* 270: 30581-7 (1995); Berrondo M, Gray J, *Proteins* 79: 2844-60 (2011)).

In saporins, there are several amino acid residues known to be important for catalytic activity, such as, e.g., tyrosine-16, tyrosine-72, tyrosine-120, glutamate-176, arginine-179, and tryptophan-208 (Bagga S et al., *J Biol Chem* 278: 4813-20 (2003); Zarovni N et al., *Canc Gene Ther* 14: 165-73 (2007); Lombardi A et al., *FASEB J* 24: 253-65 (2010)). In addition, a signal peptide may be included to reduce catalytic activity (Marshall R et al., *Plant J* 65: 218-29 (2011)).

In trichosanthins, there are several amino acid residues known to be important for catalytic activity, such as, e.g., tyrosine-70, tyrosine-111, glutamate-160, arginine-163, lysine-173, arginine-174, lysine-177, and tryptophan-192 (Wong et al., *Eur J Biochem* 221: 787-91 (1994); Li et al., *Protein Eng* 12: 999-1004 (1999); Yan et al., *Toxicon* 37: 961-72 (1999); Ding et al., *Protein Eng* 16: 351-6 (2003); Guo Q et al., *Protein Eng* 16: 391-6 (2003); Chan D et al., *Nucleic Acid Res* 35: 1660-72 (2007)).

Fungal ribotoxins enzymatically target the same universally conserved SRL ribosomal structure as members of the RIP family and most fungal ribotoxins share an RNase T1 type catalytic domain sequence and secondary structure (Lacadena J et al., *FEMS Microbiol Rev* 31: 212-37 (2007)). Most fungal ribotoxins and related enzymes share three highly conserved amino acid residues for catalysis, two histidine residues and a glutamate residue (e.g. histidine-40, glutamate-58, and histidine-92 in RNase T1). A DSKKP motif (SEQ ID NO:135) is often present in fungal ribotoxins to specifically bind the SRL (Kao R, Davies J, *J Biol Chem* 274: 12576-82 (1999)). Because fungal ribotoxin catalytic domains are superimposable, amino acid residues required for catalytic activity may be predicted in unstudied and/or new fungal ribotoxins using one or more sequence alignment methods known to the skilled worker.

For Aspf1, an internal deletion of 16 amino acid residues (positions 7-22) severely impaired its ribonucleolytic activity and cytotoxicity (Garciá-Ortega L et al., *FEBS J* 272: 2536-44 (2005)).

In mitogillin, there are several amino acid residues known to be important for catalytic activity, such as, e.g., asparagine-7, histidine-49, glutamate-95, lysine-111, arginine-120, and histidine-136 (Kao R et al., *Mol Microbiol* 29: 1019-27 (1998); Kao R, Davies J, *FEBS Lett* 466: 87-90 (2000)).

In restrictocin, there are several amino acid residues known to be important for catalytic activity, such as, e.g., tyrosine-47, histidine-49, glutamate-95, lysine-110, lysine-111, lysine-113, arginine-120, and histidine-136 (Nayak S, Batra J, *Biochemistry* 36: 13693-9 (1997); Nayak S et al., *Biochemistry* 40: 9115-24 (2001); Plantinga M et al., *Biochemistry* 50: 3004-13 (2011)).

In α-sarcin, there are several amino acid residues known to be important for catalytic activity, such as, e.g., tryptophan-48, histidine-49, histidine-50, tryptophan-51, asparagine-54, isoleucine-69, glutamate-95, glutamate-96, lysine-11, lysine-112, lysine-114, arginine-121, histidine-136, histidine-137, lysine-145 (Lacadena J et al., *Biochem J* 309: 581-6 (1995): Lacadena J et al., *Proteins* 37: 474-84 (1999); Martinez-Ruiz A et al., *Toxicon* 37: 1549-63 (1999); de Antonio C et al., *Proteins* 41: 350-61 (2000); Masip M et al., *Eur J Biochem* 268: 6190-6 (2001)).

The cytotoxicity of the A Subunits of members of the Shiga toxin family may be altered, reduced, or eliminated by mutation or truncation. The positions labeled tyrosine-77, glutamate-167, arginine-170, tyrosine-114, and tryptophan-203 have been shown to be important for the catalytic activity of Stx, Stx1, and Stx2 (Hovde C et al., *Proc Natl Acad Sci USA* 85: 2568-72 (1988); Deresiewicz R et al., *Biochemistry* 31: 3272-80 (1992); Deresiewicz R et al., *Mol Gen Genet* 241: 467-73 (1993); Ohmura M et al., *Microb Pathog* 15: 169-76 (1993); Cao C et al., *Microbiol Immunol* 38: 441-7 (1994); Suhan M, Hovde C, *Infect Immun* 66: 5252-9 (1998)). Mutating both glutamate-167 and arginine-170 eliminated the enzymatic activity of Sit-I A1 in a cell-free ribosome inactivation assay (LaPointe P et al., *J Biol Chem* 280: 23310-18 (2005)). In another approach using de novo expression of Slt-I A1 in the endoplasmic reticulum, mutating both glutamate-167 and arginine-170 eliminated Slt-I A1 fragment cytotoxicity at that expression level (LaPointe, *J Biol Chem* 280: 23310-18 (2005)). A truncation analysis demonstrated that a fragment of StxA from residues 75 to 268 still retains significant enzymatic activity in vitro (Haddad, *J Bacteriol* 175: 4970-8 (1993)). A truncated fragment of Slt-I A1 containing residues 1-239 displayed significant enzymatic activity in vitro and cytotoxicity by de novo expression in the cytosol (LaPointe, *J Biol Chem* 280: 23310-18 (2005)). Expression of a Sit-I A1 fragment truncated to residues 1-239 in the endoplasmic reticulum was not cytotoxic because it could not retrotranslocate to the cytosol (LaPointe, *J Biol Chem* 280: 23310-18 (2005)).

The most critical residues for enzymatic activity and/or cytotoxicity in the Shiga toxin A Subunits were mapped to the following residue-positions: aspargine-75, tyrosine-77, tyrosine-114, glutamate-167, arginine-170, arginine-176, and tryptophan-203 among others (Di R et al., *Toxicon* 57: 525-39 (2011)). In particular, a double-mutant construct of Stx2A containing glutamate-E167-to-lysine and arginine- 176-to-lysine mutations was completely inactivated; whereas, many single mutations in Stx1 and Stx2 showed a 10-fold reduction in cytotoxicity. Further, truncation of Stx1A to 1-239 or 1-240 reduced its cytotoxicity, and similarly, truncation of Stx2A to a conserved hydrophobic residue reduced its cytotoxicity. The most critical residues for binding eukaryotic ribosomes and/or eukaryotic ribosome inhibition in the Shiga toxin A Subunit have been mapped to the following residue-positions arginine-172, arginine-176, arginine-179, arginine-188, tyrosine-189, valine-191, and leucine-233 among others (McCluskey A et al., *PLoS One* 7: e31191 (2012)).

Shiga-like toxin 1 A Subunit truncations are catalytically active, capable of enzymatically inactivating ribosomes in vitro, and cytotoxic when expressed within a cell (LaPointe, *J Biol Chem* 280: 23310-18 (2005)). The smallest Shiga toxin A Subunit fragment exhibiting full enzymatic activity is a polypeptide composed of residues 1-239 of Slt1A (LaPointe, *J Biol Chem* 280: 23310-18 (2005)). Although the smallest fragment of the Shiga toxin A Subunit reported to retain substantial catalytic activity was residues 75-247 of StxA (Al-Jaufy, *Infect Immun* 62: 956-60 (1994)), a StxA truncation expressed de novo within a eukaryotic cell requires only up to residue 240 to reach the cytosol and exert catalytic inactivation of ribosomes (LaPointe, *J Biol Chem* 280: 23310-18 (2005)).

In certain embodiments of the CD8+ T-cell hyper-immunized and/or B-cell/CD4+ T-cell de-immunized Shiga toxin effector polypeptides and/or cell-targeted molecules of the present invention derived from SLT-1A (SEQ ID NO:1) or StxA (SEQ ID NO:2), these changes include substitution of the asparagine at position 75, tyrosine at position 77, tyrosine at position 114, glutamate at position 167, arginine at position 170, arginine at position 176, and/or substitution of the tryptophan at position 203. Examples of such substitutions will be known to the skilled worker based on the prior art, such as asparagine at position 75 to alanine, tyrosine at position 77 to serine, substitution of the tyrosine at position 114 to serine, substitution of the glutamate at position 167 to glutamate, substitution of the arginine at position 170 to alanine, substitution of the arginine at position 176 to lysine, and/or substitution of the tryptophan at position 203 to alanine. Other mutations which either enhance or reduce Shiga toxin enzymatic activity and/or cytotoxicity are within the scope of the invention and may be determined using well known techniques and assays disclosed herein.

The CD8+ T-cell hyper-immunized and/or B-cell/CD4+ T-cell de-immunized polypeptides and/or cell-targeted molecules of the invention may optionally be conjugated to one or more additional agents, which may include therapeutic and/or diagnostic agents known in the art, including such agents as described herein.

V. General Functions of the CD8+ T-Cell Hyper-Immunized and/or B-Cell/CD4+ T-Cell De-Immunized Polypeptides of the Present Invention and Cell-Targeted Molecules Comprising the Same The present invention describes various CD8+ T-cell hyper-immunized and/or B-cell/CD4+ T-cell de-immunized polypeptides which may be used as components of various compositions of matter, such as cell-targeted cytotoxic molecules and diagnostic compositions. In particular, CD8+ T-cell hyper-immunized and/or B-cell/CD4+ T-cell de-immunized polypeptides have uses as components of various protein therapeutics, such as, e.g. immunotoxins and ligand-toxin fusions, for the targeted killing of specific cell types for the treatment of a variety of diseases, including cancers, immune disorders, and microbial infections.

Any CD8+ T-cell hyper-immunized, polypeptide of the invention may be engineered into a potentially useful, therapeutic, cell-targeted molecule with the addition of a cell-targeting moiety which targets cellular internalization to a specific cell-type(s) within a chordate, such as, e.g., an amphibian, bird, fish, mammal, reptile, or shark. Similarly, any B-cell epitope de-immunized polypeptide of the invention may be engineered into a potentially useful, therapeutic, cell-targeted molecule with the addition of a cell-targeting moiety which targets cellular internalization to a specific cell-type(s) within a chordate. The present invention provides various cytotoxic cell-targeted molecules comprising CD8+ T-cell hyper-immunized and/or B-cell/CD4+ T-cell de-immunized polypeptides functionally associated with binding regions to effectuate cell targeting such that the cytotoxic cell-targeted molecules selectively delivery T-cell epitopes, kill, inhibit the growth of, deliver exogenous material to, and/or detect specific cell types. This system is modular, in that any number of diverse binding regions may be used to target to diverse cell types any CD8+ T-cell hyper-immunized and/or B-cell/CD4+ T-cell de-immunized polypeptide of the invention, including.

The presentation of a T-cell immunogenic epitope peptide by the MHC class I complex targets the presenting cell for killing by CTL-mediated cytolysis. By engineering MHC class I peptides into proteasome delivering effector polypeptide components of target-cell-internalizing therapeutics, the targeted delivery and presentation of immuno-stimulatory antigens may be accomplished by harnessing vertebrate target cells' endogenous MHC class I pathways. The presentation by targeted cells of immuno-stimulatory non-self antigens, such as, e.g., known viral epitope-peptides with high immunogenicity, can signal to other immune cells to destroy the target cells and recruit more immune cells to the target cell site within an organism.

Thus, already cytotoxic molecules, such as e.g. potential therapeutics comprising cytotoxic toxin effector regions, may be engineered using methods of the invention into more cytotoxic molecules and/or to have an additional cytotoxicity mechanism operating via effector T-cells. These multiple cytotoxic mechanisms may complement each other (such as by providing both direct target cell killing and indirect (CTL-mediated) cell killing, redundantly backup each other (such as by providing one mechanism of cell killing in the absence of the other), and/or protect against the development of therapeutic resistance (by limiting resistance to the less probable situation of the malignant or infected cell evolving to block two different cell-killing mechanisms simultaneously).

In addition, parental cytotoxic molecules which rely on toxin and/or enzymatic regions for cytotoxicity may be engineered to be cytotoxic only via T-cell epitope cytosolic delivery and presentation by both embedding a T-cell epitope and inactivating the enzymatic activity of the parental molecule, either with the embedded T-cell epitope or independently by other means such as mutation or truncation. This approach removes one cytotoxic mechanism while adding another and adds the capability of immuno-stimulation to the local area. Furthermore, parental cytotoxic molecules which rely on toxin and/or enzymatic regions for cytotoxicity may be engineered to be cytotoxic only via T-cell epitope cytosolic delivery and presentation by embedding a T-cell epitope in the enzymatic domain of the parental molecule such that the enzymatic activity is reduced or eliminated by the sequence changes that create the heterologous T-cell epitope. This allows for the one-step modification of enzymatically-cytotoxic molecules, which have the ability to internalize into cells and route to the cytosol, into enzymatically inactive, cytotoxic molecules which rely on T-cell epitope proteasome delivery and presentation for cytotoxicity and local immuno-stimulation.

A. Delivery of T-Cell Epitopes for MHC Class I Presentation on a Cell Surface

One function of certain CD8+ T-cell hyper-immunized polypeptides and cell-targeted molecules of the present invention is the delivery of one or more T-cell epitopes for MHC class I presentation by a cell. Delivery of exogenous T-cell epitope peptides to the MHC class I system of a target cell can be used to induce the target cell to present the T-cell epitope peptide in association with MHC class I molecules on the cell surface, which subsequently leads to the activation of CD8+ effector T-cells to attack the target cell.

Certain embodiments of the CD8+ T-cell hyper-immunized polypeptides and cell-targeted molecules of the present invention are capable of delivering one or more T-cell epitopes to the proteasome of a target cell. The delivered T-cell epitope are then proteolytic processed and presented by the MHC class I pathway on the outside surface of the target cell.

The applications of these T-cell epitope presenting functions of the CD8+ T-cell hyper-immunized polypeptides and cell-targeted molecules of the present invention are vast. Every nucleated cell in a mammalian organism may be capable of MHC class I pathway presentation of immunogenic T-cell epitope peptides on their cell outer surfaces complexed to MHC class I molecules. In addition, the sensitivity of T-cell epitope recognition is so exquisite that only a few MHC-I peptide complexes are required to be presented—even presentation of a single complex can be sufficient for recognition by an effector T-cell (Sykulev Y et al., *Immunity* 4: 565-71 (1996)).

In order for a heterologous T-cell epitope to be presented on a target cell surface, the polypeptide delivering the heterologous T-cell epitope-peptide must be degraded by a proteasome in the target cell such that a peptide fragment comprising the T-cell epitope is created and transported to the lumen of the ER for loading onto a MHC class I molecule.

In addition, the CD8+ T-cell hyper-immunized polypeptide must first reach the interior of a target cell and then come in contact with a proteasome in the target cell. In order to deliver a CD8+ T-cell hyper-immunized polypeptide of the present invention to the interior of a target cell, cell-targeting molecules of the present invention must be capable of target cell internalization. Once the CD8+ T-cell hyper-immunized polypeptide of the invention is internalized as a component of a cell-targeting molecule, the CD8+ T-cell hyper-immunized polypeptide will typical reside in an early endosomal compartment, such as, e.g., endocytotic vesicle. The CD8+ T-cell hyper-immunized polypeptide then has to reach a target cell's proteasome with at least one intact, heterologous T-cell epitope.

These functions can be detected and monitored by a variety of standard methods known in the art to the skilled worker. For example, the ability of cell-targeted molecules of the present invention to deliver a T-cell epitope peptide and drive presentation of the epitope peptide by the MHC class I system of target cells may be investigated using various in vitro and in vivo assays, including, e.g., the direct detection/visualization of MHC class I/peptide complexes, measurement of binding affinities for the heterologous T-cell epitope peptide to MHC Class I molecules, and/or measurement of functional consequences of MHC class I-epitope peptide complex presentation on target cells by monitoring CTL responses.

Certain assays to monitor this function of the polypeptides and molecules of the present invention involve the direct detection of a specific MHC Class I/peptide antigen complex in vitro or ex vivo. Common methods for direct visualization and quantitation of peptide-MHC class I complexes involve various immuno-detection reagents known to the skilled worker. For example, specific monoclonal antibodies can be developed to recognize a particular MHC/Class I/peptide antigen complex (Porgador A et al, *Immunity* 6: 715-26 (1997)). Similarly, soluble, multimeric T cell receptors, such as the TCR-STAR reagents (Altor, Mirmar, FL, U.S.) can be used to directly visualize or quantitate specific MHC I/antigen complexes (Zhu X et al., *J Immunol* 176: 3223-32 (2006)). These specific mAbs or soluble, multimeric T-cell receptors may be used with various detection methods, including, e.g. immunohistochemistry, flow cytometry, and enzyme-linked immuno assay (ELISA).

An alternative method for direct identification and quantification of MHC I/peptide complexes involves mass spectrometry analyses, such as, e.g., the ProPresent Antigen Presentation Assay (ProImmune, Inc., Sarasota, FL, U.S.) in which peptide-MCH class I complexes are extracted from the surfaces of cells, then the peptides are purified and identified by sequencing mass spectrometry (Falk K et al., *Nature* 351: 290-6 (1991)).

Certain assays to monitor the T-cell epitope delivery and MHC class I presentation function of the polypeptides and molecules of the present invention involve computational and/or experimental methods to monitor MHC Class I and peptide binding and stability. Several software programs are available for use by the skilled worker for predicting the binding responses of epitope peptides to MHC Class I alleles, such as, e.g., The Immune Epitope Database and Analysis Resource (IEDB) Analysis Resource MHC-I binding prediction Consensus tool (Kim Y et al., *Nucleic Acid Res* 40: W525-30 (2012). Several experimental assays have been routinely applied, such as, e.g. cell surface binding assays and/or surface plasmon resonance assays to quantify and/or compare binding kinetics (Miles K et al., *Mol Immunol* 48: 728-32 (2011)). Additionally, other MHC-peptide binding assays based on a measure of the ability of a peptide to stabilize the ternary MHC-peptide complex for a given MHC Class I allele, as a comparison to known controls, have been developed (e.g., MHC-peptide binding assay from ProImmmune, Inc.).

Alternatively, measurements of the consequence of MHC Class I/peptide antigen complex presentation on the cell surface can be performed by monitoring the cytotoxic T cell (CTL) response to the specific complex. These measurements by include direct labeling of the CTLs with MHC Class I tetramer or pentamer reagents. Tetramers or pentamers bind directly to T cell receptors of a particular specificity, determined by the Major Histocompatibility Complex (MHC) allele and peptide combination. Additionally, the quantification of released cytokines, such as interferon gamma or interleukins by ELISA or enzyme-linked immunospot (ELIspot) is commonly assayed to identify specific CTL responses. The cytotoxic capacity of CTL can be measured using a number of assays, including the classical 51 Chromium (Cr) release assay or alternative non-radioactive cytotoxicity assays (e.g., CytoTox96@ non-radioactive kits and CellTox™ CellTiter-GLO® kits available from Promega Corp., Madison, WI, U.S.), Granzyme B ELISpot, Caspase Assays or LAMP-1 translocation flow cytometric assays. To specifically monitor the killing of target cells, Carboxyfluorescein diacetate succinimidyl ester (CFSE) can be used to easily and quickly label a cell population of interest for in vitro or in vivo investigation to monitor killing of epitope specific CSFE labeled target cells (Durward M et al., *J Vis Exp* 45 pii 2250 (2010)).

In vivo responses to MHC Class I presentation can be followed by administering a MHC Class I/antigen promoting agent (e.g., a peptide, protein or inactivated/attenuated virus vaccine) followed by challenge with an active agent (e.g. a virus) and monitoring responses to that agent, typically in comparison with unvaccinated controls. Ex vivo samples can be monitored for CTL activity with methods similar to those described previously (e.g. CTL cytotoxicity assays and quantification of cytokine release).

HLA-A, HLA-B, and/or HLA-C molecules are isolated from the intoxicated cells after lysis using immune affinity (e.g., an anti-MHC antibody "pulldown" purification) and the associated peptides (i.e., the peptides presented by the isolated MHC molecules) are recovered from the purified complexes. The recovered peptides are analyzed by sequencing mass spectrometry. The mass spectrometry data is compared against a protein database library consisting of the sequence of the exogenous (non-self) peptide (T-cell epitope X) and the international protein index for humans (representing "self" or non-immunogenic peptides). The peptides are ranked by significance according to a probability database. All detected antigenic (non-self) peptide sequences are listed. The data is verified by searching against a scrambled decoy database to reduce false hits (see e.g. Ma B, Johnson R, *Mol Cell Proteomics* 11: O111.014902 (2012)). The results will demonstrate that peptides from the T-cell epitope X are presented in MHC complexes on the surface of intoxicated target cells.

The set of presented peptide-antigen-MHC complexes can vary between cells due to the antigen-specific HLA molecules expressed. T-cells can then recognize specific peptide-antigen-MHC complexes displayed on a cell surface using different TCR molecules with different antigen-specificities.

Because multiple T-cell epitopes may be delivered by a cell-targeted molecule of the invention, such as, e.g., by embedding two or more different T-cell epitopes in a single proteasome delivering effector polypeptide, a single cell-targeted molecule of the invention may be effective in chordates of the same species with different MHC class variants, such as, e.g., in humans with different HLA alleles. This may allow for the simultaneously combining different T-cell epitopes with different effectiveness in different subpopulations of subjects based on MHC complex protein diversity and polymorphisms (see e.g. Yuhki N et al., *J Hered* 98: 390-9 (2007)). For example, human MHC complex proteins, HLA proteins, vary among humans based on genetic ancestry, e.g. African (sub-Saharan), Amerindian, Caucasiod, Mongoloid, New Guinean and Australian, or Pacific islander (see e.g. Wang M, Claesson M, *Methods Mol Biol* 1184: 309-17 (2014)).

The activation of T-cell responses are desired characteristics of certain anti-cancer, anti-neoplastic, anti-tumor, and/or anti-microbial biologic drugs to stimulate the patient's own immune system toward targeted cells. Activation of a robust and strong T-cell response is also a desired characteristic of many vaccines (Aly H A, *J Immunol Methods* 382: 1-23 (2012)). The presentation of a T-cell epitope by a target cell within an organism can lead to the activation of robust immune responses to a target cell and/or its general locale within an organism. Thus, the targeted delivery of a T-cell epitope for presentation may be utilized for engineering the activation of T-cell responses during a therapeutic regime.

B. Cell Kill via Targeted Cytotoxicity and/or Recruitment of CTLs

Cell-targeted molecules of the present invention comprising CD8+ T-cell hyper-immunized and/or B-cell/CD4+ T-cell de-immunized polypeptides of the present invention can provide both: 1) cell type specific T-cell-epitope delivery for MHC class I presentation and 2) potent cytotoxicity. In addition, certain embodiments of the cell-targeted molecules of the present invention also provide de-immunization, which reduces the likelihood of certain immune responses when administered to a mammal.

In certain embodiments of the cell-targeted molecules of the present invention, upon contacting a cell physically coupled with an extracellular target biomolecule of the cell-targeting moiety (e.g. a cell-targeted binding region), the cell-targeted molecule of the invention is capable of causing death of the cell. The mechanism of cell kill may be direct, e.g. via the enzymatic activity of a toxin effector region, or indirect via CTL-mediated cytolysis, and may be under varied conditions of target cells, such as an ex vivo manipulated target cell, a target cell cultured in vitro, a target cell within a tissue sample cultured in vitro, or a target cell in vivo.

1. Indirect Cell Kill via T-Cell Epitope Delivery and MHC Class I Presentation

T-cell epitope delivering, CD8+ T-cell hyper-immunized polypeptides of the present invention, with or without B-cell epitope de-immunization, may be used as components of cell-targeted molecules for indirect cell kill. Certain embodiments of the cell-targeted molecules of the present invention are cytotoxic because they comprise a CD8+ T-cell epitope presenting polypeptide of the invention which delivers one or more T-cell epitopes to the MHC class I presentation pathway of a target cell upon target internalization of the cell-targeted molecule.

In certain embodiments of the cell-targeted molecules of the present invention, upon contacting a cell physically coupled with an extracellular target biomolecule of the cell-targeting moiety (e.g. a cell-targeted binding region), the cell-targeted molecule of the invention is capable of indirectly causing the death of the cell, such as, e.g., via the presentation of one or more T-cell epitopes by the target cell and the subsequent recruitment of CTLs.

2. Direct Cell Kill via Cell-Targeted Toxin Cytotoxicity

T-cell epitope delivering, CD8+ T-cell hyper-immunized, and/or B-cell/CD4+ T-cell de-immunized polypeptides of the present invention may be used as components of cell-targeted molecules for direct cell kill.

Because many naturally occurring toxins are adapted to killing eukaryotic cells, cytotoxic proteins designed using toxin-derived, proteasome delivering effector regions, can show potent cell-kill activity. In particular, proteasome delivering effector regions may also comprise ribotoxic toxin effector polypeptides. However, other toxin effector regions are contemplated for use in the cell-targeted molecules of the invention, such as, e.g., polypeptides from toxins which do not catalytically inactivate ribosomes but rather are cytotoxic due to other mechanisms. For example, cholix toxins, heat-labile enterotoxins, and pertussis toxins heterotrimeric G proteins by attacking the Gsalpha subunit.

The A Subunits of many members of the ABx toxin superfamily comprise enzymatic domains capable of killing a eukaryotic cell once in the cell's cytosol. The replacement of a B-cell epitope with a T-cell epitope within multiple ABx toxin-derived, polypeptides comprising toxin enzymatic domains did not significantly alter their enzymatic activity. Thus, the CD8+ T-cell hyper-immunized and/or B-cell/CD4+ T-cell de-immunized polypeptides of the present invention can potentially provide two mechanisms of cell kill.

Certain embodiments of the cell-targeted molecules of the present invention are cytotoxic because they comprise a CD8+ T-cell hyper-immunized and/or B-cell/CD4+ T-cell de-immunized polypeptide of the invention which comprises an active toxin component.

In certain embodiments of the cell-targeted molecules of the present invention, upon contacting a cell physically coupled with an extracellular target biomolecule of the cell-targeting moiety (e.g. a cell-targeted binding region), the cell-targeted molecule of the invention is capable of directly causing the death of the cell, such as, e.g., via the enzymatic activity of a toxin effector region.

C. De-Immunization Improves Applications Involving Administration to Mammals

The polypeptides and cell-targeted molecules of the present invention have improved usefulness for administration to mammalian species as either a therapeutic and/or diagnostic agent because of the reduced likelihood of producing undesired immune responses in mammals while increasing the likelihood of producing desirable immune responses in mammals.

Certain CD8+ T-cell hyper-immunized and/or B-cell/CD4+ T-cell de-immunized toxin-derived polypeptides of the present invention might differ in their antigenicity profiles when administered to various mammals, but are expected to have reduced B-cell and/or CD4+ T-cell antigenicity and/or immunogenicity. In certain embodiments, the desired biological functions of the original toxin polypeptide from which the de-immunized CD8+ T-cell hyper-immunized polypeptide was derived are preserved in the polypeptides of the invention after the B-cell epitope(s) was disrupted and the CD8+ T-cell epitope was added. In addition, B-cell epitopes often coincide or overlap with epitopes of mature CD4+ T-cells, thus the disruption of a B-cell epitope often simultaneously disrupts a CD4+ T-cell epitope.

D. Selective Cytotoxicity Among Cell Types

Certain cell-targeted molecules of the present invention have uses in the selective killing of specific target cells in the presence of untargeted, bystander cells. By targeting the delivery of immunogenic T-cell epitopes to the MHC class I pathway of target cells, the subsequent presentation of T-cell epitopes and CTL-mediated cytolysis of target cells induced by the cell-targeted molecules of the invention can be restricted to preferentially killing selected cell types in the presence of untargeted cells. In addition, the killing of target cells by the potent cytotoxic activity of various toxin effector regions can be restricted to preferentially killing target cells with the simultaneous delivery of an immunogenic T-cell epitope and a cytotoxic toxin effector polypeptide.

In certain embodiments, upon administration of the cell-targeted molecule of the present invention to a mixture of cell types, the cell-targeted molecule is capable of selectively killing those cells which are physically coupled with an extracellular target biomolecule compared to cell types not physically coupled with an extracellular target biomolecule. Because many toxins are adapted for killing eukaryotic cells, such as, e.g., members of the ABx and ribotoxin families, cytotoxic proteins designed using toxin effector regions can show potent cytotoxic activity. By targeting the delivery of enzymatically active toxin effector regions to specific cell types using high-affinity binding regions, this potent cell kill activity can be restricted to killing only those cell types desired to be targeted by their physical association with a target biomolecule of the chosen binding regions.

In certain embodiments, the cytotoxic, cell-targeted molecule of the present invention is capable of selectively or preferentially causing the death of a specific cell type within a mixture of two or more different cell types. This enables the targeted cytotoxic activity to specific cell types with a high preferentiality, such as a 3-fold cytotoxic effect, over "bystander" cell types that do not express the target biomolecule. Alternatively, the expression of the target biomolecule of the binding region may be non-exclusive to one cell type if the target biomolecule is expressed in low enough amounts and/or physically coupled in low amounts with cell types that are not to be targeted. This enables the targeted cell-killing of specific cell types with a high preferentiality, such as a 3-fold cytotoxic effect, over "bystander" cell types that do not express significant amounts of the target biomolecule or are not physically coupled to significant amounts of the target biomolecule.

In certain further embodiments, upon administration of the cytotoxic cell-targeted molecule to two different populations of cell types, the cytotoxic cell-targeted molecule is capable of causing cell death as defined by the half-maximal cytotoxic concentration ($CD_{50}$) on a population of target cells, whose members express an extracellular target biomolecule of the binding region of the cytotoxic protein, at a dose at least three-times lower than the $CD_{50}$ dose of the same cytotoxic protein to a population of cells whose members do not express an extracellular target biomolecule of the binding region of the cytotoxic protein.

In certain embodiments, the cytotoxic activity toward populations of cell types physically coupled with an extracellular target biomolecule is at least 3-fold higher than the cytotoxic activity toward populations of cell types not physically coupled with any extracellular target biomolecule of the binding region. According to the present invention, selective cytotoxicity may be quantified in terms of the ratio (a/b) of (a) cytotoxicity towards a population of cells of a specific cell type physically coupled with a target biomolecule of the binding region to (b) cytotoxicity towards a population of cells of a cell type not physically coupled with a target biomolecule of the binding region. In certain embodiments, the cytotoxicity ratio is indicative of selective cytotoxicity which is at least 3-fold, 5-fold, 10-fold, 15-fold, 20-fold, 25-fold, 30-fold, 40-fold, 50-fold, 75-fold, 100-fold, 250-fold, 500-fold, 750-fold, or 1000-fold higher for populations of cells or cell types physically coupled with a target biomolecule of the binding region compared to populations of cells or cell types not physically coupled with a target biomolecule of the binding region.

This preferential cell-killing function allows a targeted cell to be killed by certain cytotoxic, cell-targeted molecules of the present invention under varied conditions and in the presence of non-targeted bystander cells, such as ex vivo manipulated mixtures of cell types, in vitro cultured tissues with mixtures of cell types, or in vivo in the presence of multiple cell types (e.g. in situ or in a native location within a multicellular organism).

E. Delivery of Additional Exogenous Material into the Interior of Targeted Cells In addition to cytotoxic and cytostatic applications, cell-targeted molecules of the present invention optionally may be used for information gathering and diagnostic functions. Further, non-toxic variants of the cytotoxic, cell-targeted molecules of the invention, or optionally toxic variants, may be used to deliver additional exogenous materials to and/or label the interiors of cells physically coupled with an extracellular target biomolecule of the cytotoxic protein. Various types of cells and/or cell populations which express target biomolecules to at least one cellular surface may be targeted by the cell-targeted molecules of the invention for receiving exogenous materials. The functional components of the present invention are modular, in that various toxin effector regions and additional exogenous materials may be linked to various binding regions to provide diverse applications, such as non-invasive in vivo imaging of tumor cells.

Because the cell-targeted molecules of the invention, including nontoxic forms thereof, are capable of entering cells physically coupled with an extracellular target biomolecule recognized by the cell-targeted molecule's binding region, certain embodiments of the cell-targeted molecules of the invention may be used to deliver additional exogenous materials into the interior of targeted cell types. In one sense, the entire cell-targeted molecule of the invention is an exogenous material which will enter the cell; thus, the "additional" exogenous materials are heterologous materials linked to but other than the core cell-targeted molecule itself. CD8+ T-cell hyper-immunized and/or B-cell/CD4+ T-cell de-immunized polypeptides which become non-toxic after T-cell epitope addition may still be useful for delivering exogenous materials into cells (e.g. T-cell epitope replacements overlapping amino acid resides critical for catalytic function of a toxin effector region).

"Additional exogenous material" as used herein refers to one or more molecules, often not generally present within a native target cell, where the proteins of the present invention can be used to specifically transport such material to the interior of a cell. Non-limiting examples of additional exogenous materials are peptides, polypeptides, proteins, polynucleotides, small molecule chemotherapeutic agents, and detection promoting agents.

In certain embodiments, the additional exogenous material comprises a protein or polypeptide comprising an enzyme. In certain other embodiments, the additional exogenous material is a nucleic acid, such as, e.g. a ribonucleic acid that functions as a small inhibiting RNA (siRNA) or microRNA (miRNA). In certain embodiments, the additional exogenous material is an antigen, such as antigens derived from bacterial proteins, viral proteins, proteins mutated in cancer, proteins aberrantly expressed in cancer, or T-cell complementary determining regions. For example, exogenous materials include antigens, such as those characteristic of antigen-presenting cells infected by bacteria, and T-cell complementary determining regions capable of functioning as exogenous antigens. Additional examples of exogenous materials include polypeptides and proteins larger than an antigenic peptide, such as enzymes. Exogenous materials comprising polypeptides or proteins may optionally comprise one or more antigens whether known or unknown to the skilled worker.

F. Information Gathering for Diagnostic Functions

Certain cell-targeted molecules of the present invention have uses in the in vitro and/or in vivo detection of specific cells, cell types, and/or cell populations. In certain embodiments, the proteins described herein are used for both diagnosis and treatment, or for diagnosis alone. When the same cytotoxic protein is used for both diagnosis and treatment, the cytotoxic protein variant which incorporates a detection promoting agent for diagnosis may be rendered nontoxic by catalytic inactivation of a toxin effector region via one or more amino acid substitutions, including exemplary substitutions described herein. Nontoxic forms of the cytotoxic, cell-targeted molecules of the invention that are conjugated to detection promoting agents optionally may be used for diagnostic functions, such as for companion diagnostics used in conjunction with a therapeutic regimen comprising the same or a related binding region.

The ability to conjugate detection promoting agents known in the art to various cell-targeted molecules of the present invention provides useful compositions for the detection of cancer, tumor, immune, and infected cells. These diagnostic embodiments of the cell-targeted molecules of the invention may be used for information gathering via various imaging techniques and assays known in the art. For example, diagnostic embodiments of the cell-targeted molecules of the invention may be used for information gathering via imaging of intracellular organelles (e.g. endocytotic, Golgi, endoplasmic reticulum, and cytosolic compartments) of individual cancer cells, immune cells, or infected cells in a patient or biopsy sample.

Various types of information may be gathered using the diagnostic embodiments of the cell-targeted molecules of the invention whether for diagnostic uses or other uses. This information may be useful, for example, in diagnosing neoplastic cell types, determining therapeutic susceptibilities of a patient's disease, assaying the progression of anti-neoplastic therapies over time, assaying the progression of immunomodulatory therapies over time, assaying the progression of antimicrobial therapies over time, evaluating the presence of infected cells in transplantation materials, evaluating the presence of unwanted cell types in transplantation materials, and/or evaluating the presence of residual tumor cells after surgical excision of a tumor mass.

For example, subpopulations of patients might be ascertained using information gathered using the diagnostic variants of the cell-targeted molecules of the invention, and then individual patients could be categorized into subpopulations based on their unique characteristic(s) revealed using those diagnostic embodiments. For example, the effectiveness of specific pharmaceuticals or therapies might be one type of criterion used to define a patient subpopulation. For example, a nontoxic diagnostic variant of a particular cytotoxic, cell-targeted molecule of the invention may be used to differentiate which patients are in a class or subpopulation of patients predicted to respond positively to a cytotoxic variant of the same cell-targeted molecule of the invention. Accordingly, associated methods for patient identification, patient stratification, and diagnosis using CD8+ T-cell hyper-immunized and/or B-cell/CD4+ T-cell de-immunized cell-targeted molecules of the present invention, including non-toxic variants of cytotoxic, cell-targeted molecules of the present invention, are considered to be within the scope of the present invention.

VII. Production. Manufacture. and Purification of CD8+ T-Cell Hyper-Immunized and/or B-Cell/CD4+ T-Cell De-Immunized Polypeptides of the Present Invention and the Cell-Targeted Molecules Comprising the Same The CD8+ T-cell hyper-immunized and/or B-cell/CD4+ T-cell de-immunized polypeptides and cell-targeted molecules of the present invention may be produced using biochemical engineering techniques well known to those of skill in the art. For example, polypeptides and cell-targeted molecules of the invention may be manufactured by standard synthetic methods, by use of recombinant expression systems, or by any other suitable method. Thus, polypeptides and cell-targeted proteins of the present invention may be synthesized in a number of ways, including, e.g. methods comprising: (1) synthesizing a polypeptide or polypeptide component of a protein using standard solid-phase or liquid-phase methodology, either stepwise or by fragment assembly, and isolating and purifying the final peptide compound product; (2) expressing a polynucleotide that encodes a polypeptide or polypeptide component of a cell-targeted protein of the invention in a host cell and recovering the expression product from the host cell or host cell culture; or (3) cell-free in vitro expression of a polynucleotide encoding a polypeptide or polypeptide component of a cell-targeted protein of the invention, and recovering the expression product; or by any combination of the methods of (1), (2) or (3) to obtain fragments of the peptide component, subsequently joining (e.g. ligating) the fragments to obtain the peptide component, and recovering the peptide component.

It may be preferable to synthesize a CD8+ T-cell hyper-immunized and/or B-cell/CD4+ T-cell de-immunized polypeptide or a protein or polypeptide component of a cell-targeted protein of the invention by means of solid-phase or liquid-phase peptide synthesis. Polypeptides and cell-targeted molecules of the present invention may suitably be manufactured by standard synthetic methods. Thus, peptides may be synthesized by, e.g. methods comprising synthesizing the peptide by standard solid-phase or liquid-phase methodology, either stepwise or by fragment assembly, and isolating and purifying the final peptide product. In this context, reference may be made to WO 1998/11125 or, inter alia, Fields G et al., *Principles and Practice of Solid-Phase Peptide Synthesis* (Synthetic Peptides, Grant G, ed., Oxford University Press, U.K., 2nd ed., 2002) and the synthesis examples therein.

CD8+ T-cell hyper-immunized and/or B-cell/CD4+ T-cell de-immunized polypeptides and cytotoxic, cell-targeted proteins of the present invention may be prepared (produced and purified) using recombinant techniques well known in the art. In general, methods for preparing polypeptides by culturing host cells transformed or transfected with a vector comprising the encoding polynucleotide and recovering the polypeptide from cell culture are described in, e.g. Sambrook J et al., *Molecular Cloning: A Laboratory Manual* (Cold Spring Harbor Laboratory Press, NY, U.S., 1989); Dieffenbach C et al., *PCR Primer: A Laboratory Manual* (Cold Spring Harbor Laboratory Press, N.Y., U.S., 1995). Any suitable host cell may be used to produce a polypeptide and/or cell-targeted protein of the invention. Host cells may be cells stably or transiently transfected, transformed, transduced or infected with one or more expression vectors which drive expression of a polypeptide of the invention. In addition, a CD8+ T-cell hyper-immunized and/or B-cell/CD4+ T-cell de-immunized polypeptides and/or cell-targeted protein of the invention may be produced by modifying the polynucleotide encoding a polypeptide or cell-targeted protein of the invention that result in altering one or more amino acids or deleting or inserting one or more amino acids in order to achieve desired properties, such as changed cytotoxicity, changed cytostatic effects, and/or changed serum half-life.

There are a wide variety of expression systems which may be chosen to produce a polypeptide or cell-targeted protein of the present invention. For example, host organisms for expression of cell-targeted proteins of the invention include prokaryotes, such as *E. coli* and *B. subtilis*, eukaryotic cells, such as yeast and filamentous fungi (like *S. cerevisiae*, *P. pastoris*, *A. awamori*, and *K. lactis*), algae (like *C. reinhardtii*), insect cell lines, mammalian cells (like CHO cells), plant cell lines, and eukaryotic organisms such as transgenic plants (like *A. thaliana* and *N. benthamiana*).

Accordingly, the present invention also provides methods for producing a CD8+ T-cell hyper-immunized and/or B-cell/CD4+ T-cell de-immunized polypeptide and/or cell-targeted protein of the invention according to above recited methods and using a polynucleotide encoding part or all of a polypeptide of the invention or a polypeptide component of a cell-targeted protein of the invention, an expression vector comprising at least one polynucleotide of the invention capable of encoding part or all of a polypeptide of the invention when introduced into a host cell, and/or a host cell comprising a polynucleotide or expression vector of the invention.

When a polypeptide or protein is expressed using recombinant techniques in a host cell or cell-free system, it is advantageous to separate (or purify) the desired polypeptide or protein away from other components, such as host cell factors, in order to obtain preparations that are of high purity or are substantially homogeneous. Purification can be accomplished by methods well known in the art, such as centrifugation techniques, extraction techniques, chromatographic and fractionation techniques (e.g. size separation by gel filtration, charge separation by ion-exchange column, hydrophobic interaction chromatography, reverse phase chromatography, chromatography on silica or cation-exchange resins such as DEAE and the like, chromatofocusing, and Protein A SEPHAROSE® chromatography to remove contaminants), and precipitation techniques (e.g. ethanol precipitation or ammonium sulfate precipitation). Any number of biochemical purification techniques may be used to increase the purity of a CD8+ T-cell hyper-immunized and/or B-cell/CD4+ T-cell de-immunized polypeptide and/or cell-targeted molecule of the present invention. In certain embodiments, the polypeptides and cell-targeted molecules of the invention may optionally be purified in homo-multimeric forms (i.e. a protein complex of two or more identical polypeptides or cell-targeted molecules of the invention).

In the Examples below are descriptions of non-limiting examples of methods for producing a polypeptide or cell-targeted molecule of the invention, as well as specific but non-limiting aspects of production for exemplary cell-targeted molecules of the present invention.

VIII. Pharmaceutical and Diagnostic Compositions Comprising a T-Cell Hyper-Immunized and/or B-Cell/CD4+ T-Cell De-Immunized Polypeptide of the Present Invention or Cell-Targeted Molecule Comprising the Same The present invention provides polypeptides and proteins for use, alone or in combination with one or more additional therapeutic agents, in a pharmaceutical composition, for treatment or prophylaxis of conditions, diseases, disorders, or symptoms described in further detail below (e.g. cancers, malignant tumors, non-malignant tumors, growth abnormalities, immune disorders, and microbial infections). The present invention further provides pharmaceutical compositions comprising a polypeptide or cell-targeted molecule of the invention, or a pharmaceutically acceptable salt or solvate thereof, according to the invention, together with at least one pharmaceutically acceptable carrier, excipient, or vehicle. In certain embodiments, the pharmaceutical composition of the present invention may comprise homo-multimeric and/or hetero-multimeric forms of the polypeptides or cell-targeted molecules of the invention. The pharmaceutical compositions will be useful in methods of treating, ameliorating, or preventing a disease, condition, disorder, or symptom described in further detail below. Each such disease, condition, disorder, or symptom is envisioned to be a separate embodiment with respect to uses of a pharmaceutical composition according to the invention. The invention further provides pharmaceutical compositions for use in at least one method of treatment according to the invention, as described in more detail below.

As used herein, the terms "patient" and "subject" are used interchangeably to refer to any organism, commonly vertebrates such as humans and animals, which presents symptoms, signs, and/or indications of at least one disease, disorder, or condition. These terms include mammals such as the non-limiting examples of primates, livestock animals (e.g. cattle, horses, pigs, sheep, goats, etc.), companion animals (e.g. cats, dogs, etc.) and laboratory animals (e.g. mice, rabbits, rats, etc.).

As used herein, "treat," "treating," or "treatment" and grammatical variants thereof refer to an approach for obtaining beneficial or desired clinical results. The terms may refer to slowing the onset or rate of development of a condition, disorder or disease, reducing or alleviating symptoms associated with it, generating a complete or partial regression of the condition, or some combination of any of the above. For the purposes of this invention, beneficial or desired clinical results include, but are not limited to, reduction or alleviation of symptoms, diminishment of extent of disease, stabilization (e.g. not worsening) of state of disease, delay or slowing of disease progression, amelioration or palliation of the disease state, and remission (whether partial or total), whether detectable or undetectable. "Treat," "treating," or "treatment" can also mean prolonging survival relative to expected survival time if not receiving treatment. A subject (e.g. a human) in need of treatment may thus be a subject already afflicted with the disease or disorder in question. The terms "treat," "treating," or "treatment" includes inhibition or reduction of an increase in severity of a pathological state or symptoms relative to the absence of treatment, and is not necessarily meant to imply complete cessation of the relevant disease, disorder, or condition. With regard to tumors and/or cancers, treatment includes reduction in overall tumor burden and/or individual tumor size.

As used herein, the terms "prevent," "preventing," "prevention" and grammatical variants thereof refer to an approach for preventing the development of, or altering the pathology of, a condition, disease, or disorder. Accordingly, "prevention" may refer to prophylactic or preventive measures. For the purposes of this invention, beneficial or desired clinical results include, but are not limited to, prevention or slowing of symptoms, progression or development of a disease, whether detectable or undetectable. A subject (e.g. a human) in need of prevention may thus be a subject not yet afflicted with the disease or disorder in question. The term "prevention" includes slowing the onset of disease relative to the absence of treatment, and is not necessarily meant to imply permanent prevention of the relevant disease, disorder or condition. Thus "preventing" or "prevention" of a condition may in certain contexts refer to reducing the risk of developing the condition, or preventing or delaying the development of symptoms associated with the condition.

As used herein, an "effective amount" or "therapeutically effective amount" is an amount or dose of a composition (e.g. a therapeutic composition or agent) that produces at least one desired therapeutic effect in a subject, such as preventing or treating a target condition or beneficially alleviating a symptom associated with the condition. The most desirable therapeutically effective amount is an amount that will produce a desired efficacy of a particular treatment selected by one of skill in the art for a given subject in need thereof. This amount will vary depending upon a variety of factors understood by the skilled worker, including but not limited to the characteristics of the therapeutic compound (including activity, pharmacokinetics, pharmacodynamics, and bioavailability), the physiological condition of the subject (including age, sex, disease type, disease stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly (see e.g. Remington: *The Science and Practice of Pharmacy* (Gennaro A, ed., Mack Publishing Co., Easton, PA, U.S., 19th ed., 1995)).

Diagnostic compositions comprise a polypeptide or cell-targeted molecule of the invention and one or more detection promoting agents. Various detection promoting agents are known in the art, such as isotopes, dyes, colorimetric agents, contrast enhancing agents, fluorescent agents, bioluminescent agents, and magnetic agents. These agents may be incorporated into the polypeptide or cell-targeted molecule of the invention at any position. The incorporation of the agent may be via an amino acid residue(s) of the protein or via some type of linkage known in the art, including via linkers and/or chelators. The incorporation of the agent is in such a way to enable the detection of the presence of the diagnostic composition in a screen, assay, diagnostic procedure, and/or imaging technique.

When producing or manufacturing a diagnostic composition of the present invention, a cell-targeted molecule of the invention may be directly or indirectly linked to one or more detection promoting agents. There are numerous detection promoting agents known to the skilled worker which can be operably linked to the polypeptides or cell-targeted molecules of the invention for information gathering methods, such as for diagnostic and/or prognostic applications to diseases, disorders, or conditions of an organism (see e.g. Cai W et al., *J Nucl Med* 48: 304-10 (2007); Nayak T, Brechbiel M, *Bioconjug Chem* 20: 825-41 (2009); Paudyal P et al., *Oncol Rep* 22: 115-9 (2009); Qiao J et al., *PLoS ONE* 6: e18103 (2011); Sano K et al., *Breast Cancer Res* 14: R61 (2012)). For example, detection promoting agents include image enhancing contrast agents, such as fluorescent dyes (e.g. ALEXA FLUOR® 680, indocyanine green, and Cy5.5), isotopes and radionuclides, such as $^{11}$C, $^{13}$N, $^{15}$O, $^{18}$F, $^{32}$P, $^{51}$Mn, $^{52m}$Mn, $^{52}$Fe, $^{55}$Co, $^{62}$Cu, $^{64}$Cu, $^{67}$Cu, $^{67}$Ga, $^{68}$Ga, $^{72}$As, $^{73}$Se, $^{75}$Br, $^{76}$Br, $^{82m}$Rb, $^{83}$Sr, $^{86}$Y, $^{90}$Y, $^{89}$Zr, $^{94m}$Tc, $^{94}$Tc, $^{99m}$Tc, $^{110}$In, $^{111}$In, $^{120}$I, $^{123}$I, $^{124}$I, $^{125}$I, $^{131}$I, $^{154}$Gd, $^{155}$Gd, $^{156}$Gd, $^{157}$Gd, $^{158}$Gd, $^{177}$Lu, $^{186}$Re, $^{188}$Re, and $^{223}$R; paramagnetic ions, such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III); metals, such as lanthanum (III), gold (III), lead (II), and bismuth (III); ultrasound-contrast enhancing agents, such as liposomes; radiopaque agents, such as barium, gallium, and thallium compounds. Detection promoting agents may be incorporated directly or indirectly by using an intermediary functional group, such as chelators like 2-benzyl DTPA, PAMAM, NOTA, DOTA, TETA, analogs thereof, and functional equivalents of any of the foregoing (see Leyton J et al., *Clin Cancer Res* 14: 7488-96 (2008)).

There are numerous standard techniques known to the skilled worker for incorporating, affixing, and/or conjugating various detection promoting agents to proteins, especially to immunoglobulins and immunoglobulin-derived domains (Wu A, *Methods* 65: 139-47 (2014)). Similarly, there are numerous imaging approaches known to the skilled worker, such as non-invasive in vivo imaging techniques commonly used in the medical arena, for example: computed tomography imaging (CT scanning), optical imaging (including direct, fluorescent, and bioluminescent imaging), magnetic resonance imaging (MRI), positron emission tomography (PET), single-photon emission computed tomography (SPECT), ultrasound, and x-ray computed tomography imaging (see Kaur S et al., *Cancer Lett* 315: 97-111 (2012), for review).

IX. Production or Manufacture of a Pharmaceutical and/or Diagnostic Composition Comprising a T-Cell Hyper-Immunized and/or B-Cell/CD4+ T-Cell De-Immunized Polypeptide or Cell-Targeted Molecule of the Present Invention Pharmaceutically acceptable salts or solvates of any of the polypeptides and cell-targeted molecules of the invention are likewise within the scope of the present invention.

The term "solvate" in the context of the present invention refers to a complex of defined stoichiometry formed between a solute (in casu, a polypeptide compound or pharmaceutically acceptable salt thereof according to the invention) and a solvent. The solvent in this connection may, for example, be water, ethanol or another pharmaceutically acceptable, typically small-molecular organic species, such as, but not limited to, acetic acid or lactic acid. When the solvent in question is water, such a solvate is normally referred to as a hydrate.

Polypeptides and proteins of the present invention, or salts thereof, may be formulated as pharmaceutical compositions prepared for storage or administration, which typically comprise a therapeutically effective amount of a compound of the present invention, or a salt thereof, in a pharmaceutically acceptable carrier. The term "pharmaceutically acceptable carrier" includes any of the standard pharmaceutical carriers. Pharmaceutically acceptable carriers for therapeutic use are well known in the pharmaceutical art, and are described, for example, in *Remington's Pharmaceutical Sciences* (Mack Publishing Co. (A. Gennaro, ed., 1985). As used herein, "pharmaceutically acceptable carrier" includes any and all physiologically acceptable, i.e. compatible, solvents, dispersion media, coatings, antimicrobial agents, isotonic, and absorption delaying agents, and the like. Pharmaceutically acceptable carriers or diluents include those used in formulations suitable for oral, rectal, nasal or parenteral (including subcutaneous, intramuscular, intravenous, intradermal, and transdermal) administration. Exemplary pharmaceutically acceptable carriers include sterile aqueous solutions or dispersions and sterile powders for the extemporaneous preparation of sterile injectable solutions or dispersions. Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyloleate. Proper fluidity can be maintained, for example, by the use of coating materials, such as lecithin, by the maintenance of the required particle size in the case of dispersions, and by the use of surfactants. In certain embodiments, the carrier is suitable for intravenous, intramuscular, subcutaneous, parenteral, spinal or epidermal administration (e.g. by injection or infusion). Depending on selected route of administration, the protein or other pharmaceutical component may be coated in a material intended to protect the compound from the action of low pH and other natural inactivating conditions to which the active protein may encounter when administered to a patient by a particular route of administration.

The formulations of the pharmaceutical compositions of the invention may conveniently be presented in unit dosage form and may be prepared by any of the methods well known in the art of pharmacy. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms. It may be provided in single dose injectable form, for example in the form of a pen. Compositions may be formulated for any suitable route and means of administration. Subcutaneous or transdermal modes of administration may be particularly suitable for therapeutic proteins described herein.

The pharmaceutical compositions of the present invention may also contain adjuvants such as preservatives, wetting agents, emulsifying agents and dispersing agents. Preventing the presence of microorganisms may be ensured both by sterilization procedures, and by the inclusion of various antibacterial and antifungal agents, for example, paraben, chlorobutanol, phenol sorbic acid, and the like. Isotonic agents, such as sugars, sodium chloride, and the like into the compositions, may also be desirable. In addition, prolonged absorption of the injectable pharmaceutical form may be brought about by the inclusion of agents which delay absorption such as, aluminum monostearate and gelatin.

A pharmaceutical composition of the present invention also optionally includes a pharmaceutically acceptable antioxidant. Exemplary pharmaceutically acceptable antioxidants are water soluble antioxidants such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propylgallate, alpha-tocopherol, and the like; and metal chelating agents, such as citric acid, ethylenediamine tetraacetic acid (EDTA), sorbitol, tartaric acid, phosphoric acid, and the like.

In another aspect, the present invention provides pharmaceutical compositions comprising one or a combination of different polypeptides and/or cell-targeted molecules of the invention, or an ester, salt or amide of any of the foregoing, and at least one pharmaceutically acceptable carrier.

Therapeutic compositions are typically sterile and stable under the conditions of manufacture and storage. The composition may be formulated as a solution, microemulsion, liposome, or other ordered structure suitable to high drug concentration. The carrier may be a solvent or dispersion medium containing, for example, water, alcohol such as ethanol, polyol (e.g. glycerol, propylene glycol, and liquid polyethylene glycol), or any suitable mixtures. The proper fluidity may be maintained, for example, by the use of a coating such as lecithin, by the maintenance of the required particle size in the case of dispersion and by use of surfactants according to formulation chemistry well known in the art. In certain embodiments, isotonic agents, e.g. sugars, polyalcohols such as mannitol, sorbitol, or sodium chloride may be desirable in the composition. Prolonged absorption of injectable compositions may be brought about by including in the composition an agent that delays absorption for example, monostearate salts and gelatin.

Solutions or suspensions used for intradermal or subcutaneous application typically include one or more of: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and tonicity adjusting agents such as, e.g., sodium chloride or dextrose. The pH can be adjusted with acids or bases, such as hydrochloric acid or sodium hydroxide, or buffers with citrate, phosphate, acetate and the like. Such preparations may be enclosed in ampoules, disposable syringes or multiple dose vials made of glass or plastic.

Sterile injectable solutions may be prepared by incorporating a polypeptide or cell-targeted molecule of the invention in the required amount in an appropriate solvent with one or a combination of ingredients described above, as required, followed by sterilization microfiltration. Dispersions may be prepared by incorporating the active compound into a sterile vehicle that contains a dispersion medium and other ingredients, such as those described above. In the case of sterile powders for the preparation of sterile injectable solutions, the methods of preparation are vacuum drying and freeze-drying (lyophilization) that yield a powder of the active ingredient in addition to any additional desired ingredient from a sterile-filtered solution thereof.

When a therapeutically effective amount of a polypeptide or cell-targeted molecule of the invention is designed to be administered by, e.g. intravenous, cutaneous or subcutaneous injection, the binding agent will be in the form of a pyrogen-free, parenterally acceptable aqueous solution. Methods for preparing parenterally acceptable protein solutions, taking into consideration appropriate pH, isotonicity, stability, and the like, are within the skill in the art. A preferred pharmaceutical composition for intravenous, cutaneous, or subcutaneous injection will contain, in addition to binding agents, an isotonic vehicle such as sodium chloride injection, Ringer's injection, dextrose injection, dextrose and sodium chloride injection, lactated Ringer's injection, or other vehicle as known in the art. A pharmaceutical composition of the present invention may also contain stabilizers, preservatives, buffers, antioxidants, or other additives well known to those of skill in the art.

As described elsewhere herein, a polypeptide or cell-targeted molecule of the invention may be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art (see e.g. *Sustained and Controlled Release Drug Delivery Systems* (Robinson J, ed., Marcel Dekker, Inc., NY, U.S., 1978)).

In certain embodiments, the pharmaceutical composition of the present invention may be formulated to ensure a desired distribution in vivo. For example, the blood-brain barrier excludes many large and/or hydrophilic compounds. To target a therapeutic compound or composition of the invention to a particular in vivo location, they can be formulated, for example, in liposomes which may comprise one or more moieties that are selectively transported into specific cells or organs, thus enhancing targeted drug delivery. Exemplary targeting moieties include folate or biotin; mannosides; antibodies; surfactant protein A receptor; p120 catenin and the like.

Pharmaceutical compositions include parenteral formulations designed to be used as implants or particulate systems. Examples of implants are depot formulations composed of polymeric or hydrophobic components such as emulsions, ion exchange resins, and soluble salt solutions. Examples of particulate systems are microspheres, microparticles, nanocapsules, nanospheres, and nanoparticles (see e.g. Honda M et al., *Int J Nanomedicine* 8: 495-503 (2013); Sharma A et al., *Biomed Res Int* 2013: 960821 (2013); Ramishetti S, Huang L, *Ther Deliv* 3: 1429-45 (2012)). Controlled release formulations may be prepared using polymers sensitive to ions, such as, e.g. liposomes, polaxamer 407, and hydroxyapatite.

X. Polynucleotides, Expression Vectors, and Host Cells

Beyond the polypeptides and proteins of the present invention, the polynucleotides that encode the polypeptides and cell-targeted molecules of the invention, or functional portions thereof, are also encompassed within the scope of the present invention. The term "polynucleotide" is equivalent to the term "nucleic acid," each of which includes one or more of: polymers of deoxyribonucleic acids (DNAs), polymers of ribonucleic acids (RNAs), analogs of these DNAs or RNAs generated using nucleotide analogs, and derivatives, fragments and homologs thereof. The polynucleotide of the present invention may be single-, double-, or triple-stranded. Such polynucleotides are specifically disclosed to include all polynucleotides capable of encoding an exemplary protein, for example, taking into account the wobble known to be tolerated in the third position of RNA codons, yet encoding for the same amino acid as a different RNA codon (see Stothard P, *Biotechniques* 28: 1102-4 (2000)).

In one aspect, the invention provides polynucleotides which encode a CD8+ T-cell hyper-immunized and/or B-cell/CD4+ T-cell de-immunized polypeptide and/or cell-targeted protein of the invention, or a fragment or derivative thereof. The polynucleotides may include, e.g., nucleic acid sequence encoding a polypeptide at least 50%, 55%, 60%, 65%, 70%, 75%, 80%, 85%, 90%, 95%, 99% or more, identical to a polypeptide comprising one of the amino acid sequences of the protein. The invention also includes polynucleotides comprising nucleotide sequences that hybridize under stringent conditions to a polynucleotide which encodes CD8+ T-cell hyper-immunized and/or B-cell/CD4+ T-cell de-immunized polypeptide and/or cell-targeted protein of the invention, or a fragment or derivative thereof, or the antisense or complement of any such sequence.

Derivatives or analogs of the molecules (e.g., CD8+ T-cell hyper-immunized and/or B-cell/CD4+ T-cell de-immunized polypeptides and/or cell-targeted proteins comprising the same) of the present invention include, inter alia, polynucleotide (or polypeptide) molecules having regions that are substantially homologous to the polynucleotides, CD8+ T-cell hyper-immunized and/or B-cell/CD4+ T-cell de-immunized polypeptides, or cell-targeted proteins of the present invention, e.g. by at least about 45%, 50%, 70%, 80%, 95%, 98%, or even 99% identity (with a preferred identity of 80-99%) over a polynucleotide or polypeptide sequence of the same size or when compared to an aligned sequence in which the alignment is done by a computer homology program known in the art. An exemplary program is the GAP program (Wisconsin Sequence Analysis Package, Version 8 for UNIX, Genetics Computer Group, University Research Park, Madison, WI, U.S.) using the default settings, which uses the algorithm of Smith T, Waterman M, *Adv. Appl. Math.* 2: 482-9 (1981). Also included are polynucleotides capable of hybridizing to the complement of a sequence encoding the cell-targeted proteins of the invention under stringent conditions (see e.g. Ausubel F et al., *Current Protocols in Molecular Biology* (John Wiley & Sons, New York, NY, U.S., 1993)), and below. Stringent conditions are known to those skilled in the art and may be found, e.g., in *Current Protocols in Molecular Biology* (John Wiley & Sons, NY, U.S., Ch. Sec. 6.3.1-6.3.6 (1989)).

The present invention further provides expression vectors that comprise the polynucleotides within the scope of the present invention. The polynucleotides capable of encoding the CD8+ T-cell hyper-immunized and/or B-cell/CD4+ T-cell de-immunized polypeptides and/or cell-targeted proteins of the invention may be inserted into known vectors, including bacterial plasmids, viral vectors and phage vectors, using material and methods well known in the art to produce expression vectors. Such expression vectors will include the polynucleotides necessary to support production of contemplated CD8+ T-cell hyper-immunized and/or B-cell/CD4+ T-cell de-immunized polypeptides and/or cell-targeted proteins of the invention within any host cell of choice or cell-free expression systems (e.g. pTxb1 and pIVEX2.3). The specific polynucleotides comprising expression vectors for use with specific types of host cells or cell-free expression systems are well known to one of ordinary skill in the art, can be determined using routine experimentation, or may be purchased.

The term "expression vector," as used herein, refers to a polynucleotide, linear or circular, comprising one or more expression units. The term "expression unit" denotes a polynucleotide segment encoding a polypeptide of interest and capable of providing expression of the nucleic acid segment in a host cell. An expression unit typically comprises a transcription promoter, an open reading frame encoding the polypeptide of interest, and a transcription terminator, all in operable configuration. An expression vector contains one or more expression units. Thus, in the context of the present invention, an expression vector encoding a CD8+ T-cell hyper-immunized and/or B-cell/CD4+ T-cell de-immunized polypeptide and/or protein comprising a single polypeptide chain (e.g. a scFv genetically recombined with a CD8+ T-cell hyper-immunized and/or B-cell/CD4+ T-cell de-immunized Shiga toxin effector region) includes at least an expression unit for the single polypeptide chain, whereas a protein comprising, e.g. two or more polypeptide chains (e.g. one chain comprising a $V_L$ domain and a second chain comprising a $V_H$ domain linked to a toxin effector region) includes at least two expression units, one for each of the two polypeptide chains of the protein. For expression of multi-chain cell-targeted proteins of the invention, an expression unit for each polypeptide chain may also be separately contained on different expression vectors (e.g. expression may be achieved with a single host cell into which expression vectors for each polypeptide chain has been introduced).

Expression vectors capable of directing transient or stable expression of polypeptides and proteins are well known in the art. The expression vectors generally include, but are not limited to, one or more of the following: a heterologous signal sequence or peptide, an origin of replication, one or more marker genes, an enhancer element, a promoter, and a transcription termination sequence, each of which is well known in the art. Optional regulatory control sequences, integration sequences, and useful markers that can be employed are known in the art.

The term "host cell" refers to a cell which can support the replication or expression of the expression vector. Host cells may be prokaryotic cells, such as *E. coli* or eukaryotic cells (e.g. yeast, insect, amphibian, bird, or mammalian cells). Creation and isolation of host cell lines comprising a polynucleotide of the invention or capable of producing a polypeptide and/or cell-targeted protein of the invention can be accomplished using standard techniques known in the art.

CD8+ T-cell hyper-immunized and/or B-cell/CD4+ T-cell de-immunized polypeptides and/or proteins within the scope of the present invention may be variants or derivatives of the polypeptides and proteins described herein that are produced by modifying the polynucleotide encoding a polypeptide and/or protein by altering one or more amino acids or deleting or inserting one or more amino acids that may render it more suitable to achieve desired properties, such as more optimal expression by a host cell.

XI. Delivery Devices and Kits

In certain embodiments, the invention relates to a device comprising one or more compositions of matter of the invention, such as a pharmaceutical composition, for delivery to a subject in need thereof. Thus, a delivery device comprising one or more compounds of the invention can be used to administer to a patient a composition of matter of the invention by various delivery methods, including: intravenous, subcutaneous, intramuscular or intraperitoneal injection; oral administration; transdermal administration; pulmonary or transmucosal administration; administration by implant, osmotic pump, cartridge or micro pump; or by other means recognized by a person of skill in the art.

Also within the scope of the invention are kits comprising at least one composition of matter of the invention, and optionally, packaging and instructions for use. Kits may be useful for drug administration and/or diagnostic information gathering. A kit of the invention may optionally comprise at least one additional reagent (e.g., standards, markers and the like). Kits typically include a label indicating the intended use of the contents of the kit. The kit may further comprise reagents and other tools for detecting a cell type (e.g. tumor cell) in a sample or in a subject, or for diagnosing whether a patient belongs to a group that responds to a therapeutic strategy which makes use of a compound, composition or related method of the invention as described herein.

XII. Methods of Generating T-Cell Hyper-Immunized and/or B-Cell/CD4+ T-Cell De-Immunized Polypeptides of the Present Invention The present invention provides methods of creating T-cell hyper-immunized and/or B-cell/CD4+ T-cell de-immunized polypeptides of the present invention by modifying polypeptides already capable of intracellularly routing to a cytosol, ER, or lysosome of a cell from an endosomal compartment of the cell; the method comprising the step of adding a heterologous T-cell epitope to the polypeptide. In certain further methods of the present invention, the heterologous T-cell epitope is embedded or inserted within a polypeptide capable of intracellularly routing to a cytosol, ER, or lysosome of a cell from an endosomal compartment of the cell.

In certain embodiments of the methods of the present invention, a CD8+ T-cell hyper-immunized and/or B-cell/CD4+ T-cell de-immunized polypeptide of the present invention is created by modifying a polypeptide already capable of intracellularly routing to a cytosol, ER, or lysosome of a cell from an endosomal compartment of the cell; the method comprising the step of adding a heterologous T-cell epitope to the polypeptide. In certain further methods of the present invention, the heterologous T-cell epitope is embedded or inserted within a polypeptide capable of intracellularly routing to a cytosol, ER, or lysosome of a cell from an endosomal compartment of the cell.

In certain embodiments of the methods of the present invention, a polypeptide already capable of intracellularly routing to a cytosol, ER, or lysosome of a cell from an endosomal compartment of the cell is created into a T-cell hyper-immunized polypeptide of the present invention; the method comprising the step of adding a heterologous T-cell epitope to the polypeptide. In certain further embodiments of the methods of the present invention, a polypeptide already capable of intracellularly routing to a cytosol, ER, or lysosome of a cell from an endosomal compartment of the cell is created into a CD8+ T-cell hyper-immunized polypeptide of the present invention; the method comprising the step of adding a heterologous T-cell epitope to the polypeptide. In certain further methods of the present invention, the heterologous T-cell epitope is embedded or inserted within a polypeptide capable of intracellularly routing to a cytosol, ER, or lysosome of a cell from an endosomal compartment of the cell.

In certain embodiments of the methods of the present invention, a polypeptide capable of delivering a T-cell epitope for presentation by a MHC class I molecule is created; the method comprising the step of adding a heterologous T-cell epitope to a polypeptide capable of intracellular delivery of the T-cell epitope from an endosomal compartment of a cell to a proteasome of the cell. In certain further methods of the present invention, the heterologous T-cell epitope is embedded or inserted within a polypeptide capable of intracellularly routing to a cytosol, ER, or lysosome of a cell from an endosomal compartment of the cell.

In certain embodiments of the methods of the present invention, a T-cell hyper-immunized and/or B-cell/CD4+ T-cell de-immunized polypeptide is created; the method comprising the step of inserting or embedding a heterologous T-cell epitope into an endogenous B-cell epitope region of a polypeptide already capable of intracellularly routing to a cytosol, ER, or lysosome of a cell from an endosomal compartment of the cell.

In certain embodiments of the methods of the present invention, a CD8+ T-cell hyper-immunized and B-cell/CD4+ T-cell de-immunized polypeptide of the present invention is created; the method comprising the step of embedding or inserting a heterologous T-cell epitope into an endogenous B-cell epitope region of a polypeptide already capable of intracellularly routing to a cytosol, ER, or lysosome of a cell from an endosomal compartment of the cell.

In certain embodiments of the methods of the present invention, a polypeptide already capable of intracellularly routing to a cytosol, ER, or lysosome of a cell from an endosomal compartment of the cell is created into a T-cell hyper-immunized and/or B-cell/CD4+ T-cell de-immunized polypeptide of the present invention; the method comprising the step of embedding or inserting a heterologous T-cell epitope into an endogenous B-cell epitope region of the polypeptide. In certain further embodiments of the methods of the present invention, a polypeptide already capable of intracellularly routing to a cytosol, ER, or lysosome of a cell from an endosomal compartment of the cell is created into a CD8+ T-cell hyper-immunized polypeptide of the present invention; the method comprising the step of embedding or inserting a heterologous T-cell epitope into an endogenous B-cell epitope region of the polypeptide.

In certain embodiments of the methods of the present invention, a de-immunized polypeptide capable of delivering a T-cell epitope for presentation by a MHC class I molecule is created; the method comprising the step of embedding or inserting a heterologous T-cell epitope into an endogenous B-cell epitope region of a polypeptide capable of intracellular delivery of the T-cell epitope from an endosomal compartment of a cell to a proteasome of the cell.

In certain embodiments of the methods of the present invention, a de-immunized polypeptide is created which has reduced B-cell immunogenicity when administered to a chordate. In certain embodiments of the methods of the present invention, is a method for reducing B-cell immunogenicity in a polypeptide, the method comprising the step of disrupting a B-cell epitope region within a polypeptide with one or more amino acid residue(s) comprised by a heterologous T-cell epitope added to the polypeptide. In certain further embodiments, the disrupting step further comprises creating one or more amino acid substitutions in the B-cell epitope region. In certain further embodiments, the disrupting step further comprises creating one or more amino acid insertions in the B-cell epitope region.

Certain embodiments of the methods of the present invention are methods for reducing B-cell immunogenicity in a polypeptide while simultaneously increasing CD8+ T-cell immunogenicity after administration to a chordate, the methods comprising the step of disrupting a B-cell epitope region within a polypeptide with one or more amino acid residue(s) comprised by a heterologous CD8+ T-cell epitope added to the polypeptide. In certain further embodiments, the disrupting step further comprises creating one or more amino acid substitutions in the B-cell epitope region. In certain further embodiments, the disrupting step further comprises creating one or more amino acid insertions in the B-cell epitope region.

Certain embodiments of the methods of the present invention are methods for reducing B-cell immunogenicity in a polypeptide while simultaneously increasing CD8+ T-cell immunogenicity after administration to a chordate, the methods comprising the steps of: 1) identifying a B-cell epitope in a polypeptide; and 2) disrupting the identified B-cell epitope with one or more amino acid residue(s) comprised by a heterologous CD8+ T-cell epitope added to the polypeptide. In certain further embodiments, the disrupting step further comprises the creation of one or more amino acid substitutions in the B-cell epitope region. In certain further embodiments, the disrupting step further comprises creating one or more amino acid insertions in the B-cell epitope region.

Certain embodiments of the methods of the present invention are methods for reducing B-cell immunogenicity in a polypeptide while simultaneously increasing CD8+ T-cell immunogenicity after administration to a chordate, the methods comprising the steps of: 1) identifying a B-cell epitope in a polypeptide; and 2) disrupting the identified B-cell epitope with one or more amino acid residue(s) comprised by a heterologous CD8+ T-cell epitope added to the polypeptide. In certain further embodiments, the disrupting step further comprises the creation of one or more amino acid substitutions in the B-cell epitope region. In certain further embodiments, the disrupting step further comprises creating one or more amino acid insertions in the B-cell epitope region.

In certain embodiments of the methods of the present invention, a CD4+ T-cell de-immunized polypeptide is created which has reduced CD4+ T-cell immunogenicity when administered to a chordate. In certain embodiments of the methods of the present invention, is a method for reducing CD4+ T-cell immunogenicity in a polypeptide, the method comprising the step of disrupting a CD4+ T-cell epitope region within a polypeptide with one or more amino acid residue(s) comprised by a heterologous CD8+ T-cell epitope added to the polypeptide. In certain further embodiments, the disrupting step further comprises creating one or more amino acid substitutions in the B-cell epitope region. In certain further embodiments, the disrupting step further comprises creating one or more amino acid insertions in the CD4+ T-cell epitope region.

Certain embodiments of the methods of the present invention are methods for reducing CD4+ T-cell immunogenicity in a polypeptide while simultaneously increasing CD8+ T-cell immunogenicity after administration to a chordate, the methods comprising the step of disrupting a CD4+ T-cell epitope region within a polypeptide with one or more amino acid residue(s) comprised by a heterologous CD8+ T-cell epitope added to the polypeptide. In certain further embodiments, the disrupting step further comprises creating one or more amino acid substitutions in the CD4+ T-cell epitope region. In certain further embodiments, the disrupting step further comprises creating one or more amino acid insertions in the CD4+ T-cell epitope region.

Certain embodiments of the methods of the present invention are methods for reducing CD4+ T-cell immunogenicity in a polypeptide while simultaneously increasing CD8+ T-cell immunogenicity after administration to a chordate, the methods comprising the steps of: 1) identifying a CD4+ T-cell epitope in a polypeptide; and 2) disrupting the identified CD4+ T-cell epitope with one or more amino acid residue(s) comprised by a heterologous CD8+ T-cell epitope added to the polypeptide. In certain further embodiments, the disrupting step further comprises the creation of one or more amino acid substitutions in the CD4+ T-cell epitope region. In certain further embodiments, the disrupting step further comprises creating one or more amino acid insertions in the CD4+ T-cell epitope region.

Certain embodiments of the methods of the present invention are methods for reducing CD4+ T-cell immunogenicity in a polypeptide while simultaneously increasing CD8+ T-cell immunogenicity after administration to a chordate, the methods comprising the steps of: 1) identifying a CD4+ T-cell epitope in a polypeptide; and 2) disrupting the identified CD4+ T-cell epitope with one or more amino acid residue(s) comprised by a heterologous CD8+ T-cell epitope added to the polypeptide. In certain further embodiments, the disrupting step further comprises the creation of one or more amino acid substitutions in the CD4+ T-cell epitope region. In certain further embodiments, the disrupting step further comprises creating one or more amino acid insertions in the CD4+ T-cell epitope region.

XII. Methods for Using a T-Cell Hyper-Immunized and/or B-Cell/CD4+ T-Cell De-Immunized Polypeptide of the Present Invention, Cell-Targeted Molecule Comprising the Same, or Pharmaceutical and/or Diagnostic Composition Thereof Generally, it is an object of the invention to provide pharmacologically active agents, as well as compositions comprising the same, that can be used in the prevention and/or treatment of diseases, disorders, and conditions, such as certain cancers, tumors, growth abnormalities, immune disorders, or further pathological conditions mentioned herein. Accordingly, the present invention provides methods of using the polypeptides, cell-targeted molecules, and pharmaceutical compositions of the present invention for the delivering of T-cell epitopes to the MHC class I presentation pathway of target cells, targeted killing of cells, for delivering additional exogenous materials into targeted cells, for labeling of the interiors of targeted cells, for collecting diagnostic information, and for treating diseases, disorders, and conditions as described herein.

Already cytotoxic molecules, such as e.g. potential therapeutics comprising cytotoxic toxin region polypeptides, may be engineered to be more cytotoxic and/or to have redundant, backup cytotoxicities operating via completely different mechanisms. These multiple cytotoxic mechanisms may complement each other (such as by providing both two mechanisms of cell killing, direct and indirect, as well as mechanisms of immuno-stimulation to the local area), redundantly backup each other (such as by providing direct cell killing in the absence of the other), and/or protect against developed resistance (by limiting resistance to the less probable situation of the malignant or infected cell blocking two different mechanisms simultaneously).

In addition, parental cytotoxic molecules which rely on toxin effector and/or enzymatic regions for cytotoxicity may be engineered by mutating the parental molecule to be enzymatically inactive but to be cytotoxic via T-cell epitope delivery to the MHC class I system of a target cell and subsequent presentation to the surface of the target cell. This approach removes one cytotoxic mechanism while adding another and adds the capability of immuno-stimulation to the local area of the target cell by T-cell epitope presentation. Furthermore, parental cytotoxic molecules which rely on enzymatic regions for cytotoxicity may be engineered to be cytotoxic only via T-cell epitope delivery to the MHC class I system by embedding a T-cell epitope in the enzymatic domain of the parental molecule such that the enzymatic activity is reduced or eliminated. This allows for the one-step modification of enzymatically-cytotoxic molecules, which have the ability once in an endosomal compartment to route to the cytosol and/or ER, into enzymatically inactive, cytotoxic molecules which rely on T-cell epitope delivery to the MHC class I system of a target cell and subsequent presentation on the surface of the target cell for cytotoxicity. Any of the polypeptides of the invention can be engineered into cell-targeted cytotoxic molecules with potential as therapeutics by the linking of a variety of cell-targeting binding regions which target specific cell-type(s) within a mixture of two or more cell types, such as, e.g., within an organism.

In particular, it is an object of the invention to provide such pharmacologically active agents, compositions, and/or methods that have certain advantages compared to the agents, compositions, and/or methods that are currently known in the art. Accordingly, the present invention provides methods of using polypeptides and proteins with characterized by polypeptide sequences and pharmaceutical compositions thereof. For example, any of the polypeptide sequences in SEQ ID NOs: 1-60 may be specifically utilized as a component of the cell-targeted molecules used in the following methods.

The present invention provides methods of killing a cell comprising the step of contacting the cell, either in vitro or in vivo, with a polypeptide, protein, or pharmaceutical composition of the present invention. The polypeptides, proteins, and pharmaceutical compositions of the present invention can be used to kill a specific cell type upon contacting a cell or cells with one of the claimed compositions of matter. In certain embodiments, a cytotoxic polypeptide, protein, or pharmaceutical composition of the present invention can be used to kill specific cell types in a mixture of different cell types, such as mixtures comprising cancer cells, infected cells, and/or hematological cells. In certain embodiments, a cytotoxic polypeptide, protein, or pharmaceutical composition of the present invention can be used to kill cancer cells in a mixture of different cell types. In certain embodiments, a cytotoxic polypeptide, protein, or pharmaceutical composition of the present invention can be used to kill specific cell types in a mixture of different cell types, such as pre-transplantation tissues. In certain embodiments, a polypeptide, protein, or pharmaceutical composition of the present invention can be used to kill specific cell types in a mixture of cell types, such as pre-administration tissue material for therapeutic purposes. In certain embodiments, a polypeptide, protein, or pharmaceutical composition of the present invention can be used to selectively kill cells infected by viruses or microorganisms, or otherwise selectively kill cells expressing a particular extracellular target biomolecule, such as a cell surface biomolecule. The polypeptides, proteins, and pharmaceutical compositions of the present invention have varied applications, including, e.g., uses in depleting unwanted cell types from tissues either in vitro or in vivo, uses in modulating immune responses to treat graft-versus-host disease, uses as antiviral agents, uses as anti-parasitic agents, and uses in purging transplantation tissues of unwanted cell types.

In certain embodiments, a cytotoxic polypeptide, protein, or pharmaceutical composition of the present invention, alone or in combination with other compounds or pharmaceutical compositions, can show potent cell-kill activity when administered to a population of cells, in vitro or in vivo in a subject such as in a patient in need of treatment. By targeting the delivery of enzymatically active toxin regions and T-cell epitopes using high-affinity binding regions to specific cell types, this potent cell-kill activity can be restricted to specifically and selectively kill certain cell types within an organism, such as certain cancer cells, neoplastic cells, malignant cells, non-malignant tumor cells, or infected cells.

The present invention provides a method of killing a cell in a patient in need thereof, the method comprising the step of administering to the patient at least one cytotoxic polypeptide or protein of the present invention, or a pharmaceutical composition thereof.

Certain embodiments of the cytotoxic polypeptide, protein, or pharmaceutical compositions thereof can be used to kill a cancer cell in a patient by targeting an extracellular biomolecule found physically coupled with a cancer or tumor cell. The terms "cancer cell" or "cancerous cell" refers to various neoplastic cells which grow and divide in an abnormally accelerated fashion and will be clear to the skilled person. The term "tumor cell" includes both malignant and non-malignant cells. Generally, cancers and/or tumors can be defined as diseases, disorders, or conditions that are amenable to treatment and/or prevention. The cancers and tumors (either malignant or non-malignant) which are comprised of cancer cells and/or tumor cells which may benefit from methods and compositions of the invention will be clear to the skilled person. Neoplastic cells are often associated with one or more of the following: unregulated growth, lack of differentiation, local tissue invasion, angiogenesis, and metastasis.

Certain embodiments of the cytotoxic polypeptide or cell-targeted molecule of the present invention, or pharmaceutical compositions thereof, can be used to kill an immune cell (whether healthy or malignant) in a patient by targeting an extracellular biomolecule found physically coupled with an immune cell.

Certain embodiments of the cytotoxic polypeptide or cell-targeted molecule of the present invention, or pharmaceutical compositions thereof, can be used to kill an infected cell in a patient by targeting an extracellular biomolecule found physically coupled with an infected cell.

It is within the scope of the present invention to utilize the cell-targeted molecule of the present invention or pharmaceutical composition thereof for the purposes of purging patient cell populations (e.g. bone marrow) of malignant, neoplastic, or otherwise unwanted T-cells and/or B-cells and then reinfusing the T-cell and/or B-cells depleted material into the patient (see e.g. van Heeckeren W et al., *Br J Haematol* 132: 42-55 (2006); (see e.g. Alpdogan O, van den Brink M, *Semin Oncol* 39: 629-42 (2012)).

It is within the scope of the present invention to utilize the cell-targeted molecule of the present invention or pharmaceutical composition thereof for the purposes of ex vivo depletion of T cells and/or B-cells from isolated cell populations removed from a patient. In one non-limiting example, the cell-targeted molecule of the invention can be used in a method for prophylaxis of organ and/or tissue transplant rejection wherein the donor organ or tissue is perfused prior to transplant with a cytotoxic, cell-targeted molecule of the invention or a pharmaceutical composition thereof in order to purge the organ of donor T-cells and/or B-cells (see e.g. Alpdogan O, van den Brink M, *Semin Oncol* 39: 629-42 (2012)).

It is also within the scope of the present invention to utilize the cell-targeted molecule of the invention or pharmaceutical composition thereof for the purposes of depleting T-cells and/or B-cells from a donor cell population as a prophylaxis against graft-versus-host disease, and induction of tolerance, in a patient to undergo a bone marrow and or stem cell transplant (see e.g. van Heeckeren W et al., *Br J Haematol* 132: 42-55 (2006); (see e.g. Alpdogan O, van den Brink M, *Semin Oncol* 39: 629-42 (2012)).

Certain embodiments of the cytotoxic polypeptide or cell-targeted molecule of the invention, or pharmaceutical compositions thereof, can be used to kill an infected cell in a patient by targeting an extracellular biomolecule found physically coupled with an infected cell.

Certain embodiments of the cell-targeted molecules of the present invention, or pharmaceutical compositions thereof, can be used to "seed" a locus within an organism with non-self, T-cell epitope-peptide presenting cells in order to activate the immune system to police the locus. In certain further embodiments of this "seeding" method of the present invention, the locus is a tumor mass or infected tissue site. In preferred embodiments of this "seeding" method of the present invention, the non-self, T-cell epitope-peptide is selected from the group consisting of: peptides not already presented by the target cells of the cell-targeted molecule, peptides not present within any protein expressed by the target cell, peptides not present within the proteome of the target cell, peptides not present in the extracellular microenvironment of the site to be seeded, and peptides not present in the tumor mass or infect tissue site to be targeted.

This "seeding" method functions to label one or more target cells within a chordate with one or more MHC class I presented T-cell epitopes for recognition by effector T-cells and activation of downstream immune responses. By exploiting the cell internalizing, intracellularly routing, and T-cell epitope delivering functions of the cell-targeted molecules of the invention, the target cells which display the delivered T-cell epitope are harnessed to induce recognition of the presenting target cell by host T-cells and induction of further immune responses including target cell killing by CTLs. This "seeding" method of using a cell-targeted molecule of the present invention can provide a temporary vaccination-effect by inducing adaptive immune responses to attack the cells within the seeded microenvironment, such as, e.g. a tumor mass or infected tissue site, whether presenting a cell-targeted molecule-delivered T-cell epitope(s) or not. This "seeding" method may also induce the breaking of immuno-tolerance to a target cell population, a tumor mass, and/or infected tissue site within an organism.

Additionally, the present invention provides a method of treating a disease, disorder, or condition in a patient comprising the step of administering to a patient in need thereof a therapeutically effective amount of at least one of the cytotoxic polypeptide or cell-targeted molecule of the present invention, or a pharmaceutical composition thereof. Contemplated diseases, disorders, and conditions that can be treated using this method include cancers, malignant tumors, non-malignant tumors, growth abnormalities, immune disorders, and microbial infections. Administration of a "therapeutically effective dosage" of a compound of the invention can result in a decrease in severity of disease symptoms, an increase in frequency and duration of disease symptom-free periods, or a prevention of impairment or disability due to the disease affliction.

The therapeutically effective amount of a compound of the present invention will depend on the route of administration, the type of mammal being treated, and the physical characteristics of the specific patient under consideration. These factors and their relationship to determining this amount are well known to skilled practitioners in the medical arts. This amount and the method of administration can be tailored to achieve optimal efficacy, and may depend on such factors as weight, diet, concurrent medication and other factors, well known to those skilled in the medical arts. The dosage sizes and dosing regimen most appropriate for human use may be guided by the results obtained by the present invention, and may be confirmed in properly designed clinical trials. An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the skilled person.

An acceptable route of administration may refer to any administration pathway known in the art, including but not limited to aerosol, enteral, nasal, ophthalmic, oral, parenteral, rectal, vaginal, or transdermal (e.g. topical administration of a cream, gel or ointment, or by means of a transdermal patch). "Parenteral administration" is typically associated with injection at or in communication with the intended site of action, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal administration.

For administration of a pharmaceutical composition of the present invention, the dosage range will generally be from about 0.0001 to 100 milligrams per kilogram (mg/kg), and more, usually 0.01 to 5 mg/kg, of the host body weight. Exemplary dosages may be 0.25 mg/kg body weight, 1 mg/kg body weight, 3 mg/kg body weight, 5 mg/kg body weight or 10 mg/kg body weight or within the range of 1-10 mg/kg. An exemplary treatment regime is a once or twice daily administration, or a once or twice weekly administration, once every two weeks, once every three weeks, once every four weeks, once a month, once every two or three months or once every three to 6 months. Dosages may be selected and readjusted by the skilled health care professional as required to maximize therapeutic benefit for a particular patient.

Pharmaceutical compositions of the present invention will typically be administered to the same patient on multiple occasions. Intervals between single dosages can be, for example, 2-5 days, weekly, monthly, every two or three months, every six months, or yearly. Intervals between administrations can also be irregular, based on regulating blood levels or other markers in the subject or patient. Dosage regimens for a compound of the invention include intravenous administration of 1 mg/kg body weight or 3 mg/kg body weight with the compound administered every two to four weeks for six dosages, then every three months at 3 mg/kg body weight or 1 mg/kg body weight.

A pharmaceutical composition of the present invention may be administered via one or more routes of administration, using one or more of a variety of methods known in the art. As will be appreciated by the skilled worker, the route and/or mode of administration will vary depending upon the desired results. Routes of administration for polypeptides, proteins, and pharmaceutical compositions of the invention include, e.g. intravenous, intramuscular, intradermal, intraperitoneal, subcutaneous, spinal, or other parenteral routes of administration, for example by injection or infusion. In other embodiments, a polypeptide, protein, or pharmaceutical composition of the invention may be administered by a non-parenteral route, such as a topical, epidermal or mucosal route of administration, for example, intranasally, orally, vaginally, rectally, sublingually, or topically.

Therapeutic polypeptides, proteins, or pharmaceutical compositions of the present invention may be administered with one or more of a variety of medical devices known in the art. For example, in one embodiment, a pharmaceutical composition of the invention may be administered with a needleless hypodermic injection device. Examples of well-known implants and modules useful in the present invention are in the art, including e.g., implantable micro-infusion pumps for controlled rate delivery; devices for administering through the skin; infusion pumps for delivery at a precise infusion rate; variable flow implantable infusion devices for continuous drug delivery; and osmotic drug delivery systems. These and other such implants, delivery systems, and modules are known to those skilled in the art.

A polypeptide, protein, or pharmaceutical composition of the present invention may be administered alone or in combination with one or more other therapeutic or diagnostic agents. A combination therapy may include a cytotoxic, cell-targeted molecule of the invention or pharmaceutical composition thereof combined with at least one other therapeutic agent selected based on the particular patient, disease or condition to be treated. Examples of other such agents include, inter alia, a cytotoxic, anti-cancer or chemotherapeutic agent, an anti-inflammatory or anti-proliferative agent, an antimicrobial or antiviral agent, growth factors, cytokines, an analgesic, a therapeutically active small molecule or polypeptide, a single chain antibody, a classical antibody or fragment thereof, or a nucleic acid molecule which modulates one or more signaling pathways, and similar modulating therapeutics which may complement or otherwise be beneficial in a therapeutic or prophylactic treatment regimen.

Treatment of a patient with a polypeptide, protein, or pharmaceutical composition of the present invention preferably leads to cell death of targeted cells and/or the inhibition of growth of targeted cells. As such, cytotoxic, cell-targeted molecules of the present invention, and pharmaceutical compositions comprising them, will be useful in methods for treating a variety of pathological disorders in which killing or depleting target cells may be beneficial, such as, inter alia, cancer, tumors, other growth abnormalities, immune disorders, and infected cells. The present invention provides methods for suppressing cell proliferation, and treating cell disorders, including neoplasia, overactive B-cells, and overactive T-cells.

In certain embodiments, polypeptides, proteins, and pharmaceutical compositions of the present invention can be used to treat or prevent cancers, tumors (malignant and non-malignant), growth abnormalities, immune disorders, and microbial infections. In a further aspect, the above ex vivo method can be combined with the above in vivo method to provide methods of treating or preventing rejection in bone marrow transplant recipients, and for achieving immunological tolerance.

In certain embodiments, the present invention provides methods for treating malignancies or neoplasms and other blood cell associated cancers in a mammalian subject, such as a human, the method comprising the step of administering to a subject in need thereof a therapeutically effective amount of a cytotoxic protein or pharmaceutical composition of the invention.

The cytotoxic polypeptides, proteins, and pharmaceutical compositions of the present invention have varied applications, including, e.g., uses in removing unwanted T-cells, uses in modulating immune responses to treat graft-versus-host disease, uses as antiviral agents, uses as antimicrobial agents, and uses in purging transplantation tissues of unwanted cell types. The cytotoxic polypeptides, proteins, and pharmaceutical compositions of the present invention are commonly anti-neoplastic agents—meaning they are capable of treating and/or preventing the development, maturation, or spread of neoplastic or malignant cells by inhibiting the growth and/or causing the death of cancer or tumor cells.

In certain embodiments, a polypeptide, protein, or pharmaceutical composition of the present invention is used to treat a B-cell-, plasma cell- or antibody-mediated disease or disorder, such as for example leukemia, lymphoma, myeloma, Human Immunodeficiency Virus-related diseases, amyloidosis, hemolytic uremic syndrome, polyarteritis, septic shock, Crohn's Disease, rheumatoid arthritis, ankylosing spondylitis, psoriatic arthritis, ulcerative colitis, psoriasis, asthma, Sjorgren's syndrome, graft-versus-host disease, graft rejection, diabetes, vasculitis, scleroderma, and systemic lupus erythematosus.

In another aspect, certain embodiments of the polypeptides, proteins, and pharmaceutical compositions of the present invention are antimicrobial agents—meaning they are capable of treating and/or preventing the acquisition, development, or consequences of microbiological pathogenic infections, such as caused by viruses, bacteria, fungi, prions, or protozoans.

It is within the scope of the present invention to provide a prophylaxis or treatment for diseases or conditions mediated by T-cells or B-cells by administering the cytotoxic protein or the invention, or a pharmaceutical composition thereof, to a patient for the purpose of killing T-cells or B-cells in the patient. This usage is compatible with preparing or conditioning a patient for bone marrow transplantation, stem cell transplantation, tissue transplantation, or organ transplantation, regardless of the source of the transplanted material, e.g. human or non-human sources.

It is within the scope of the present invention to provide a bone marrow recipient for prophylaxis or treatment of host-versus-graft disease via the targeted cell-killing of host T-cells using a cytotoxic polypeptide, protein, or pharmaceutical composition of the present invention.

The cytotoxic polypeptides, proteins, and pharmaceutical compositions of the present invention can be utilized in a method of treating cancer comprising administering to a patient, in need thereof, a therapeutically effective amount of a cytotoxic polypeptide, protein, or pharmaceutical composition of the present invention. In certain embodiments of the methods of the present invention, the cancer being treated is selected from the group consisting of: bone cancer (such as multiple myeloma or Ewing's sarcoma), breast cancer, central/peripheral nervous system cancer (such as brain cancer, neurofibromatosis, or glioblastoma), gastrointestinal cancer (such as stomach cancer or colorectal cancer), germ cell cancer (such as ovarian cancers and testicular cancers, glandular cancer (such as pancreatic cancer, parathyroid cancer, pheochromocytoma, salivary gland cancer, or thyroid cancer), head-neck cancer (such as nasopharyngeal cancer, oral cancer, or pharyngeal cancer), hematological cancers (such as leukemia, lymphoma, or myeloma), kidney-urinary tract cancer (such as renal cancer and bladder cancer), liver cancer, lung/pleura cancer (such as mesothelioma, small cell lung carcinoma, or non-small cell lung carcinoma), prostate cancer, sarcoma (such as angiosarcoma, fibrosarcoma, Kaposi's sarcoma, or synovial sarcoma), skin cancer (such as basal cell carcinoma, squamous cell carcinoma, or melanoma), and uterine cancer.

The polypeptides, proteins, and pharmaceutical compositions of the present invention can be utilized in a method of treating an immune disorder comprising administering to a patient, in need thereof, a therapeutically effective amount of the cytotoxic protein or a pharmaceutical composition of the present invention. In certain embodiments of the methods of the present invention, the immune disorder is related to an inflammation associated with a disease selected from the group consisting of: amyloidosis, ankylosing spondylitis, asthma, Crohn's disease, diabetes, graft rejection, graft-versus-host disease, Hashimoto's thyroiditis, hemolytic uremic syndrome, HIV-related diseases, lupus erythematosus, multiple sclerosis, polyarteritis, psoriasis, psoriatic arthritis, rheumatoid arthritis, scleroderma, septic shock, Sjorgren's syndrome, ulcerative colitis, and vasculitis.

Among certain embodiments of the present invention is using the polypeptide or cell-targeted molecule of the present invention as a component of a pharmaceutical composition or medicament for the treatment or prevention of a cancer, tumor, other growth abnormality, immune disorder, and/or microbial infection. For example, immune disorders presenting on the skin of a patient may be treated with such a medicament in efforts to reduce inflammation. In another example, skin tumors may be treated with such a medicament in efforts to reduce tumor size or eliminate the tumor completely.

Certain cytotoxic polypeptides, proteins, and pharmaceutical compositions of the present invention may be used in molecular neurosurgery applications such as immunolesioning and neuronal tracing (see, Wiley R, Lappi D, *Adv Drug Deliv Rev* 55: 1043-54 (2003), for review). For example, the targeting domain may be selected or derived from various ligands, such as neurotransmitters and neuropeptides, which target specific neuronal cell types by binding neuronal surface receptors, such as a neuronal circuit specific G-protein coupled receptor. Similarly, the targeting domain may be selected from or derived from antibodies that bind neuronal surface receptors. Because certain toxins robustly direct their own retrograde axonal transport, certain cytotoxic, cell-targeted molecules of the invention may be used to kill a neuron(s) which expresses the extracellular target at a site of cytotoxic protein injection distant from the cell body (see Llewellyn-Smith I et al., *J Neurosci Methods* 103: 83-90 (2000)). These neuronal cell type specific targeting cytotoxic polypeptides and proteins have uses in neuroscience research, such as for elucidating mechanisms of sensations (see e.g. Mishra S, Hoon M, *Science* 340: 968-71 (2013), and creating model systems of neurodegenerative diseases, such as Parkinson's and Alzheimer's (see e.g. Hamlin A et al., *PLoS One* e53472 (2013)).

Among certain embodiment of the present invention is a method of using a polypeptide, protein, pharmaceutical composition, and/or diagnostic composition of the present invention to label or detect the interiors of neoplastic cells and/or immune cell types. Based on the ability of certain polypeptides, proteins, and pharmaceutical compositions of the invention to enter specific cell types and route within cells via retrograde intracellular transport, the interior compartments of specific cell types are labeled for detection. This can be performed on cells in situ within a patient or on cells and tissues removed from an organism, e.g. biopsy material.

Among certain embodiment of the present invention is a method of using a polypeptide, protein, pharmaceutical composition, and/or diagnostic composition of the present invention to detect the presence of a cell type for the purpose of information gathering regarding diseases, conditions and/or disorders. The method comprises contacting a cell with a diagnostically sufficient amount of a cytotoxic molecule to detect the cytotoxic molecule by an assay or diagnostic technique. The phrase "diagnostically sufficient amount" refers to an amount that provides adequate detection and accurate measurement for information gathering purposes by the particular assay or diagnostic technique utilized. Generally, the diagnostically sufficient amount for whole organism in vivo diagnostic use will be a non-cumulative dose of between 0.1 mg to 100 mg of the detection promoting agent linked cell-targeted molecule of the invention per kg of subject per subject. Typically, the amount of polypeptide or cell-targeted molecule of the invention used in these information gathering methods will be as low as possible provided that it is still a diagnostically sufficient amount. For example, for in vivo detection in an organism, the amount of polypeptide, protein, or pharmaceutical composition of the invention administered to a subject will be as low as feasibly possible.

The cell-type specific targeting of polypeptides and cell-targeted molecules of the present invention combined with detection promoting agents provides a way to detect and image cells physically coupled with an extracellular target biomolecule of a binding region of the molecule of the invention. Imaging of cells using the polypeptides or cell-targeted molecules of the present invention may be performed in vitro or in vivo by any suitable technique known in the art. Diagnostic information may be collected using various methods known in the art, including whole body imaging of an organism or using ex vivo samples taken from an organism. The term "sample" used herein refers to any number of things, but not limited to, fluids such as blood, urine, serum, lymph, saliva, anal secretions, vaginal secretions, and semen, and tissues obtained by biopsy procedures. For example, various detection promoting agents may be utilized for non-invasive in vivo tumor imaging by techniques such as magnetic resonance imaging (MRI), optical methods (such as direct, fluorescent, and bioluminescent imaging), positron emission tomography (PET), single-photon emission computed tomography (SPECT), ultrasound, x-ray computed tomography, and combinations of the aforementioned (see, Kaur S et al., *Cancer Lett* 315: 97-111 (2012), for review).

Among certain embodiment of the present invention is a method of using a polypeptide, protein, or pharmaceutical composition of the present invention as a diagnostic composition to label or detect the interiors of cancer, tumor, and/or immune cell types (see e.g., Koyama Y et al., *Clin Cancer Res* 13: 2936-45 (2007); Ogawa M et al., *Cancer Res* 69: 1268-72 (2009); Yang L et al., Small 5: 235-43 (2009)). Based on the ability of certain polypeptides, proteins, and pharmaceutical compositions of the invention to enter specific cell types and route within cells via retrograde intracellular transport, the interior compartments of specific cell types are labeled for detection. This can be performed on cells in sit within a patient or on cells and tissues removed from an organism, e.g. biopsy material.

Diagnostic compositions of the present invention may be used to characterize a disease, disorder, or condition as potentially treatable by a related pharmaceutical composition of the present invention. Certain compositions of matter of the present invention may be used to determine whether a patient belongs to a group that responds to a therapeutic strategy which makes use of a compound, composition or related method of the present invention as described herein or is well suited for using a delivery device of the invention.

Diagnostic compositions of the present invention may be used after a disease, e.g. a cancer, is detected in order to better characterize it, such as to monitor distant metastases, heterogeneity, and stage of cancer progression. The phenotypic assessment of disease disorder or infection can help prognostic and prediction during therapeutic decision making. In disease reoccurrence, certain methods of the invention may be used to determine if local or systemic problem.

Diagnostic compositions of the present invention may be used to assess responses to therapeutic(s) regardless of the type of therapeutic, e.g. small molecule drug, biological drug, or cell-based therapy. For example, certain embodiments of the diagnostics of the invention may be used to measure changes in tumor size, changes in antigen positive cell populations including number and distribution, or monitoring a different marker than the antigen targeted by a therapy already being administered to a patient (see Smith- Jones P et al., *Nat. Biotechnol* 22: 701-6 (2004); Evans M et al., *Proc. Natl. Acad. Sci. U.S.A.* 108: 9578-82 (2011)).

Certain embodiments of the method used to detect the presence of a cell type may be used to gather information regarding diseases, disorders, and conditions, such as, for example bone cancer (such as multiple myeloma or Ewing's sarcoma), breast cancer, central/peripheral nervous system cancer (such as brain cancer, neurofibromatosis, or glioblastoma), gastrointestinal cancer (such as stomach cancer or colorectal cancer), germ cell cancer (such as ovarian cancers and testicular cancers, glandular cancer (such as pancreatic cancer, parathyroid cancer, pheochromocytoma, salivary gland cancer, or thyroid cancer), head-neck cancer (such as nasopharyngeal cancer, oral cancer, or pharyngeal cancer), hematological cancers (such as leukemia, lymphoma, or myeloma), kidney-urinary tract cancer (such as renal cancer and bladder cancer), liver cancer, lung/pleura cancer (such as mesothelioma, small cell lung carcinoma, or non-small cell lung carcinoma), prostate cancer, sarcoma (such as angiosarcoma, fibrosarcoma, Kaposi's sarcoma, or synovial sarcoma), skin cancer (such as basal cell carcinoma, squamous cell carcinoma, or melanoma), uterine cancer, AIDS, amyloidosis, ankylosing spondylitis, asthma, autism, cardiogenesis, Crohn's disease, diabetes, erythematosus, gastritis, graft rejection, graft-versus-host disease, Grave's disease, Hashimoto's thyroiditis, hemolytic uremic syndrome, HIV-related diseases, lupus erythematosus, lymphoproliferative disorders, multiple sclerosis, myasthenia gravis, neuroinflammation, polyarteritis, psoriasis, psoriatic arthritis, rheumatoid arthritis, scleroderma, septic shock, Sjorgren's syndrome, systemic lupus erythematosus, ulcerative colitis, vasculitis, cell proliferation, inflammation, leukocyte activation, leukocyte adhesion, leukocyte chemotaxis, leukocyte maturation, leukocyte migration, neuronal differentiation, acute lymphoblastic leukemia (ALL), T acute lymphocytic leukemia/lymphoma (ALL), acute myelogenous leukemia, acute myeloid leukemia (AML), B-cell chronic lymphocytic leukemia (B-CLL), B-cell prolymphocytic lymphoma, Burkitt's lymphoma (BL), chronic lymphocytic leukemia (CLL), chronic myelogenous leukemia (CML-BP), chronic myeloid leukemia (CML), diffuse large B-cell lymphoma, follicular lymphoma, hairy cell leukemia (HCL), Hodgkin's Lymphoma (HL), intravascular large B-cell lymphoma, lymphomatoid granulomatosis, lymphoplasmacytic lymphoma, MALT lymphoma, mantle cell lymphoma, multiple myeloma (MM), natural killer cell leukemia, nodal marginal B-cell lymphoma, Non-Hodgkin's lymphoma (NHL), plasma cell leukemia, plasmacytoma, primary effusion lymphoma, pro-lymphocytic leukemia, promyelocytic leukemia, small lymphocytic lymphoma, splenic marginal zone lymphoma, T-cell lymphoma (TCL), heavy chain disease, monoclonal gammopathy, monoclonal immunoglobulin deposition disease, myelodusplastic syndromes (MDS), smoldering multiple myeloma, and Waldenstrom macroglobulinemia.

In certain embodiments, the polypeptides and cell-targeted molecules of the present invention, or pharmaceutical compositions thereof, are used for both diagnosis and treatment, or for diagnosis alone. In some situations, it would be desirable to determine or verify the HLA variant(s) and/or HLA alleles expressed in the subject and/or diseased tissue from the subject, such as, e.g., a patient in need of treatment, before selecting a polypeptide or cell-targeted molecule of the invention for treatment.

The present invention is further illustrated by the following non-limiting examples of 1) CD8+ T-cell hyper-immunized and/or B-cell/CD4+ T-cell de-immunized polypeptides, 2) CD8+ T-cell epitope presenting toxin-derived polypeptides, and 3) selectively cytotoxic, cell-targeted proteins comprising the aforementioned polypeptides and capable of specifically targeting certain cell types.

EXAMPLES

The following examples demonstrate certain embodiments of the present invention. However, it is to be understood that these examples are for illustration purposes only and do not intend, nor should any be construed, to be wholly definitive as to conditions and scope of this invention. The experiments in the following examples were carried out using standard techniques, which are well known and routine to those of skill in the art, except where otherwise described in detail.

The presentation of a T-cell immunogenic epitope peptide by the MHC class I system targets the presenting cell for killing by CTL-mediated lysis and also triggers immune stimulation in the local microenvironment. By engineering immunogenic epitope sequences within toxin effector polypeptide components of target-cell-internalizing therapeutics, the targeted delivery and presentation of immuno-stimulatory antigens may be accomplished. The presentation of immuno-stimulatory non-self antigens, such as e.g. known viral antigens with high immunogenicity, by target cells signals to other immune cells to destroy the target cells as well as to recruit more immune cells to the area.

In the examples, T-cell epitopes were embedded or inserted into Shiga toxin effector polypeptides and diphtheria toxin effector polypeptides, which may serve as components of target-cell-internalizing molecules, by engineering internal regions to comprise one or more T-cell epitopes. Thus, there is no terminal fusion of an additional amino acid residue, peptide, or polypeptide component to the starting polypeptide.

In the examples, most of the T-cell epitopes were embedded into toxin effector polypeptide components of target-cell-internalizing molecules by engineering multiple amino acid substitutions but without changing the total number of amino acid residues in the exemplary toxin effector polypeptides as compared to the parental toxin effector polypeptide. Thus, for all of the diphtheria toxin effector polypeptides and most of the Shiga toxin effector polypeptides tested in the Examples, there was no insertion of additional amino acids but rather only substitutions for existing amino acids resulting in the maintenance of the original length of the parental polypeptide.

Novel toxin-derived effector polypeptides, which can function as components of cell-targeted molecules (such as e.g. immunotoxins and ligand-toxin fusions), were created which can promote cellular internalization, sub-cellular routing to the cytosol, and delivery of the T-cell epitope to the cytosol for presentation by the MHC I class pathway to the target cell surface to signal to CTLs.

Certain novel toxin-derived effector polypeptides were also de-immunized by embedding or inserting a T-cell epitope in a B-cell epitope region using one or more methods of the present invention. In order to simultaneously de-immunize and provide for T-cell epitope presentation on the target cell surface within the same toxin polypeptide region, predicted B-cell epitope regions were disrupted by replacing them with known T-cell epitopes predicted to bind to MHC Class I molecules. Amino acid sequences from toxin-derived polypeptides were analyzed to predict antigenic and/or immunogenic B-cell epitopes in silico. Various T-cell epitope embedded, toxin-derived polypeptides were experimentally tested for retention of toxin effector functions.

The preservation of toxin effector functions of exemplary T-cell epitope presenting toxin effector polypeptides of the invention were tested and compared to toxin effector polypeptides comprising wild-type toxin polypeptide sequences, referred to herein as "wild-type" or "WT," which did not comprise any internal modification or mutation to the toxin effector region.

The following examples of exemplary CD8+ T-cell epitope presenting Shiga toxin-derived polypeptides of the invention demonstrate methods of simultaneously providing for T-cell epitope delivery for MHC class I presentation while retaining one or more Shiga toxin effector functions. Further, the following examples of exemplary CD8+ T-cell epitope presenting and/or B-cell/CD4+ T-cell de-immunized Shiga toxin-derived polypeptides of the invention demonstrate methods of simultaneously providing for 1) T-cell epitope delivery for MHC class I presentation, 2) retaining one or more toxin effector functions, and 3) de-immunization of the toxin effector region.

The exemplary cell-targeted molecules of the invention bound to target biomolecules expressed by targeted cell types and entered the targeted cells. The internalized exemplary cell-targeted proteins of the invention effectively routed their de-immunized toxin effector regions to the cytosol and effectively delivered immunogenic T-cell epitopes to the target cells' MHC class I pathway resulting in presentation of the T-cell epitope peptide on the surface of target cells regions.

Example 1. Embedding or Inserting T-Cell Epitopes within Polypeptide Components of Cell-Targeting Molecules In this example, T-cell epitope sequences were selected from human viral proteins and embedded or inserted into Shiga toxin effector polypeptides. In some variants, the T-cell epitope was embedded or inserted into B-cell epitope regions in order to disrupt natively occurring B-cell epitopes. In other variants, the T-cell epitope is embedded into regions not predicted to contain any B-cell epitopes and, thus, these modifications are not predicted to disrupt any dominant B-cell epitopes. In some of the above variants, the T-cell epitope is embedded into regions predicted to disrupt catalytic activity.

A. Selecting T-Cell Epitope Peptides for Embedding or Insertion

In this example, known T-cell epitope peptides were selected for embedding and inserting into Shiga toxin effector regions which have the intrinsic ability to intracellularly route to the cytosol. For example, there are many known immunogenic viral proteins and peptide components of viral proteins from human viruses, such as human influenza A viruses and human CMV viruses. Immunogenic viral peptides were chosen that are capable of binding to human MHC class I molecules and/or eliciting human CTL-mediated responses.

Seven peptides predicted to be T-cell epitopes (SEQ ID NOs:4-10) were scored for the ability to bind to common human MHC class I human leukocyte antigen (HLA) variants encoded by the more prevalent alleles in human populations using the Immune Epitope Database (IEDB) Analysis Resource MHC-I binding prediction's consensus tool and recommended parameters (Kim Y et al., *Nucleic Acids Res* 40: W252-30 (2012)). The IEDB MHC-I binding prediction analysis predicted the "ANN affinity"—an estimated binding affinity between the input peptide and the selected human HLA variant where $IC_{50}$ values less than 50 nanomolar (nM) are considered high affinity, $IC_{50}$ values between 50 and 500 nM are considered intermediate affinity, and $IC_{50}$ values between 500 and 5000 nM are considered low affinity. The IEDB MHC-I binding prediction analysis indicated the best binders by the lowest percentile ranks. Table 1 shows the IEDB MHC-I binding prediction percentile rank and predicted binding affinity of the seven tested T cell epitope-peptides (SEQ ID NOs:4-10) binding to the selected human HLA variants.

TABLE 1

Predictions for Various Viral Protein-Derived T-Cell Epitopes Binding to Various Human MHC Class I Complexes

| T-cell epitope | | | IEDB MHC-I binding prediction | |
|---|---|---|---|---|
| Name | Sequence | HLA Allele | Percentile Rank | Predicted Affinity |
| F2 | GILGFVFTL (SEQ ID NO: 4) | HLA-A*32:01 HLA-A*02:01 HLA-A*02:06 | 0.80 0.80 2.20 | intermediate high high |
| F2-2 | DILGFVFTL (SEQ ID NO: 5) | HLA-A*32:01 HLA-A*02:01 HLA-A*02:06 | 1.40 4.60 9.55 | intermediate low intermediate |
| F2-3 | DILGFDFTL (SEQ ID NO: 6) | HLA-A*32:01 HLA-A*02:01 HLA-A*02:06 | 2.80 8.20 11.25 | low low low |
| F2-4 | GILGDVFTL (SEQ ID NO: 7) | HLA-A*02:01 HLA-A*02:06 HLA-A*32:01 | 1.40 2.40 3.10 | high high low |
| F3 | ILRGSVAHK (SEQ ID NO: 8) | HLA-A*03:01 HLA-A*30:01 HLA-A*31:01 | 0.25 0.70 4.25 | high high intermediate |

TABLE 1-continued

Predictions for Various Viral Protein-Derived T-Cell
Epitopes Binding to Various Human MHC Class I Complexes

| T-cell epitope | | | IEDB MHC-I binding prediction | |
|---|---|---|---|---|
| Name | Sequence | HLA Allele | Percentile Rank | Predicted Affinity |
| F3-4 | ILRFSVAHK | HLA-A*03:01 | 0.25 | high |
| | (SEQ ID NO: 9) | HLA-A*30:01 | 0.80 | high |
| | | HLA-A*31:01 | 3.30 | intermediate |
| C2 | NLVPMVATV | HLA-A*02:03 | 0.30 | high |
| | (SEQ ID NO: 10) | HLA-A*02:01 | 1.00 | high |
| | | HLA-A*02:06 | 1.10 | high |

The results of the IEDB MHC-I binding prediction analysis show that some peptides were predicted to bind with high affinity to multiple human MHC class I molecules, whereas other peptides were predicted to bind with more moderate affinities to the analyzed human MHC class I molecules.

B. Identifying B-Cell Epitope Regions in Toxins and Toxin Effector Polypeptides

Toxin derived polypeptides with intrinsic subcellular routing characteristics suitable for proteasome delivery were chosen for de-immunization in order to reduce the possibility of undesirable immune responses after administration to chordate, such as, e.g., the production of anti-toxin antibodies. Amino acid sequences from toxins and toxin-derived polypeptides were analyzed to predict antigenic and/or immunogenic B-cell epitopes in silico.

Polypeptide effectors derived from both a Shiga toxin and a diphtheria toxin were analyzed for B-cell epitopes.

Shiga Toxin Derived Effector Polypeptides

First, B-cell epitope regions were identified within Shiga toxin A Subunits. Computational methods were utilized to predict antigenic and/or immunogenic B-cell epitopes in Shiga toxin A subunit sequences with the potential to elicit responses by mammalian immune systems after administration.

Linear B-cell epitopes were predicted within the A Subunits of Shiga toxins using the polypeptide sequence and 3D structural data of Shiga-Like Toxin Chain A (PDB ID: iDM0_A) and the REVEAL® system provided by ProImmune, Inc. (Sarasota, FL, U.S.). In parallel, B-cell epitopes were predicted within the amino acid sequences of the A Subunit of Shiga toxins using the BcePred webserver (Saha S, Raghava G, Lecture Notes in Comput Sci 3239: 197-204 (2004)), Bepipred Linear Epitope Prediction (Larsen J et al., Immunome Res 2: 2 (2006)), ElliPro Antibody epitope prediction (Haste Andersen P et al., Protein Sci 15: 2558-67 (2006); Ponomarenko J, Bourne P, BMC Struct Biol 7: 64 (2007)), and/or the Epitopia server (Rubinstein N et al., BMC Bioinformatics 10: 287 (2009)). The Epitopia server prediction was used to identify immunogenic B-cell epitopes as any stretch of linear amino acid residues comprising a majority of residues predicted on Epitopia's immunogenicity scale to be "high" (scored as 4 or 5). The various computational methods revealed similar predictions for B-cell epitope regions in the three prototypical Shiga toxin A Subunits (Tables 2-4).

TABLE 2

B-Cell Epitope Predictions for the Mature, Native
A Subunit of Shiga-like Toxin 1 (SEQ ID NO: 1)

| Epitope Region | natively positioned amino acid positions | | | | |
|---|---|---|---|---|---|
| | REVEAL | BcePred | Bepipred | ElliPro | Epitopia |
| 1 | | | | | 1-15 |
| 2 | | 29-35 | 28-34 | 27-37 | 18-23 |
| 3 | 42-48 | 39-46 | 43-47 | | 44-49 |
| 4 | 58-66 | 55-61 | 56-64 | 57-66 | 52-62 |
| 5 | 96-103 | 105-111 | 100-115 | 96-110 | 94-102, 109-114 |
| 6 | 144-151 | 141-147 | 147-151 | 144-153 | |
| 7 | 183-189 | 181-187 | 183-185 | 180-190 | 179-188 |
| 8 | | | 211-219 | | 211-220 |
| 9 | 243-251 | | | 243-257 | 245-259 |
| 10 | 257-268 | 261-267 | 254-268 | | |
| 11 | 289-293 | 285-291 | | 262-293 | 262-281 |

TABLE 3

B-Cell Epitope Predictions for the Mature,
Native A Subunit of Shiga Toxin (SEQ ID NO: 2)
natively positioned amino acid positions

| REVEAL | BcePred | Bepipred | ElliPro |
|---|---|---|---|
| | 29-35 | 28-34 | 27-37 |
| 42-48 | 39-46 | 44-47 | |
| 58-66 | 55-61 | 56-64 | 57-66 |
| 96-103 | 105-111 | 100-115 | 96-110 |
| 144-151 | 141-147 | 147-151 | 144-153 |
| 183-189 | 181-187 | 183-185 | 180-190 |
| | | 211-219 | |
| 243-251 | | | 243-257 |
| 257-268 | 261-267 | 254-268 | |
| 289-293 | 285-291 | | 262-293 |

TABLE 4

B-Cell Epitope Predictions for the Mature, Native
A Subunit of Shiga-like Toxin 2 (SEQ ID NO: 3)
natively positioned amino acid positions

| BcePred | Bepipred | ElliPro |
|---|---|---|
| 3-11 | 8-14 | |
| 29-35 | 28-36 | 26-37 |
| | | 42-48 |
| | 57-62 | 56-66 |
| 108-115 | 109-115 | 96-110 |
| 141-156 | | 140-153 |
| | 179-188 | 180-191 |
| | 210-218 | 210-217 |

TABLE 4-continued

B-Cell Epitope Predictions for the Mature, Native
A Subunit of Shiga-like Toxin 2 (SEQ ID NO: 3)
natively positioned amino acid positions

| BcePred | Bepipred | ElliPro |
|---------|----------|---------|
| 240-257 | 244-258  | 241-255 |
|         |          | 262-278 |
|         |          | 281-297 |

In addition to Shiga toxin-derived toxin effector polypeptides, which are capable of inducing cellular internalization and directing their own subcellular routing to the cytosol, cytosolic routing effector regions from other proteins may be chosen as a source for polypeptides to modify into a polypeptide of the present invention, such as, e.g., from other ABx and/or RIP toxins.

Diphtheria Toxin Derived Effector Polypeptides

Diphtheria toxins have been used to design immunotoxins and ligand-toxin fusion molecules wherein the diphtheria derived component can provide cellular internalization and cytosolic routing effector functions. A computational method was utilized to predict antigenic and/or immunogenic B-cell epitope regions in the diphtheria toxin A subunit with the potential to elicit responses in mammalian immune systems. B-cell epitope regions were predicted in the A Subunit of diphtheria toxin (SEQ ID NO:44) using the BcePred webserver (Saha S, Raghava G, *Lecture Notes in Comput Sci* 3239: 197-204 (2004)). This computational method revealed seven putative B-cell epitope regions in the prototypical Diphtheria Toxin A Subunit (Table 5). In addition, the Immune Epitope Database (IEDB) curated by the National Institutes of Allergy and Infectious Diseases of the U.S. (NIAID) is said to provide all experimentally characterized B-cell nd T-cell epitopes of diphtheria toxins. Currently, the IEDB provides 7 epitopes with at least one positive measurement regarding peptidic epitopes related to the diphtheria toxin A subunit and the diphtheria toxin effector polypeptide SEQ ID NO:44 used in the Examples (see Table 5 and region 182-201 and 225-238 of SEQ ID NO:44).

TABLE 5

B-Cell Epitope Predictions for the Mature, Native
A Subunit of Diphtheria Toxin (SEQ ID NO: 44)

| Epitope Region | Natively positioned amino acids | |
|---|---|---|
|   | BcePred | IEDB |
| 1 | 3-10 |  |
| 2 |  | 15-31 |
| 3 | 33-43 | 32-54 |
| 4 | 71-77 |  |
| 5 |  | 93-113 |
| 6 | 125-131 |  |
| 7 | 138-146 | 141-167 |
| 8 | 165-175 | 141-167 |
| 9 | 185-191 | 181-193 |

C. Identifying CD4+ T-Cell Epitope Regions in Toxins and Toxin Effector Polypeptides The Shiga toxin A subunit was analyzed for the presence of any CD4+ T-cell epitopes. T-cell epitopes were predicted for the mature A Subunit of Shiga-like toxin 1 (SEQ ID NO:1) by the REVEAL™ Immunogenicity System (IS) T-cell assay performed by ProImmune Inc. (Sarasota, FL, U.S.). This assay uses multiple overlapping peptide sequences from the subject protein to test for the elicitation of any immune response by CD4+ T-cells from healthy donor cell samples depleted of CD8+ T-cells. There were seven T-cell epitope regions identified using this assay at the following natively positioned groups of amino acid residues: CD4+ T-cell epitope region #1: 4-33, CD4+ T-cell epitope region #2: 34-78, CD4+ T-cell epitope region #3: 77-103, CD4+ T-cell epitope region #4: 128-168, CD4+ T-cell epitope region #5: 160-183, CD4+ T-cell epitope region #6: 236-258, and CD4+ T-cell epitope region #7: 274-293.

The diphtheria toxin A subunit and a wild-type (WT), diphtheria toxin effector polypeptide used as a parental polypeptide for generation of the diphtheria toxin effector polypeptides in the Examples, were investigated on NIAD's IEDB for T-cell epitopes. Currently, the IEDB provides over 25 peptidic epitopes with at least one positive measurement regarding T-cell immunogenic related to the diphtheria toxin A subunit and the diphtheria toxin effector polypeptides in the Examples. There were several T-cell epitope regions identified by the IEDB in diphtheria toxins, such as, e.g., the following regions corresponding to overlapping immunogenic peptides in the polypeptide of SEQ ID NO:45 at amino acid residue positions: 2-21, 22-41, 32-71, 72-91, 82-221, 212-231, 232-251, and 251-301.

D. Generating Toxin Effector Polypeptides with Embedded or Inserted T-Cell Epitopes Disrupting Endogenous B-Cell Epitope Regions and/or Endogenous CD4+ T-Cell Epitope Regions Exemplary toxin-derived effector polypeptides of the invention were created using both a Shiga toxin and a diphtheria toxin.

Shiga Toxin Derived Effector Polypeptides

A nucleic acid encoding a cytotoxic protein comprising a Shiga toxin effector region and an immunoglobulin-type binding region for cell targeting was produced using techniques known in the art. The Shiga toxin effector region in the parental cytotoxic protein of this example comprised amino acids 1-251 of SEQ ID NO:1.

Using standard techniques known in the art, a series of mutations were engineered into the nucleic acid encoding the parental cytotoxic protein and variants of the cytotoxic protein were produced which comprised multiple amino acid substitutions as compared to the parental cytotoxic protein. The mutations were selected to disrupt at least one predicted B-cell epitope region described in Table 2 by embedding at least one T-cell epitope peptide described in Table 1. For most of the exemplary polypeptides of the invention described in the Examples, the amino acid sequence for each T-cell epitope was embedded by manipulating the nucleic acid sequences encoding the region of interest such that the total number of encoded amino acid residues in the variants remained unchanged from the total number of amino acid residues in the parental cytotoxic protein. Ten different polynucleotides were generated which each encoded a different exemplary cytotoxic, cell-targeted protein of the invention comprising a different exemplary Shiga toxin effector polypeptide component of the invention. These exemplary polynucleotides were used to produce ten exemplary cytotoxic, cell-targeted proteins of the invention using standard techniques known in the art. In certain experiments, the full-length coding sequence of the cytotoxic protein of this example began or ended with a polynucleotide encoding a Strep-tag® II to facilitate detection and purification. Proteins were purified using methods known to the skilled worker.

Eleven cytotoxic proteins were derived from the parental cytotoxic protein, each comprising an exemplary Shiga toxin effector polypeptide of the invention (selected from SEQ ID NOs:11-21) and a disruption of at least one of the predicted B-cell epitope regions in Table 2 using one of the T-cell epitopes described in Table 1. The exact modification to the parental Shiga toxin effector polypeptide for each of the eleven cytotoxic proteins is shown in Table 6. Table 6 lists the sequence of each embedded T-cell epitope, the native position in the Shiga toxin A Subunit of the modification, and the disrupted stretch of amino acids in the B-cell epitope region.

TABLE 6

Exemplary Shiga Toxin Effector Polypeptides with T-Cell Epitopes Embedded or inserted into B-Cell Epitope Regions and/or CD4+ T-Cell Epitope Regions

| Position (native residue positions) | T-Cell Epitope Name | T-Cell Epitope Embedded | B-Cell Epitope Region | B-Cell Epitope Region Replaced |
|---|---|---|---|---|
| 4-12 | F3-4 | ILRFSVAHK (SEQ ID NO: 9) | 1 | TLDFSTAKT (SEQ ID NO: 136) |
| 43-51 | C2 | NLVPMVATV (SEQ ID NO: 10) | 3 | SGSGDNLFA (SEQ ID NO: 137) |
| 44-52 | F2 | GILGFVFTL (SEQ ID NO: 4) | 3 | GSGDNLFAV (SEQ ID NO: 138) |
| 44-52 | C2 | NLVPMVATV (SEQ ID NO: 10) | 3 | GSGDNLFAV (SEQ ID NO: 138) |
| 53-61 | F2-2 | DILGFVFTL (SEQ ID NO: 5) | 4 | DVRGIDPEE (SEQ ID NO: 139) |
| 53-61 | F2-3 | DILGFDFTL (SEQ ID NO: 6) | 4 | DVRGIDPEE (SEQ ID NO: 139) |
| 53-61 | C2 | NLVPMVATV (SEQ ID NO: 10) | 4 | DVRGIDPEE (SEQ ID NO: 139) |
| 104-112 | C2 | NLVPMVATV (SEQ ID NO: 10) | 5 | TAVTLSGDS (SEQ ID NO: 140) |
| 180-188 | F2-4 | GILGDVFTL (SEQ ID NO: 7) | 7 | TTLDDLSGR (SEQ ID NO: 141) |
| 53-61 | F2 | GILGFVFTL (SEQ ID NO: 4) | 4 | DVRGIDPE (SEQ ID NO: 142) |
| 245/246 | F3 | ILRGSVARK (SEQ ID NO: 8) | 9 | none (inserted at 246) |

The first nine cytotoxic proteins each comprised a Shiga toxin effector polypeptide comprising an embedded T-cell epitope (see Table 6)—meaning without any change to the overall total number of amino acid residues in the Shiga toxin effector polypeptide component of the parental cytotoxic protein. Each of the first nine modifications listed in Table 6 exemplifies an embedded T-cell epitope which disrupts a B-cell epitope region. As these nine modifications are exact replacements, the T-cell epitope sequence and B-cell epitope region sequence disrupted are identical in length and match one-for-one each amino acid as listed in order from amino-terminus to carboxy-terminus. The tenth Shiga toxin effector polypeptide in Table 6, 53-61-F2, comprises both a partial replacement and an insertion of one amino acid at position 61 which shifts the remaining carboxy-terminal, wild-type (WT), amino acid residues by one position. The eleventh Shiga toxin effector polypeptide in Table 6 is a complete insertion of the entire T-cell epitope between natively positioned amino acid residues 245 and 246. This insertion lies within B-cell epitope region #9 natively positioned at amino acids 243-259 of SLT-1A.

Computational analysis in silico predicted that at least one B-cell epitope present in the wild-type Shiga toxin was eliminated for eight of the T-cell epitope embedded or inserted Shiga toxin effector polypeptide variants, and no new B-cell epitopes were predicted to be generated by embedding or inserting a T-cell epitope in any of the exemplary Shiga toxin effector polypeptides in Table 6 (see also Example 3, infra).

In addition, the Shiga toxin effector polypeptides represented by SEQ ID NOs:11-17 amd 19-21 each comprises a disruption of a predicted endogenous CD4+ T-cell epitope(s).

Diphtheria Toxin Derived Effector Polypeptides

Similar to the above descriptions of modifying Shiga toxin-derived polypeptides, T-cell epitopes were embedded into diphtheria toxin-derived polypeptides with proteasome delivery effector function to create exemplary T-cell epitope embedded, diphtheria toxin effector polypeptides of the invention. The T-cell epitopes were selected from a peptide in Table 1 and embedded to disrupt at least one predicted B-cell epitope region described in Table 5.

All the diphtheria toxin-derived polypeptides of this example comprised the catalytic domain from the diphtheria toxin A Subunit continuous with the translocation domain from the diphtheria toxin B Subunit, a furin cleavage motif between the A and B subunit derived, toxin effector polypeptide regions, and a predicted disulfide bond between cysteines in the A and B subunit derived, toxin effector polypeptide regions. Thus, the diphtheria toxin-derived polypeptides in this example comprise both a proteasome delivery effector region and ribotoxic toxin effector polypeptide. The polypeptide sequences of exemplary, T-cell epitope embedded, diphtheria toxin effector polypeptides of the invention are provided as SEQ ID NOs: 46, 47, and 48.

Using standard techniques, a series of mutations were made in the diphtheria toxin effector polypeptide in order to embed a T-cell epitope in a position overlapping a predicted B-cell epitope region (see Table 5). Table 7 shows examples of T-cell epitope embedded, diphtheria toxin effector polypeptides by denoting the position of embedded T-cell epitope based on the native diphtheria toxin polypeptide sequence in SEQ ID NO:44, the T-cell epitope name, the T-cell epitope peptide sequence, the predicted B-cell epitope region disrupted, and the replaced amino acid sequence in the native diphtheria toxin polypeptide sequence.

TABLE 7

Exemplary Diphtheria Toxin Effector Polypeptides with T-Cell Epitopes Embedded into B-Cell Epitope Regions

| Position (native positions) | T-Cell Epitope | T-Cell Epitope Embedded | B-Cell Epitope Region | B-Cell Epitope Region Replaced | B-Cell Epitope Prediction original epitope | neo-epitope |
|---|---|---|---|---|---|---|
| 34-42 | F2 | GILGFVFTL (SEQ ID NO: 4) | 2 | GIQKPKSGT (SEQ ID NO: 143) | eliminated | none |
| 69-77 | C2 | NLYPMVATV (SEQ ID NO: 10) | 3 | NENPLSGKA (SEQ ID NO: 144) | eliminated | none |
| 168-176 | F3 | ILRGSVAFIK (SEQ ID NO: 8) | 6 | ETRGKRGQD (SEQ ID NO: 145) | eliminated | none |

The T-cell epitope embedded, diphtheria toxin effector polypeptide variants (SEQ ID NOs: 46, 47, and 48) were analyzed for any change in the predicted B cell epitopes as described above. In all three T-cell epitope embedded, diphtheria toxin effector polypeptide variants, the predicted B-cell epitope in the wild-type diphtheria toxin amino acid sequence was eliminated, and no new B-cell epitopes were predicted (Table 7).

Three T-cell epitope embedded, diphtheria toxin effector polypeptide variants (SEQ ID NOs: 46, 47, and 48), and the parental diphtheria toxin effector polypeptide comprising only wild-type toxin amino acid sequences (SEQ ID NO:45), were each designed with an amino-terminal methionine and a carboxy-terminal polyhistidine-tag (6×His tag (SEQ ID NO:146)) to facilitate expression and purification. Both exemplary T-cell epitope embedded, diphtheria toxin effector polypeptide variants of the invention and the parental diphtheria toxin effector polypeptide comprising only wild-type toxin amino acid sequences were produced by a bacterial expression system known in the art and purified under conditions known in the art, such as, e.g., nickel-nitrilotriacetic acid (Ni-NTA) resin chromatography.

E. Generating Shiga Toxin Effector Polypeptides with Embedded T-Cell Epitopes which do not Disrupt any B-Cell Epitope Region Recognizing all the B-cell epitope region predictions from all the methods described in the Examples (Table 2), regions of SLT-1A that were not predicted to contain any B-cell epitope were identified. T-cell epitope peptide sequences from Table 1 are embedded in those regions identified to lack B-cell epitopes by replacing the native amino acids by substitutions to create three different exemplary Shiga toxin effector polypeptides of the invention as shown in Table 8. Table 8 shows the identified regions in the mature, native SLT-1A polypeptide sequence and the replacement T-cell epitope sequences constructed into the Shiga toxin effector polypeptides (see SEQ ID NOs: 22-39).

TABLE 8

T-Cell Epitopes Embedded Outside B-Cell Epitope Regions in Shiga Toxin Effector Polypeptides

| Position (native residue positions) | T-Cell Epitope Name | T-Cell Epitope Embedded | WT Region Replaced |
|---|---|---|---|
| 66-74 | F2 | GILGFVFTL (SEQ ID NO: 4) | NLRLIVERN (SEQ ID NO: 147) |
| 75-83 | F2 | GILGFVFTL (SEQ ID NO: 4) | NLYVTGFVN (SEQ ID NO: 148) |
| 157-165 | F2 | GILGFVFTL (SEQ ID NO: 4) | AMLRFVTVT (SEQ ID NO: 149) |
| 164-172 | F2 | GILGFVFTL (SEQ ID NO: 4) | VTAEALRFR (SEQ ID NO: 150) |
| 221-229 | F2 | GILGFVFTL (SEQ ID NO: 4) | VGRISFGSI (SEQ ID NO: 151) |
| 231-239 | F2 | GILGFVFTL (SEQ ID NO: 4) | AILGSVALI (SEQ ID NO: 152) |
| 66-74 | F3 | ILRGSVAHK (SEQ ID NO: 8) | NIRLIVERN (SEQ ID NO: 147) |
| 75-83 | F3 | ILRGSVAHK (SEQ ID NO: 8) | NLYVTGFVN (SEQ ID NO: 148) |
| 157-165 | F3 | ILRGSVAHK (SEQ ID NO: 8) | AMLRFVTVT (SEQ ID NO: 149) |

TABLE 8-continued

T-Cell Epitopes Embedded Outside B-Cell Epitope
Regions in Shiga Toxin Effector Polypeptides

| Position (native residue positions) | T-Cell Epitope Name | T-Cell Epitope Embedded | WT Region Replaced |
|---|---|---|---|
| 164-172 | F3 | ILRGSVAHK (SEQ ID NO: 8) | VTAEALRFR (SEQ ID NO: 150) |
| 221-229 | F3 | ILRGSVAHK (SEQ ID NO: 8) | VGRISFGSI (SEQ ID NO: 151) |
| 231-239 | F3 | ILRGSVAHK (SEQ ID NO: 8) | AILGSVALI (SEQ ID NO: 152) |
| 66-74 | C2 | NLVPMVATV (SEQ ID NO: 10) | NLRLIVERN (SEQ ID NO: 147) |
| 75-83 | C2 | NLVPMVATV (SEQ ID NO: 10) | NLYVTGFVN (SEQ ID NO: 148) |
| 157-165 | C2 | NLVPMVATV (SEQ ID NO: 10) | AMLRFVTVT (SEQ ID NO: 149) |
| 164-172 | C2 | NLVPMVATV (SEQ ID NO: 10) | VTAEALRFR (SEQ ID NO: 150) |
| 221-229 | C2 | NLVPMVATV (SEQ ID NO: 10) | VGRISFGSI (SEQ ID NO: 151) |
| 231-239 | C2 | NLVPMVATV (SEQ ID NO: 10) | AILGSVALI (SEQ ID NO: 152) |

The Shiga toxin effector polypeptide sequences comprising, as exact replacements, the embedded T-cell epitopes in Table 8 were analyzed using the BcePred program. None of the embedded T-cell epitope exact replacements in Table 8 disrupted any of the six epitope regions predicted by that program. One of the embedded T-cell epitope replacement sequences in Table 8, variant 75-83-F3, resulted in the prediction of a new B-cell epitope. Embedding T-cell epitopes near the regions (66-74) and/or (157-165) may interfere with the Shiga toxin effector function of catalytic activity because of their proximity to at least one amino acid known to be required for SLT-1A catalytic activity (e.g. Y77 and E167).

In addition, the Shiga toxin effector polypeptides represented by SEQ ID NOs: 22-39 all comprise a disruption of a predicted endogenous CD4+ T-cell epitope(s) except for the polypeptides with heterologous T-cell epitopes embedded at position 221-229, which are represented by SEQ ID NOs: 26, 32, and 38.

F. Generating Toxin Effector Polypeptides with Embedded T-Cell Epitopes which Disrupt Toxin Catalytic Function The most critical residues for enzymatic activity of the Shiga toxin A Subunits include tyrosine-77 (Y77) and glutamate-167 (E167) (Di, Toxicon 57: 525-39 (2011)). T-cell epitope peptide sequences from Table 1 are embedded into Shiga toxin effector polypeptides such that either Y77 or E167 is mutated in order to reduce or eliminate Shiga toxin enzymatic activity. Six different exemplary Shiga toxin effector polypeptides of the invention comprising a heterologous T-cell epitope disrupting a catalytic amino acid residue are shown in Table 9. Table 9 shows the position of the embedded T-cell epitopes in the mature, native SLT-1A polypeptide sequence, the replacement T-cell epitope sequences which are embedded, the replaced sequences in the mature, native SLT-1A polypeptide sequence, and a resulting catalytic residue disruption (see also SEQ ID NOs: 23, 29, 40, 41, 42, and 43).

TABLE 9

T-Cell Epitopes Embedded in Shiga Toxin Effector
Polypeptides to Inactivate Shiga Toxin Catalytic Function

| Position (native residue positions) | T-Cell Epitope Name | T-Cell Epitope Embedded | WT Region Replaced | Catalytic Residue Change |
|---|---|---|---|---|
| 75-83 | C2 | NLVPMVATV (SEQ ID NO: 10) | NLYVTGFVN (SEQ ID NO: 148) | Y77V |
| 75-83 | F3 | ILRGSVAHK (SEQ ID NO: 8) | NLYVTGFVN (SEQ ID NO: 148) | Y77R |
| 77-85 | F2 | GILGFVFTL (SEQ ID NO: 4) | YVTGFVNRT (SEQ ID NO: 153) | Y77G |

TABLE 9-continued

T-Cell Epitopes Embedded in Shiga Toxin Effector
Polypeptides to Inactivate Shiga Toxin Catalytic Function

| Position (native residue positions) | T-Cell Epitope Name | T-Cell Epitope Embedded | WT Region Replaced | Catalytic Residue Change |
|---|---|---|---|---|
| 159-167 | F2 | GILGFVFTL (SEQ ID NO: 4) | LRFVTVTAE (SEQ ID NO: 154) | E167L |
| 159-167 | F3 | ILRGSVAHK (SEQ ID NO: 8) | LRFVTVTAE (SEQ ID NO: 154) | E167K |
| 162-170 | C2 | NLYPMVATV (SEQ ID NO: 10) | VTVTAEALR (SEQ ID NO: 155) | E167V |

All of the Shiga toxin effector polypeptides represented by SEQ ID NOs: 23, 29, 40, 42, and 43 comprise disruptions of a predicted endogenous CD4+ T-cell epitope(s). In addition, among the exemplary Shiga toxin effector polypeptides with embedded T-cell epitopes which do not disrupt any B-cell epitope region shown in Table 8, at least eight of them disrupt a catalytic amino acid residue of the Shiga toxin effector region (see SEQ ID NOs: 23, 25, 29, 31 35, and 37).

In addition to embedding and inserting at a single site, multiple immunogenic T-cell epitopes for MHC class I presentation are embedded and/or inserted within the same Shiga toxin-derived polypeptides or diphtheria toxin-derived polypeptides for use in the targeted delivery of a plurality of T-cell epitopes simultaneously, such as, e.g., disrupting a B-cell epitope region with a first embedded T-cell epitope and disrupting a toxin catalytic function with a second embedded T-cell epitope. However, it should be noted that a single embedded T-cell epitope can simultaneously disrupt both a B-cell epitope region and a toxin catalytic function.

Example 2. Testing Toxin-Derived Effector Polypeptides for Retention of Ribotoxic Toxin Effector Function Exemplary toxin-derived effector polypeptides of the invention were tested for retention of ribotoxic toxin effector function.

Shiga Toxin Derived Effector Polypeptides' Retention of Ribotoxicity

The retention of the enzymatic activity of the parental Shiga toxin effector polypeptide after embedding or inserting one or more T-cell epitopes was determined using a ribosome inhibition assay. The results of this assay in this example were based on performing the assay with each Shiga toxin effector polypeptide as a component of a cytotoxic protein. The specific cytotoxicities of different cytotoxic proteins comprising different Shiga toxin effector polypeptides were measured using a tissue culture cell-based toxicity assay. The enzymatic and cytotoxic activities of the exemplary cytotoxic, cell-targeted proteins of the invention were compared to the parental Shiga toxin effector polypeptide alone (no cell-targeting binding region) and a "WT" cytotoxic protein comprising the same cell-targeting domain (e.g. binding region comprising an immunoglobulin-type binding region capable of binding an extracellular target biomolecule with high affinity) but with a wild-type Shiga toxin effector region (WT).

The ribosome inactivation capabilities of cytotoxic proteins comprising embedded or inserted T-cell epitopes were determined using a cell-free, in vitro protein translation assay using the TNT® Quick Coupled Transcription/Translation kit (L1170 Promega Madison, WI, U.S.). The kit includes Luciferase T7 Control DNA (L4821 Promega Madison, WI, U.S.) and TNT® Quick Master Mix. The ribosome activity reaction was prepared according to manufacturer's instructions. A series of 10-fold dilutions of the protein to be tested, comprising either a mutated Shiga toxin effector polypeptide region or WT region, was prepared in an appropriate buffer and a series of identical TNT reaction mixture components were created for each dilution. Each sample in the dilution series was combined with each of the TNT reaction mixtures along with the Luciferase T7 Control DNA. The test samples were incubated for 1.5 hours at 30 degrees Celsius (° C.). After the incubation, Luciferase Assay Reagent (E1483 Promega, Madison, WI, U.S.) was added to all test samples and the amount of luciferase protein translation was measured by luminescence according to manufacturer's instructions. The level of translational inhibition was determined by non-linear regression analysis of log-transformed concentrations of total protein versus relative luminescence units. Using statistical software (GraphPad Prism, San Diego, CA, U.S.), the half maximal inhibitory concentration ($IC_{50}$) value was calculated for each sample using the Prism software function of log(inhibitor) vs. response (three parameters) [Y=Bottom+((Top−Bottom)/(1+10^(X−Log $IC_{50}$)))] under the heading dose-response-inhibition. The $IC_{50}$ values were calculated for each de-immunized protein comprising a B cell epitope replacement/disruption Shiga toxin effector polypeptide region and a control protein comprising a wild-type Shiga toxin effector region (WT).

The exemplary Shiga toxin effector polypeptide regions of the invention exhibited ribosome inhibition comparable to a wild-type Shiga toxin effector polypeptide (WT) as indicated in Table 10. As reported in Table 10, any construct comprising a Shiga toxin effector polypeptide of the invention which exhibited an $IC_{50}$ within 10-fold of the positive control construct comprising a wild-type Shiga toxin effector region was considered to exhibit ribosome inhibition activity comparable to wild-type.

TABLE 10

Retention of Shiga Toxin Function(s): In vitro catalytic activity and in vivo specific cytotoxicity of exemplary Shiga toxin effector polypeptides

| Exemplary Shiga Toxin Effector Polypeptide | Shiga Toxin Functions | |
|---|---|---|
| Position-T-Cell-Epitope | Ribosome Inactivation | Specific Cytotoxicity |
| 4-12-F3-4 | comparable to WT | comparable to WT |
| 43-51-C2 | comparable to WT | comparable to WT |
| 44-52-F2 | comparable to WT | comparable to WT |
| 53-61-F2 | comparable to WT | comparable to WT |
| 53-61-F2-2 | comparable to WT | comparable to WT |
| 53-61-F2-3 | comparable to WT | comparable to WT |
| 53-61-C2 | comparable to WT | comparable to WT |
| 104-112-C2 | comparable to WT | comparable to WT |
| 180-188-F2-4 | comparable to WT | comparable to WT |
| 245-F3 | comparable to WT | comparable to WT |

The retention of cytotoxicity by exemplary Shiga toxin effector polypeptides of the invention after T-cell epitope embedding/insertion was determined by a cell-kill assay in the context of the Shiga toxin effector polypeptide as a component of a cytotoxic protein. The cytotoxicity levels of proteins comprising Shiga toxin effector polypeptides, comprising an embedded or inserted T-cell epitope, were determined using extracellular target expressing cells as compared to cells that do not express a target biomolecule of the cytotoxic protein's binding region. Cells were plated ($2 \times 10^3$ cells per well for adherent cells, plated the day prior to protein addition or $7.5 \times 10^3$ cells per well for suspension cells, plated the same day as protein addition) in 20 µL cell culture medium in 384-well plates. A series of 10-fold dilutions of each protein comprising a mutated Shiga toxin effector polypeptide region to be tested was prepared in an appropriate buffer, and then 5 µL of the dilutions or buffer control were added to the cells. Control wells containing only media were used for baseline correction. The cell samples were incubated with the proteins or just buffer for 3 days at 37° C. and in an atmosphere of 5% carbon dioxide ($CO_2$). The total cell survival or percent viability was determined using a luminescent readout using the CellTiter-Glo® Luminescent Cell Viability Assay (G7573 Promega Madison, WI, U.S.) according to the manufacturer's instructions.

The Percent Viability of experimental wells was calculated using the following equation: (Test RLU−Average Media RLU)/(Average Cells RLU−Average Media RLU)*100. Log polypeptide concentration versus Percent Viability was plotted in Prism (GraphPad Prism, San Diego, CA, U.S.) and log (inhibitor) versus response (3 parameter) analysis was used to determine the half-maximal cytotoxic concentration ($CD_{50}$) value for the tested proteins. The $CD_{50}$ was calculated for each protein comprising an exemplary Shiga toxin effector polypeptide of the invention in Table 10, positive-control cytotoxic protein comprising a wild-type Shiga toxin effector region, and the wild-type SLT-1A Subunit alone (no targeting domain)—both were considered WT positive controls.

The protein comprising exemplary Shiga toxin effector polypeptides of the invention exhibited cell-specific cytotoxicities comparable to a wild-type (WT) Shiga toxin effector polypeptide as indicated in Table 10. As reported in Table 10 with regard to specific cytotoxicity, "comparable to WT" means a protein comprising a Shiga toxin effector polypeptide, comprising an embedded or inserted T-cell epitope, exhibited a $CD_{50}$ to a target positive cell population within 10-fold of a protein comprising a wild-type (WT) Shiga toxin effector region and/or less than 50-fold of the SLT-1A subunit alone.

In addition, the same protein constructs comprising exemplary Shiga toxin effector polypeptides of the invention exhibited specific cytotoxicity to biomolecular-target-expressing cells as compared to biomolecular-target-negative cells (i.e. cells which did not express, at a cellular surface, the biomolecular target of the cell-target binding region of the protein construct). Thus, all the proteins comprising the exemplary Shiga toxin effector polypeptides in Table 10 were cytotoxic proteins exhibiting Shiga toxin effector functions comparable to wild-type (WT), and each cytotoxic protein comprised a disruption in one or more predicted, B-cell epitope regions.

Diphtheria Toxin Derived Effector Polypeptides' Retention of Ribotoxicity

The catalytic activity of exemplary, T-cell epitope embedded, diphtheria toxin effector polypeptides were compared to diphtheria toxin effector polypeptides comprising only wild-type amino acid sequences, referred to herein as "wild-type" or "WT." Both T-cell epitope embedded, diphtheria toxin effector polypeptide variants retained ribosome inactivation activity.

The retention of enzymatic activity of diphtheria toxin effector polypeptide variants with embedded T-cell epitopes in the context of a cell-targeted molecule was tested using a ribosome inhibition assay and a wild-type (WT) diphtheria toxin effector polypeptide as a positive control. The ribosome inactivation capabilities of these toxin effector polypeptides was determined using a cell-free, in vitro protein translation assay using the TNT® Quick Coupled Transcription/Translation kit (L1170 Promega Madison, WI, U.S.) as described above unless otherwise noted. First, the diphtheria toxin effector polypeptides were cleaved in vitro with furin (New England Biolabs, Ipswich, MA, U.S.) under standard conditions. Then the cleaved proteins were diluted in buffer to make a series of dilutions for each sample. Each dilution in each series was combined with each of the TNT reaction mixtures along with the Luciferase T7 Control DNA and tested for ribosome inactivation activity as described above.

Figures 2, 3:
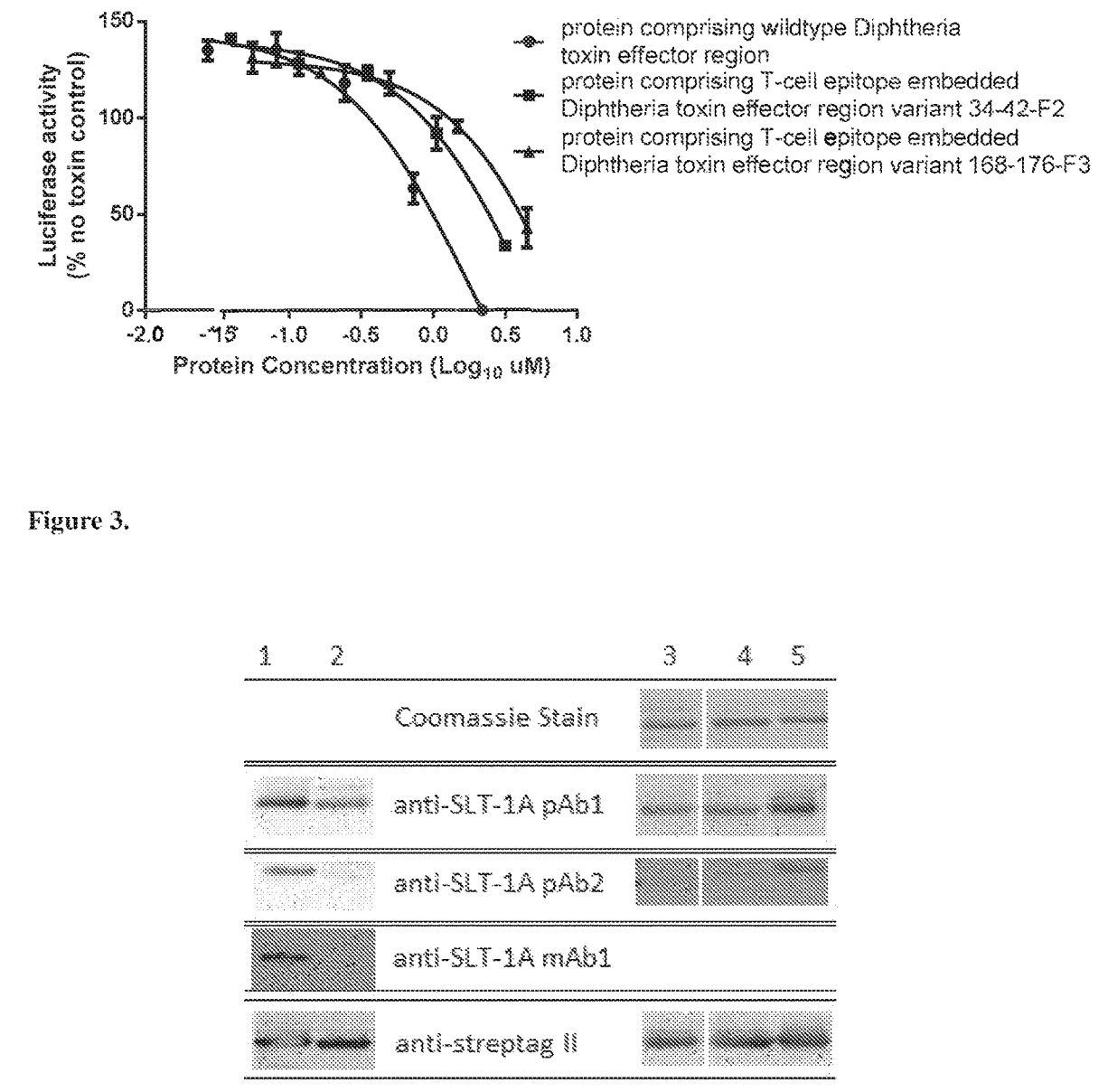

The $IC_{50}$ was calculated, as described above, for the diphtheria toxin effector polypeptides. FIG. 2 and Table 11 show the results of this in vitro assay for retention of diphtheria ribotoxic toxin effector function by exemplary, T-cell embedded, diphtheria toxin effector polypeptides of the invention. The activities of the T-cell embedded, diphtheria toxin effector polypeptides were comparable to the wild-type (WT) positive control because the $IC_{50}$ values were within ten-fold of the wild-type diphtheria toxin effector polypeptide control (FIG. 2; Table 11).

TABLE 11

Retention of catalytic activity by exemplary T-cell epitope embedded, Diphtheria toxin effector polypeptides

| Diphtheria Toxin Effector Polypeptide | $IC_{50}$ (µM) | Fold Change from WT |
|---|---|---|
| Wild-type (WT) | 1.80 | 1.0 |
| T-cell epitope embedded, diphtheria toxin effector polypeptide variant 34-42-F2 | 4.94 | 2.8 |
| T-cell epitope embedded, diphtheria toxin effector polypeptide variant 168-176-F3 | 13.3 | 7.5 |

TABLE 11-continued

Retention of catalytic activity by exemplary T-cell epitope embedded, Diphtheria toxin effector polypeptides

| Exemplary Diphtheria Toxin Effector Polypeptide | Diphtheria Toxin Function: Ribosome Inactivation |
|---|---|
| 34-42-F2 | comparable to WT |
| 168-176-F3 | comparable to WT |

Example 3. Testing the De-Immunization Effects of Disruption of B-Cell Epitope Regions and CD4+ T-Cell Epitope Regions in T-Cell Epitope Embedded, Toxin Effector Polypeptides The disruption of B-cell epitope regions in Shiga toxin effector polypeptides using embedded or inserted T-cell epitopes was tested for de-immunization by investigating levels of antigenicity and/or immunogenicity compared to wild-type (WT) Shiga toxin effector polypeptides comprising only wild-type amino acid sequences.

Testing De-Immunization via Western Analysis

To analyze de-immunization, the antigenicity or immunogenicity levels of Shiga toxin effector polypeptides was tested both in silico and by Western blotting using preformed antibodies which recognize wild-type Shiga toxin effector polypeptides.

Each Shiga toxin effector polypeptide described in Table 6 (SEQ ID NOs: 11-21) was checked for the disruption of predicted B-cell epitopes using the BcePred webserver using the following parameters: flexibility readout with the default settings of hydrophilicity 2, accessibility 2, exposed surface 2.4, antigenic propensity 1.8, flexibility 1.9, turns 1.9, polarity 2.3, and combined 1.9 (Saha S, Raghava G, *Lecture Notes in Comput Sci* 3239: 197-204 (2004)). Three predicted immunogenic epitope regions identified in the wild-type SLT-1A Subunit by other programs (see Table 2) were not predicted by the BcePred flexibility approach with the default settings and, thus, could not be analyzed.

The T-cell epitope embedding or insertion in the following exemplary Shiga toxin effector polypeptides of the invention SEQ ID NOs: 11-21 resulted in the elimination of the predicted B-cell epitope intended for disruption without the introduction of any epitopes de novo (neo-epitopes) (Table 12). None of the tested exemplary Shiga toxin effector polypeptides of the invention resulted in the generation of any de novo predicted B-cell epitopes using the BcePred flexibility approach with the default settings (Table 12). Any B-cell epitope region not predicted by the BcePred flexibility approach with the default settings was indicated with "not identified" and the result after T-cell epitope embedding or insertion was indicated with "N/A" to denote "not applicable.

TABLE 12

Analysis of B-Cell Epitope Region Disruption by Embedded or Inserted T-Cell Epitopes

| | B-Cell Epitope Region Disruption with T-Cell Epitope Replacement | | BcePred Flexibility B-Cell Epitope Predictions | | |
|---|---|---|---|---|---|
| T-Cell Epitope Position | T-Cell Epitope Embedded | B-Cell Epitope Region Disrupted | WT Shiga Toxin Sequence (parental) | Modified Shiga Toxin Sequence | Neo-Epitope Prediction |
| 4-12 | ILRFSVAHK (SEQ ID NO: 9) | 1 | not identified | N/A | none |
| 43-51 | NLVPMVATV (SEQ ID NO: 10) | 3 | 39-46 | eliminated | none |
| 44-52 | GILGFVFTL (SEQ ID NO: 4) | 3 | 39-46 | eliminated | none |
| 44-52 | NLVPMVATV (SEQ ID NO: 10) | 3 | 39-46 | eliminated | none |
| 53-61 | GILGFVFTL (SEQ ID NO: 4) | 4 | 55-61 | eliminated | none |
| 53-61 | DILGFVFTL (SEQ ID NO: 5) | 4 | 55-61 | eliminated | none |
| 53-61 | DILGFDFTL (SEQ ID NO: 6) | 4 | 55-61 | eliminated | none |
| 53-61 | NLVPMVATV (SEQ ID NO: 10) | 4 | 55-61 | eliminated | none |
| 104-112 | NLVPMVATV (SEQ ID NO: 10) | 5 | 105-111 | eliminated | none |
| 180-188 | GILGDVFTL (SEQ ID NO: 7) | 7 | 181-187 | eliminated | none |
| 245/246 | ILRFSVAHK (SEQ ID NO: 9) | 9 | not identified | N/A | none |

The relative antigenicity levels of Shiga toxin effector polypeptides was tested for de-immunization by Western blotting using pre-formed antibodies, both polyclonal and monoclonal antibodies, which recognize the wild-type (WT) Shiga toxin effector polypeptides comprising amino acids 1-251 of SEQ ID NO: 1.

Western blotting was performed on cytotoxic proteins comprising a Shiga toxin effector polypeptide comprising either only a wild-type (WT) Shiga toxin sequence or one of various modified Shiga toxin sequences comprising a B-cell epitope region disruption via replacement with a T-cell epitope (SEQ ID NOs: 11-19). These cytotoxic proteins were loaded in equal amounts to replicate, 4-20%/sodium dodecyl sulfate (SDS), polyacrylamide gels (Lonza, Basel, CH) and electrophoresed under denaturing conditions. The resulting gels were either analyzed by Coomassie staining or transferred to polyvinyl difluoride (PVDF) membranes using the iBlot® (Life Technologies, Carlsbad, CA, U.S.) system according to manufacturer's instructions. The resulting membranes were probed under standard conditions using the following antibodies: rabbit polyclonal α-NWSHPQFEK (A00626, Genscript, Piscataway, NJ, U.S.) which recognizes the polypeptide NWSHPQFEK (SEQ ID NO:156) also known as Streptag® II, mouse monoclonal α-Stx (mAb1 or anti-SLT-1A mAb1) (BEI NR-867 BEI Resources, Manassas, VA, U.S.; cross reactive with Shiga toxin and Shiga-like toxin 1 A subunits), rabbit polyclonal antibody α-SLT-1A (pAb1 or anti-SLT-1A pAb1) (Harlan Laboratories, Inc. Indianapolis, IN, U.S., custom antibody production raised against the SLT-1A amino acids 1-251), and rabbit polyclonal antibody α-SLT-1A (pAb2 or anti-SLT-1A pAb2) (Genscript, Piscataway, NJ, U.S., custom antibody production), which was raised against the peptides RGIDPEEGRFNN (SEQ ID NO:157) and HGQDSVRVGR (SEQ ID NO:158). The peptide sequence RGIDPEEGRFNN (SEQ ID NO:157) is located at amino acids 55-66 in SLT-1A and StxA, spanning a predicted B cell epitope, and the peptide sequence HGQDSVRVGR (SEQ ID NO:158) is located at 214-223 in SLT-1A and StxA, spanning a predicted B-cell epitope.

Figure 4:
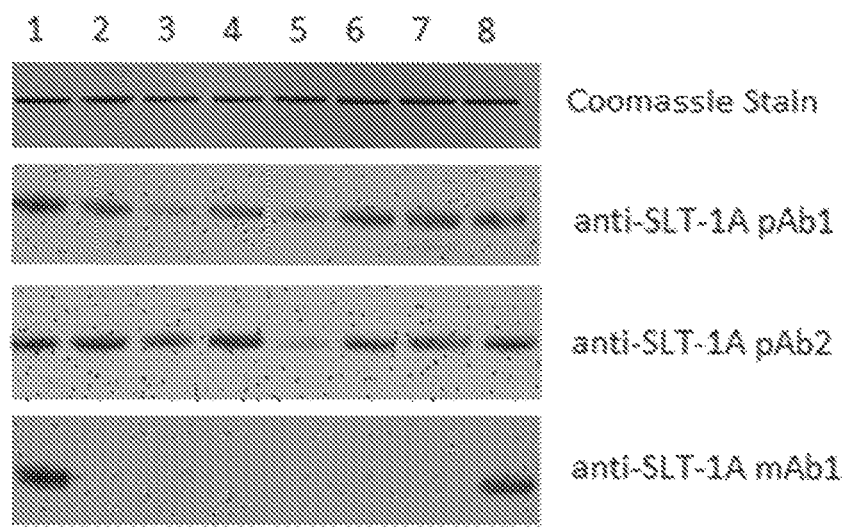
FIG. 4 shows Western blot analyses of cell-targeted, cytotoxic proteins comprising T-cell hyper-immunized toxin effector polypeptides with different B-cell epitope regions disrupted by different T-cell epitopes. Embedding T cell epitopes into various B-cell epitope regions disrupted epitope(s) recognized by various anti-SLT-1A antibodies by western analysis. Lane 1 contains a cytotoxic protein with a WT Shiga toxin effector region; lane 2 contains a cytotoxic protein comprising 4-12-F3; lane 3 contains a cytotoxic protein comprising 44-52-F2; lane 4 contains a cytotoxic protein comprising 43-51-C2; lane 5 contains a cytotoxic protein comprising 53-61-C2; lane 6 contains a cytotoxic protein comprising 104-112-C2; lane 7 contains a cytotoxic protein comprising 180-188-F2-4; and lane 8 contains a cytotoxic protein with a WT Shiga toxin effector region.

Membrane bound antibodies were detected using standard conditions and, when appropriate, using horseradish peroxidase (HRP) conjugated secondary antibodies (goat anti-rabbit-HRP or goat anti-mouse-HRP, Thermo Scientific, Rockford, IL, U.S.). FIGS. 3-4 show images of Western blots with the lanes of the gels and/or membranes numbered and the figure legends indicate by the same respective numbering which Shiga toxin effector polypeptide was a component of the cytotoxic protein sample loaded into each lane. For each gel, the Coomassie staining and/or anti-streptag II Western blot signal serve as total cytotoxic protein loading controls. All the modified Shiga toxin effector polypeptides had reduced or abolished recognition by one or more antibodies that can recognize wild-type SLT-1A indicating a reduced antigenicity and successful de-immunization. The result of the Western blot analyses shown in FIGS. 3 and 4 are summarized in Table 13.

TABLE 13

Epitope Disruption Analysis by Western: Exemplary Shiga toxin effector polypeptides tested show reduced or abolished antibody binding

| Cytotoxic Protein comprising: | Western Blot Result | | |
|---|---|---|---|
| | anti-SLT-1A pAb1 | anti-SLT-1A pAb2 | anti-SLT-1A mAb1 |
| WT Shiga toxin effector region | present | present | present |

Exemplary Shiga toxin effector polypeptide comprising a B-cell epitope region disrupted with the T-cell epitope below:

| T-Cell Epitope Position | T-Cell Epitope Embedded | B-Cell Epitope Region Disrupted | | | |
|---|---|---|---|---|---|
| 4-12 | ILRFSVAHK (SEQ ID NO: 9) | 1 | reduced | present | abolished |
| 43-51 | NLVPMVATV (SEQ ID NO: 10) | 3 | reduced | present | abolished |
| 44-52 | GILGFVFTL (SEQ ID NO: 4) | 3 | strongly reduced | reduced | abolished |
| 53-61 | GILGFVFTL (SEQ ID NO: 4) | 4 | reduced | abolished | abolished |
| 53-61 | DILGFVFTL (SEQ ID NO: 5) | 4 | reduced | abolished | not tested |
| 53-61 | DILGFDFTL (SEQ ID NO: 6) | 4 | reduced | abolished | not tested |
| 53-61 | NLVPMVATV (SEQ ID NO: 10) | 4 | strongly reduced | strongly reduced | abolished |

TABLE 13-continued

Epitope Disruption Analysis by Western: Exemplary Shiga
toxin effector polypeptides tested show reduced or abolished
antibody binding

| 104-112 | NLVPMVATV (SEQ ID NO: 10) | 5 | present | present | abolished |
| 180-188 | GILGDVFTL (SEQ ID NO: 7) | 7 | present | present | abolished |

Testing CD4+ T-Cell De-Immunization

Disruptions in predicted CD4+ T-cell epitope regions are tested for reductions in CD4+ T-cell immunogenicity using assays of human CD4+ T-cell proliferation in the presence of exogenously administered polypeptides and assays of human CD4+ dendritic T-cell stimulation in the presence of human monocytes treated with administered polypeptides.

T-cell proliferation assays known to the skilled worker are used to test the effectiveness of CD4+ T-cell epitope de-immunization in exemplary toxin effector polypeptides comprising T-cell epitopes embedded or inserted into predicted CD4+ T-cell epitopes. The T-cell proliferation assay of this example involves the labeling of CD4+ T-cells and then measuring changes in proliferation using flow cytometric methods in response to the administration of different peptides derived from either a polypeptide de-immunized using the methods of embedding or inserting a heterologous CD8+ T-cell epitope (e.g., SEQ ID NOs: 11-43) or a reference polypeptide that does not have any heterologous T-cell epitope associated with it.

A series of overlapping peptides derived from a polypeptide are synthesized and tested in the CFSE CD4+ T cell proliferation assay (ProImmune Inc., Sarasota, FL, U.S). Human CD8+ T-cell depleted, peripheral blood mononuclear cells (PBMCs) labeled with CFSE are cultured with 5 µM of each peptide of interest for seven days in six replicate wells. Each assay plate includes a set of untreated control wells. The assay also incorporates reference antigen controls, comprising synthetic peptides for known MHC class II antigens.

The CD8+ T-cell depleted, PBMCs that proliferate in response to an administered peptide will show a reduction in CFSE fluorescence intensity as measured directly by flow cytometry. For a naïve T-cell analysis, the Percentage Stimulation above background is determined for each stimulated sample, through comparison with results from an unstimulated sample, such as by ranking with regard to fluorescent signal, as negative, dim, or high. Counts for the CD4+ CFSE T-cell dim population in each sample are expressed as a proportion of the total CD4+ T-cell population. The replicate values are used to calculate Percentage Stimulation above Background (proportion of CD4+ T-cell CFSE dim cells with antigen stimulation, minus proportion of CD4+ T-cell CFSE dim cells without antigen stimulation). The mean and standard error of the mean are calculated from the replicate values. A result is considered "positive" if the Percentage Stimulation above background is greater than 0.5% and also greater than twice the standard error above background. To allow for comparison of peptides, a Response Index is calculated. This index is based on multiplying the magnitude of response (Percentage Stimulation above background) for each peptide by the number of responding donors (Percentage Antigenicity) for each peptide.

Determining Relative CD4+ T-Cell Immunogenicity

The relative CD4+ T-cell immunogenicity of exemplary, full-length polypeptides of the invention is determined using the following dendritic cell (DC) T-cell proliferation assay. This DC T-cell assay measures CD4+ T-cell responses to exogenously administered polypeptides or proteins. The DC T-cell assay is performed using ProImmune's DC-T assay service to determine the relative levels of CD4+ T-cell driven immunogenicity between polypeptides, proteins, and cell-targeted molecules of the invention as compared to the starting parental polypeptides, proteins, or cell-targeted molecules which lack the addition of any heterologous T-cell epitope. The DC T-cell assay of this example involves testing human dendritic cells for antigen presentation of peptides derived from the administered polypeptide, protein, or cell-targeted molecule samples.

Briefly, healthy human donor tissues are used to isolate typed samples based on high-resolution MHC Class II tissue-typing. A cohort of 20, 40 or 50 donors is used. First, monocytes obtained from human donor PBMCs are cultured in a defined medium to generate immature dendritic cells. Then, the immature dendritic cells are stimulated with a well-defined control antigen and induced into a more mature phenotype by further culture in a defined medium. Next, CD8+ T-cell depleted donor PBMCs from the same human donor sample are labeled with CFSE. The CFSE-labeled, CD8+ T-cell depleted PBMCs are then cultured with the antigen-primed, dendritic cells for seven days to allow for CD4+ dendritic cell stimulation, after which eight replicates for each sample are tested. As negative controls, each dendritic cell culture series also includes a set of untreated dendritic cells. For a positive control, the assay incorporates two well-defined reference antigens, each comprising a full-length protein.

To evaluate dendritic cell based immunogenicity, the frequency of donor cell responses is analyzed across the study cohort. Positive responses in the assay are considered indicative of a potential in vivo CD4+ T-cell response. A positive response, measured as a percentage of stimulation above background, is defined as percentages greater than 0.5 percent (%) in 2 or more independent donor samples. The strength of positive donor cell responses is determined by taking the mean percentage stimulation above background obtained across accepted donors for each sample. A Response Index is calculated by multiplying the value of the strength of response by the frequency of the donors responding to determine levels of CD4+ T-cell immunogenicity for each sample. In addition, a Response index, representing the relative CD4+ T-cell immunogenicity is determined by comparing the results from two samples, one comprising a CD8+ T cell epitope embedded in a predicted CD4+ T-cell epitope region and a second variant which lacks any disruption to the same predicted CD4+ T-cell region to determine if the disruption reduces the CD4+ T-cell response of human donor cells.

Testing De-Immunization via Relative Immunogenicity In Vivo

The relative immunogenicity levels of Shiga toxin effector polypeptides are tested for de-immunization using mammalian models of the human immune system. Mice are intravenously administered cytotoxic proteins or polypeptides comprising either wild-type (WT) or de-immunized forms of the Shiga toxin effector polypeptide component 3 times per week for two weeks or more. Blood samples are taken from the injected mice and tested by enzyme-linked immunosorbent assay (ELISA) for reactivity to the cytotoxic proteins and/or the Shiga toxin effector polypeptide. Reduced immunogenic responses will be elicited in mice injected with the de-immunized Shiga toxin effector polypeptide, or compositions comprising the same, as compared to mice injected only with the wild-type form of the Shiga toxin effector polypeptide, or composition comprising the same. The relatively reduced immunogenic response will indicate that the de-immunized Shiga toxin effector polypeptides are de-immunized with regard to having reduced immunogenic potential after administration to a mammal and allowing time for the mammal's immune system to respond.

In addition, diphtheria toxin effector polypeptides of the invention (e.g. SEQ ID NOs: 46-48) are tested for de-immunization using the methods of this example to verify the disruption of one or more B-cell epitope regions in each diphtheria toxin effector polypeptides comprising an embedded or inserted T-cell epitope.

Example 4. Testing Cellular Internalization, Sub-Cellular Routing, and Presentation of an Embedded T-Cell Epitope on the Surfaces of Target Cells by Exemplary Shiga Toxin Effector Polypeptides of the Invention In this example, the ability of exemplary cell-targeted proteins of the invention, which each comprise an exemplary Shiga toxin effector polypeptide of the invention, to deliver T-cell epitopes to the MHC class I pathway of target cells for presentation to the target cell surface was investigated. In addition, cell-targeted proteins comprising diphtheria toxin effector polypeptides of the invention (e.g. SEQ ID NOs: 46-48) are tested using the methods of this example to verify their ability to deliver embedded T-cell epitopes to the MHC class I presentation system.

Using standard techniques known in the art, various exemplary cell-targeted proteins of the invention were made where each comprises a cell-type-targeting region and a Shiga toxin effector polypeptide of the invention (see e.g. WO2014164680 and WO2014164693). A cell-targeted protein of the invention comprises both a Shiga toxin effector polypeptide of the invention and a cell-targeting binding region capable of exhibiting high-affinity binding to an extracellular target biomolecule physically-coupled to the surface of a specific cell type(s). The cell-targeted proteins of the invention are capable of selectively targeting cells expressing the target biomolecule of their cell-targeting binding region and internalizing into these target cells.

A flow cytometry method was used to demonstrate delivery and extracellular display of a T-cell epitope (inserted or embedded in a Shiga toxin effector region) in complex with MHC Class I molecules on the surfaces of target cells. This flow cytometry method utilizes soluble human T-cell receptor (TCR) multimer reagents (Soluble T-Cell Antigen Receptor STAR™ Multimer, Altor Bioscience Corp., Miramar, FL, U.S.), each with high-affinity binding to a different epitope-human HLA complex.

Each STAR™ TCR multimer reagent is derived from a specific T-cell receptor and allows detection of a specific peptide-MHC complex based on the ability of the chosen TCR to recognize a specific peptide presented in the context of a particular MHC class I molecule. These TCR multimers are composed of recombinant human TCRs which have been biotinylated and multimerized with streptavidin. The TCR multimers are labeled with phycoerythrin (PE). These TCR multimer reagents allow the detection of specific peptide-MHC Class I complexes presented on the surfaces of human cells because each soluble TCR multimer type recognizes and stably binds to a specific peptide-MHC complex under varied conditions (Zhu X et al., *J Immunol* 176: 3223-32 (2006)). These TCR multimer reagents allow the identification and quantitation by flow cytometry of peptide-MHC class I complexes present on the surfaces of cells.

The TCR CMV-pp65-PE STAR™ multimer reagent (Altor Bioscience Corp., Miramar, FL, U.S.) was used in this Example. MHC class I pathway presentation of the CMV C2 peptide (NLVPMVATV (SEQ ID NO:10)) by human cells expressing the HLA-A2 can be detected with the TCR CMV-pp65-PE STAR™ multimer reagent which exhibits high affinity recognition of the CMV-pp65 epitope-peptide (residues 495-503, NLVPMVATV (SEQ ID NO:10)) complexed to human HLA-A2 and which is labeled with PE.

The target cells used in this Example were immortalized human cancer cells available from the ATCC (Manassas VA, U.S.). Using standard flow cytometry methods known in the art, the target cells were confirmed to express on their cell surfaces both the HLA-A2 MHC-Class I molecule and the extracellular target biomolecule of the cell-targeting moiety of the proteins used in this Example.

The target cells were treated with the exemplary cell-targeted proteins of the invention, each comprising different Shiga toxin effector polypeptides comprising a T-cell epitope embedded into a predicted B-cell epitope region. One of each of the exemplary cell-targeted proteins of the invention tested in this Example comprised one of the following Shiga toxin effector polypeptides: 43-51-C2 (SEQ ID NO:13), 53-61-C2 (SEQ ID NO:17), and 104-112-C2 (SEQ ID NO:18). Sets of target cells were treated by exogenous administration of the different exemplary cell-targeted proteins of the invention at concentrations similar to those used by others taking into account cell-type specific sensitivities to Shiga toxins (see e.g. Noakes K et al., *FEBS Lett* 453: 95-9 (1999)). The treated cells were then incubated for six hours in standard conditions, including at 37° C. and an atmosphere with 5% carbon dioxide, to allow for intoxication mediated by a Shiga toxin effector region. Then the cells were washed with cell culture medium, re-suspended in fresh cell culture medium, and incubated for 20 hours prior to staining with the TCR CMV-pp65-PE STAR™ multimer reagent.

As controls, sets of target cells were treated in three conditions: 1) without any treatment ("untreated") meaning that no exogenous molecules were added, 2) with exogenously administered CMV C2 peptide (CMV-pp65, aa495-503: sequence NLVPMVATV (SEQ ID NO:10), synthesized by BioSynthesis, Lewisville, TX, U.S.), and 3) with exogenously administered CMV C2 peptide (NLVPMVATV (SEQ ID NO:10), as above) combined with a Peptide Loading Enhancer ("PLE," Altor Bioscience Corp., Miramar, FL). The C2 peptide combined with PLE treatment allowed for exogenous peptide loading and served as a positive control. Cells displaying the appropriate MHC class I haplotype can be forced to load the appropriate exogenously applied peptide from an extracellular space (i.e. in the absence of cellular internalization of the applied peptide) or in the presence of PLE, which is a mixture of B2-microglobulin and other components.

After the treatments, all the sets of cells were washed and incubated with the TCR CMV-pp65-PE STAR multimer reagent for one hour on ice. The cells were washed and the fluorescence of the samples was measured by flow cytometry using an Accuri™ C6 flow cytometer (BD Biosciences, San Jose, CA, U.S.) to detect the presence of and quantify any TCR CMV-pp65-PE STAR™ multimer bound to cells in the population (sometimes referred to herein as "staining").

Figure 5:
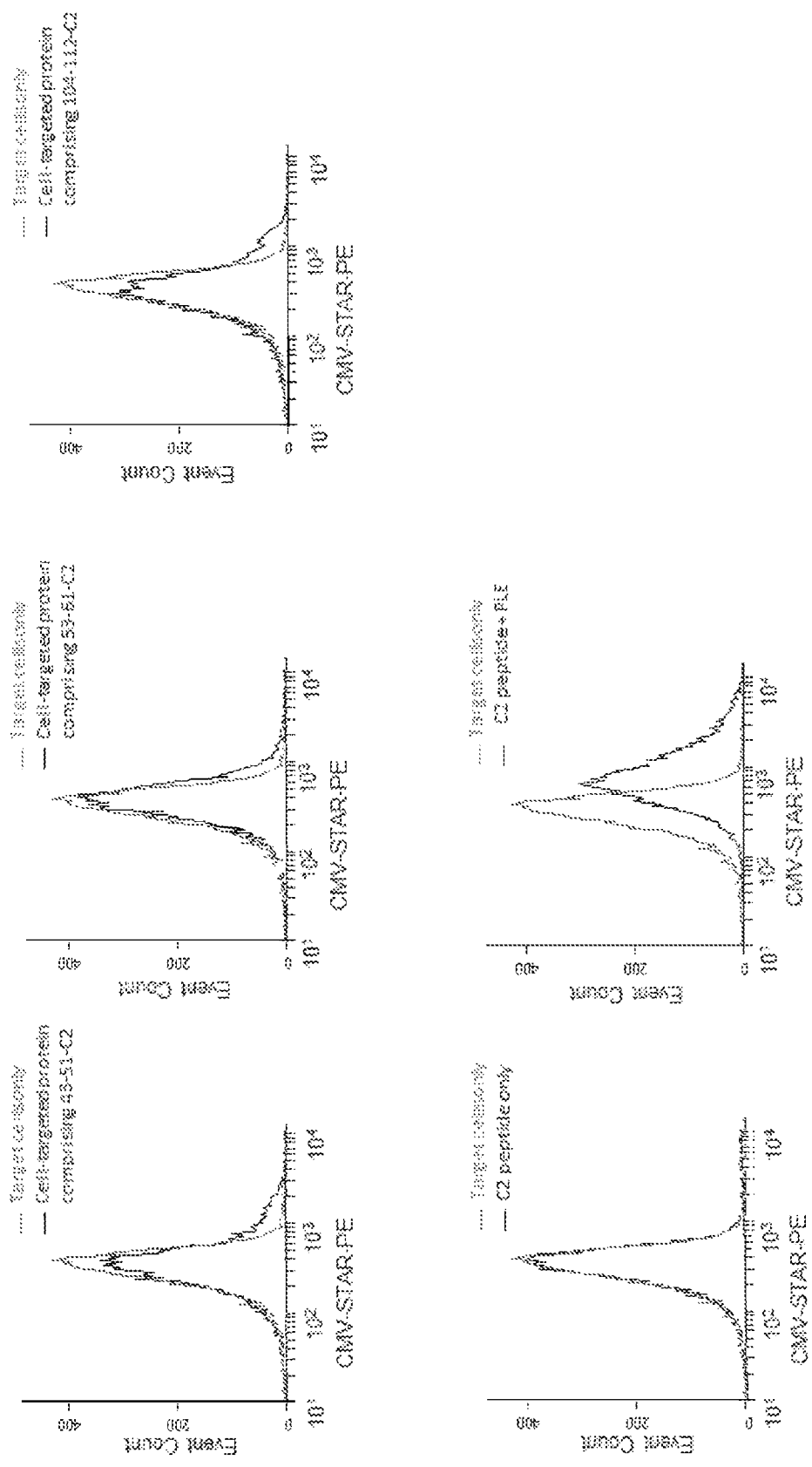
FIG. 5 shows overlays of the results of flow cytometric analysis for cell-surface presentation of T-cell epitope-peptide/MHC class I complexes in sets of cells receiving different treatments: untreated, treated with an exemplary cell-targeted protein of the present invention, treated with exogenous epitope-peptide and PLE, and treated with exogenous epitope-peptide only. Cells treated with three exemplary cell-targeted proteins of the present invention, each comprising a de-immunized Shiga toxin effector polypeptide comprising an embedded T-cell epitope disrupting a B-cell epitope region, displayed the embedded epitope-peptide complexed to WIC molecules on their cell surfaces.

The results of the flow cytometric analysis of the sets of differently treated cells are shown in FIG. 5 and Table 14. The untreated control was used to identify the positive and negative cell populations by employing a gate which results in less than 1% of cells from the untreated control in the "positive" gate (representing background signal). The same gate was then applied to the other samples to characterize the positive population for each sample. In FIG. 5, the flow cytometry histograms are given with the counts (number of cells) on the Y-axis and the relative fluorescent units (RFU) on the X-axis (log scale). The grey line in all histograms shows the profile of the untreated cells and the black line shows the profile of treated cells according to the treatment indicated. In Table 14, the percentage of cells in a treatment set which stained positive for the C2-epitope-peptide-HLA-A2 complex is given. Positive cells in this assay were cells which were bound by the TCR-CMV-pp65-PE STAR reagent and counted in the positive gate described above. Table 14 also shows for each set the corresponding indexed, mean, fluorescent intensity ("iMFI," the fluorescence of the positive population multiplied by the percent positive) in RFU.

TABLE 14

Flow Cytometry Results for Exemplary Cell-targeted proteins of the invention: Peptide-epitope C2-MHC class I complexes detected on the surfaces of intoxicated, target cells

| Target cell treatment: exogenously administered molecule(s) | TCR CMV-pp65-PE Flow Cytometry | |
| --- | --- | --- |
| | Percentage of Positive Cells | iMFI (RFU) |
| Untreated | 0.96% | 20 |
| Cell-targeted protein with Shiga toxin effector region 43-51-C2 | 7.6% | 113 |
| Cell-targeted protein with Shiga toxin effector region 53-61-C2 | 4.5% | 64 |
| Cell-targeted protein with Shiga toxin effector region 104-112-C2 | 6.7% | 89 |
| C2 peptide only | 0.95% | 19 |
| C2 peptide and PLE | 36.7% | 728 |

Cells administered with exogenous protein comprising 43-51-C2, 53-61-C2, and 104-112-C2 showed a positive signal for cell-surface, C2-peptide-HLA-A2 complexes on 7.6%, 4.5%, and 6.7% of the cells in their population, respectively. In contrast, cell populations that were "untreated" and treated with "C2 peptide only" contained less than 1% positive cells (0.96 and 0.95 percent, respectively). Due to processing efficiency and kinetics, which were not measured, it is possible that the percent of presented C2-peptide-HLA-A2 complex detected at a single timepoint in a "cell-targeted protein" treatment sample may not accurately reflect the maximum presentation possible by these exemplary cell-targeted proteins of the invention.

The positive control "C2 peptide and PLE" population contained 36.7% positive cells; however, the peptide can only be loaded onto the surface from an extracellular space ("exogenously") and in the presence of PLE as shown by comparing with the "C2 peptide only" results which had a similar background staining level (0.95%) as the untreated control.

The detection of the exogenously administered, embedded T-cell epitope C2 complexed with human MHC Class I molecules (C2 epitope-peptide/HLA-A2) on the cell surface of intoxicated target cells demonstrated that cell-targeted proteins comprising the exemplary Shiga toxin effector regions 43-51-C2, 53-61-C2, or 104-112-C2 were capable of entering target cells, performing sufficient sub-cellular routing, and delivering enough embedded T-cell epitope to the MHC class I pathway for surface presentation on the target cell surface.

Example 5. Testing Cytotoxic T-Cell Mediated Cytolysis of Intoxicated Target Cells and Other Immune Responses Triggered by MHC Class I Presentation of T-Cell Epitopes Delivered by Proteins of the Present Invention In this example, standard assays known in the art are used to investigate the functional consequences of target cells' MHC class I presentation of T-cell epitopes delivered by exemplary cell-targeted proteins of the invention. The functional consequences to investigate include CTL activation, CTL mediated target cell killing, and CTL cytokine release by CTLs.

A CTL-based cytotoxicity assay is used to assess the consequences of epitope presentation. The assay involves tissue-cultured target cells and T-cells. Target cells are intoxicated as described in Example 4. Briefly, target cells are incubated for six hours in standard conditions with different exogenously administered proteins, where certain proteins comprise a Shiga toxin effector polypeptide of the invention or a diphtheria toxin effector polypeptide of the invention. Next, CTLs are added to the intoxicated target cells and incubated to allow for the T-cells to recognize and bind any target-cells displaying epitope-peptide/MHC class I complexes. Then certain functional consequences are investigated using standard methods known to the skilled worker, including CTL binding to target cells, target cell killing by CTL-mediated cytolysis, and the release of cytokines, such as interferon gamma or interleukins by ELISA or ELIspot.

The activation of CTLs by target cells displaying epitope-peptide/MHC class I complexes is quantified using commercially available CTL response assays, e.g. CytoTox96@ non-radioactive assays (Promega, Madison, WI, U.S.), Granzyme B ELISpot assays (Mabtech, Inc., Cincinnati, OH, U.S.), caspase activity assays, and LAMP-1 translocation flow cytometric assays. To specifically monitor CTL-mediated killing of target cells, carboxyfluorescein succinimidyl ester (CFSE) is used to target-cells for in vitro and in vivo investigation as described in the art (see e.g. Durward M et al., *J Vis Exp* 45 pii 2250 (2010)).

Example 6. A Cytotoxic Protein Comprising a T-Cell Hyper-Immunized and B-Cell/CD4+ T-Cell De-Immunized Shiga Toxin Effector Polypeptide and a Binding Region Specific to CD20 (αCD20 Fused with SLT-1A)

In this example, a T-cell hyper-immunized and B-cell/CD4+ T-cell de-immunized Shiga toxin effector region is derived from the A subunit of Shiga-like Toxin 1 (SLT-1A) as described above. An immunoglobulin-type binding region αCD20-antigen is derived from an immunoglobulin-type domain recognizing human CD20 (see e.g. Haisma et al., *Blood* 92: 184-90 (1999); Geng S et al., *Cell Mol Immunol* 3: 439-43 (2006): Olafesn T et al., *Protein Eng Des Sel* 23: 243-9 (2010)), which comprises an immunoglobulin-type binding region capable of binding an extracellular part of CD20. CD20 is expressed on multiple cancer cell types, such as, e.g., B-cell lymphoma cells, hairy cell leukemia cells, B-cell chronic lymphocytic leukemia cells, and melanoma cells. In addition, CD20 is an attractive target for therapeutics to treat certain autoimmune diseases, disorders, and conditions involving overactive B-cells.

Construction, Production, and Purification of the Cytotoxic Protein SLT-1A::αCD20

The immunoglobulin-type binding region αCD20 and Shiga toxin effector region (such as, e.g., SEQ ID NOs:11-43) are linked together. For example, a fusion protein is produced by expressing a polynucleotide encoding the αCD20-antigen-binding protein SLT-1A::αCD20 (see, e.g., SEQ ID NOs: 49, 50, and 51). Expression of the SLT-1A::αCD20 cytotoxic protein is accomplished using either bacterial and/or cell-free, protein translation systems as described in the previous examples.

Determining the In Vitro Characteristics of the Cytotoxic Protein SLT-1A::αCD20

The binding characteristics, the maximum specific binding ($B_{max}$) and equilibrium binding constants ($K_D$), of the cytotoxic protein of this example for CD20+ cells and CD20− cells is determined by fluorescence-based, flow-cytometry. The $B_{max}$ for SLT-1A::αCD20 to CD20+ cells is measured to be approximately 50,000-200,000 MFI with a $K_D$ within the range of 0.01-100 nM, whereas there is no significant binding to CD20− cells in this assay.

The ribosome inactivation abilities of the SLT-1A::αCD20 cytotoxic protein is determined in a cell-free, in vitro protein translation as described above in the previous examples. The inhibitory effect of the cytotoxic protein of this example on cell-free protein synthesis is significant. The $IC_{50}$ of SLT-1A::αCD20 on protein synthesis in this cell-free assay is approximately 0.1-100 pM.

Determining the Cytotoxicity of the Cytotoxic Protein SLT-1A::αCD20 Using a CD20+ Cell-Kill Assay The cytotoxicity characteristics of SLT-1A::αCD20 are determined by the general cell-kill assay as described above in the previous examples using CD20+ cells. In addition, the selective cytotoxicity characteristics of SLT-1A::αCD20 are determined by the same general cell-kill assay using CD20− cells as a comparison to the CD20+ cells. The $CD_{50}$ of the cytotoxic protein of this example is approximately 0.01-100 nM for CD20+ cells depending on the cell line. The $CD_{50}$ of the cytotoxic protein is approximately 10-10,000 fold greater (less cytotoxic) for cells not expressing CD20 on a cellular surface as compared to cells which do express CD20 on a cellular surface. In addition, the cytotoxicity of SLT-1A::αCD20 is investigated for both direct cytotoxicity and indirect cytotoxicity by T-cell epitope delivery and presentation leading to CTL-mediated cytotoxicity.

Determining the In Vivo Effects of the Cytotoxic Protein SLT-1A::αCD20 Using Animal Models Animal models are used to determine the in vivo effects of the cytotoxic protein SLT-1A::αCD20 on neoplastic cells. Various mice strains are used to test the effect of the cytotoxic protein after intravenous administration on xenograft tumors in mice resulting from the injection into those mice of human neoplastic cells which express CD20 on their cell surfaces. *Cell* killing is investigated for both direct cytotoxicity and indirect cytotoxicity by T-cell epitope delivery and presentation leading to CTL-mediated cytotoxicity.

Example 7. A Cytotoxic Protein Comprising a T-Cell Hyper-Immunized and B-Cell/CD4+ T-Cell De-Immunized Shiga Toxin Effector Polypeptide and a Binding Region Specific to HER2 ("αHER2-V$_H$H Fused with SLT-1A")

In this example, the CD8+ T-cell hyper-immunized and B-cell/CD4+ T-cell de-immunized Shiga toxin effector region is derived from the A subunit of Shiga-like Toxin 1 (SLT-1A) as described above. The immunoglobulin-type binding region is αHER2 V$_H$H derived from a single-domain variable region of the camelid antibody (VHH) protein 5F7, as described in U.S. Patent Application Publication 2011/0059090.

Construction, Production, and Purification of the Cytotoxic Protein "αHER2-V$_H$H fused with SLT-1A"

The immunoglobulin-type binding region and Shiga toxin effector region are linked together to form a fused protein (see, e.g., SEQ ID NOs: 52, 53, and 54). In this example, a polynucleotide encoding the αHER2-VHH variable region derived from protein 5F7 may be cloned in frame with a polynucleotide encoding a linker known in the art and in frame with a polynucleotide encoding the Shiga toxin effector region comprising amino acids of SEQ ID NOs:11-43. Variants of "αHER2-V$_H$H fused with SLT-1A" cytotoxic proteins are created such that the binding region is optionally located adjacent to the amino-terminus of the Shiga toxin effector region and optionally comprises a carboxy-terminal endoplasmic reticulum signal motif of the KDEL family. Expression of the "αHER2-V$_H$H fused with SLT-1A" cytotoxic protein variants is accomplished using either bacterial and/or cell-free, protein translation systems as described in the previous examples.

Determining the In Vitro Characteristics of the Cytotoxic Protein "αHER2-V$_H$H fused with SLT-1A"

The binding characteristics of the cytotoxic protein of this example for HER2+ cells and HER2− cells is determined by a fluorescence-based, flow-cytometry. The $B_{max}$ for "αHER2-VHH fused with SLT-1A" variants to HER2+ cells is measured to be approximately 50,000-200,000 MFI with a $K_D$ within the range of 0.01-100 nM, whereas there is no significant binding to HER2− cells in this assay.

The ribosome inactivation abilities of the "αHER2-V$_H$H fused with SLT-1A" cytotoxic proteins are determined in a cell-free, in vitro protein translation as described above in the previous examples. The inhibitory effect of the cytotoxic protein of this example on cell-free protein synthesis is significant. The $IC_{50}$ of "αHER2-V$_H$H fused with SLT-1A" variants on protein synthesis in this cell-free assay is approximately 0.1-100 pM.

Determining the Cytotoxicity of the Cytotoxic Protein "αHER2-VHH Fused with SLT-1A" Using a HER2+ Cell-Kill Assay The cytotoxicity characteristics of "αHER2-VHH fused with SLT-1A" variants are determined by the general cell-kill assay as described above in the previous examples using HER2+ cells. In addition, the selective cytotoxicity characteristics of "αHER2-V$_H$H fused with SLT-1A" are determined by the same general cell-kill assay using HER2− cells as a comparison to the HER2+ cells. The $CD_{50}$ of the cytotoxic protein of this example is approximately 0.01-100 nM for HER2+ cells depending on the cell line. The $CD_{50}$ of the cytotoxic protein is approximately 10-10,000 fold greater (less cytotoxic) for cells not expressing HER2 on a cellular surface as compared to cells which do express HER2 on a cellular surface. In addition, the cytotoxicity of αHER2-V$_H$H fused with SLT-1A is investigated for both direct cytotoxicity and indirect cytotoxicity by T-cell epitope delivery and presentation leading to CTL-mediated cytotoxicity.

Determining the In Vivo Effects of the Cytotoxic Protein αHER2-VHH fused with SLT-1A Using Animal Models Animal models are used to determine the in vivo effects of the cytotoxic protein αHER2-V$_H$H fused with SLT-1A on neoplastic cells. Various mice strains are used to test the effect of the cytotoxic protein after intravenous administration on xenograft tumors in mice resulting from the injection into those mice of human neoplastic cells which express HER2 on their cell surfaces. Cell killing is investigated for both direct cytotoxicity and indirect cytotoxicity by T-cell epitope delivery and presentation leading to CTL-mediated cytotoxicity.

Example 8. A Cytotoxic Protein Comprising a T-Cell Hyper-Immunized and B-Cell/CD4+ T-Cell De-Immunized Shiga Toxin Effector Polypeptide and a Binding Region Derived from the Antibody αEpstein-Barr-Antigen In this example, the CD8+ T-cell hyper-immunized and B-cell/CD4+ T-cell de-immunized Shiga toxin effector region is a de-immunized Shiga toxin effector polypeptide derived from the A subunit of Shiga-like Toxin 1 (SLT-1A) as described above. An immunoglobulin-type binding region αEpstein-Barr-antigen is derived from a monoclonal antibody against an Epstein Barr antigen (Fang C et al., *J Immunol Methods* 287: 21-30 (2004)), which comprises an immunoglobulin-type binding region capable of binding a human cell infected by the Epstein-Barr virus or a transformed cell expressing an Epstein-Barr antigen. The Epstein-Barr antigen is expressed on multiple cell types, such as cells infected by an Epstein-Barr virus and cancer cells (e.g. lymphoma and naspharnygeal cancer cells). In addition, Epstein-Barr infection is associated with other diseases, e.g., multiple sclerosis.

Construction, Production, and Purification of the Cytotoxic Protein SLT-1A::αEpsteinBarr::KDEL The immunoglobulin-type binding region αEpstein-Barr-antigen and Shiga toxin effector region are linked together, and a carboxy-terminal KDEL (SEQ ID NO:61) is added to form a protein. For example, a fusion protein is produced by expressing a polynucleotide encoding the αEpstein-Barr-antigen-binding protein SLT-1A::αEpsteinBarr::KDEL. Expression of the SLT-1A::αEpsteinBarr::KDEL cytotoxic protein is accomplished using either bacterial and/or cell-free, protein translation systems as described in the previous examples.

Determining the In Vitro Characteristics of the Cytotoxic Protein SLT-1A::αEpsteinBarr::KDEL The binding characteristics of the cytotoxic protein of this example for Epstein-Barr antigen positive cells and Epstein-Barr antigen negative cells is determined by fluorescence-based, flow-cytometry. The B$_{max}$ for SLT-1A::αEpsteinBarr::KDEL to Epstein-Barr antigen positive cells is measured to be approximately 50,000-200,000 MFI with a K$_D$ within the range of 0.01-100 nM, whereas there is no significant binding to Epstein-Barr antigen negative cells in this assay.

The ribosome inactivation abilities of the SLT-1A::αEpsteinBarr::KDEL cytotoxic protein is determined in a cell-free, in vitro protein translation as described above in the previous examples. The inhibitory effect of the cytotoxic protein of this example on cell-free protein synthesis is significant. The IC$_{50}$ of SLT-1A::αEpsteinBarr::KDEL on protein synthesis in this cell-free assay is approximately 0.1-100 pM.

Determining the Cytotoxicity of the Cytotoxic Protein SLT-1A::αEpsteinBarr::KDEL Using a Cell-Kill Assay The cytotoxicity characteristics of SLT-1A::αEpsteinBarr::KDEL are determined by the general cell-kill assay as described above in the previous examples using Epstein-Barr antigen positive cells. In addition, the selective cytotoxicity characteristics of SLT-1A::αEpsteinBarr::KDEL are determined by the same general cell-kill assay using Epstein-Barr antigen negative cells as a comparison to the Epstein-Barr antigen positive cells. The CD$_{50}$ of the cytotoxic protein of this example is approximately 0.01-100 nM for Epstein-Barr antigen positive cells depending on the cell line. The CD$_{50}$ of the cytotoxic protein is approximately 10-10,000 fold greater (less cytotoxic) for cells not expressing the Epstein-Barr antigen on a cellular surface as compared to cells which do express the Epstein-Barr antigen on a cellular surface. In addition, the cytotoxicity of SLT-1A::αEpsteinBarr::KDEL is investigated for both direct cytotoxicity and indirect cytotoxicity by T-cell epitope delivery and presentation leading to CTL-mediated cytotoxicity.

Determining the In Vivo Effects of the Cytotoxic Protein SLT-1A::αEpsteinBarr::KDEL Using Animal Models Animal models are used to determine the in vivo effects of the cytotoxic protein SLT-1A::αEpsteinBarr::KDEL on neoplastic cells. Various mice strains are used to test the effect of the cytotoxic protein after intravenous administration on xenograft tumors in mice resulting from the injection into those mice of human neoplastic cells which express Epstein-Barr antigens on their cell surfaces. Cell killing is investigated for both direct cytotoxicity and indirect cytotoxicity by T-cell epitope delivery and presentation leading to CTL-mediated cytotoxicity.

Example 9. A Cytotoxic Protein Comprising a T-Cell Hyper-Immunized and B-Cell/CD4+ T-Cell De-Immunized Shiga Toxin Effector Polypeptide and a Binding Region Derived from the Antibody αLeishmania-Antigen In this example, the Shiga toxin effector region is a CD8+ T-cell hyper-immunized and B-cell/CD4+ T-cell de-immunized Shiga toxin effector polypeptide derived from the A subunit of Shiga-like Toxin 1 (SLT-1A) as described above. An immunoglobulin-type binding region αLeishmania-antigen is derived from an antibody generated, using techniques known in the art, to a cell-surface Leishmania antigen present on human cells harboring an intracellular trypanosomatid protozoa (see Silveira T et al., *Int J Parasitol* 31: 1451-8 (2001); Kenner J et al., *J Cutan Pathol* 26: 130-6 (1999); Berman J and Dwyer, *Clin Exp Immunol* 44: 342-348 (1981)).

Construction, Production, and Purification of the Cytotoxic Protein SLT-1A::αLeishmania::KDEL The immunoglobulin-type binding region α-Leishmania-antigen and Shiga toxin effector region are linked together, and a carboxy-terminal KDEL (SEQ ID NO:61) is added to form a protein. For example, a fusion protein is produced by expressing a polynucleotide encoding the Leishmania-antigen-binding protein SLT-1A::αLeishmania::KDEL. Expression of the SLT-1A::αLeishmania::KDEL cytotoxic protein is accomplished using either bacterial and/or cell-free, protein translation systems as described in the previous examples.

Determining the In Vitro Characteristics of the Cytotoxic Protein SLT-1A::αLeishmania::KDEL The binding characteristics of the cytotoxic protein of this example for Leishmania antigen positive cells and Leishmania antigen negative cells is determined by fluorescence-based, flow-cytometry. The $B_{max}$ for SLT-1A::αLeishmania::KDEL to Leishmania antigen positive cells is measured to be approximately 50,000-200,000 MFI with a $K_D$ within the range of 0.01-100 nM, whereas there is no significant binding to Leishmania antigen negative cells in this assay.

The ribosome inactivation abilities of the SLT-1A::αLeishmania::KDEL cytotoxic protein is determined in a cell-free, in vitro protein translation as described above in the previous examples. The inhibitory effect of the cytotoxic protein of this example on cell-free protein synthesis is significant. The $IC_{50}$ of SLT-1A::αLeishmania::KDEL on protein synthesis in this cell-free assay is approximately 0.1-100 pM.

Determining the Cytotoxicity of the Cytotoxic Protein SLT-1A::αLeishmania::KDEL Using a Cell-Kill Assay The cytotoxicity characteristics of SLT-1A::αLeishmania::KDEL are determined by the general cell-kill assay as described above in the previous examples using Leishmania antigen positive cells. In addition, the selective cytotoxicity characteristics of SLT-1A::αLeishmania::KDEL are determined by the same general cell-kill assay using Leishmania antigen negative cells as a comparison to the Leishmania antigen positive cells. The $CD_{50}$ of the cytotoxic protein of this example is approximately 0.01-100 nM for Leishmania antigen positive cells depending on the cell line. The $CD_{50}$ of the cytotoxic protein is approximately 10-10,000 fold greater (less cytotoxic) for cells not expressing the Leishmania antigen on a cellular surface as compared to cells which do express the Leishmania antigen on a cellular surface. In addition, the cytotoxicity of SLT-1A::αLeishmania::KDEL is investigated for both direct cytotoxicity and indirect cytotoxicity by T-cell epitope delivery and presentation leading to CTL-mediated cytotoxicity.

Example 10. A Cytotoxic Protein Comprising a T-Cell Hyper-Immunized and B-Cell/CD4+ T-Cell De-Immunized Shiga Toxin Effector Polypeptide and a Binding Region Derived from an Immunoglobulin-Type Binding Region αNeurotensin-Receptor In this example, the Shiga toxin effector region is a CD8+ T-cell hyper-immunized and B-cell/CD4+ T-cell de-immunized Shiga toxin effector polypeptide derived from the A subunit of Shiga-like Toxin 1 (SLT-1A) as described above. An immunoglobulin-type binding region αNeurotensin-Receptor is derived from the DARPin™ (GenBank Accession: 2P2C_R) or a monoclonal antibody (Ovigne J et al., *Neuropeptides* 32: 247-56 (1998)) which binds the human neurotensin receptor. The neurotensin receptor is expressed by various cancer cells, such as breast cancer, colon cancer, lung cancer, melanoma, and pancreatic cancer cells.

Construction, Production, and Purification of the Cytotoxic Protein SLT-1A::αNeurotensinR::KDEL The immunoglobulin-type binding region αNeurotensinR and Shiga toxin effector region are linked together, and a carboxy-terminal KDEL (SEQ ID NO:61) is added to form a protein. For example, a fusion protein is produced by expressing a polynucleotide encoding the neurotensin-receptor-binding protein SLT-1A::αNeurotensinR::KDEL. Expression of the SLT-1A::αNeurotensinR::KDEL cytotoxic protein is accomplished using either bacterial and/or cell-free, protein translation systems as described in the previous examples.

Determining the In Vitro Characteristics of the Cytotoxic Protein SLT-1A::αNeurotensinR::KDEL The binding characteristics of the cytotoxic protein of this example for neurotensin receptor positive cells and neurotensin receptor negative cells is determined by fluorescence-based, flow-cytometry. The $B_{max}$ for SLT-1A::αNeurotensinR::KDEL to neurotensin receptor positive cells is measured to be approximately 50,000-200,000 MFI with a $K_D$ within the range of 0.01-100 nM, whereas there is no significant binding to neurotensin receptor negative cells in this assay.

The ribosome inactivation abilities of the SLT-1A::αNeurotensinR::KDEL cytotoxic protein is determined in a cell-free, in vitro protein translation as described above in the previous examples. The inhibitory effect of the cytotoxic protein of this example on cell-free protein synthesis is significant. The $IC_{50}$ of SLT-1A::αNeurotensinR::KDEL on protein synthesis in this cell-free assay is approximately 0.1-100 pM.

Determining the Cytotoxicity of the Cytotoxic Protein SLT-1A::αNeurotensinR::KDEL Using a Cell-Kill Assay The cytotoxicity characteristics of SLT-1A::αNeurotensinR::KDEL are determined by the general cell-kill assay as described above in the previous examples using neurotensin receptor positive cells. In addition, the selective cytotoxicity characteristics of SLT-1A::αNeurotensinR::KDEL are determined by the same general cell-kill assay using neurotensin receptor negative cells as a comparison to the neurotensin receptor positive cells. The $CD_{50}$ of the cytotoxic protein of this example is approximately 0.01-100 nM for neurotensin receptor positive cells depending on the cell line. The $CD_{50}$ of the cytotoxic protein is approximately 10-10,000 fold greater (less cytotoxic) for cells not expressing neurotensin receptor on a cellular surface as compared to cells which do express neurotensin receptor on a cellular surface. In addition, the cytotoxicity of SLT-1A::αNeurotensinR::KDEL is investigated for both direct cytotoxicity and indirect cytotoxicity by T-cell epitope delivery and presentation leading to CTL-mediated cytotoxicity.

Determining the In Vivo Effects of the Cytotoxic Protein SLT-1A::αNeurotensinR::KDEL Using Animal Models Animal models are used to determine the in vivo effects of the cytotoxic protein SLT-1A::αNeurotensinR::KDEL on neoplastic cells. Various mice strains are used to test the effect of the cytotoxic protein after intravenous administration on xenograft tumors in mice resulting from the injection into those mice of human neoplastic cells which express neurotensin receptors on their cell surfaces. Cell killing is investigated for both direct cytotoxicity and indirect cytotoxicity by T-cell epitope delivery and presentation leading to CTL-mediated cytotoxicity.

Example 11. A Cytotoxic Protein Comprising a T-Cell Hyper-Immunized and B-Cell/CD4+ T-Cell De-Immunized Shiga Toxin Effector Polypeptide and a Binding Region Derived from an Immunoglobulin-Type Binding Region αEGFR In this example, the Shiga toxin effector region is CD8+ T-cell hyper-immunized and B-cell/CD4+ T-cell de-immunized Shiga toxin effector polypeptide derived from the A subunit of Shiga-like Toxin 1 (SLT-1A). The binding region αEGFR is derived from the AdNectin™ (GenBank Accession: 3QWQ_B), the Affibody™ (GenBank Accession: 2KZI_A; U.S. Pat. No. 8,598,113), or an antibody, all of which bind one or more human epidermal growth factor receptors. The expression of epidermal growth factor receptors are associated with human cancer cells, such as, e.g., lung cancer cells, breast cancer cells, and colon cancer cells.
Construction, Production, and Purification of the Cytotoxic Protein SLT-1A::αEGFR::KDEL The immunoglobulin-type binding region αEGFR and Shiga toxin effector region are linked together, and a carboxy-terminal KDEL (SEQ ID NO:61) is added to form a protein. For example, a fusion protein is produced by expressing a polynucleotide encoding the EGFR binding protein SLT-1A::αEGFR::KDEL. Expression of the SLT-1A::αEGFR::KDEL cytotoxic protein is accomplished using either bacterial and/or cell-free, protein translation systems as described in the previous examples.
Determining the In Vitro Characteristics of the Cytotoxic Protein SLT-1A::αEGFR::KDEL The binding characteristics of the cytotoxic protein of this example for EGFR+ cells and EGFR− cells is determined by fluorescence-based, flow-cytometry. The $B_{max}$ for SLT-1A::αEGFR::KDEL to EGFR+ cells is measured to be approximately 50,000-200,000 MFI with a $K_D$ within the range of 0.01-100 nM, whereas there is no significant binding to EGFR− cells in this assay.

The ribosome inactivation abilities of the SLT-1A::αEGFR::KDEL cytotoxic protein is determined in a cell-free, in vitro protein translation as described above in the previous examples. The inhibitory effect of the cytotoxic protein of this example on cell-free protein synthesis is significant. The $IC_{50}$ of SLT-1A::αEGFR::KDEL on protein synthesis in this cell-free assay is approximately 0.1-100 pM.
Determining the Cytotoxicity of the Cytotoxic Protein SLT-1A::αEGFR::KDEL Using a Cell-Kill Assay The cytotoxicity characteristics of SLT-1A::αEGFR::KDEL are determined by the general cell-kill assay as described above in the previous examples using EGFR+ cells. In addition, the selective cytotoxicity characteristics of SLT-1A::αEGFR::KDEL are determined by the same general cell-kill assay using EGFR-cells as a comparison to the Leishmania antigen positive cells. The $CD_{50}$ of the cytotoxic protein of this example is approximately 0.01-100 nM for EGFR+ cells depending on the cell line. The $CD_{50}$ of the cytotoxic protein is approximately 10-10,000 fold greater (less cytotoxic) for cells not expressing EGFR on a cellular surface as compared to cells which do express EGFR on a cellular surface. In addition, the cytotoxicity of SLT-1A::αEGFR::KDEL is investigated for both direct cytotoxicity and indirect cytotoxicity by T-cell epitope delivery and presentation leading to CTL-mediated cytotoxicity.
Determining the In Vivo Effects of the Cytotoxic Protein SLT-1A::αEGFR::KDEL Using Animal Models Animal models are used to determine the in vivo effects of the cytotoxic protein SLT-1A::αEGFR::KDEL on neoplastic cells. Various mice strains are used to test the effect of the cytotoxic protein after intravenous administration on xenograft tumors in mice resulting from the injection into those mice of human neoplastic cells which express EGFR(s) on their cell surfaces. Cell killing is investigated for both direct cytotoxicity and indirect cytotoxicity by T-cell epitope delivery and presentation leading to CTL-mediated cytotoxicity.

Example 12. A Cytotoxic Protein Comprising a T-Cell Hyper-Immunized and B-Cell/CD4+ T-Cell De-Immunized Shiga Toxin Effector Polypeptide and a Binding Region Derived from the Antibody αCCR5

In this example, the Shiga toxin effector region is a CD8+ T-cell hyper-immunized and B-cell/CD4+ T-cell de-immunized Shiga toxin effector polypeptide derived from the A subunit of Shiga-like Toxin 1 (SLT-1A). An immunoglobulin-type binding region αCCR5 is derived from a monoclonal antibody against human CCR5 (CD195) (Bernstone L et al., Hybridoma 31: 7-19 (2012)). CCR5 is predominantly expressed on T-cells, macrophages, dendritic cells, and microglia. In addition, CCR5 plays a role in the pathogenesis and spread of the Human Immunodeficiency Virus (HIV).
Construction, Production, and Purification of the Cytotoxic Protein SLT-1A::αCCR5::KDEL The immunoglobulin-type binding region αCCR5 and Shiga toxin effector region are linked together, and a carboxy-terminal KDEL (SEQ ID NO:61) is added to form a protein. For example, a fusion protein is produced by expressing a polynucleotide encoding the αCCR5-binding protein SLT-1A::αCCR5::KDEL. Expression of the SLT-1A::αCCR5::KDEL cytotoxic protein is accomplished using either bacterial and/or cell-free, protein translation systems as described in the previous examples.
Determining the In Vitro Characteristics of the Cytotoxic Protein SLT-1A::αCCR5

The binding characteristics of the cytotoxic protein of this example for CCR5+ cells and CCR5− cells is determined by fluorescence-based, flow-cytometry. The $B_{max}$ for SLT-1A::αCCR5::KDEL to CCR5+ positive cells is measured to be approximately 50,000-200,000 MFI with a $K_D$ within the range of 0.01-100 nM, whereas there is no significant binding to CCR5− cells in this assay.

The ribosome inactivation abilities of the SLT-1A::αCCR5::KDEL cytotoxic protein is determined in a cell-free, in vitro protein translation as described above in the previous examples. The inhibitory effect of the cytotoxic protein of this example on cell-free protein synthesis is significant. The $IC_{50}$ of SLT-1A::αCCR5::KDEL on protein synthesis in this cell-free assay is approximately 0.1-100 pM.
Determining the Cytotoxicity of the Cytotoxic Protein SLT-1A::αCCR5::KDEL Using a Cell-Kill Assay The cytotoxicity characteristics of SLT-1A::αCCR5::KDEL are determined by the general cell-kill assay as described above in the previous examples using CCR5+ cells. In addition, the selective cytotoxicity characteristics of SLT-1A::αCCR5::KDEL are determined by the same general cell-kill assay using CCR5-cells as a comparison to the CCR5+ cells. The $CD_{50}$ of the cytotoxic protein of this example is approximately 0.01-100 nM for CCR5+ cells depending on the cell line. The $CD_{50}$ of the cytotoxic protein is approximately 10-10,000 fold greater (less cytotoxic) for cells not expressing CCR5 on a cellular surface as compared to cells which do express CCR5 on a cellular surface. In addition, the cytotoxicity of SLT-1A::αCCR5::KDEL is investigated for both direct cytotoxicity and indirect cytotoxicity by T-cell epitope delivery and presentation leading to CTL-mediated cytotoxicity.
Determining the In Vivo Effects of the Cytotoxic Protein SLT-1A::αCCR5::KDEL Using Animal Models Animal models are used to determine the in vivo effects of the cytotoxic protein SLT-1A::αCCR5::KDEL on depleting T-cells from donor materials (see Tsirigotis P et al., *Immunotherapy* 4: 407-24 (2012)). Non-human primates are used to determine in vivo effects of SLT-1A::αCCR5. Graft-versus-host disease is analyzed in rhesus macaques after kidney transplantation when the donated organs are pretreated with SLT-1A::αCCR5::KDEL (see Weaver T et al., *Nat Med* 15: 746-9 (2009)). In vivo depletion of peripheral blood T lymphocytes in cynomolgus primates is observed after parenteral administration of different doses of SLT-1A::αCCR5::KDEL. Cell killing is investigated for both direct cytotoxicity and indirect cytotoxicity by T-cell epitope delivery and presentation leading to CTL-mediated cytotoxicity. The use of SLT-1A::αCCR5::KDEL to block HIV infection is tested by giving an acute dose of SLT-1A::αCCR5::KDEL to non-human primates in order to severely deplete circulating T-cells upon exposure to a simian immunodeficiency virus (SIV) (see Sellier P et al., *PLoS One* 5: e10570 (2010)).

Example 13. A Cytotoxic Protein Comprising a T-Cell Hyper-Immunized and B-Cell/CD4+ T-Cell De-Immunized Shiga Toxin Effector Polypeptide and a Binding Region Derived from an Anti-Env Immunoglobulin Domain In this example, the Shiga toxin effector region is a CD8+ T-cell hyper-immunized and B-cell/CD4+ T-cell de-immunized Shiga toxin effector polypeptide derived from the A subunit of Shiga toxin (StxA). An immunoglobulin-type binding region αEnv is derived from existing antibodies that bind HIV envelope glycoprotein (Env), such as GP41, GP120, GP140, or GP160 (see e.g. Chen W et al., *J Mol Bio* 382: 779-89 (2008); Chen W et al., *Expert Opin Biol Ther* 13: 657-71 (2013); van den Kerkhof T et al., *Retrovirology* 10: 102 (2013)) or from antibodies generated using standard techniques (see Prabakaran et al., *Front Microbiol* 3: 277 (2012)). Envs are HIV surface proteins that are also displayed on the cell surfaces of HIV-infected cells during HIV replication. Although Envs are expressed in infected cells predominantly in endosomal compartments, sufficient amounts of Envs could be present on a cell surface to be targeted by a highly potent cytotoxic, cell-targeted protein of the invention. In addition, Env-targeting cytotoxic proteins might bind HIV virions and enter newly infected cells during the fusion of virions with a host cell.

Because HIV displays a high rate of mutation, it is preferable to use an immunoglobulin domain that binds a functional constrained part of an Env, such as shown by broadly neutralizing antibodies that bind Envs from multiple strains of HIV (van den Kerkhof T et al., *Retrovirology* 10: 102 (2013)). Because the Envs present on an infected cell's surface are believed to present sterically restricted epitopes (Chen W et al., *J Virol* 88: 1125-39 (2014)), it is preferable to use smaller than 100 kD and ideally smaller than 25 kD, such as sdAbs or VHH domains.

Construction. Production, and Purification of the Cytotoxic Protein SLT-1A::αEnv::KDEL The immunoglobulin-type binding region αEnv and Shiga toxin effector region are linked together, and a carboxy-terminal KDEL (SEQ ID NO:61) is added to form a cytotoxic protein. For example, a fusion protein is produced by expressing a polynucleotide encoding the αEnv-binding protein SLT-1A::αEnv::KDEL. Expression of the SLT-1A::αEnv::KDEL cytotoxic protein is accomplished using either bacterial and/or cell-free, protein translation systems as described in the previous examples.

Determining the In Vitro Characteristics of the Cytotoxic Protein SLT-1A::αEnv::KDEL The binding characteristics of the cytotoxic protein of this example for Env+ cells and Env– cells is determined by fluorescence-based, flow-cytometry assay. The $B_{max}$ for SLT-1A::αEnv::KDEL to Env+ positive cells is measured to be approximately 50,000-200,000 MFI with a $K_D$ within the range of 0.01-100 nM, whereas there is no significant binding to Env– cells in this assay.

The ribosome inactivation abilities of the SLT-1A::αEnv::KDEL cytotoxic protein is determined in a cell-free, in vitro protein translation as described above in the previous examples. The inhibitory effect of the cytotoxic protein of this example on cell-free protein synthesis is significant. The $IC_{50}$ of SLT-1A::αEnv::KDEL on protein synthesis in this cell-free assay is approximately 0.1-100 pM.

Determining the Cytotoxicity of the Cytotoxic Protein SLT-1A::αEnv::KDEL Using a Cell-Kill Assay The cytotoxicity characteristics of SLT-1A::αEnv::KDEL are determined by the general cell-kill assay as described above in the previous examples using Env+ cells. In addition, the selective cytotoxicity characteristics of SLT-1A::αEnv::KDEL are determined by the same general cell-kill assay using Env-cells as a comparison to the Env+ cells. The $CD_{50}$ of the cytotoxic protein of this example is approximately 0.01-100 nM for Env+ cells depending on the cell line and/or the HIV strain used to infect the cells to make them Env+. The $CD_{50}$ of the cytotoxic protein is approximately 10-10,000 fold greater (less cytotoxic) for cells not expressing Env on a cellular surface as compared to cells which do express Env on a cellular surface. In addition, the cytotoxicity of SLT-1A::αEnv::KDEL is investigated for both direct cytotoxicity and indirect cytotoxicity by T-cell epitope delivery and presentation leading to CTL-mediated cytotoxicity.

Determining the In Vivo Effects of the Cytotoxic Protein SLT-1A::αEnv::KDEL Using Animal Models The use of SLT-1A::αEnv::KDEL to inhibit HIV infection is tested by administering SLT-1A::αEnv::KDEL to simian immunodeficiency virus (SIV) infected non-human primates (see Sellier P et al., *PLoS One* 5: e10570 (2010)). Cell killing is investigated for both direct cytotoxicity and indirect cytotoxicity by T-cell epitope delivery and presentation leading to CTL-mediated cytotoxicity.

Example 14. A Cytotoxic Protein Comprising a T-Cell Hyper-Immunized and B-Cell/CD4+ T-Cell De-Immunized Shiga Toxin Effector Polypeptide and a Binding Region Derived from the Antibody αUL18

In this example, the Shiga toxin effector region is a CD8+ T-cell hyper-immunized and B-cell/CD4+ T-cell de-immunized Shiga toxin effector polypeptide derived from the A subunit of Shiga-like Toxin 1 (SLT-1A). An immunoglobulin-type binding region αUL18 is derived from an antibody generated, using techniques known in the art, to the cell-surface cytomegalovirus protein UL18, which is present on human cells infected with cytomegalovirus (Yang Z, Bjorkman P, *Proc Natl Acad Sci USA* 105: 10095-100 (2008)). The human cytomegalovirus infection is associated with various cancers and inflammatory disorders.

Construction, Production, and Purification of the Cytotoxic Protein SLT-1A::αUL18::KDEL The immunoglobulin-type binding region αUL18 and Shiga toxin effector region are linked together, and a carboxy-terminal KDEL (SEQ ID NO:61) is added to form a protein. For example, a fusion protein is produced by expressing a polynucleotide encoding the αUL18-binding protein SLT-1A::αUL18::KDEL. Expression of the SLT-1A::αUL18::KDEL cytotoxic protein is accomplished using either bacterial and/or cell-free, protein translation systems as described in the previous examples.

Determining the In Vitro Characteristics of the Cytotoxic Protein SLT-1A::αUL18::KDEL The binding characteristics of the cytotoxic protein of this example for cytomegalovirus protein UL18 positive cells and cytomegalovirus protein UL18 negative cells is determined by fluorescence-based, flow-cytometry. The $B_{max}$ for SLT-1A::αUL18::KDEL to cytomegalovirus protein UL18 positive cells is measured to be approximately 50,000-200,000 MFI with a $K_D$ within the range of 0.01-100 nM, whereas there is no significant binding to cytomegalovirus protein UL18 negative cells in this assay.

The ribosome inactivation abilities of the SLT-1A::αUL18::KDEL cytotoxic protein is determined in a cell-free, in vitro protein translation as described above in the previous examples. The inhibitory effect of the cytotoxic protein of this example on cell-free protein synthesis is significant. The $IC_{50}$ of SLT-1A::αUL18::KDEL on protein synthesis in this cell-free assay is approximately 0.1-100 pM.

Determining the Cytotoxicity of the Cytotoxic Protein SLT-1A::αUL18::KDEL Using a Cell-Kill Assay The cytotoxicity characteristics of SLT-1A::αUL18::KDEL are determined by the general cell-kill assay as described above in the previous examples using cytomegalovirus protein UL18 positive cells. In addition, the selective cytotoxicity characteristics of SLT-1A::αUL18::KDEL are determined by the same general cell-kill assay using cytomegalovirus protein UL18 negative cells as a comparison to the cytomegalovirus protein UL18 positive cells. The $CD_{50}$ of the cytotoxic protein of this example is approximately 0.01-100 nM for cytomegalovirus protein UL18 positive cells depending on the cell line. The $CD_{50}$ of the cytotoxic protein is approximately 10-10,000 fold greater (less cytotoxic) for cells not expressing the cytomegalovirus protein UL18 on a cellular surface as compared to cells which do express the cytomegalovirus protein UL18 on a cellular surface. In addition, the cytotoxicity of SLT-1A::αUL18::KDEL is investigated for both direct cytotoxicity and indirect cytotoxicity by T-cell epitope delivery and presentation leading to CTL-mediated cytotoxicity.

Example 15. A Cytotoxic Protein Comprising a T-Cell Hyper-Immunized and B-Cell/CD4+ T-Cell De-Immunized Diphtheria Toxin Effector Polypeptide and a Binding Region Specific to CD20 (αCD20 Fused with Diphtheria Toxin)

In this example, a CD8+ T-cell hyper-immunized and B-cell/CD4+ T-cell de-immunized diphtheria toxin effector region is derived from the A subunit of diphtheria toxin 1 as described above. An immunoglobulin-type binding region αCD20-antigen is derived from an immunoglobulin-type domain recognizing human CD20 (see e.g. Haisma et al., *Blood* 92: 184-90 (1999); Geng S et al., *Cell Mol Immunol* 3: 439-43 (2006); Olafesn T et al., *Protein Eng Des Sel* 23: 243-9 (2010)), which comprises an immunoglobulin-type binding region capable of binding an extracellular part of CD20. CD20 is expressed on multiple cancer cell types, such as, e.g., B-cell lymphoma cells, hairy cell leukemia cells, B-cell chronic lymphocytic leukemia cells, and melanoma cells. In addition, CD20 is an attractive target for therapeutics to treat certain autoimmune diseases, disorders, and conditions involving overactive B-cells.

Construction, Production, and Purification of the Cytotoxic Protein Diphtheria Toxin::αCD20

The immunoglobulin-type binding region αCD20 and diphtheria toxin effector region (such as, e.g., SEQ ID NOs: 46, 47, and 48) are linked together. For example, a fusion protein is produced by expressing a polynucleotide encoding the αCD20-antigen-binding protein diphtheria toxin:: αCD20 (see, e.g., SEQ ID NOs: 55, 56, and 57). Expression of the SLT diphtheria toxin::αCD20 cytotoxic protein is accomplished using either bacterial and/or cell-free, protein translation systems as described in the previous examples.

Determining the In Vitro Characteristics of the Cytotoxic Protein Diphtheria Toxin::αCD20

The binding characteristics of the cytotoxic protein of this example for CD20+ cells and CD20− cells is determined by fluorescence-based, flow-cytometry assay as described in previous patents. The $B_{max}$ for diphtheria toxin::αCD20 to CD20+ cells is measured to be approximately 50,000-200,000 MFI with a $K_D$ within the range of 0.01-100 nM, whereas there is no significant binding to CD20− cells in this assay.

The ribosome inactivation abilities of the diphtheria toxin::αCD20 cytotoxic protein is determined in a cell-free, in vitro protein translation as described above in the previous examples. The inhibitory effect of the cytotoxic protein of this example on cell-free protein synthesis is significant. The $IC_{50}$ of diphtheria toxin::αCD20 on protein synthesis in this cell-free assay is approximately 0.1-100 pM.

Determining the Cytotoxicity of the Cytotoxic Protein Diphtheria Toxin::αCD20 Using a CD20+ Cell-Kill Assay The cytotoxicity characteristics of diphtheria toxin:: αCD20 are determined by the general cell-kill assay as described above in the previous examples using CD20+ cells. In addition, the selective cytotoxicity characteristics of diphtheria toxin::αCD20 are determined by the same general cell-kill assay using CD20− cells as a comparison to the CD20+ cells. The $CD_{50}$ of the cytotoxic protein of this example is approximately 0.01-100 nM for CD20+ cells depending on the cell line. The $CD_{50}$ of the cytotoxic protein is approximately 10-10,000 fold greater (less cytotoxic) for cells not expressing CD20 on a cellular surface as compared to cells which do express CD20 on a cellular surface. In addition, the cytotoxicity of diphtheria toxin::αCD20 is investigated for both direct cytotoxicity and indirect cytotoxicity by T-cell epitope delivery and presentation leading to CTL-mediated cytotoxicity.

Determining the In Vivo Effects of the Cytotoxic Protein Diphtheria Toxin::αCD20 Using Animal Models Animal models are used to determine the in vivo effects of the cytotoxic protein diphtheria toxin::αCD20 on neoplastic cells. Various mice strains are used to test the effect of the cytotoxic protein after intravenous administration on xenograft tumors in mice resulting from the injection into those mice of human neoplastic cells which express CD20 on their cell surfaces. *Cell* killing is investigated for both direct cytotoxicity and indirect cytotoxicity by T-cell epitope delivery and presentation leading to CTL-mediated cytotoxicity.

Example 16. A Cytotoxic Protein Comprising a T-Cell Hyper-Immunized and B-Cell/CD4+ T-Cell De-Immunized Diphtheria Toxin Effector Polypeptide and a Binding Region Specific to HER2 ("αHER2-$V_H$H Fused with Diphtheria Toxin")

In this example, the CD8+ T-cell hyper-immunized and B-cell/CD4+ T-cell de-immunized diphtheria toxin effector region is derived from the A subunit of diphtheria toxin as described above. The immunoglobulin-type binding region is αHER2 $V_HH$ derived from a single-domain variable region of the camelid antibody (VHH) protein 5F7, as described in U.S. Patent Application Publication 2011/0059090.

Construction, Production, and Purification of the Cytotoxic Protein "αHER2-VHH fused with Diphtheria Toxin"

The immunoglobulin-type binding region and diphtheria toxin effector region are linked together to form a fused protein (see, e.g., SEQ ID NOs: 58, 59, and 60). In this example, a polynucleotide encoding the αHER2-VHH variable region derived from protein 5F7 may be cloned in frame with a polynucleotide encoding a linker known in the art and in frame with a polynucleotide encoding the diphtheria toxin effector region comprising amino acids of SEQ ID NOs: 46, 47, or 48. Variants of "αHER2-$V_HH$ fused with diphtheria toxin" cytotoxic proteins are created such that the binding region is optionally located adjacent to the amino-terminus of the diphtheria toxin effector region and optionally comprises a carboxy-terminal endoplasmic reticulum signal motif of the KDEL family. Expression of the "αHER2-$V_HH$ fused with diphtheria toxin" cytotoxic protein variants is accomplished using either bacterial and/or cell-free, protein translation systems as described in the previous examples.

Determining the In Vitro Characteristics of the Cytotoxic Proteins "αHER2-VHH fused with Diphtheria Toxin"

The binding characteristics of the cytotoxic protein of this example for HER2+ cells and HER2− cells is determined by fluorescence-based, flow-cytometry assay as described in previous patents. The $B_{max}$ for "αHER2-VHH fused with diphtheria toxin" to HER2+ cells is measured to be approximately 50,000-200,000 MFI with a $K_D$ within the range of 0.01-100 nM, whereas there is no significant binding to HER2− cells in this assay.

The ribosome inactivation abilities of the "αHER2-$V_HH$ fused with diphtheria toxin" cytotoxic proteins is determined in a cell-free, in vitro protein translation as described above in the previous examples. The inhibitory effect of the cytotoxic protein of this example on cell-free protein synthesis is significant. The $IC_{50}$ of "αHER2-VHH fused with diphtheria toxin" on protein synthesis in this cell-free assay is approximately 0.1-100 pM.

Determining the Cytotoxicity of the Cytotoxic Protein "αHER2-VHH fused with Diphtheria Toxin" Using a HER2+ Cell-Kill Assay The cytotoxicity characteristics of "αHER2-$V_HH$ fused with diphtheria toxin" are determined by the general cell-kill assay as described above in the previous examples using HER2+ cells. In addition, the selective cytotoxicity characteristics of "αHER2-VHH fused with diphtheria toxin" are determined by the same general cell-kill assay using HER2− cells as a comparison to the HER2+ cells. The $CD_{50}$ of the cytotoxic protein of this example is approximately 0.01-100 nM for HER2+ cells depending on the cell line. The $CD_{50}$ of the cytotoxic protein is approximately 10-10,000 fold greater (less cytotoxic) for cells not expressing HER2 on a cellular surface as compared to cells which do express HER2 on a cellular surface. In addition, the cytotoxicity of "αHER2-VHH fused with diphtheria toxin" is investigated for both direct cytotoxicity and indirect cytotoxicity by T-cell epitope delivery and presentation leading to CTL-mediated cytotoxicity.

Determining the In Vivo Effects of the Cytotoxic Protein "αHER2-VHH fused with Diphtheria Toxin" Using Animal Models Animal models are used to determine the in vivo effects of the cytotoxic protein "αHER2-$V_HH$ fused with diphtheria toxin" on neoplastic cells. Various mice strains are used to test the effect of the cytotoxic protein after intravenous administration on xenograft tumors in mice resulting from the injection into those mice of human neoplastic cells which express HER2 on their cell surfaces. Cell killing is investigated for both direct cytotoxicity and indirect cytotoxicity by T-cell epitope delivery and presentation leading to CTL-mediated cytotoxicity.

Example 17. T-Cell Hyper-Immunized and/or B-Cell/CD4+ T-Cell De-Immunized Shiga Toxin Derived Cytotoxic Proteins Targeting Various Cell Types In this example, the Shiga toxin effector region comprises T-cell hyper-immunized and/or B-cell/CD4+ T-cell de-immunized Shiga toxin effector polypeptide derived from the A subunit of Shiga-like Toxin 1 (SLT-1A), Shiga toxin (StxA), and/or Shiga-like Toxin 2 (SLT-2A) with any one or more of the aforementioned B-cell epitope regions disrupted via one or more embedded or inserting T-cell epitopes. A binding region is derived from the immunoglobulin domain from the molecule chosen from column 1 of Table 15 and which binds the extracellular target biomolecule indicated in column 2 of Table 15. The exemplary cytotoxic proteins of this example are optionally created with a carboxy-terminal KDEL-type signal motif and/or detection promoting agent(s) using reagents and techniques known in the art. The exemplary cytotoxic proteins of this example are tested as described in the previous examples using cells expressing the appropriate extracellular target biomolecules. The exemplary proteins of this example may be used, e.g., to diagnose and treat diseases, conditions, and/or disorders indicated in column 3 of Table 15.

TABLE 15

Various Binding Regions for Cell Targeting of Cytotoxic Proteins

| Source of binding region | Extracellular target | Application(s) |
| --- | --- | --- |
| alemtuzumab | CD52 | B-cell cancers, such as lymphoma and leukemia, and B-cell related immune disorders, such as autoimmune disorders |
| basiliximab | CD25 | T-cell disorders, such as prevention of organ transplant rejections, and some B-cell lineage cancers |

TABLE 15-continued

Various Binding Regions for Cell Targeting of Cytotoxic Proteins

| Source of binding region | Extracellular target | Application(s) |
|---|---|---|
| brentuximab | CD30 | hematological cancers, B-cell related immune disorders, and T-cell related immune disorders |
| catumaxomab | EpCAM | various cancers, such as ovarian cancer, malignant ascites, gastric cancer |
| cetuximab | EGFR | various cancers, such as colorectal cancer and head and neck cancer |
| daclizumab | CD25 | B-cell lineage cancers and T-cell disorders, such as rejection of organ transplants |
| daratumumab | CD38 | hematological cancers, B-cell related immune disorders, and T-cell related immune disorders |
| dinutuximab | ganglioside GD2 | Various cancers, such as breast cancer, myeloid cancers, and neuroblastoma |
| efalizumab | LFA-1 (CD11a) | autoimmune disorders, such as psoriasis |
| ertumaxomab | HER2/neu | various cancers and tumors, such as breast cancer and colorectal cancer |
| gemtuzumab | CD33 | myeloid cancer or immune disorder |
| ibritumomab | CD20 | B-cell cancers, such as lymphoma and leukemia, and B-cell related immune disorders, such as autoimmune disorders |
| ipilimumab | CD152 | T-cell related disorders and various cancers, such as leukemia, melanoma |
| muromonab | CD3 | prevention of organ transplant rejections |
| natalizumab | integrin α4 | autoimmune disorders, such as multiple sclerosis and Crohn's disease |
| obinutuzumab | CD20 | B-cell cancers, such as lymphoma and leukemia, and B-cell related immune disorders, such as autoimmune disorders |
| ocaratuzumab | CD20 | B-cell cancers, such as lymphoma and leukemia, and B-cell related immune disorders, such as autoimmune disorders |
| ocrelizumab | CD20 | B-cell cancers, such as lymphoma and leukemia, and B-cell related immune disorders, such as autoimmune disorders |
| ofatumumab | CD20 | B-cell cancers, such as lymphoma and leukemia, and B-cell related immune disorders, such as autoimmune disorders |
| palivizumab | F protein of respiratory syncytial virus | treat respiratory syncytial virus |
| panitumumab | EGFR | various cancers, such as colorectal cancer and head and neck cancer |
| pertuzumab | HER2/neu | various cancers and tumors, such as breast cancer and colorectal cancer |
| pro 140 | CCR5 | HIV infection and T-cell disorders |

TABLE 15-continued

Various Binding Regions for Cell Targeting of Cytotoxic Proteins

| Source of binding region | Extracellular target | Application(s) |
| --- | --- | --- |
| ramucirumab | VEGFR2 | various cancers and cancer related disorders, such as solid tumors |
| rituximab | CD20 | B-cell cancers, such as lymphoma and leukemia, and B-cell related immune disorders, such as autoimmune disorders |
| tocilizumab or atlizumab | IL-6 receptor | autoimmune disorders, such as rheumatoid arthritis |
| tositumomab | CD20 | B-cell cancers, such as lymphoma and leukemia, and B-cell related immune disorders, such as autoimmune disorders |
| trastuzumab | HER2/neu | various cancers and tumors, such as breast cancer and colorectal cancer |
| ublituximab | CD20 | B-cell cancers, such as lymphoma and leukemia, and B-cell related immune disorders, such as autoimmune disorders |
| vedolizumab | integrin α4β7 | autoimmune disorders, such as Crohn's disease and ulcerative colitis |
| CD20 binding scFv(s) Geng S et al., *Cell Mol Immunol* 3: 439-43 (2006); Olafesn T et al., *Protein Eng Des Sel* 23: 243-9 (2010) | CD20 | B-cell cancers, such as lymphoma and leukemia, and B-cell related immune disorders, such as autoimmune disorders |
| CD22 binding scFv(s) Kawas S et al., *MAbs* 3: 479-86 (2011) | CD22 | B-cell cancers or B-cell related immune disorders |
| CD25 binding scFv(s) Muramatsu H et al., *Cancer Lett* 225: 225-36 (2005) | CD25 | various cancers of the B-cell lineage and immune disorders related to T-cells |
| CD30 binding monoclonal antibody(s) Klimka A et al., *Br J Cancer* 83: 252-60 (2000) | CD30 | B-cell cancers or B-cell/T-cell related immune disorders |
| CD33 binding monoclonal antibody(s) Benedict C et al., *J Immunol Methods* 201: 223-31 (1997) | CD33 | myeloid cancer or immune disorder |
| CD38 binding immunoglobulin domains U.S. Pat. No. 8,153,765 | CD38 | hematological cancers, B-cell related immune disorders, and T-cell related immune disorders |
| CD40 binding scFv(s) Ellmark P et al., *Immunology* 106: 456-63 (2002) | CD40 | various cancers and immune disorders |
| CD52 binding monoclonal antibody(s) U.S. Pat. No. 7,910,104 B2 | CD52 | B-cell cancers, such as lymphoma and leukemia, and B-cell related immune disorders, such as autoimmune disorders |
| CD56 binding monoclonal antibody(s) Shin J et al., *Hybridoma* 18: 521-7 (1999) | CD56 | immune disorders and various cancers, such as lung cancer, Merkel cell carcinoma, myeloma |
| CD79 binding monoclonal antibody(s) Zhang L et al., *Ther Immunol* 2: 191-202 (1995) | CD79 | B-cell cancers or B-cell related immune disorders |

TABLE 15-continued

Various Binding Regions for Cell Targeting of Cytotoxic Proteins

| Source of binding region | Extracellular target | Application(s) |
|---|---|---|
| CD248 binding scFv(s) Zhao A et al., *J Immunol Methods* 363: 221-32 (2011) | CD248 | various cancers, such as inhibiting angiogenesis |
| EpCAM binding monoclonal antibody(s) Schanzer J et al., *J Immunother* 29: 477-88 (2006) | EpCAM | various cancers, such as ovarian cancer, malignant ascites, gastric cancer |
| PSMA binding monoclonal antibody(s) Frigerio B et al., *Eur J Cancer* 49: 2223-32 (2013) | PSMA | prostate cancer |
| Eph-B2 binding monoclonal antibody(s) Abéngozar M et al., *Blood* 119: 4565-76 (2012) | Eph-B2 | for various cancers such as colorectal cancer and prostate cancer |
| Endoglin binding monoclonal antibody(s) Völkel T et al., *Biochim Biophys Res Acta* 1663: 158-66 (2004) | Endoglin | various cancers, such as breast cancer and colorectal cancers |
| FAP binding monoclonal antibody(s) Zhang J et al., *FASEB J* 27: 581-9 (2013) | FAP | various cancers, such as sarcomas and bone cancers |
| CEA binding antibody(s) and scFv(s) Neumaier M et al., *Cancer Res* 50: 2128-34 (1990); Pavoni E et al., *BMC Cancer* 6: 4 (2006); Yazaki P et al., *Nucl Med Biol* 35: 151-8 (2008), Zhao J et al., *Oncol Res* 17: 217-22 (2008) | CEA | various cancers, such as gastrointestinal cancer, pancreatic cancer, lung cancer, and breast cancer |
| CD24 binding monoclonal antibody(s) Kristiansen G et al., *Lab Invest* 90: 1102-16 (2010) | CD24 | various cancers, such as bladder cancer |
| LewisY antigen binding scFv(s) Power B et al., *Protein Sci* 12: 734-47 (2003); monoclonal antibody BR96 Feridani A et al., *Cytometry* 71: 361-70 (2007) | LewisY antigens | various cancers, such as cervical cancer and uterine cancer |
| adalimumab | TNF-α | various cancers and immune disorders, such as Rheumatoid arthritis, Crohn's Disease, Plaque Psoriasis, Psoriatic Arthritis, Ankylosing Spondylitis, Juvenile Idiopathic Arthritis, Hemolytic disease of the newborn |
| afelimomab | TNF-α | various cancers and immune disorders |
| ald518 | IL-6 | various cancers and immune disorders, such as rheumatoid arthritis |
| anrukinzumab or ima-638 | IL-13 | various cancers and immune disorders |
| briakinumab | IL-12, IL-23 | various cancers and immune disorders, such as psoriasis, rheumatoid arthritis, inflammatory bowel diseases, multiple sclerosis |

TABLE 15-continued

Various Binding Regions for Cell Targeting of Cytotoxic Proteins

| Source of binding region | Extracellular target | Application(s) |
| --- | --- | --- |
| brodalumab | IL-17 | various cancers and immune disorders, such as inflammatory diseases |
| canakinumab | IL-1 | various cancers and immune disorders, such as rheumatoid arthritis |
| certolizumab | TNF-α | various cancers and immune disorders, such as Crohn's disease |
| fezakinumab | IL-22 | various cancers and immune disorders, such as rheumatoid arthritis, psoriasis |
| ganitumab | IGF-I | various cancers |
| golimumab | TNF-α | various cancers and immune disorders, such as rheumatoid arthritis, psoriatic arthritis, ankylosing spondylitis |
| infliximab | TNF-α | various cancers and immune disorders, such as rheumatoid arthritis, ankylosing spondylitis, psoriatic arthritis, psoriasis, Crohn's disease, ulcerative colitis |
| ixekizumab | IL-17A | various cancers and immune disorders, such as autoimmune diseases |
| mepolizumab | IL-5 | various immune disorders and cancers, such as B-cell cancers |
| nerelimomab | TNF-α | various cancers and immune disorders |
| olokizumab | IL6 | various cancers and immune disorders |
| ozoralizumab | TNF-α | inflammation |
| perakizumab | IL17A | various cancers and immune disorders, such as arthritis |
| placulumab | human TNF | various immune disorders and cancers |
| sarilumab | IL6 | various cancers and immune disorders, such as rheumatoid arthritis, ankylosing spondylitis |
| siltuximab | IL-6 | various cancers and immune disorders |
| sirukumab | IL-6 | various cancers and immune disorders, such as rheumatoid arthritis |
| tabalumab | BAFF | B-cell cancers |
| ticilimumab or tremelimumab | CTLA-4 | various cancers |
| tildrakizumab | IL23 | immunologically mediated inflammatory disorders |
| tnx-650 | IL-13 | various cancers and immune disorders, such as B-cell cancers |
| tocilizumab or atlizumab | IL-6 receptor | various cancers and immune disorders, such as rheumatoid arthritis |
| ustekinumab | IL-12, IL-23 | various cancers and immune disorders, such as multiple sclerosis, psoriasis, psoriatic arthritis |
| Various growth factors: VEGF, EGF1, EGF2, FGF | VEGFR, EGFR, FGFR | various cancer, such as breast cancer and colon cancer, and to inhibit vascularization |

TABLE 15-continued

Various Binding Regions for Cell Targeting of Cytotoxic Proteins

| Source of binding region | Extracellular target | Application(s) |
|---|---|---|
| Various cytokines: IL-2, IL-6, IL-23, CCL2, BAFFs, TNFs, RAXKL | IL-2R, IL-6R, IL-23R, CD80/CD86, TNFRSF13/TNFRSF17, TNFR | various immune disorders and cancers |
| Broadly neutralizing antibodies identified from patient samples Prabakaran et al., *Front Microbiol* 3: 277 (2012) | Influenza surface antigens, e.g. h

```
Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg Met Ala Ser Asp Glu
                245                 250                 255

Phe Pro Ser Met Cys Pro Ala Asp Gly Arg Val Arg Gly Ile Thr His
            260                 265                 270

Asn Lys Ile Leu Trp Asp Ser Ser Thr Leu Gly Ala Ile Leu Met Arg
        275                 280                 285

Arg Thr Ile Ser Ser
    290

<210> SEQ ID NO 2
<211> LENGTH: 293
<212> TYPE: PRT
<213> ORGANISM: Shigella dysenteriae
<220> FEATURE:
<223> OTHER INFORMATION: Shiga toxin Subunit A (StxA)

<400> SEQUENCE: 2

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Thr Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175
```

Gly Phe Arg Thr Thr Leu Asp Asp Leu Ser Gly Arg Ser Tyr Val Met
180 185 190

Thr Ala Glu Asp Val Asp Leu Thr Leu Asn Trp Gly Arg Leu Ser Ser
195 200 205

Val Leu Pro Asp Tyr His Gly Gln Asp Ser Val Arg Val Gly Arg Ile
210 215 220

Ser Phe Gly Ser Ile Asn Ala Ile Leu Gly Ser Val Ala Leu Ile Leu
225 230 235 240

Asn Cys His His His Ala Ser Arg Val Ala Arg Met Ala Ser Asp Glu
245 250 255

Phe Pro Ser Met Cys Pro Ala Asp Gly Arg Val Arg Gly Ile Thr His
260 265 270

Asn Lys Ile Leu Trp Asp Ser Ser Thr Leu Gly Ala Ile Leu Met Arg
275 280 285

Arg Thr Ile Ser Ser
290

<210> SEQ ID NO 3
<211> LENGTH: 297
<212> TYPE: PRT
<213> ORGANISM: Escherichia coli
<220> FEATURE:
<223> OTHER INFORMATION: Shiga-like toxin 2 Subunit A (SLT-2A)

<400> SEQUENCE: 3

Asp Glu Phe Thr Val Asp Phe Ser Ser Gln Lys Ser Tyr Val Asp Ser
1 5 10 15

Leu Asn Ser Ile Arg Ser Ala Ile Ser Thr Pro Leu Gly Asn Ile Ser
20 25 30

Gln Gly Gly Val Ser Val Ser Val Ile Asn His Val Leu Gly Gly Asn
35 40 45

Tyr Ile Ser Leu Asn Val Arg Gly Leu Asp Pro Tyr Ser Glu Arg Phe
50 55 60

Asn His Leu Arg Leu Ile Met Glu Arg Asn Asn Leu Tyr Val Ala Gly
65 70 75 80

Phe Ile Asn Thr Glu Thr Asn Ile Phe Tyr Arg Phe Ser Asp Phe Ser
85 90 95

His Ile Ser Val Pro Asp Val Ile Thr Val Ser Met Thr Thr Asp Ser
100 105 110

Ser Tyr Ser Ser Leu Gln Arg Ile Ala Asp Leu Glu Arg Thr Gly Met
115 120 125

Gln Ile Gly Arg His Ser Leu Val Gly Ser Tyr Leu Asp Leu Met Glu
130 135 140

Phe Arg Gly Arg Ser Met Thr Arg Ala Ser Ser Arg Ala Met Leu Arg
145 150 155 160

Phe Val Thr Val Ile Ala Glu Ala Leu Arg Phe Arg Gln Ile Gln Arg
165 170 175

Gly Phe Arg Pro Ala Leu Ser Glu Ala Ser Pro Leu Tyr Thr Met Thr
180 185 190

Ala Gln Asp Val Asp Leu Thr Leu Asn Trp Gly Arg Ile Ser Asn Val
195 200 205

Leu Pro Glu Tyr Arg Gly Glu Glu Gly Val Arg Ile Gly Arg Ile Ser
210 215 220

Phe Asn Ser Leu Ser Ala Ile Leu Gly Ser Val Ala Val Ile Leu Asn
225 230 235 240

```
Cys His Ser Thr Gly Ser Tyr Ser Val Arg Ser Val Ser Gln Lys Gln
                245                 250                 255

Lys Thr Glu Cys Gln Ile Val Gly Asp Arg Ala Ala Ile Lys Val Asn
        260                 265                 270

Asn Val Leu Trp Glu Ala Asn Thr Ile Ala Ala Leu Leu Asn Arg Lys
            275                 280                 285

Pro Gln Asp Leu Thr Glu Pro Asn Gln
    290                 295

<210> SEQ ID NO 4
<211> LENGTH: 9
<212> TYPE: PRT
<213> ORGANISM: Influenza A virus
<220> FEATURE:
<223> OTHER INFORMATION: T-cell epitope-peptide F2

<400> SEQUENCE: 4

Gly Ile Leu Gly Phe Val Phe Thr Leu
1               5

<210> SEQ ID NO 5
<211> LENGTH: 9
<212> TYPE: PRT
<213> ORGANISM: Influenza A virus
<220> FEATURE:
<223> OTHER INFORMATION: T-cell epitope-peptide F2-2

<400> SEQUENCE: 5

Asp Ile Leu Gly Phe Val Phe Thr Leu
1               5

<210> SEQ ID NO 6
<211> LENGTH: 9
<212> TYPE: PRT
<213> ORGANISM: Influenza A virus
<220> FEATURE:
<223> OTHER INFORMATION: T-cell epitope-peptide F2-3

<400> SEQUENCE: 6

Asp Ile Leu Gly Phe Asp Phe Thr Leu
1               5

<210> SEQ ID NO 7
<211> LENGTH: 9
<212> TYPE: PRT
<213> ORGANISM: Influenza A virus
<220> FEATURE:
<223> OTHER INFORMATION: T-cell epitope-peptide F2-4

<400> SEQUENCE: 7

Gly Ile Leu Gly Asp Val Phe Thr Leu
1               5

<210> SEQ ID NO 8
<211> LENGTH: 9
<212> TYPE: PRT
<213> ORGANISM: Influenza A virus
<220> FEATURE:
<223> OTHER INFORMATION: T-cell epitope-peptide F3

<400> SEQUENCE: 8

Ile Leu Arg Gly Ser Val Ala His Lys
1               5

<210> SEQ ID NO 9
```

-continued

```
<211> LENGTH: 9
<212> TYPE: PRT
<213> ORGANISM: Influenza A virus
<220> FEATURE:
<223> OTHER INFORMATION: T-cell epitope-peptide F3-4

<400> SEQUENCE: 9

Ile Leu Arg Phe Ser Val Ala His Lys
1               5

<210> SEQ ID NO 10
<211> LENGTH: 9
<212> TYPE: PRT
<213> ORGANISM: Human cytomegalovirus
<220> FEATURE:
<223> OTHER INFORMATION: T-cell epitope-peptide C2

<400> SEQUENCE: 10

Asn Leu Val Pro Met Val Ala Thr Val
1               5

<210> SEQ ID NO 11
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: T-cell epitope embedded Shiga toxin effector
      polypeptide variant 4-12-F3-4

<400> SEQUENCE: 11

Lys Glu Phe Ile Leu Arg Phe Ser Val Ala His Lys Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220
```

```
Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250

<210> SEQ ID NO 12
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: T-cell epitope embedded Shiga toxin effector
      polypeptide variant 44-52-F2

<400> SEQUENCE: 12

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ile Leu Gly Phe
        35                  40                  45

Val Phe Thr Leu Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250

<210> SEQ ID NO 13
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: T-cell epitope embedded Shiga toxin effector
``` polypeptide variant 43-51-C2

<400> SEQUENCE: 13

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Asn Leu Val Pro Met Val
        35                  40                  45

Ala Thr Val Val Asp Val Arg Gly Ile Asp Pro Glu Glu Gly Arg Phe
    50                  55                  60

Asn Asn Leu Arg Leu Ile Val Glu Arg Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250

<210> SEQ ID NO 14
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: T-cell epitope partially embedded and inserted
      Shiga toxin effector polypeptide variant 53-61-F2

<400> SEQUENCE: 14

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Gly Ile Leu Gly Phe Val Thr Leu Glu Gly Arg
    50                  55                  60

Phe Asn Asn Leu Arg Leu Ile Val Glu Arg Asn Asn Leu Tyr Val Thr

```
                65                  70                  75                  80
        Gly Phe Val Asn Arg Thr Asn Asn Val Phe Tyr Arg Phe Ala Asp Phe
                            85                  90                  95

Ser His Val Thr Phe Pro Gly Thr Thr Ala Val Thr Leu Ser Gly Asp
                           100                 105                 110

Ser Ser Tyr Thr Thr Leu Gln Arg Val Ala Gly Ile Ser Arg Thr Gly
                           115                 120                 125

Met Gln Ile Asn Arg His Ser Leu Thr Thr Ser Tyr Leu Asp Leu Met
                130                 135                 140

Ser His Ser Gly Thr Ser Leu Thr Gln Ser Val Ala Arg Ala Met Leu
        145                 150                 155                 160

Arg Phe Val Thr Val Thr Ala Glu Ala Leu Arg Phe Arg Gln Ile Gln
                            165                 170                 175

Arg Gly Phe Arg Thr Thr Leu Asp Asp Leu Ser Gly Arg Ser Tyr Val
                            180                 185                 190

Met Thr Ala Glu Asp Val Asp Leu Thr Leu Asn Trp Gly Arg Leu Ser
                            195                 200                 205

Ser Val Leu Pro Asp Tyr His Gly Gln Asp Ser Val Arg Val Gly Arg
                210                 215                 220

Ile Ser Phe Gly Ser Ile Asn Ala Ile Leu Gly Ser Val Ala Leu Ile
        225                 230                 235                 240

Leu Asn Cys His His His Ala Ser Arg Val Ala Arg
                            245                 250

<210> SEQ ID NO 15
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: T-cell epitope embedded Shiga toxin effector
      polypeptide variant 53-61-F2-2

<400> SEQUENCE: 15

Lys Glu Phe Thr Leu Asp Phe Ser Thr Ala Lys Thr Tyr Val Asp Ser
1               5                  10                  15

Leu Asn Val Ile Arg Ser Ala Ile Gly Thr Pro Leu Gln Thr Ile Ser
                20                  25                  30

Ser Gly Gly Thr Ser Leu Leu Met Ile Asp Ser Gly Ser Gly Asp Asn
            35                  40                  45

Leu Phe Ala Val Asp Ile Leu Gly Phe Val Phe Thr Leu Gly Arg Phe
        50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160
```

```
Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250

<210> SEQ ID NO 16
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: T-cell epitope embedded Shiga toxin effector
      polypeptide variant 53-61-F2-3

<400> SEQUENCE: 16

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Ile Leu Gly Phe Asp Phe Thr Leu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250
```

<210> SEQ ID NO 17
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: T-cell epitope embedded Shiga toxin effector
      polypeptide variant 53-61-C2

<400> SEQUENCE: 17

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asn Leu Val Pro Met Val Ala Thr Val Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250

<210> SEQ ID NO 18
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: T-cell epitope embedded Shiga toxin effector
      polypeptide variant 104-112-C2

<400> SEQUENCE: 18

Lys Glu Phe Thr Leu Asp Phe Ser Thr Ala Lys Thr Tyr Val Asp Ser
1               5                   10                  15

```
Leu Asn Val Ile Arg Ser Ala Ile Gly Thr Pro Leu Gln Thr Ile Ser
             20                  25                  30

Ser Gly Gly Thr Ser Leu Leu Met Ile Asp Ser Gly Ser Gly Asp Asn
         35                  40                  45

Leu Phe Ala Val Asp Val Arg Gly Ile Asp Pro Glu Glu Gly Arg Phe
 50                  55                  60

Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Asn Leu Val Pro Met Val Ala Thr Val
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250

<210> SEQ ID NO 19
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: T-cell epitope embedded Shiga toxin effector
      polypeptide variant 180-188-F2-4

<400> SEQUENCE: 19

Lys Glu Phe Thr Leu Asp Phe Ser Thr Ala Lys Thr Tyr Val Asp Ser
1               5                  10                  15

Leu Asn Val Ile Arg Ser Ala Ile Gly Thr Pro Leu Gln Thr Ile Ser
             20                  25                  30

Ser Gly Gly Thr Ser Leu Leu Met Ile Asp Ser Gly Ser Gly Asp Asn
         35                  40                  45

Leu Phe Ala Val Asp Val Arg Gly Ile Asp Pro Glu Glu Gly Arg Phe
 50                  55                  60

Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Thr Ala Val Thr Leu Ser Gly Asp Ser
```

```
            100             105             110
Ser Tyr Thr Thr Leu Gln Arg Val Ala Gly Ile Ser Arg Thr Gly Met
        115             120             125

Gln Ile Asn Arg His Ser Leu Thr Thr Ser Tyr Leu Asp Leu Met Ser
130             135             140

His Ser Gly Thr Ser Leu Thr Gln Ser Val Ala Arg Ala Met Leu Arg
145             150             155             160

Phe Val Thr Val Thr Ala Glu Ala Leu Arg Phe Arg Gln Ile Gln Arg
                165             170             175

Gly Phe Arg Gly Ile Leu Gly Asp Val Phe Thr Leu Ser Tyr Val Met
            180             185             190

Thr Ala Glu Asp Val Asp Leu Thr Leu Asn Trp Gly Arg Leu Ser Ser
        195             200             205

Val Leu Pro Asp Tyr His Gly Gln Asp Ser Val Arg Val Gly Arg Ile
    210             215             220

Ser Phe Gly Ser Ile Asn Ala Ile Leu Gly Ser Val Ala Leu Ile Leu
225             230             235             240

Asn Ser His His His Ala Ser Arg Val Ala Arg
                245             250

<210> SEQ ID NO 20
<211> LENGTH: 260
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: T-cell epitope inserted Shiga toxin effector
      polypeptide variant 245/246-F3

<400> SEQUENCE: 20

Lys Glu Phe Thr Leu Asp Phe Ser Thr Ala Lys Thr Tyr Val Asp Ser
1               5               10              15

Leu Asn Val Ile Arg Ser Ala Ile Gly Thr Pro Leu Gln Thr Ile Ser
            20              25              30

Cys Gly Gly Thr Ser Leu Leu Met Ile Asp Ser Gly Ser Gly Asp Asn
        35              40              45

Leu Phe Ala Val Asp Val Arg Gly Ile Asp Pro Glu Glu Gly Arg Phe
    50              55              60

Asn Asn Leu Arg Leu Ile Val Glu Arg Asn Asn Leu Tyr Val Thr Gly
65              70              75              80

Phe Val Asn Arg Thr Asn Asn Val Phe Tyr Arg Phe Ala Asp Phe Ser
                85              90              95

His Val Thr Phe Pro Gly Thr Thr Ala Val Thr Leu Ser Gly Asp Ser
            100             105             110

Ser Tyr Thr Thr Leu Gln Arg Val Ala Gly Ile Ser Arg Thr Gly Met
        115             120             125

Gln Ile Asn Arg His Ser Leu Thr Thr Ser Tyr Leu Asp Leu Met Ser
130             135             140

His Ser Gly Thr Ser Leu Thr Gln Ser Val Ala Arg Ala Met Leu Arg
145             150             155             160

Phe Val Thr Val Thr Ala Glu Ala Leu Arg Phe Arg Gln Ile Gln Arg
                165             170             175

Gly Phe Arg Thr Thr Leu Asp Asp Leu Ser Gly Arg Ser Tyr Val Met
            180             185             190
```

Thr Ala Glu Asp Val Asp Leu Thr Leu Asn Trp Gly Arg Leu Ser Ser
                195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Ser His His His Ile Leu Arg Gly Ser Val Ala His Lys Ala Ser
                245                 250                 255

Arg Val Ala Arg
            260

<210> SEQ ID NO 21
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: T-cell epitope embedded Shiga toxin effector
      polypeptide variant 44-52-C2

<400> SEQUENCE: 21

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Asn Leu Val Pro Met
        35                  40                  45

Val Ala Thr Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250

<210> SEQ ID NO 22

-continued

```
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: T-cell epitope embedded Shiga toxin effector
      polypeptide variant 66-74-F2

<400> SEQUENCE: 22

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Gly Ile Leu Gly Phe Val Phe Thr Leu Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250

<210> SEQ ID NO 23
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: T-cell epitope embedded Shiga toxin effector
      polypeptide variant 75-83-F2

<400> SEQUENCE: 23

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30
```

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Gly Ile Leu Gly Phe Val
65                  70                  75                  80

Phe Thr Leu Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250

<210> SEQ ID NO 24
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: T-cell epitope embedded Shiga toxin effector
      polypeptide variant 157-165-F2

<400> SEQUENCE: 24

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met

```
            115                 120                 125
Gln Ile Asn Arg His Ser Leu Thr Thr Ser Tyr Leu Asp Leu Met Ser
        130                 135                 140

His Ser Gly Thr Ser Leu Thr Gln Ser Val Ala Arg Gly Ile Leu Gly
145                 150                 155                 160

Phe Val Phe Thr Leu Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
                180                 185                 190

Thr Ala Glu Asp Val Asp Leu Thr Leu Asn Trp Gly Arg Leu Ser Ser
                195                 200                 205

Val Leu Pro Asp Tyr His Gly Gln Asp Ser Val Arg Val Gly Arg Ile
210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250

<210> SEQ ID NO 25
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: T-cell epitope embedded Shiga toxin effector
      polypeptide variant 164-172-F2

<400> SEQUENCE: 25

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
                20                  25                  30

Ser Gly Gly Thr Ser Leu Leu Met Ile Asp Ser Gly Ser Gly Asp Asn
            35                  40                  45

Leu Phe Ala Val Asp Val Arg Gly Ile Asp Pro Glu Glu Gly Arg Phe
        50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
                100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
        130                 135                 140

His Ser Gly Thr Ser Leu Thr Gln Ser Val Ala Arg Ala Met Leu Arg
145                 150                 155                 160

Phe Val Thr Gly Ile Leu Gly Phe Val Phe Thr Leu Gln Ile Gln Arg
                165                 170                 175

Gly Phe Arg Thr Thr Leu Asp Asp Leu Ser Gly Arg Ser Tyr Val Met
                180                 185                 190

Thr Ala Glu Asp Val Asp Leu Thr Leu Asn Trp Gly Arg Leu Ser Ser
                195                 200                 205
```

```
Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250

<210> SEQ ID NO 26
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: T-cell epitope embedded Shiga toxin effector
      polypeptide variant 221-229-F2

<400> SEQUENCE: 26

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Gly Ile Leu Gly
    210                 215                 220

Phe Val Phe Thr Leu Asn Ala Ile Leu Gly Ser Val Ala Leu Ile Leu
225                 230                 235                 240

Asn Cys His His His Ala Ser Arg Val Ala Arg
                245                 250

<210> SEQ ID NO 27
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<223> OTHER INFORMATION: T-cell epitope embedded Shiga toxin effector
      polypeptide variant 231-239-F2

<400> SEQUENCE: 27

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Gly Ile Leu Gly Phe Val Phe Thr Leu Leu
225                 230                 235                 240

Asn Cys His His His Ala Ser Arg Val Ala Arg
                245                 250

<210> SEQ ID NO 28
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: T-cell epitope embedded Shiga toxin effector
      polypeptide variant 66-74-F3

<400> SEQUENCE: 28

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60
```

```
Asn Ile Leu Arg Gly Ser Val Ala His Lys Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Thr Ala Val Thr Leu Ser Gly Asp Ser
                100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
                180                 185                 190

Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Val Gly Arg Ile
        210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250

<210> SEQ ID NO 29
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: T-cell epitope embedded Shiga toxin effector
      polypeptide variant 75-83-F3

<400> SEQUENCE: 29

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
                20                  25                  30

Ser Gly Gly Thr Ser Leu Leu Met Ile Asp Ser Gly Ser Gly Asp Asn
            35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Ile Leu Arg Gly Ser Val
65                  70                  75                  80

Ala His Lys Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
                100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
```

```
145                 150                 155                 160
Phe Val Thr Val Thr Ala Glu Ala Leu Arg Phe Arg Gln Ile Gln Arg
                165                 170                 175
Gly Phe Arg Thr Thr Leu Asp Asp Leu Ser Gly Arg Ser Tyr Val Met
                180                 185                 190
Thr Ala Glu Asp Val Asp Leu Thr Leu Asn Trp Gly Arg Leu Ser Ser
                195                 200                 205
Val Leu Pro Asp Tyr His Gly Gln Asp Ser Val Arg Val Gly Arg Ile
            210                 215                 220
Ser Phe Gly Ser Ile Asn Ala Ile Leu Gly Ser Val Ala Leu Ile Leu
225                 230                 235                 240
Asn Cys His His His Ala Ser Arg Val Ala Arg
                245                 250

<210> SEQ ID NO 30
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: T-cell epitope embedded Shiga toxin effector
      polypeptide variant 157-165-F3

<400> SEQUENCE: 30

Lys Glu Phe Thr Leu Asp Phe Ser Thr Ala Lys Thr Tyr Val Asp Ser
1               5                   10                  15
Leu Asn Val Ile Arg Ser Ala Ile Gly Thr Pro Leu Gln Thr Ile Ser
            20                  25                  30
Ser Gly Gly Thr Ser Leu Leu Met Ile Asp Ser Gly Ser Gly Asp Asn
        35                  40                  45
Leu Phe Ala Val Asp Val Arg Gly Ile Asp Pro Glu Glu Gly Arg Phe
    50                  55                  60
Asn Asn Leu Arg Leu Ile Val Glu Arg Asn Asn Leu Tyr Val Thr Gly
65                  70                  75                  80
Phe Val Asn Arg Thr Asn Asn Val Phe Tyr Arg Phe Ala Asp Phe Ser
                85                  90                  95
His Val Thr Phe Pro Gly Thr Thr Ala Val Thr Leu Ser Gly Asp Ser
            100                 105                 110
Ser Tyr Thr Thr Leu Gln Arg Val Ala Gly Ile Ser Arg Thr Gly Met
        115                 120                 125
Gln Ile Asn Arg His Ser Leu Thr Thr Ser Tyr Leu Asp Leu Met Ser
    130                 135                 140
His Ser Gly Thr Ser Leu Thr Gln Ser Val Ala Arg Ile Leu Arg Gly
145                 150                 155                 160
Ser Val Ala His Lys Ala Glu Ala Leu Arg Phe Arg Gln Ile Gln Arg
                165                 170                 175
Gly Phe Arg Thr Thr Leu Asp Asp Leu Ser Gly Arg Ser Tyr Val Met
                180                 185                 190
Thr Ala Glu Asp Val Asp Leu Thr Leu Asn Trp Gly Arg Leu Ser Ser
                195                 200                 205
Val Leu Pro Asp Tyr His Gly Gln Asp Ser Val Arg Val Gly Arg Ile
            210                 215                 220
Ser Phe Gly Ser Ile Asn Ala Ile Leu Gly Ser Val Ala Leu Ile Leu
225                 230                 235                 240
```

Asn Cys His His His Ala Ser Arg Val Ala Arg
                245                 250

<210> SEQ ID NO 31
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: T-cell epitope embedded Shiga toxin effector
      polypeptide variant 164-172-F3

<400> SEQUENCE: 31

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
                20                  25                  30

Ser Gly Gly Thr Ser Leu Leu Met Ile Asp Ser Gly Ser Gly Asp Asn
            35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
                100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Ile Leu Arg Gly Ser Val Ala His Lys Gln Ile Gln Arg
                165                 170                 175

Gly Phe Arg Thr Thr Leu Asp Asp Leu Ser Gly Arg Ser Tyr Val Met
                180                 185                 190

Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250

<210> SEQ ID NO 32
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: T-cell epitope embedded Shiga toxin effector
      polypeptide variant 221-229-F3

<400> SEQUENCE: 32

```
Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
                100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Ile Leu Arg Gly
    210                 215                 220

Ser Val Ala His Lys Asn Ala Ile Leu Gly Ser Val Ala Leu Ile Leu
225                 230                 235                 240

Asn Cys His His His Ala Ser Arg Val Ala Arg
                245                 250

<210> SEQ ID NO 33
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: T-cell epitope embedded Shiga toxin effector
      polypeptide variant 231-239-F3

<400> SEQUENCE: 33

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95
```

His Val Thr Phe Pro Gly Thr Thr Ala Val Thr Leu Ser Gly Asp Ser
                100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
                195                 200                 205

Val Leu Pro Asp Tyr His Gly Gln Asp Ser Val Arg Val Gly Arg Ile
        210                 215                 220

Ser Phe Gly Ser Ile Asn Ile Leu Arg Gly Ser Val Ala His Lys Leu
225                 230                 235                 240

Asn Cys His His His Ala Ser Arg Val Ala Arg
                245                 250

<210> SEQ ID NO 34
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: T-cell epitope embedded Shiga toxin effector
      polypeptide variant 66-74-C2

<400> SEQUENCE: 34

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Val Pro Met Val Ala Thr Val Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
                100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met

```
                180                 185                 190
Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Val Gly Arg Ile
        210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250

<210> SEQ ID NO 35
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: T-cell epitope embedded Shiga toxin effector
      polypeptide variant 75-83-C2

<400> SEQUENCE: 35

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Val Pro Met Val
65                  70                  75                  80

Ala Thr Val Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250

<210> SEQ ID NO 36
<211> LENGTH: 251
```

<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: T-cell epitope embedded Shiga toxin effector
      polypeptide variant 157-165-C2

<400> SEQUENCE: 36

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Asn Leu Val Pro
145                 150                 155                 160

Met Val Ala Thr Val Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250

<210> SEQ ID NO 37
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: T-cell epitope embedded Shiga toxin effector
      polypeptide variant 164-172-C2

<400> SEQUENCE: 37

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
            35                  40                  45

Leu Phe Ala Val Asp Val Arg Gly Ile Asp Pro Glu Glu Gly Arg Phe
 50                  55                  60

Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Leu Arg
145                 150                 155                 160

Phe Val Thr Asn Leu Val Pro Met Val Ala Thr Val Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Val Gly Arg Ile
            210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250

<210> SEQ ID NO 38
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: T-cell epitope embedded Shiga toxin effector
      polypeptide variant 221-229-C2

<400> SEQUENCE: 38

Lys Glu Phe Thr Leu Asp Phe Ser Thr Ala Lys Thr Tyr Val Asp Ser
 1               5                  10                  15

Leu Asn Val Ile Arg Ser Ala Ile Gly Thr Pro Leu Gln Thr Ile Ser
             20                  25                  30

Ser Gly Gly Thr Ser Leu Leu Met Ile Asp Ser Gly Ser Gly Asp Asn
            35                  40                  45

Leu Phe Ala Val Asp Val Arg Gly Ile Asp Pro Glu Glu Gly Arg Phe
 50                  55                  60

Asn Asn Leu Arg Leu Ile Val Glu Arg Asn Asn Leu Tyr Val Thr Gly
 65                  70                  75                  80

Phe Val Asn Arg Thr Asn Asn Val Phe Tyr Arg Phe Ala Asp Phe Ser
                 85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
            115                 120                 125

```
Gln Ile Asn Arg His Ser Leu Thr Thr Ser Tyr Leu Asp Leu Met Ser
        130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
                180                 185                 190

Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Asn Leu Val Pro
        210                 215                 220

Met Val Ala Thr Val Asn Ala Ile Leu Gly Ser Val Ala Leu Ile Leu
225                 230                 235                 240

Asn Cys His His His Ala Ser Arg Val Ala Arg
                245                 250

<210> SEQ ID NO 39
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: T-cell epitope embedded Shiga toxin effector
      polypeptide variant 231-239-C2

<400> SEQUENCE: 39

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
                20                  25                  30

Ser Gly Gly Thr Ser Leu Leu Met Ile Asp Ser Gly Ser Gly Asp Asn
            35                  40                  45

Leu Phe Ala Val Asp Val Arg Gly Ile Asp Pro Glu Glu Gly Arg Phe
        50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
                100                 105                 110

Ser Tyr Thr Thr Leu Gln Arg Val Ala Gly Ile Ser Arg Thr Gly Met
            115                 120                 125

Gln Ile Asn Arg His Ser Leu Thr Thr Ser Tyr Leu Asp Leu Met Ser
        130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
                180                 185                 190

Thr Ala Glu Asp Val Asp Leu Thr Leu Asn Trp Gly Arg Leu Ser Ser
            195                 200                 205

Val Leu Pro Asp Tyr His Gly Gln Asp Ser Val Arg Val Gly Arg Ile
```

```
                210               215                 220
Ser Phe Gly Ser Ile Asn Asn Leu Val Pro Met Val Ala Thr Val Leu
225                 230                 235                 240

Asn Cys His His His Ala Ser Arg Val Ala Arg
                245                 250

<210> SEQ ID NO 40
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: T-cell epitope embedded Shiga toxin effector
      polypeptide variant 77-85-F2

<400> SEQUENCE: 40

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
                20                  25                  30

Ser Gly Gly Thr Ser Leu Leu Met Ile Asp Ser Gly Ser Gly Asp Asn
            35                  40                  45

Leu Phe Ala Val Asp Val Arg Gly Ile Asp Pro Glu Glu Gly Arg Phe
50                  55                  60

Asn Asn Leu Arg Leu Ile Val Glu Arg Asn Asn Leu Gly Ile Leu Gly
65                  70                  75                  80

Phe Val Phe Thr Leu Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

Phe Val Thr Val Thr Ala Glu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250

<210> SEQ ID NO 41
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

<223> OTHER INFORMATION: T-cell epitope embedded Shiga toxin effector
polypeptide variant 159-167-F2

<400> SEQUENCE: 41

```
Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
130                 135                 140

His Ser Gly Thr Ser Leu Thr Gln Ser Val Ala Arg Ala Met Gly Ile
145                 150                 155                 160

Leu Gly Phe Val Phe Thr Leu Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250
```

<210> SEQ ID NO 42
<211> LENGTH: 251
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: T-cell epitope embedded Shiga toxin effector
polypeptide variant 159-167-F3

<400> SEQUENCE: 42

```
Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
50                  55                  60
```

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Ile Leu
145                 150                 155                 160

Arg Gly Ser Val Ala His Lys Ala Leu Arg Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250

<210> SEQ ID NO 43
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: T-cell epitope embedded Shiga toxin effector
      polypeptide variant 162-170-C2

<400> SEQUENCE: 43

Lys Glu Phe Thr Leu Asp Phe Ser Thr Ala Lys Thr Tyr Val Asp Ser
1               5                   10                  15

Leu Asn Val Ile Arg Ser Ala Ile Gly Thr Pro Leu Gln Thr Ile Ser
            20                  25                  30

Ser Gly Gly Thr Ser Leu Leu Met Ile Asp Ser Gly Ser Gly Asp Asn
        35                  40                  45

Leu Phe Ala Val Asp Val Arg Gly Ile Asp Pro Glu Glu Gly Arg Phe
    50                  55                  60

Asn Asn Leu Arg Leu Ile Val Glu Arg Asn Asn Leu Tyr Val Thr Gly
65                  70                  75                  80

Phe Val Asn Arg Thr Asn Asn Val Phe Tyr Arg Phe Ala Asp Phe Ser
                85                  90                  95

His Val Thr Phe Pro Gly Thr Thr Ala Val Thr Leu Ser Gly Asp Ser
            100                 105                 110

Ser Tyr Thr Thr Leu Gln Arg Val Ala Gly Ile Ser Arg Thr Gly Met
        115                 120                 125

Gln Ile Asn Arg His Ser Leu Thr Thr Ser Tyr Leu Asp Leu Met Ser
    130                 135                 140

His Ser Gly Thr Ser Leu Thr Gln Ser Val Ala Arg Ala Met Leu Arg
145                 150                 155                 160

```
Phe Asn Leu Val Pro Met Val Ala Thr Val Phe Arg Gln Ile Gln Arg
                165                 170                 175

Gly Phe Arg Thr Thr Leu Asp Asp Leu Ser Gly Arg Ser Tyr Val Met
            180                 185                 190

Thr Ala Glu Asp Val Asp Leu Thr Leu Asn Trp Gly Arg Leu Ser Ser
        195                 200                 205

Val Leu Pro Asp Tyr His Gly Gln Asp Ser Val Arg Val Gly Arg Ile
    210                 215                 220

Ser Phe Gly Ser Ile Asn Ala Ile Leu Gly Ser Val Ala Leu Ile Leu
225                 230                 235                 240

Asn Cys His His His Ala Ser Arg Val Ala Arg
                245                 250

<210> SEQ ID NO 44
<211> LENGTH: 193
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Diphtheria Toxin A Subunit

<400> SEQUENCE: 44

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg

<210> SEQ ID NO 45
<211> LENGTH: 398
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

<223> OTHER INFORMATION: Diphtheria toxin effector polypeptide
comprising wild-type diphtheria toxin sequences

<400> SEQUENCE: 45

```
Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
    370                 375                 380

His Lys Thr Gln Pro Gly Gly Ser His His His His His
385                 390                 395
```

-continued

<210> SEQ ID NO 46
<211> LENGTH: 398
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: T-cell epitope embedded diphtheria toxin
      effector polypeptide variant 34-42-F2

<400> SEQUENCE: 46

```
Met Gly Ala Asp Asp Val Val Asp Ser Ser Lys Ser Phe Val Met Glu
 1               5                  10                  15

Asn Phe Ser Ser Tyr His Gly Thr Lys Pro Gly Tyr Val Asp Ser Ile
            20                  25                  30

Gln Lys Gly Ile Leu Gly Phe Val Phe Thr Leu Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Glu Thr Arg Gly Lys Arg Gly Gln
                165                 170                 175

Asp Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
```

```
                    340                 345                 350
Asp Ile Gly Phe Ala Ala Tyr Asn Phe Val Glu Ser Ile Ile Asn Leu
            355                 360                 365

Phe Gln Val Val His Asn Ser Tyr Asn Arg Pro Ala Tyr Ser Pro Gly
        370                 375                 380

His Lys Thr Gln Pro Gly Gly Ser His His His His His
385                 390                 395
```

<210> SEQ ID NO 47
<211> LENGTH: 398
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: T-cell epitope embedded diphtheria toxin effector polypeptide variant 168-176-F3

<400> SEQUENCE: 47

```
Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95

Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
        115                 120                 125

Gly Asp Gly Ala Ser Arg Val Val Leu Ser Leu Pro Phe Ala Glu Gly
    130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Ile Leu Arg Gly Ser Val Ala His
                165                 170                 175

Lys Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
        195                 200                 205

Val Ile Arg Asp Lys Thr Lys Thr Lys Ile Glu Ser Leu Lys Glu His
    210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285
```

```
Val Ile Asp Ser Glu Thr Ala Asp Asn Leu Glu Lys Thr Thr Ala Ala
            290                 295                 300
Leu Ser Ile Leu Pro Gly Ile Gly Ser Val Met Gly Ile Ala Asp Gly
305                 310                 315                 320
Ala Val His His Asn Thr Glu Glu Ile Val Ala Gln Ser Ile Ala Leu
                325                 330                 335
Ser Ser Leu Met Val Ala Gln Ala Ile Pro Leu Val Gly Glu Leu Val
            340                 345                 350
Asp Ile Gly Phe Ala Ala Tyr Asn Phe Val Glu Ser Ile Ile Asn Leu
                355                 360                 365
Phe Gln Val Val His Asn Ser Tyr Asn Arg Pro Ala Tyr Ser Pro Gly
370                 375                 380
His Lys Thr Gln Pro Gly Gly Ser His His His His His His
385                 390                 395

<210> SEQ ID NO 48
<211> LENGTH: 398
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: T-cell epitope embedded diphtheria toxin
      effector polypeptide variant 69-77-C2

<400> SEQUENCE: 48

Met Gly Ala Asp Asp Val Val Asp Ser Ser Lys Ser Phe Val Met Glu
1               5                   10                  15
Asn Phe Ser Ser Tyr His Gly Thr Lys Pro Gly Tyr Val Asp Ser Ile
                20                  25                  30
Gln Lys Gly Ile Gln Lys Pro Lys Ser Gly Thr Gln Gly Asn Tyr Asp
            35                  40                  45
Asp Asp Trp Lys Gly Phe Tyr Ser Thr Asp Asn Lys Tyr Asp Ala Ala
50                  55                  60
Gly Tyr Ser Val Asp Asn Leu Val Pro Met Val Ala Thr Val Gly Gly
65                  70                  75                  80
Val Val Lys Val Thr Tyr Pro Gly Leu Thr Lys Val Leu Ala Leu Lys
                85                  90                  95
Val Asp Asn Ala Glu Thr Ile Lys Lys Glu Leu Gly Leu Ser Leu Thr
            100                 105                 110
Glu Pro Leu Met Glu Gln Val Gly Thr Glu Glu Phe Ile Lys Arg Phe
        115                 120                 125
Gly Asp Gly Ala Ser Arg Val Val Leu Ser Leu Pro Phe Ala Glu Gly
    130                 135                 140
Ser Ser Ser Val Glu Tyr Ile Asn Asn Trp Glu Gln Ala Lys Ala Leu
145                 150                 155                 160
Ser Val Glu Leu Glu Ile Asn Phe Glu Thr Arg Gly Lys Arg Gly Gln
                165                 170                 175
Asp Ala Met Tyr Glu Tyr Met Ala Gln Ala Cys Ala Gly Asn Arg Val
            180                 185                 190
Arg Arg Ser Val Gly Ser Ser Leu Ser Cys Ile Asn Leu Asp Trp Asp
        195                 200                 205
Val Ile Arg Asp Lys Thr Lys Thr Lys Ile Glu Ser Leu Lys Glu His
    210                 215                 220
Gly Pro Ile Lys Asn Lys Met Ser Glu Ser Pro Asn Lys Thr Val Ser
225                 230                 235                 240
```

```
Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
        275                 280                 285

Val Ile Asp Ser Glu Thr Ala Asp Asn Leu Glu Lys Thr Thr Ala Ala
    290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
        355                 360                 365

Phe Gln Val Val His Asn Ser Tyr Asn Arg Pro Ala Tyr Ser Pro Gly
    370                 375                 380

His Lys Thr Gln Pro Gly Gly Ser His His His His His His
385                 390                 395
```

<210> SEQ ID NO 49
<211> LENGTH: 512
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Cytotoxic Protein: alpha-CD20 fused with
      de-immunized SLT-1A

```
            180                 185                 190
Ala Ser Gly Val Pro Ala Arg Phe Ser Gly Ser Gly Ser Gly Thr Ser
        195                 200                 205

Tyr Ser Leu Thr Ile Ser Arg Val Glu Ala Glu Asp Ala Ala Thr Tyr
    210                 215                 220

Tyr Cys Gln Gln Trp Ile Ser Asn Pro Pro Thr Phe Gly Ala Gly Thr
225                 230                 235                 240

Lys Leu Glu Leu Lys Glu Phe Pro Lys Pro Ser Thr Pro Pro Gly Ser
                245                 250                 255

Ser Gly Gly Ala Pro Lys Glu Phe Thr Leu Asp Phe Ser Thr Ala Lys
            260                 265                 270

Thr Tyr Val Asp Ser Leu Asn Val Ile Arg Ser Ala Ile Gly Thr Pro
        275                 280                 285

Leu Gln Thr Ile Ser Ser Gly Gly Thr Ser Leu Leu Met Ile Asp Ser
    290                 295                 300

Asn Leu Val Pro Met Val Ala Thr Val Asp Val Arg Gly Ile Asp Pro
305                 310                 315                 320

Glu Glu Gly Arg Phe Asn Asn Leu Arg Leu Ile Val Glu Arg Asn Asn
                325                 330                 335

Leu Tyr Val Thr Gly Phe Val Asn Arg Thr Asn Asn Val Phe Tyr Arg
            340                 345                 350

Phe Ala Asp Phe Ser His Val Thr Phe Pro Gly Thr Thr Ala Val Thr
        355                 360                 365

Leu Ser Gly Asp Ser Ser Tyr Thr Thr Leu Gln Arg Val Ala Gly Ile
    370                 375                 380

Ser Arg Thr Gly Met Gln Ile Asn Arg His Ser Leu Thr Thr Ser Tyr
385                 390                 395                 400

Leu Asp Leu Met Ser His Ser Gly Thr Ser Leu Thr Gln Ser Val Ala
                405                 410                 415

Arg Ala Met Leu Arg Phe Val Thr Val Thr Ala Glu Ala Leu Arg Phe
            420                 425                 430

Arg Gln Ile Gln Arg Gly Phe Arg Thr Thr Leu Asp Asp Leu Ser Gly
        435                 440                 445

Arg Ser Tyr Val Met Thr Ala Glu Asp Val Asp Leu Thr Leu Asn Trp
    450                 455                 460

Gly Arg Leu Ser Ser Val Leu Pro Asp Tyr His Gly Gln Asp Ser Val
465                 470                 475                 480

Arg Val Gly Arg Ile Ser Phe Gly Ser Ile Asn Ala Ile Leu Gly Ser
                485                 490                 495

Val Ala Leu Ile Leu Asn Cys His His His Ala Ser Arg Val Ala Arg
            500                 505                 510

<210> SEQ ID NO 50
<211> LENGTH: 511
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Cytotoxic Protein: alpha-CD20 fused with
      de-immunized SLT-1A variant #2

<400> SEQUENCE: 50

Met Gln Val Gln Leu Val Gln Ser Gly Ala Glu Leu Val Lys Pro Gly
1               5                   10                  15
```

```
Ala Ser Val Lys Met Ser Cys Lys Ala Ser Gly Tyr Thr Phe Thr Ser
            20                  25                  30

Tyr Asn Met His Trp Val Lys Gln Thr Pro Gly Gln Gly Leu Glu Trp
            35                  40                  45

Ile Gly Ala Ile Tyr Pro Gly Asn Gly Asp Thr Ser Tyr Asn Gln Lys
            50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Ser Glu Asp Ser Ala Val Tyr Tyr
            85                  90                  95

Cys Ala Arg Ala Gln Leu Arg Pro Asn Tyr Trp Tyr Phe Asp Val Trp
            100                 105                 110

Gly Ala Gly Thr Thr Val Thr Val Ser Ser Gly Gly Gly Ser Gly Gly
            115                 120                 125

Gly Gly Gly Ser Gly Gly Gly Ser Gly Gly Gly Ser Gly Gly
            130                 135                 140

Gly Gly Ser Asp Ile Val Leu Ser Gln Ser Pro Ala Ile Leu Ser Ala
145                 150                 155                 160

Ser Pro Gly Glu Lys Val Thr Met Thr Cys Arg Ala Ser Ser Ser Val
            165                 170                 175

Ser Tyr Met His Trp Tyr Gln Gln Lys Pro Gly Ser Ser Pro Lys Pro
            180                 185                 190

Trp Ile Tyr Ala Thr Ser Asn Leu Ala Ser Gly Val Pro Ala Arg Phe
            195                 200                 205

Ser Gly Ser Gly Ser Gly Thr Ser Tyr Ser Leu Thr Ile Ser Arg Val
            210                 215                 220

Glu Ala Glu Asp Ala Ala Thr Tyr Tyr Cys Gln Gln Trp Ile Ser Asn
225                 230                 235                 240

Pro Pro Thr Phe Gly Ala Gly Thr Lys Leu Glu Leu Lys Gly Gly Gly
            245                 250                 255

Gly Ser Gly Gly Lys Glu Phe Thr Leu Asp Phe Ser Thr Ala Lys Thr
            260                 265                 270

Tyr Val Asp Ser Leu Asn Val Ile Arg Ser Ala Ile Gly Thr Pro Leu
            275                 280                 285

Gln Thr Ile Ser Ser Gly Gly Thr Ser Leu Leu Met Ile Asp Ser Gly
            290                 295                 300

Ser Gly Asp Asn Leu Phe Ala Val Asn Leu Val Pro Met Val Ala Thr
305                 310                 315                 320

Val Gly Arg Phe Asn Asn Leu Arg Leu Ile Val Glu Arg Asn Asn Leu
            325                 330                 335

Tyr Val Thr Gly Phe Val Asn Arg Thr Asn Asn Val Phe Tyr Arg Phe
            340                 345                 350

Ala Asp Phe Ser His Val Thr Phe Pro Gly Thr Thr Ala Val Thr Leu
            355                 360                 365

Ser Gly Asp Ser Ser Tyr Thr Thr Leu Gln Arg Val Ala Gly Ile Ser
            370                 375                 380

Arg Thr Gly Met Gln Ile Asn Arg His Ser Leu Thr Thr Ser Tyr Leu
385                 390                 395                 400

Asp Leu Met Ser His Ser Gly Thr Ser Leu Thr Gln Ser Val Ala Arg
            405                 410                 415

Ala Met Leu Arg Phe Val Thr Val Thr Ala Glu Ala Leu Arg Phe Arg
            420                 425                 430

Gln Ile Gln Arg Gly Phe Arg Thr Thr Leu Asp Asp Leu Ser Gly Arg
```

```
            435                 440                 445
Ser Tyr Val Met Thr Ala Glu Asp Val Asp Leu Thr Leu Asn Trp Gly
    450                 455                 460

Arg Leu Ser Ser Val Leu Pro Asp Tyr His Gly Gln Asp Ser Val Arg
465                 470                 475                 480

Val Gly Arg Ile Ser Phe Gly Ser Ile Asn Ala Ile Leu Gly Ser Val
                    485                 490                 495

Ala Leu Ile Leu Asn Cys His His Ala Ser Arg Val Ala Arg
                500                 505                 510
```

<210> SEQ ID NO 51
<211> LENGTH: 513
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Cytotoxic Protein: alpha-CD20 fused with
      de-immunized SLT-1A variant #3

<400> SEQUENCE: 51

```
Met Gln Val Gln Leu Gln Gln Pro Gly Ala Glu Leu Val Lys Pro Gly
1               5                   10                  15

Ala Ser Val Lys Met Ser Cys Lys Ala Ser Gly Tyr Thr Phe Thr Ser
                20                  25                  30

Tyr Asn Met His Trp Val Lys Gln Thr Pro Gly Arg Gly Leu Glu Trp
            35                  40                  45

Ile Gly Ala Ile Tyr Pro Gly Asn Gly Asp Thr Ser Tyr Asn Gln Lys
    50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Ser Glu Asp Ser Ala Val Tyr Tyr
                85                  90                  95

Cys Ala Arg Ser Thr Tyr Tyr Gly Gly Asp Trp Tyr Phe Asn Val Trp
                100                 105                 110

Gly Ala Gly Thr Thr Val Thr Val Ser Ala Gly Ser Thr Ser Gly Ser
            115                 120                 125

Gly Lys Pro Gly Ser Gly Glu Gly Ser Thr Lys Gly Gln Ile Val Leu
    130                 135                 140

Ser Gln Ser Pro Ala Ile Leu Ser Ala Ser Pro Gly Glu Lys Val Thr
145                 150                 155                 160

Met Thr Cys Arg Ala Ser Ser Ser Val Ser Tyr Ile His Trp Phe Gln
                165                 170                 175

Gln Lys Pro Gly Ser Ser Pro Lys Pro Trp Ile Tyr Ala Thr Ser Asn
            180                 185                 190

Leu Ala Ser Gly Val Pro Val Arg Phe Ser Gly Ser Gly Ser Gly Thr
    195                 200                 205

Ser Tyr Ser Leu Thr Ile Ser Arg Val Glu Ala Glu Asp Ala Ala Thr
210                 215                 220

Tyr Tyr Cys Gln Gln Trp Thr Ser Asn Pro Pro Thr Phe Gly Gly Gly
                225                 230                 235                 240

Thr Lys Leu Glu Ile Lys Glu Phe Pro Lys Pro Ser Thr Pro Pro Gly
                245                 250                 255

Ser Ser Gly Gly Ala Pro Lys Glu Phe Thr Leu Asp Phe Ser Thr Ala
            260                 265                 270
```

```
Lys Thr Tyr Val Asp Ser Leu Asn Val Ile Arg Ser Ala Ile Gly Thr
            275                 280                 285

Pro Leu Gln Thr Ile Ser Ser Gly Gly Thr Ser Leu Leu Met Ile Asp
        290                 295                 300

Ser Gly Ser Gly Asp Asn Leu Phe Ala Val Asp Val Arg Gly Ile Asp
305                 310                 315                 320

Pro Glu Glu Gly Arg Phe Asn Asn Leu Arg Leu Ile Val Glu Arg Asn
                325                 330                 335

Asn Leu Tyr Val Thr Gly Phe Val Asn Arg Thr Asn Asn Val Phe Tyr
            340                 345                 350

Arg Phe Ala Asp Phe Ser His Val Thr Phe Pro Gly Thr Asn Leu Val
        355                 360                 365

Pro Met Val Ala Thr Val Ser Tyr Thr Thr Leu Gln Arg Val Ala Gly
    370                 375                 380

Ile Ser Arg Thr Gly Met Gln Ile Asn Arg His Ser Leu Thr Thr Ser
385                 390                 395                 400

Tyr Leu Asp Leu Met Ser His Ser Gly Thr Ser Leu Thr Gln Ser Val
                405                 410                 415

Ala Arg Ala Met Leu Arg Phe Val Thr Val Thr Ala Glu Ala Leu Arg
            420                 425                 430

Phe Arg Gln Ile Gln Arg Gly Phe Arg Thr Thr Leu Asp Asp Leu Ser
        435                 440                 445

Gly Arg Ser Tyr Val Met Thr Ala Glu Asp Val Asp Leu Thr Leu Asn
    450                 455                 460

Trp Gly Arg Leu Ser Ser Val Leu Pro Asp Tyr His Gly Gln Asp Ser
465                 470                 475                 480

Val Arg Val Gly Arg Ile Ser Phe Gly Ser Ile Asn Ala Ile Leu Gly
                485                 490                 495

Ser Val Ala Leu Ile Leu Asn Cys His His Ala Ser Arg Val Ala
            500                 505                 510

Arg

<210> SEQ ID NO 52
<211> LENGTH: 385
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Cytotoxic Protein: anti-HER2-VHH fused with
      de-immunized SLT-1A variant #1

<400> SEQUENCE: 52

Met Glu Val Gln Leu Val Glu Ser Gly Gly Gly

Lys Arg Phe Arg Thr Ala Ala Gln Gly Thr Asp Tyr Trp Gly Gln Gly
100 105 110

Thr Gln Val Thr Val Ser Ser Ala His His Ser Glu Asp Pro Ser Ser
115 120 125

Lys Ala Pro Lys Ala Pro Lys Glu Phe Thr Leu Asp Phe Ser Thr Ala
130 135 140

Lys Thr Tyr Val Asp Ser Leu Asn Val Ile Arg Ser Ala Ile Gly Thr
145 150 155 160

Pro Leu Gln Thr Ile Ser Ser Gly Gly Thr Ser Leu Leu Met Ile Asp
165 170 175

Ser Asn Leu Val Pro Met Val Ala Thr Val Asp Val Arg Gly Ile Asp
180 185 190

Pro Glu Glu Gly Arg Phe Asn Asn Leu Arg Leu Ile Val Glu Arg Asn
195 200 205

Asn Leu Tyr Val Thr Gly Phe Val Asn Arg Thr Asn Asn Val Phe Tyr
210 215 220

Arg Phe Ala Asp Phe Ser His Val Thr Phe Pro Gly Thr Thr Ala Val
225 230 235 240

Thr Leu Ser Gly Asp Ser Ser Tyr Thr Thr Leu Gln Arg Val Ala Gly
245 250 255

Ile Ser Arg Thr Gly Met Gln Ile Asn Arg His Ser Leu Thr Thr Ser
260 265 270

Tyr Leu Asp Leu Met Ser His Ser Gly Thr Ser Leu Thr Gln Ser Val
275 280 285

Ala Arg Ala Met Leu Arg Phe Val Thr Val Thr Ala Glu Ala Leu Arg
290 295 300

Phe Arg Gln Ile Gln Arg Gly Phe Arg Thr Thr Leu Asp Asp Leu Ser
305 310 315 320

Gly Arg Ser Tyr Val Met Thr Ala Glu Asp Val Asp Leu Thr Leu Asn
325 330 335

Trp Gly Arg Leu Ser Ser Val Leu Pro Asp Tyr His Gly Gln Asp Ser
340 345 350

Val Arg Val Gly Arg Ile Ser Phe Gly Ser Ile Asn Ala Ile Leu Gly
355 360 365

Ser Val Ala Leu Ile Leu Asn Cys His His His Ala Ser Arg Val Ala
370 375 380

Arg
385

<210> SEQ ID NO 53
<211> LENGTH: 387
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Cytotoxic Protein: anti-HER2-VHH fused with de-immunized SLT-1A variant #2

<400> SEQUENCE: 53

Met Lys Glu Phe Thr Leu Asp Phe Ser Thr Ala Lys Thr Tyr Val Asp
1 5 10 15

Ser Leu Asn Val Ile Arg Ser Ala Ile Gly Thr Pro Leu Gln Thr Ile
20 25 30

Ser Ser Gly Gly Thr Ser Leu Leu Met Ile Asp Ser Gly Ser Gly Asp
35 40 45

```
Asn Leu Phe Ala Val Asn Leu Val Pro Met Val Ala Thr Val Gly Arg
 50                  55                  60

Phe Asn Asn Leu Arg Leu Ile Val Glu Arg Asn Asn Leu Tyr Val Thr
 65                  70                  75                  80

Gly Phe Val Asn Arg Thr Asn Asn Val Phe Tyr Arg Phe Ala Asp Phe
                 85                  90                  95

Ser His Val Thr Phe Pro Gly Thr Thr Ala Val Thr Leu Ser Gly Asp
                100                 105                 110

Ser Ser Tyr Thr Thr Leu Gln Arg Val Ala Gly Ile Ser Arg Thr Gly
            115                 120                 125

Met Gln Ile Asn Arg His Ser Leu Thr Thr Ser Tyr Leu Asp Leu Met
130                 135                 140

Ser His Ser Gly Thr Ser Leu Thr Gln Ser Val Ala Arg Ala Met Leu
145                 150                 155                 160

Arg Phe Val Thr Val Thr Ala Glu Ala Leu Arg Phe Arg Gln Ile Gln
                165                 170                 175

Arg Gly Phe Arg Thr Thr Leu Asp Asp Leu Ser Gly Arg Ser Tyr Val
                180                 185                 190

Met Thr Ala Glu Asp Val Asp Leu Thr Leu Asn Trp Gly Arg Leu Ser
            195                 200                 205

Ser Val Leu Pro Asp Tyr His Gly Gln Asp Ser Val Arg Val Gly Arg
210                 215                 220

Ile Ser Phe Gly Ser Ile Asn Ala Ile Leu Gly Ser Val Ala Leu Ile
225                 230                 235                 240

Leu Asn Cys His His His Ala Ser Arg Val Ala Arg Glu Phe Pro Lys
                245                 250                 255

Pro Ser Thr Pro Pro Gly Ser Ser Gly Gly Ala Pro Met Glu Val Gln
                260                 265                 270

Leu Val Glu Ser Gly Gly Gly Leu Val Gln Ala Gly Gly Ser Leu Arg
            275                 280                 285

Leu Ser Cys Ala Ala Ser Gly Ile Thr Phe Ser Ile Asn Thr Met Gly
290                 295                 300

Trp Tyr Arg Gln Ala Pro Gly Lys Gln Arg Glu Leu Val Ala Leu Ile
305                 310                 315                 320

Ser Ser Ile Gly Asp Thr Tyr Tyr Ala Asp Ser Val Lys Gly Arg Phe
                325                 330                 335

Thr Ile Ser Arg Asp Asn Ala Lys Asn Thr Val Tyr Leu Gln Met Asn
                340                 345                 350

Ser Leu Lys Pro Glu Asp Thr Ala Val Tyr Tyr Cys Lys Arg Phe Arg
            355                 360                 365

Thr Ala Ala Gln Gly Thr Asp Tyr Trp Gly Gln Gly Thr Gln Val Thr
370                 375                 380

Val Ser Ser
385

<210> SEQ ID NO 54
<211> LENGTH: 390
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Cytotoxic Protein: anti-HER2-VHH fused with
      de-immunized SLT-1A variant #3 (alpha-HER2-VHH::SLT-1A::KDEL)
```

```
<400> SEQUENCE: 54

Met Glu Val Gln Leu Val Glu Ser Gly Gly Gly Leu Val Gln Ala Gly
1               5                   10                  15

Gly Ser Leu Arg Leu Ser Cys Ala Ala Ser Gly Ile Thr Phe Ser Ile
            20                  25                  30

Asn Thr Met Gly Trp Tyr Arg Gln Ala Pro Gly Lys Gln Arg Glu Leu
        35                  40                  45

Val Ala Leu Ile Ser Ser Ile Gly Asp Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Lys Arg Phe Arg Thr Ala Ala Gln Gly Thr Asp Tyr Trp Gly Gln Gly
            100                 105                 110

Thr Gln Val Thr Val Ser Ser Glu Phe Pro Lys Pro Ser Thr Pro Pro
        115                 120                 125

Gly Ser Ser Gly Gly Ala Pro Lys Glu Phe Thr Leu Asp Phe Ser Thr
130                 135                 140

Ala Lys Thr Tyr Val Asp Ser Leu Asn Val Ile Arg Ser Ala Ile Gly
145                 150                 155                 160

Thr Pro Leu Gln Thr Ile Ser Ser Gly Gly Thr Ser Leu Leu Met Ile
                165                 170                 175

Asp Ser Gly Ser Gly Asp Asn Leu Phe Ala Val Asp Val Arg Gly Ile
            180                 185                 190

Asp Pro Glu Glu Gly Arg Phe Asn Asn Leu Arg Leu Ile Val Glu Arg
        195                 200                 205

Asn Asn Leu Tyr Val Thr Gly Phe Val Asn Arg Thr Asn Asn Val Phe
    210                 215                 220

Tyr Arg Phe Ala Asp Phe Ser His Val Thr Phe Pro Gly Thr Asn Leu
225                 230                 235                 240

Val Pro Met Val Ala Thr Val Ser Tyr Thr Thr Leu Gln Arg Val Ala
                245                 250                 255

Gly Ile Ser Arg Thr Gly Met Gln Ile Asn Arg His Ser Leu Thr Thr
            260                 265                 270

Ser Tyr Leu Asp Leu Met Ser His Ser Gly Thr Ser Leu Thr Gln Ser
        275                 280                 285

Val Ala Arg Ala Met Leu Arg Phe Val Thr Val Thr Ala Glu Ala Leu
    290                 295                 300

Arg Phe Arg Gln Ile Gln Arg Gly Phe Arg Thr Thr Leu Asp Asp Leu
305                 310                 315                 320

Ser Gly Arg Ser Tyr Val Met Thr Ala Glu Asp Val Asp Leu Thr Leu
                325                 330                 335

Asn Trp Gly Arg Leu Ser Ser Val Leu Pro Asp Tyr His Gly Gln Asp
            340                 345                 350

Ser Val Arg Val Gly Arg Ile Ser Phe Gly Ser Ile Asn Ala Ile Leu
        355                 360                 365

Gly Ser Val Ala Leu Ile Leu Asn Cys His His His Ala Ser Arg Val
370                 375                 380

Ala Arg Lys Asp Glu Leu
385                 390

<210> SEQ ID NO 55
```

```
<211> LENGTH: 652
<212> TYPE: PRT
<213> ORGANISM: Artificial Sequence
<220> FEATURE:
<223> OTHER INFORMATION:

```
                  355                 360                 365

Leu Ser Leu Thr Glu Pro Leu Met Glu Gln Val Gly Thr Glu Phe
            370                 375                 380

Ile Lys Arg Phe Gly Asp Gly Ala Ser Arg Val Val Leu Ser Leu Pro
385                 390                 395                 400

Phe Ala Glu Gly Ser Ser Val Glu Tyr Ile Asn Asn Trp Glu Gln
                405                 410                 415

Ala Lys Ala Leu Ser Val Glu Leu Glu Ile Asn Phe Glu Thr Arg Gly
                420                 425                 430

Lys Arg Gly Gln Asp Ala Met Tyr Glu Tyr Met Ala Gln Ala Cys Ala
            435                 440                 445

Gly Asn Arg Val Arg Arg Ser Val Gly Ser Ser Leu Ser Cys Ile Asn
            450                 455                 460

Leu Asp Trp Asp Val Ile Arg Asp Lys Thr Lys Thr Lys Ile Glu Ser
465                 470                 475                 480

Leu Lys Glu His Gly Pro Ile Lys Asn Lys Met Ser Glu Ser Pro Asn
                485                 490                 495

Lys Thr Val Ser Glu Glu Lys Ala Lys Gln Tyr Leu Glu Glu Phe His
            500                 505                 510

Gln Thr Ala Leu Glu His Pro Glu Leu Ser Glu Leu Lys Thr Val Thr
            515                 520                 525

Gly Thr Asn Pro Val Phe Ala Gly Ala Asn Tyr Ala Ala Trp Ala Val
            530                 535                 540

Asn Val Ala Gln Val Ile Asp Ser Glu Thr Ala Asp Asn Leu Glu Lys
545                 550                 555                 560

Thr Thr Ala Ala Leu Ser Ile Leu Pro Gly Ile Gly Ser Val Met Gly
                565                 570                 575

Ile Ala Asp Gly Ala Val His His Asn Thr Glu Glu Ile Val Ala Gln
                580                 585                 590

Ser Ile Ala Leu Ser Ser Leu Met Val Ala Gln Ala Ile Pro Leu Val
            595                 600                 605

Gly Glu Leu Val Asp Ile Gly Phe Ala Ala Tyr Asn Phe Val Glu Ser
            610                 615                 620

Ile Ile Asn Leu Phe Gln Val Val His Asn Ser Tyr Asn Arg Pro Ala
625                 630                 635                 640

Tyr Ser Pro Gly His Lys Thr Gln Pro Gly Gly Ser
                645                 650

<210> SEQ ID NO 56
<211> LENGTH: 651
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Cytotoxic Protein: alpha-CD20 fused with
      de-immunized diphtheria toxin variant #2

<400> SEQUENCE: 56

Met Gln Val Gln Leu Val Gln Ser Gly Ala Glu Leu Val Lys Pro Gly
1               5                   10                  15

Ala Ser Val Lys Met Ser Cys Lys Ala Ser Gly Tyr Thr Phe Thr Ser
                20                  25                  30

Tyr Asn Met His Trp Val Lys Gln Thr Pro Gly Gln Gly Leu Glu Trp
            35                  40                  45
```

```
Ile Gly Ala Ile Tyr Pro Gly Asn Gly Asp Thr Ser Tyr Asn Gln Lys
 50                  55                  60

Phe Lys Gly Lys Ala Thr Leu Thr Ala Asp Lys Ser Ser Ser Thr Ala
 65                  70                  75                  80

Tyr Met Gln Leu Ser Ser Leu Thr Ser Glu Asp Ser Ala Val Tyr Tyr
                 85                  90                  95

Cys Ala Arg Ala Gln Leu Arg Pro Asn Tyr Trp Tyr Phe Asp Val Trp
                100                 105                 110

Gly Ala Gly Thr Thr Val Thr Val Ser Ser Gly Gly Gly Ser Gly
                115                 120                 125

Gly Gly Gly Ser Gly Gly Gly Ser Gly Gly Gly Ser Gly Gly
        130                 135                 140

Gly Gly Ser Asp Ile Val Leu Ser Gln Ser Pro Ala Ile Leu Ser Ala
145                 150                 155                 160

Ser Pro Gly Glu Lys Val Thr Met Thr Cys Arg Ala Ser Ser Ser Val
                165                 170                 175

Ser Tyr Met His Trp Tyr Gln Gln Lys Pro Gly Ser Ser Pro Lys Pro
                180                 185                 190

Trp Ile Tyr Ala Thr Ser Asn Leu Ala Ser Gly Val Pro Ala Arg Phe
                195                 200                 205

Ser Gly Ser Gly Ser Gly Thr Ser Tyr Ser Leu Thr Ile Ser Arg Val
        210                 215                 220

Glu Ala Glu Asp Ala Ala Thr Tyr Tyr Cys Gln Gln Trp Ile Ser Asn
225                 230                 235                 240

Pro Pro Thr Phe Gly Ala Gly Thr Lys Leu Glu Leu Lys Gly Gly Gly
                245                 250                 255

Gly Ser Gly Gly Gly Ala Asp Asp Val Val Asp Ser Ser Lys Ser Phe
        260                 265                 270

Val Met Glu Asn Phe Ser Ser Tyr His Gly Thr Lys Pro Gly Tyr Val
                275                 280                 285

Asp Ser Ile Gln Lys Gly Ile Gln Lys Pro Lys Ser Gly Thr Gln Gly
        290                 295                 300

Asn Tyr Asp Asp Asp Trp Lys Gly Phe Tyr Ser Thr Asp Asn Lys Tyr
305                 310                 315                 320

Asp Ala Ala Gly Tyr Ser Val Asp Asn Glu Asn Pro Leu Ser Gly Lys
                325                 330                 335

Ala Gly Gly Val Val Lys Val Thr Tyr Pro Gly Leu Thr Lys Val Leu
                340                 345                 350

Ala Leu Lys Val Asp Asn Ala Glu Thr Ile Lys Lys Glu Leu Gly Leu
                355                 360                 365

Ser Leu Thr Glu Pro Leu Met Glu Gln Val Gly Thr Glu Glu Phe Ile
        370                 375                 380

Lys Arg Phe Gly Asp Gly Ala Ser Arg Val Val Leu Ser Leu Pro Phe
385                 390                 395                 400

Ala Glu Gly Ser Ser Ser Val Glu Tyr Ile Asn Asn Trp Glu Gln Ala
                405                 410                 415

Lys Ala Leu Ser Val Glu Leu Glu Ile Asn Phe Ile Leu Arg Gly Ser
                420                 425                 430

Val Ala His Lys Ala Met Tyr Glu Tyr Met Ala Gln Ala Cys Ala Gly
                435                 440                 445

Asn Arg Val Arg Arg Ser Val Gly Ser Ser Leu Ser Cys Ile Asn Leu
        450                 455                 460

Asp Trp Asp Val Ile Arg Asp Lys Thr Lys Thr Lys Ile Glu Ser Leu
```

```
                465                 470                 475                 480
Lys Glu His Gly Pro Ile Lys Asn Lys Met Ser Glu Ser Pro Asn Lys
                    485                 490                 495

Thr Val Ser Glu Glu Lys Ala Lys Gln Tyr Leu Glu Glu Phe His Gln
                500                 505                 510

Thr Ala Leu Glu His Pro Glu Leu Ser Glu Leu Lys Thr Val Thr Gly
            515                 520                 525

Thr Asn Pro Val Phe Ala Gly Ala Asn Tyr Ala Ala Trp Ala Val Asn
        530                 535                 540

Val Ala Gln Val Ile Asp Ser Glu Thr Ala Asp Asn Leu Glu Lys Thr
545                 550                 555                 560

Thr Ala Ala Leu Ser Ile Leu Pro Gly Ile Gly Ser Val Met Gly Ile
                565                 570                 575

Ala Asp Gly Ala Val His His Asn Thr Glu Glu Ile Val Ala Gln Ser
                580                 585                 590

Ile Ala Leu Ser Ser Leu Met Val Ala Gln Ala Ile Pro Leu Val Gly
            595                 600                 605

Glu Leu Val Asp Ile Gly Phe Ala Ala Tyr Asn Phe Val Glu Ser Ile
        610                 615                 620

Ile Asn Leu Phe Gln Val Val His Asn Ser Tyr Asn Arg Pro Ala Tyr
625                 630                 635                 640

Ser Pro Gly His Lys Thr Gln Pro Gly Gly Ser
                645                 650
```

<210> SEQ ID NO 57
<211> LENGTH: 653
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Cytotoxic Protein: alpha-CD20 fused with
      de-immunized diphtheria toxin variant #3

<400> SEQUENCE: 57

```
Met Gln Val Gln Leu Gln Gln Pro Gly Ala Glu Leu Val Lys Pro Gly
1               5                   10                  15

Ala Ser Val Lys Met Ser Cys Lys Ala Ser Gly Tyr Thr Phe Thr Ser
                20                  25                  30

Tyr Asn Met His Trp Val Lys Gln Thr Pro Gly Arg Gly Leu Glu Trp
            35                  40                  45

Ile Gly Ala Ile Tyr Pro Gly Asn Gly Asp Thr Ser Tyr Asn Gln Lys
        50                  55                  60

Phe Lys Gly Lys Ala Thr Leu Thr Ala Asp Lys Ser Ser Ser Thr Ala
65                  70                  75                  80

Tyr Met Gln Leu Ser Ser Leu Thr Ser Glu Asp Ser Ala Val Tyr Tyr
                85                  90                  95

Cys Ala Arg Ser Thr Tyr Tyr Gly Gly Asp Trp Tyr Phe Asn Val Trp
            100                 105                 110

Gly Ala Gly Thr Thr Val Thr Val Ser Ala Gly Ser Thr Ser Gly Ser
        115                 120                 125

Gly Lys Pro Gly Ser Gly Glu Gly Ser Thr Lys Gly Gln Ile Val Leu
    130                 135                 140

Ser Gln Ser Pro Ala Ile Leu Ser Ala Ser Pro Gly Glu Lys Val Thr
145                 150                 155                 160
```

```
Met Thr Cys Arg Ala Ser Ser Val Ser Tyr Ile His Trp Phe Gln
                165                 170                 175
Gln Lys Pro Gly Ser Ser Pro Lys Pro Trp Ile Tyr Ala Thr Ser Asn
            180                 185                 190
Leu Ala Ser Gly Val Pro Val Arg Phe Ser Gly Ser Gly Ser Gly Thr
            195                 200                 205
Ser Tyr Ser Leu Thr Ile Ser Arg Val Glu Ala Glu Asp Ala Ala Thr
            210                 215                 220
Tyr Tyr Cys Gln Gln Trp Thr Ser Asn Pro Thr Phe Gly Gly Gly
225                 230                 235                 240
Thr Lys Leu Glu Ile Lys Glu Phe Pro Lys Pro Ser Thr Pro Pro Gly
            245                 250                 255
Ser Ser Gly Gly Ala Pro Gly Ala Asp Asp Val Val Asp Ser Ser Lys
            260                 265                 270
Ser Phe Val Met Glu Asn Phe Ser Ser Tyr His Gly Thr Lys Pro Gly
            275                 280                 285
Tyr Val Asp Ser Ile Gln Lys Gly Ile Gln Lys Pro Lys Ser Gly Thr
            290                 295                 300
Gln Gly Asn Tyr Asp Asp Asp Trp Lys Gly Phe Tyr Ser Thr Asp Asn
305                 310                 315                 320
Lys Tyr Asp Ala Ala Gly Tyr Ser Val Asp Asn Leu Val Pro Met Val
                325                 330                 335
Ala Thr Val Gly Gly Val Val Lys Val Thr Tyr Pro Gly Leu Thr Lys
            340                 345                 350
Val Leu Ala Leu Lys Val Asp Asn Ala Glu Thr Ile Lys Lys Glu Leu
            355                 360                 365
Gly Leu Ser Leu Thr Glu Pro Leu Met Glu Gln Val Gly Thr Glu Glu
            370                 375                 380
Phe Ile Lys Arg Phe Gly Asp Gly Ala Ser Arg Val Val Leu Ser Leu
385                 390                 395                 400
Pro Phe Ala Glu Gly Ser Ser Ser Val Glu Tyr Ile Asn Asn Trp Glu
                405                 410                 415
Gln Ala Lys Ala Leu Ser Val Glu Leu Glu Ile Asn Phe Glu Thr Arg
            420                 425                 430
Gly Lys Arg Gly Gln Asp Ala Met Tyr Glu Tyr Met Ala Gln Ala Cys
            435                 440                 445
Ala Gly Asn Arg Val Arg Arg Ser Val Gly Ser Ser Leu Ser Cys Ile
            450                 455                 460
Asn Leu Asp Trp Asp Val Ile Arg Asp Lys Thr Lys Thr Lys Ile Glu
465                 470                 475                 480
Ser Leu Lys Glu His Gly Pro Ile Lys Asn Lys Met Ser Glu Ser Pro
                485                 490                 495
Asn Lys Thr Val Ser Glu Glu Lys Ala Lys Gln Tyr Leu Glu Glu Phe
            500                 505                 510
His Gln Thr Ala Leu Glu His Pro Glu Leu Ser Glu Leu Lys Thr Val
            515                 520                 525
Thr Gly Thr Asn Pro Val Phe Ala Gly Ala Asn Tyr Ala Ala Trp Ala
            530                 535                 540
Val Asn Val Ala Gln Val Ile Asp Ser Glu Thr Ala Asp Asn Leu Glu
545                 550                 555                 560
Lys Thr Thr Ala Ala Leu Ser Ile Leu Pro Gly Ile Gly Ser Val Met
                565                 570                 575
Gly Ile Ala Asp Gly Ala Val His His Asn Thr Glu Glu Ile Val Ala
```

```
                        580                 585                 590
Gln Ser Ile Ala Leu Ser Ser Leu Met Val Ala Gln Ala Ile Pro Leu
                595                 600                 605

Val Gly Glu Leu Val Asp Ile Gly Phe Ala Ala Tyr Asn Phe Val Glu
        610                 615                 620

Ser Ile Ile Asn Leu Phe Gln Val Val His Asn Ser Tyr Asn Arg Pro
625                 630                 635                 640

Ala Tyr Ser Pro Gly His Lys Thr Gln Pro Gly Gly Ser
                645                 650

<210> SEQ ID NO 58
<211> LENGTH: 525
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Cytotoxic Protein: anti-HER2-VHH fused with
      de-immunized diphtheria toxin variant #1

<400> SEQUENCE: 58

Met Glu Val Gln Leu Val Glu Ser Gly Gly Gly Leu Val Gln Ala Gly
1               5                   10                  15

Gly Ser Leu Arg Leu Ser Cys Ala Ala Ser Gly Ile Thr Phe Ser Ile
            20                  25                  30

Asn Thr Met Gly Trp Tyr Arg Gln Ala Pro Gly Lys Gln Arg Glu Leu
        35                  40                  45

Val Ala Leu Ile Ser Ser Ile Gly Asp Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Lys Arg Phe Arg Thr Ala Ala Gln Gly Thr Asp Tyr Trp Gly Gln Gly
            100                 105                 110

Thr Gln Val Thr Val Ser Ser Ala His His Ser Glu Asp Pro Ser Ser
        115                 120                 125

Lys Ala Pro Lys Ala Pro Gly Ala Asp Asp Val Val Asp Ser Ser Lys
    130                 135                 140

Ser Phe Val Met Glu Asn Phe Ser Ser Tyr His Gly Thr Lys Pro Gly
145                 150                 155                 160

Tyr Val Asp Ser Ile Gln Lys Gly Ile Leu Gly Phe Val Phe Thr Leu
                165                 170                 175

Gln Gly Asn Tyr Asp Asp Asp Trp Lys Gly Phe Tyr Ser Thr Asp Asn
            180                 185                 190

Lys Tyr Asp Ala Ala Gly Tyr Ser Val Asp Asn Glu Asn Pro Leu Ser
        195                 200                 205

Gly Lys Ala Gly Gly Val Val Lys Val Thr Tyr Pro Gly Leu Thr Lys
    210                 215                 220

Val Leu Ala Leu Lys Val Asp Asn Ala Glu Thr Ile Lys Lys Glu Leu
225                 230                 235                 240

Gly Leu Ser Leu Thr Glu Pro Leu Met Glu Gln Val Gly Thr Glu Glu
                245                 250                 255

Phe Ile Lys Arg Phe Gly Asp Gly Ala Ser Arg Val Val Leu Ser Leu
            260                 265                 270
```

-continued

```
Pro Phe Ala Glu Gly Ser Ser Val Glu Tyr Ile Asn Asn Trp Glu
            275                 280                 285

Gln Ala Lys Ala Leu Ser Val Glu Leu Glu Ile Asn Phe Glu Thr Arg
        290                 295                 300

Gly Lys Arg Gly Gln Asp Ala Met Tyr Glu Tyr Met Ala Gln Ala Cys
305                 310                 315                 320

Ala Gly Asn Arg Val Arg Arg Ser Val Gly Ser Ser Leu Ser Cys Ile
                325                 330                 335

Asn Leu Asp Trp Asp Val Ile Arg Asp Lys Thr Lys Thr Lys Ile Glu
            340                 345                 350

Ser Leu Lys Glu His Gly Pro Ile Lys Asn Lys Met Ser Glu Ser Pro
        355                 360                 365

Asn Lys Thr Val Ser Glu Glu Lys Ala Lys Gln Tyr Leu Glu Glu Phe
    370                 375                 380

His Gln Thr Ala Leu Glu His Pro Glu Leu Ser Glu Leu Lys Thr Val
385                 390                 395                 400

Thr Gly Thr Asn Pro Val Phe Ala Gly Ala Asn Tyr Ala Ala Trp Ala
                405                 410                 415

Val Asn Val Ala Gln Val Ile Asp Ser Glu Thr Ala Asp Asn Leu Glu
            420                 425                 430

Lys Thr Thr Ala Ala Leu Ser Ile Leu Pro Gly Ile Gly Ser Val Met
        435                 440                 445

Gly Ile Ala Asp Gly Ala Val His His Asn Thr Glu Glu Ile Val Ala
450                 455                 460

Gln Ser Ile Ala Leu Ser Ser Leu Met Val Ala Gln Ala Ile Pro Leu
465                 470                 475                 480

Val Gly Glu Leu Val Asp Ile Gly Phe Ala Ala Tyr Asn Phe Val Glu
                485                 490                 495

Ser Ile Ile Asn Leu Phe Gln Val Val His Asn Ser Tyr Asn Arg Pro
            500                 505                 510

Ala Tyr Ser Pro Gly His Lys Thr Gln Pro Gly Gly Ser
        515                 520                 525

<210> SEQ ID NO 59
<211> LENGTH: 527
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Cytotoxic Protein: anti-HER2-VHH fused with
      de-immunized diphtheria toxin variant #2

<400> SEQUENCE: 59

Met Gly Ala Asp Asp Val Val Asp Ser Ser Lys Ser Phe Val Met Glu
1               5                   10                  15

Asn Phe Ser Ser Tyr His Gly Thr Lys Pro Gly Tyr Val Asp Ser Ile
            20                  25                  30

Gln Lys Gly Ile Gln Lys Pro Lys Ser Gly Thr Gln Gly Asn Tyr Asp
        35                  40                  45

Asp Asp Trp Lys Gly Phe Tyr Ser Thr Asp Asn Lys Tyr Asp Ala Ala
    50                  55                  60

Gly Tyr Ser Val Asp Asn Glu Asn Pro Leu Ser Gly Lys Ala Gly Gly
65                  70                  75                  80

Val Val Lys Val Thr Tyr Pro Gly Leu Thr Lys Val Leu Ala Leu Lys
                85                  90                  95
```

```
Val Asp Asn Ala Glu Thr Ile Lys Lys Glu Leu Gly Leu Ser Leu Thr
            100                 105                 110

Glu Pro Leu Met Glu Gln Val Gly Thr Glu Glu Phe Ile Lys Arg Phe
            115                 120                 125

Gly Asp Gly Ala Ser Arg Val Val Leu Ser Leu Pro Phe Ala Glu Gly
            130                 135                 140

Ser Ser Ser Val Glu Tyr Ile Asn Asn Trp Glu Gln Ala Lys Ala Leu
145                 150                 155                 160

Ser Val Glu Leu Glu Ile Asn Phe Ile Leu Arg Gly Ser Val Ala His
                165                 170                 175

Lys Ala Met Tyr Glu Tyr Met Ala Gln Ala Cys Ala Gly Asn Arg Val
            180                 185                 190

Arg Arg Ser Val Gly Ser Ser Leu Ser Cys Ile Asn Leu Asp Trp Asp
            195                 200                 205

Val Ile Arg Asp Lys Thr Lys Thr Lys Ile Glu Ser Leu Lys Glu His
            210                 215                 220

Gly Pro Ile Lys Asn Lys Met Ser Glu Ser Pro Asn Lys Thr Val Ser
225                 230                 235                 240

Glu Glu Lys Ala Lys Gln Tyr Leu Glu Glu Phe His Gln Thr Ala Leu
                245                 250                 255

Glu His Pro Glu Leu Ser Glu Leu Lys Thr Val Thr Gly Thr Asn Pro
            260                 265                 270

Val Phe Ala Gly Ala Asn Tyr Ala Ala Trp Ala Val Asn Val Ala Gln
            275                 280                 285

Val Ile Asp Ser Glu Thr Ala Asp Asn Leu Glu Lys Thr Thr Ala Ala
            290                 295                 300

Leu Ser Ile Leu Pro Gly Ile Gly Ser Val Met Gly Ile Ala Asp Gly
305                 310                 315                 320

Ala Val His His Asn Thr Glu Glu Ile Val Ala Gln Ser Ile Ala Leu
                325                 330                 335

Ser Ser Leu Met Val Ala Gln Ala Ile Pro Leu Val Gly Glu Leu Val
            340                 345                 350

Asp Ile Gly Phe Ala Ala Tyr Asn Phe Val Glu Ser Ile Ile Asn Leu
            355                 360                 365

Phe Gln Val Val His Asn Ser Tyr Asn Arg Pro Ala Tyr Ser Pro Gly
370                 375                 380

His Lys Thr Gln Pro Gly Gly Ser Glu Phe Pro Lys Pro Ser Thr Pro
385                 390                 395                 400

Pro Gly Ser Ser Gly Gly Ala Pro Met Glu Val Gln Leu Val Glu Ser
                405                 410                 415

Gly Gly Gly Leu Val Gln Ala Gly Gly Ser Leu Arg Leu Ser Cys Ala
            420                 425                 430

Ala Ser Gly Ile Thr Phe Ser Ile Asn Thr Met Gly Trp Tyr Arg Gln
            435                 440                 445

Ala Pro Gly Lys Gln Arg Glu Leu Val Ala Leu Ile Ser Ser Ile Gly
            450                 455                 460

Asp Thr Tyr Tyr Ala Asp Ser Val Lys Gly Arg Phe Thr Ile Ser Arg
465                 470                 475                 480

Asp Asn Ala Lys Asn Thr Val Tyr Leu Gln Met Asn Ser Leu Lys Pro
                485                 490                 495

Glu Asp Thr Ala Val Tyr Tyr Cys Lys Arg Phe Arg Thr Ala Ala Gln
            500                 505                 510
```

Gly Thr Asp Tyr Trp Gly Gln Gly Thr Gln Val Thr Val Ser Ser
            515                 520                 525

<210> SEQ ID NO 60
<211> LENGTH: 530
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Cytotoxic Protein: anti-HER2-VHH fused with
      de-immunized diphtheria toxin variant #3
      (alpha-HER2-VHH::diphtheria Toxin:KDEL)

<400> SEQUENCE: 60

Met Glu Val Gln Leu Val Glu Ser Gly Gly Gly Leu Val Gln Ala Gly
1               5                   10                  15

Gly Ser Leu Arg Leu Ser Cys Ala Ala Ser Gly Ile Thr Phe Ser Ile
            20                  25                  30

Asn Thr Met Gly Trp Tyr Arg Gln Ala Pro Gly Lys Gln Arg Glu Leu
        35                  40                  45

Val Ala Leu Ile Ser Ser Ile Gly Asp Thr Tyr Tyr Ala Asp Ser Val
50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Lys Arg Phe Arg Thr Ala Ala Gln Gly Thr Asp Tyr Trp Gly Gln Gly
            100                 105                 110

Thr Gln Val Thr Val Ser Ser Glu Phe Pro Lys Pro Ser Thr Pro Pro
        115                 120                 125

Gly Ser Ser Gly Gly Ala Pro Gly Ala Asp Asp Val Val Asp Ser Ser
    130                 135                 140

Lys Ser Phe Val Met Glu Asn Phe Ser Ser Tyr His Gly Thr Lys Pro
145                 150                 155                 160

Gly Tyr Val Asp Ser Ile Gln Lys Gly Ile Gln Lys Pro Lys Ser Gly
                165                 170                 175

Thr Gln Gly Asn Tyr Asp Asp Asp Trp Lys Gly Phe Tyr Ser Thr Asp
            180                 185                 190

Asn Lys Tyr Asp Ala Ala Gly Tyr Ser Val Asp Asn Leu Val Pro Met
        195                 200                 205

Val Ala Thr Val Gly Gly Val Val Lys Val Thr Tyr Pro Gly Leu Thr
    210                 215                 220

Lys Val Leu Ala Leu Lys Val Asp Asn Ala Glu Thr Ile Lys Lys Glu
225                 230                 235                 240

Leu Gly Leu Ser Leu Thr Glu Pro Leu Met Glu Gln Val Gly Thr Glu
                245                 250                 255

Glu Phe Ile Lys Arg Phe Gly Asp Gly Ala Ser Arg Val Val Leu Ser
            260                 265                 270

Leu Pro Phe Ala Glu Gly Ser Ser Val Glu Tyr Ile Asn Asn Trp
        275                 280                 285

Glu Gln Ala Lys Ala Leu Ser Val Glu Leu Glu Ile Asn Phe Glu Thr
    290                 295                 300

Arg Gly Lys Arg Gly Gln Asp Ala Met Tyr Glu Tyr Met Ala Gln Ala
305                 310                 315                 320

Cys Ala Gly Asn Arg Val Arg Arg Ser Val Gly Ser Ser Leu Ser Cys

```
                    325                 330                 335
Ile Asn Leu Asp Trp Asp Val Ile Arg Asp Lys Thr Lys Thr Lys Ile
            340                 345                 350
Glu Ser Leu Lys Glu His Gly Pro Ile Lys Asn Lys Met Ser Glu Ser
        355                 360                 365
Pro Asn Lys Thr Val Ser Glu Lys Ala Lys Gln Tyr Leu Glu Glu
    370                 375                 380
Phe His Gln Thr Ala Leu Glu His Pro Glu Leu Ser Glu Leu Lys Thr
385                 390                 395                 400
Val Thr Gly Thr Asn Pro Val Phe Ala Gly Ala Asn Tyr Ala Ala Trp
                405                 410                 415
Ala Val Asn Val Ala Gln Val Ile Asp Ser Glu Thr Ala Asp Asn Leu
            420                 425                 430
Glu Lys Thr Thr Ala Ala Leu Ser Ile Leu Pro Gly Ile Gly Ser Val
        435                 440                 445
Met Gly Ile Ala Asp Gly Ala Val His His Asn Thr Glu Glu Ile Val
    450                 455                 460
Ala Gln Ser Ile Ala Leu Ser Ser Leu Met Val Ala Gln Ala Ile Pro
465                 470                 475                 480
Leu Val Gly Glu Leu Val Asp Ile Gly Phe Ala Ala Tyr Asn Phe Val
                485                 490                 495
Glu Ser Ile Ile Asn Leu Phe Gln Val Val His Asn Ser Tyr Asn Arg
            500                 505                 510
Pro Ala Tyr Ser Pro Gly His Lys Thr Gln Pro Gly Gly Ser Lys Asp
        515                 520                 525
Glu Leu
    530

<210> SEQ ID NO 61
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Lys Asp Glu Leu
1

<210> SEQ ID NO 62
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

His Asp Glu Phe
1

<210> SEQ ID NO 63
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63
```

```
His Asp Glu Leu
1

<210> SEQ ID NO 64
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Asp Glu Phe
1

<210> SEQ ID NO 65
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Arg Asp Glu Leu
1

<210> SEQ ID NO 66
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Trp Asp Glu Leu
1

<210> SEQ ID NO 67
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Tyr Asp Glu Leu
1

<210> SEQ ID NO 68
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

His Glu Glu Phe
1

<210> SEQ ID NO 69
<211> LENGTH: 4
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 69

His Glu Glu Leu
1

<210> SEQ ID NO 70
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Lys Glu Glu Leu
1

<210> SEQ ID NO 71
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Arg Glu Glu Leu
1

<210> SEQ ID NO 72
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Lys Ala Glu Leu
1

<210> SEQ ID NO 73
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Lys Cys Glu Leu
1

<210> SEQ ID NO 74
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Lys Phe Glu Leu
1
```

```
<210> SEQ ID NO 75
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Lys Gly Glu Leu
1

<210> SEQ ID NO 76
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Lys His Glu Leu
1

<210> SEQ ID NO 77
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Lys Leu Glu Leu
1

<210> SEQ ID NO 78
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Lys Asn Glu Leu
1

<210> SEQ ID NO 79
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Lys Gln Glu Leu
1

<210> SEQ ID NO 80
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 80

Lys Arg Glu Leu
1

<210> SEQ ID NO 81
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Lys Ser Glu Leu
1

<210> SEQ ID NO 82
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Lys Val Glu Leu
1

<210> SEQ ID NO 83
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Lys Trp Glu Leu
1

<210> SEQ ID NO 84
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Lys Tyr Glu Leu
1

<210> SEQ ID NO 85
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Lys Glu Asp Leu
1

<210> SEQ ID NO 86
<211> LENGTH: 4
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 86

Lys Ile Glu Leu
1

<210> SEQ ID NO 87
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Asp Lys Glu Leu
1

<210> SEQ ID NO 88
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Phe Asp Glu Leu
1

<210> SEQ ID NO 89
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Lys Asp Glu Phe
1

<210> SEQ ID NO 90
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Lys Lys Glu Leu
1

<210> SEQ ID NO 91
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

His Ala Asp Leu
1
```

```
<210> SEQ ID NO 92
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

His Ala Glu Leu
1

<210> SEQ ID NO 93
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

His Ile Glu Leu
1

<210> SEQ ID NO 94
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

His Asn Glu Leu
1

<210> SEQ ID NO 95
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

His Thr Glu Leu
1

<210> SEQ ID NO 96
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Lys Thr Glu Leu
1

<210> SEQ ID NO 97
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 97

His Val Glu Leu
1

<210> SEQ ID NO 98
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Asn Asp Glu Leu
1

<210> SEQ ID NO 99
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gln Asp Glu Leu
1

<210> SEQ ID NO 100
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Arg Glu Asp Leu
1

<210> SEQ ID NO 101
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Arg Asn Glu Leu
1

<210> SEQ ID NO 102
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Arg Thr Asp Leu
1

<210> SEQ ID NO 103
<211> LENGTH: 4
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Arg Thr Glu Leu
1

<210> SEQ ID NO 104
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ser Asp Glu Leu
1

<210> SEQ ID NO 105
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Thr Asp Glu Leu
1

<210> SEQ ID NO 106
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ser Lys Glu Leu
1

<210> SEQ ID NO 107
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ala Leu Glu Asp Glu Leu
1               5

<210> SEQ ID NO 108
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

His Ala Glu Asp Glu Leu
```

```
1               5
```

<210> SEQ ID NO 109
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

```
His Leu Glu Asp Glu Leu
1               5
```

<210> SEQ ID NO 110
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

```
Lys Leu Glu Asp Glu Leu
1               5
```

<210> SEQ ID NO 111
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

```
Ile Arg Ser Asp Glu Leu
1               5
```

<210> SEQ ID NO 112
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

```
Glu Arg Ser Thr Glu Leu
1               5
```

<210> SEQ ID NO 113
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

```
Arg Pro Ser Thr Glu Leu
1               5
```

<210> SEQ ID NO 114
<211> LENGTH: 6
<212> TYPE: PRT
<213> ORGANISM: Artificial Sequence
<220> FEATURE:
<223> OTHER INFORMATION: Description of Artificial Sequence: Synthetic

```
                           peptide

<400> SEQUENCE: 114

Ala Ser Gly Gly Pro Glu
1               5

<210> SEQ ID NO 115
<211> LENGTH: 54
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (5)..(6)
<223> OTHER INFORMATION: May or may not be present
<220> FEATURE:
<221> NAME/KEY: MISC_FEATURE
<222> LOCATION: (10)..(11)
<223> OTHER INFORMATION: May or may not be present
<220> FEATURE:
<221> NAME/KEY: MISC_FEATURE
<222> LOCATION: (15)..(16)
<223> OTHER INFORMATION: May or may not be present
<220> FEATURE:
<221> NAME/KEY: MISC_FEATURE
<222> LOCATION: (20)..(21)
<223> OTHER INFORMATION: May or may not be present
<220> FEATURE:
<221> NAME/KEY: MISC_FEATURE
<222> LOCATION: (25)..(26)
<223> OTHER INFORMATION: May or may not be present
<220> FEATURE:
<221> NAME/KEY: MISC_FEATURE
<222> LOCATION: (30)..(31)
<223> OTHER INFORMATION: May or may not be present
<220> FEATURE:
<221> NAME/KEY: MISC_FEATURE
<222> LOCATION: (35)..(36)
<223> OTHER INFORMATION: May or may not be present
<220> FEATURE:
<221> NAME/KEY: MISC_FEATURE
<222> LOCATION: (40)..(41)
<223> OTHER INFORMATION: May or may not be present
<220> FEATURE:
<221> NAME/KEY: MISC_FEATURE
<222> LOCATION: (45)..(46)
<223> OTHER INFORMATION: May or may not be present
<220> FEATURE:
<221> NAME/KEY: MISC_FEATURE
<222> LOCATION: (50)..(51)
<223> OTHER INFORMATION: May or may not be present
<220> FEATURE:
<221> NAME/KEY: MISC_FEATURE
<222> LOCATION: (3)..(52)
<223> OTHER INFORMATION: This region may encompass 1-10 'Gly(2-4)Ser'
      repeating units wherein some positions may be
      absent

<400> SEQUENCE: 115

Ala Met Gly Gly Gly Gly Ser Gly Gly Gly Ser Gly Gly Gly Gly
1               5                   10                  15

Ser Gly Gly Gly Gly Ser Gly Gly Gly Ser Gly Gly Gly Gly Ser
                20                  25                  30

Gly Gly Gly Gly Ser Gly Gly Gly Gly Ser Gly Gly Gly Ser Gly
        35                  40                  45

Gly Gly Gly Ser Ala Met
    50

<210> SEQ ID NO 116
<211> LENGTH: 210
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (2)..(6)
<223> OTHER INFORMATION: May or may not be present
<220> FEATURE:
<221> NAME/KEY: MISC_FEATURE
<222> LOCATION: (9)..(13)
<223> OTHER INFORMATION: May or may not be present
<220> FEATURE:
<221> NAME/KEY: MISC_FEATURE
<222> LOCATION: (16)..(20)
<223> OTHER INFORMATION: May or may not be present
<220> FEATURE:
<221> NAME/KEY: MISC_FEATURE
<222> LOCATION: (23)..(27)
<223> OTHER INFORMATION: May or may not be present
<220> FEATURE:
<221> NAME/KEY: MISC_FEATURE
<222> LOCATION: (30)..(34)
<223> OTHER INFORMATION: May or may not be present
<220> FEATURE:
<221> NAME/KEY: MISC_FEATURE
<222> LOCATION: (37)..(41)
<223> OTHER INFORMATION: May or may not be present
<220> FEATURE:
<221> NAME/KEY: MISC_FEATURE
<222> LOCATION: (44)..(48)
<223> OTHER INFORMATION: May or may not be present
<220> FEATURE:
<221> NAME/KEY: MISC_FEATURE
<222> LOCATION: (51)..(55)
<223> OTHER INFORMATION: May or may not be present
<220> FEATURE:
<221> NAME/KEY: MISC_FEATURE
<222> LOCATION: (58)..(62)
<223> OTHER INFORMATION: May or may not be present
<220> FEATURE:
<221> NAME/KEY: MISC_FEATURE
<222> LOCATION: (65)..(69)
<223> OTHER INFORMATION: May or may not be present
<220> FEATURE:
<221> NAME/KEY: MISC_FEATURE
<222> LOCATION: (72)..(76)
<223> OTHER INFORMATION: May or may not be present
<220> FEATURE:
<221> NAME/KEY: MISC_FEATURE
<222> LOCATION: (79)..(83)
<223> OTHER INFORMATION: May or may not be present
<220> FEATURE:
<221> NAME/KEY: MISC_FEATURE
<222> LOCATION: (86)..(90)
<223> OTHER INFORMATION: May or may not be present
<220> FEATURE:
<221> NAME/KEY: MISC_FEATURE
<222> LOCATION: (93)..(97)
<223> OTHER INFORMATION: May or may not be present
<220> FEATURE:
<221> NAME/KEY: MISC_FEATURE
<222> LOCATION: (100)..(104)
<223> OTHER INFORMATION: May or may not be present
<220> FEATURE:
<221> NAME/KEY: MISC_FEATURE
<222> LOCATION: (107)..(111)
<223> OTHER INFORMATION: May or may not be present
<220> FEATURE:
<221> NAME/KEY: MISC_FEATURE
<222> LOCATION: (114)..(118)
<223> OTHER INFORMATION: May or may not be present
<220> FEATURE:
<221> NAME/KEY: MISC_FEATURE
<222> LOCATION: (121)..(125)
<223> OTHER INFORMATION: May or may not be present
<220> FEATURE:
<221> NAME/KEY: MISC_FEATURE
```

```
<222> LOCATION: (128)..(132)
<223> OTHER INFORMATION: May or may not be present
<220> FEATURE:
<221> NAME/KEY: MISC_FEATURE
<222> LOCATION: (135)..(139)
<223> OTHER INFORMATION: May or may not be present
<220> FEATURE:
<221> NAME/KEY: MISC_FEATURE
<222> LOCATION: (142)..(146)
<223> OTHER INFORMATION: May or may not be present
<220> FEATURE:
<221> NAME/KEY: MISC_FEATURE
<222> LOCATION: (149)..(153)
<223> OTHER INFORMATION: May or may not be present
<220> FEATURE:
<221> NAME/KEY: MISC_FEATURE
<222> LOCATION: (156)..(160)
<223> OTHER INFORMATION: May or may not be present
<220> FEATURE:
<221> NAME/KEY: MISC_FEATURE
<222> LOCATION: (163)..(167)
<223> OTHER INFORMATION: May or may not be present
<220> FEATURE:
<221> NAME/KEY: MISC_FEATURE
<222> LOCATION: (170)..(174)
<223> OTHER INFORMATION: May or may not be present
<220> FEATURE:
<221> NAME/KEY: MISC_FEATURE
<222> LOCATION: (177)..(181)
<223> OTHER INFORMATION: May or may not be present
<220> FEATURE:
<221> NAME/KEY: MISC_FEATURE
<222> LOCATION: (184)..(188)
<223> OTHER INFORMATION: May or may not be present
<220> FEATURE:
<221> NAME/KEY: MISC_FEATURE
<222> LOCATION: (191)..(195)
<223> OTHER INFORMATION: May or may not be present
<220> FEATURE:
<221> NAME/KEY: MISC_FEATURE
<222> LOCATION: (198)..(202)
<223> OTHER INFORMATION: May or may not be present
<220> FEATURE:
<221> NAME/KEY: MISC_FEATURE
<222> LOCATION: (205)..(209)
<223> OTHER INFORMATION: May or may not be present
<220> FEATURE:
<221> NAME/KEY: MISC_FEATURE
<222> LOCATION: (1)..(210)
<223> OTHER INFORMATION: This sequence may encompass 1-30 '(Gly)X-Ser'
     repeating units, wherein X represents 1-6 and wherein some
     positions may be absent

<400> SEQUENCE: 116

Gly Gly Gly Gly Gly Gly Ser Gly Gly Gly Gly Gly Ser Gly Gly
1               5                   10                  15

Gly Gly Gly Gly Ser Gly Gly Gly Gly Gly Ser Gly Gly Gly Gly
            20                  25                  30

Gly Gly Ser Gly Gly Gly Gly Gly Ser Gly Gly Gly Gly Gly Gly
        35                  40                  45

Ser Gly Gly Gly Gly Gly Gly Ser Gly Gly Gly Gly Gly Ser Gly
    50                  55                  60

Gly Gly Gly Gly Gly Ser Gly Gly Gly Gly Ser Gly Gly Gly Gly
65                  70                  75                  80

Gly Gly Gly Ser Gly Gly Gly Gly Gly Ser Gly Gly Gly Gly Gly
                85                  90                  95

Gly Ser Gly Gly Gly Gly Gly Ser Gly Gly Gly Gly Gly Gly Ser
            100                 105                 110

Gly Gly Gly Gly Gly Gly Ser Gly Gly Gly Gly Gly Ser Gly Gly
        115                 120                 125
```

Gly Gly Gly Gly Ser Gly Gly Gly Gly Ser Gly Gly Gly
    130                 135                 140
Gly Gly Ser Gly Gly Gly Gly Gly Ser Gly Gly Gly Gly
145                 150                 155                 160
Ser Gly Gly Gly Gly Gly Ser Gly Gly Gly Gly Ser Gly
                165                 170                 175
Gly Gly Gly Gly Ser Gly Gly Gly Gly Ser Gly Gly Gly
            180                 185                 190
Gly Gly Gly Ser Gly Gly Gly Gly Gly Ser Gly Gly Gly Gly
        195                 200                 205

Gly Ser
    210

<210> SEQ ID NO 117
<211> LENGTH: 210
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (2)..(6)
<223> OTHER INFORMATION: May or may not be present
<220> FEATURE:
<221> NAME/KEY: MISC_FEATURE
<222> LOCATION: (9)..(13)
<223> OTHER INFORMATION: May or may not be present
<220> FEATURE:
<221> NAME/KEY: MISC_FEATURE
<222> LOCATION: (16)..(20)
<223> OTHER INFORMATION: May or may not be present
<220> FEATURE:
<221> NAME/KEY: MISC_FEATURE
<222> LOCATION: (23)..(27)
<223> OTHER INFORMATION: May or may not be present
<220> FEATURE:
<221> NAME/KEY: MISC_FEATURE
<222> LOCATION: (30)..(34)
<223> OTHER INFORMATION: May or may not be present
<220> FEATURE:
<221> NAME/KEY: MISC_FEATURE
<222> LOCATION: (37)..(41)
<223> OTHER INFORMATION: May or may not be present
<220> FEATURE:
<221> NAME/KEY: MISC_FEATURE
<222> LOCATION: (44)..(48)
<223> OTHER INFORMATION: May or may not be present
<220> FEATURE:
<221> NAME/KEY: MISC_FEATURE
<222> LOCATION: (51)..(55)
<223> OTHER INFORMATION: May or may not be present
<220> FEATURE:
<221> NAME/KEY: MISC_FEATURE
<222> LOCATION: (58)..(62)
<223> OTHER INFORMATION: May or may not be present
<220> FEATURE:
<221> NAME/KEY: MISC_FEATURE
<222> LOCATION: (65)..(69)
<223> OTHER INFORMATION: May or may not be present
<220> FEATURE:
<221> NAME/KEY: MISC_FEATURE
<222> LOCATION: (72)..(76)
<223> OTHER INFORMATION: May or may not be present
<220> FEATURE:
<221> NAME/KEY: MISC_FEATURE
<222> LOCATION: (79)..(83)
<223> OTHER INFORMATION: May or may not be present
<220> FEATURE:
<221> NAME/KEY: MISC_FEATURE
<222> LOCATION: (86)..(90)
<223> OTHER INFORMATION: May or may not be present
<220> FEATURE:

```
<221> NAME/KEY: MISC_FEATURE
<222> LOCATION: (93)..(97)
<223> OTHER INFORMATION: May or may not be present
<220> FEATURE:
<221> NAME/KEY: MISC_FEATURE
<222> LOCATION: (100)..(104)
<223> OTHER INFORMATION: May or may not be present
<220> FEATURE:
<221> NAME/KEY: MISC_FEATURE
<222> LOCATION: (107)..(111)
<223> OTHER INFORMATION: May or may not be present
<220> FEATURE:
<221> NAME/KEY: MISC_FEATURE
<222> LOCATION: (114)..(118)
<223> OTHER INFORMATION: May or may not be present
<220> FEATURE:
<221> NAME/KEY: MISC_FEATURE
<222> LOCATION: (121)..(125)
<223> OTHER INFORMATION: May or may not be present
<220> FEATURE:
<221> NAME/KEY: MISC_FEATURE
<222> LOCATION: (128)..(132)
<223> OTHER INFORMATION: May or may not be present
<220> FEATURE:
<221> NAME/KEY: MISC_FEATURE
<222> LOCATION: (135)..(139)
<223> OTHER INFORMATION: May or may not be present
<220> FEATURE:
<221> NAME/KEY: MISC_FEATURE
<222> LOCATION: (142)..(146)
<223> OTHER INFORMATION: May or may not be present
<220> FEATURE:
<221> NAME/KEY: MISC_FEATURE
<222> LOCATION: (149)..(153)
<223> OTHER INFORMATION: May or may not be present
<220> FEATURE:
<221> NAME/KEY: MISC_FEATURE
<222> LOCATION: (156)..(160)
<223> OTHER INFORMATION: May or may not be present
<220> FEATURE:
<221> NAME/KEY: MISC_FEATURE
<222> LOCATION: (163)..(167)
<223> OTHER INFORMATION: May or may not be present
<220> FEATURE:
<221> NAME/KEY: MISC_FEATURE
<222> LOCATION: (170)..(174)
<223> OTHER INFORMATION: May or may not be present
<220> FEATURE:
<221> NAME/KEY: MISC_FEATURE
<222> LOCATION: (177)..(181)
<223> OTHER INFORMATION: May or may not be present
<220> FEATURE:
<221> NAME/KEY: MISC_FEATURE
<222> LOCATION: (184)..(188)
<223> OTHER INFORMATION: May or may not be present
<220> FEATURE:
<221> NAME/KEY: MISC_FEATURE
<222> LOCATION: (191)..(195)
<223> OTHER INFORMATION: May or may not be present
<220> FEATURE:
<221> NAME/KEY: MISC_FEATURE
<222> LOCATION: (198)..(202)
<223> OTHER INFORMATION: May or may not be present
<220> FEATURE:
<221> NAME/KEY: MISC_FEATURE
<222> LOCATION: (205)..(209)
<223> OTHER INFORMATION: May or may not be present
<220> FEATURE:
<221> NAME/KEY: MISC_FEATURE
<222> LOCATION: (1)..(210)
<223> OTHER INFORMATION: This sequence may encompass 1-30 '(Ser)X-Gly'
      repeating units, wherein X represents 1-6 and wherein some
      positions may be absent

<400> SEQUENCE: 117

Ser Ser Ser Ser Ser Ser Gly Ser Ser Ser Ser Ser Gly Ser Ser
1               5                   10                  15
```

Ser Ser Ser Ser Gly Ser Ser Ser Ser Gly Ser Ser Ser
        20                  25                  30

Ser Ser Gly Ser Ser Ser Ser Ser Gly Ser Ser Ser Ser
        35                  40                  45

Gly Ser Ser Ser Ser Ser Gly Ser Ser Ser Ser Gly Ser
50                  55                  60

Ser Ser Ser Ser Gly Ser Ser Ser Ser Gly Ser Ser Ser
65                  70                  75                  80

Ser Ser Ser Gly Ser Ser Ser Ser Gly Ser Ser Ser Ser
            85                  90                  95

Ser Gly Ser Ser Ser Ser Ser Gly Ser Ser Ser Ser Gly
        100                 105                 110

Ser Ser Ser Ser Ser Gly Ser Ser Ser Ser Gly Ser Ser
            115                 120                 125

Ser Ser Ser Ser Gly Ser Ser Ser Ser Gly Ser Ser Ser
        130                 135                 140

Ser Ser Gly Ser Ser Ser Ser Gly Ser Ser Ser Ser Ser
145                 150                 155                 160

Gly Ser Ser Ser Ser Ser Gly Ser Ser Ser Ser Gly Ser
            165                 170                 175

Ser Ser Ser Ser Gly Ser Ser Ser Ser Gly Ser Ser Ser
        180                 185                 190

Ser Ser Gly Ser Ser Ser Ser Gly Ser Ser Ser Ser Ser
            195                 200                 205

Ser Gly
    210

<210> SEQ ID NO 118
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(150)
<223> OTHER INFORMATION: This sequence may encompass 1-30 'Gly-Gly-Gly-
      Gly-Ser' repeating units wherein some positions may be
      absent

<400> SEQUENCE: 118

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser Gly Gly Gly Gly Ser Gly
            85                  90                  95

Gly Gly Gly Ser Gly Gly Gly Gly Ser Gly Gly Gly Gly Ser Gly Gly
        100                 105                 110

Gly Gly Ser Gly Gly Gly Gly Ser Gly Gly Gly Gly Ser Gly Gly Gly
        115                 120                 125

Gly Ser Gly Gly Gly Gly Ser Gly Gly Gly Ser Gly Gly Gly
            130                 135                 140

Ser Gly Gly Gly Gly Ser
145                 150

<210> SEQ ID NO 119
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (2)..(30)
<223> OTHER INFORMATION: May or may not be present wherein some
      positions may be absent

<400> SEQUENCE: 119

Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly
            20                  25                  30

<210> SEQ ID NO 120
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gly Lys Ser Ser Gly Ser Gly Ser Glu Ser Lys Ser
1               5                   10

<210> SEQ ID NO 121
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Gly Ser Thr Ser Gly Ser Gly Lys Ser Ser Glu Gly Lys Gly
1               5                   10

<210> SEQ ID NO 122
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Gly Ser Thr Ser Gly Ser Gly Lys Ser Ser Glu Gly Ser Gly Ser Thr
1               5                   10                  15

Lys Gly

<210> SEQ ID NO 123
<211> LENGTH: 18
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 123

Gly Ser Thr Ser Gly Ser Gly Lys Pro Gly Ser Gly Glu Gly Ser Thr
1               5                   10                  15

Lys Gly

<210> SEQ ID NO 124
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Glu Gly Lys Ser Ser Gly Ser Gly Ser Glu Ser Lys Glu Phe
1               5                   10

<210> SEQ ID NO 125
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Ser Arg Ser Ser Gly
1               5

<210> SEQ ID NO 126
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Ser Gly Ser Ser Cys
1               5

<210> SEQ ID NO 127
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Ala Met Gly Arg Ser Gly Gly Cys Ala Gly Asn Arg Val Gly Ser
1               5                   10                  15

Ser Leu Ser Cys Gly Gly Leu Asn Leu Gln Ala Met
            20                  25

<210> SEQ ID NO 128
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Gly Gly Gly Gly Ser Gly Gly Gly Ser Gly Gly Gly Ser
1               5                   10                  15

<210> SEQ ID NO 129
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Gly Gly Gly Ser
1

<210> SEQ ID NO 130
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Gly Gly Gly Gly Ser
1               5

<210> SEQ ID NO 131
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Gly Gly Gly Gly Ser Gly Gly Gly
1               5

<210> SEQ ID NO 132
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gly Gly Ser Gly Gly Gly Gly
1               5

<210> SEQ ID NO 133
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Gly Ser Thr Ser Gly Gly Gly Ser Gly Gly Ser Gly Gly Gly
1               5                   10                  15

Ser Ser

<210> SEQ ID NO 134
<211> LENGTH: 18

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gly Ser Thr Ser Gly Ser Gly Lys Pro Gly Ser Ser Glu Gly Ser Thr
1               5                   10                  15

Lys Gly

<210> SEQ ID NO 135
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Asp Ser Lys Lys Pro
1               5

<210> SEQ ID NO 136
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Thr Leu Asp Phe Ser Thr Ala Lys Thr
1               5

<210> SEQ ID NO 137
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Ser Gly Ser Gly Asp Asn Leu Phe Ala
1               5

<210> SEQ ID NO 138
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Gly Ser Gly Asp Asn Leu Phe Ala Val
1               5

<210> SEQ ID NO 139
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139
```

Asp Val Arg Gly Ile Asp Pro Glu Glu
1               5

<210> SEQ ID NO 140
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Thr Ala Val Thr Leu Ser Gly Asp Ser
1               5

<210> SEQ ID NO 141
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Thr Thr Leu Asp Asp Leu Ser Gly Arg
1               5

<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Asp Val Arg Gly Ile Asp Pro Glu
1               5

<210> SEQ ID NO 143
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gly Ile Gln Lys Pro Lys Ser Gly Thr
1               5

<210> SEQ ID NO 144
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Asn Glu Asn Pro Leu Ser Gly Lys Ala
1               5

<210> SEQ ID NO 145
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 145

Glu Thr Arg Gly Lys Arg Gly Gln Asp
1               5

<210> SEQ ID NO 146
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 146

His His His His His His
1               5

<210> SEQ ID NO 147
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Asn Leu Arg Leu Ile Val Glu Arg Asn
1               5

<210> SEQ ID NO 148
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Asn Leu Tyr Val Thr Gly Phe Val Asn
1               5

<210> SEQ ID NO 149
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ala Met Leu Arg Phe Val Thr Val Thr
1               5

<210> SEQ ID NO 150
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Val Thr Ala Glu Ala Leu Arg Phe Arg
1               5
```

```
<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Val Gly Arg Ile Ser Phe Gly Ser Ile
1               5

<210> SEQ ID NO 152
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Ala Ile Leu Gly Ser Val Ala Leu Ile
1               5

<210> SEQ ID NO 153
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Tyr Val Thr Gly Phe Val Asn Arg Thr
1               5

<210> SEQ ID NO 154
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Leu Arg Phe Val Thr Val Thr Ala Glu
1               5

<210> SEQ ID NO 155
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Val Thr Val Thr Ala Glu Ala Leu Arg
1               5

<210> SEQ ID NO 156
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 156

Asn Trp Ser His Pro Gln Phe Glu Lys
1               5

<210> SEQ ID NO 157
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Arg Gly Ile Asp Pro Glu Glu Gly Arg Phe Asn Asn
1               5                   10

<210> SEQ ID NO 158
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

His Gly Gln Asp Ser Val Arg Val Gly Arg
1               5                   10
```

The invention claimed is:

1. A cell-targeting molecule comprising
   (i). a binding region capable of specifically binding an extracellular target biomolecule physically coupled to the surface of a cell, and
   (ii) a Shiga toxin effector polypeptide comprising an amino acid sequence having at least 90% identity to amino acids 1 to 251 of SEQ ID NO: 1;

wherein the amino acid sequence comprises at least four endogenous B-cell epitope regions, and comprises: amino acid substitutions V541, R55L, I57F, P59F, E60T, and E61L in SEQ ID NO: 1, wherein the endogenous B-cell epitope regions are natively positioned in a wild-type Shiga toxin A Subunit within amino acid residues: 39-48 of SEQ ID NO:1; 94-115 of SEQ ID NO:1; 179-190 of SEQ ID NO:1; and 243-251 of SEQ ID NO:1;

wherein the amino acid sequence comprises an asparagine at the amino acid residue corresponding to position 75 of SEQ ID NO: 1, a tyrosine at the amino acid residue corresponding to position 77 of SEQ ID NO: 1, a tyrosine at the amino acid residue corresponding to position 114 of SEQ ID NO: 1, a glutamate at the amino acid residue corresponding to position 167 of SEQ ID NO: 1, an arginine at the amino acid residue corresponding to position 170 of SEQ ID NO: 1, an arginine at the amino acid residue corresponding to position 176 of SEQ ID NO: 1, and a tryptophan at the amino acid residue corresponding to position 203 of SEQ ID NO: 1; and wherein the amino acid sequence has at least 95% sequence identity to SEQ ID NO: 16.

2. The cell-targeting molecule of claim 1, wherein the amino acid sequence has at least 95% sequence identity to amino acids 1 to 251 of SEQ ID NO: 1.

3. The cell-targeting molecule of claim 1, wherein the binding region is fused to the carboxy terminus of the Shiga toxin effector polypeptide to form a single, continuous polypeptide.

4. The cell-targeting molecule of claim 1, wherein the binding region comprises an immunoglobulin-type binding region.

5. The cell-targeting molecule of claim 4, wherein the immunoglobulin-type binding region comprises a polypeptide selected from: single-domain antibody fragment, single-chain variable fragment, antibody variable fragment, complementary determining region 3 fragment, constrained FR3-CDR3-FR4 polypeptide, Fd fragment, antigen-binding fragment, fibronectin-derived 10th fibronectin type III domain, tenascin type III domain, ankyrin repeat motif domain, low-density-lipoprotein-receptor-derived A-domain, lipocalin, Kunitz domain, Protein-A-derived Z domain, gamma-B crystallin-derived domain, ubiquitin-derived domain, Sac7d-derived polypeptide, Fyn-derived SH2 domain, miniprotein, C-type lectin-like domain scaffold, a heavy-chain antibody domain derived from a camelid $V_HH$ fragment, heavy-chain antibody domain derived from cartilaginous fish, immunoglobulin new antigen receptor (IgNAR), $V_{NAR}$ fragment, multimerizing scFv fragment, bivalent minibody, bispecific tandem scFv, bispecific tandem $V_HH$, and bispecific minibody.

6. The cell-targeting molecule of claim 5, wherein the multimerizing scFv fragment is a diabody, triabody, or tetrabody.

7. The cell-targeting molecule of claim 1, wherein the binding region comprises one or more polypeptides capable of specifically binding the extracellular target biomolecule.

8. The cell-targeting molecule of claim 1, which comprises the linker peptide $(G_xS)_n$ wherein x is 1 to 6 and n is 1 to 30.

9. The cell-targeting molecule of claim 8, wherein x is 4 and n is 1.

10. The cell-targeting molecule of claim 1, wherein the extracellular target biomolecule is CD20, CD38, CTLA-4, HER2/neu/ErbB2, or CS1/SLAMF7.

11. A pharmaceutical composition comprising the cell-targeting molecule of claim 1 and a pharmaceutically acceptable excipient or carrier.

\* \* \* \* \*